(12) United States Patent
Meister et al.

(10) Patent No.: US 10,407,677 B2
(45) Date of Patent: Sep. 10, 2019

(54) HIGH COMPLEXITY SIRNA POOLS

(71) Applicants: INTANA BIOSCIENCE GMBH, Munich (DE); UNIVERSITÄT REGENSBURG, Regensburg (DE)

(72) Inventors: Gunter Meister, Regenstauf (DE); Michael Hannus, Dresden (DE)

(73) Assignees: INTANA BIOSCIENCE GmbH, Munich (DE); siTools Biotech GmbH, Munich (DE)

( * ) Notice: Subject to any disclaimer, the term of this patent is extended or adjusted under 35 U.S.C. 154(b) by 145 days.

(21) Appl. No.: 14/396,905

(22) PCT Filed: Apr. 25, 2013

(86) PCT No.: PCT/EP2013/058603
§ 371 (c)(1),
(2) Date: Oct. 24, 2014

(87) PCT Pub. No.: WO2013/160393
PCT Pub. Date: Oct. 31, 2013

(65) Prior Publication Data
US 2015/0132848 A1    May 14, 2015

(30) Foreign Application Priority Data

Apr. 26, 2012 (EP) .................................. 12165702
Apr. 26, 2012 (GB) .................................. 1207291.4
Oct. 26, 2012 (EP) .................................. 12190148

(51) Int. Cl.
*C12N 15/11* (2006.01)

(52) U.S. Cl.
CPC ........ *C12N 15/111* (2013.01); *C12N 2310/14* (2013.01); *C12N 2310/51* (2013.01); *C12N 2330/31* (2013.01)

(58) Field of Classification Search
CPC combination set(s) only.
See application file for complete search history.

(56) References Cited

U.S. PATENT DOCUMENTS

| | | | |
|---|---|---|---|
| 2005/0260754 A1 | 11/2005 | Kock et al. | |
| 2006/0166913 A1* | 7/2006 | Suzuki | C12N 15/111 514/44 A |
| 2007/0031844 A1* | 2/2007 | Khvorova | A61K 31/713 435/6.11 |
| 2011/0251258 A1 | 10/2011 | Samarsky et al. | |

FOREIGN PATENT DOCUMENTS

| | | |
|---|---|---|
| EP | 1681347 A1 | 7/2006 |
| WO | WO 2004/035765 A2 | 4/2004 |
| WO | WO 2004/046320 A2 | 6/2004 |
| WO | WO 2004/106517 A1 | 12/2004 |
| WO | WO 2007/010840 A1 | 1/2007 |
| WO | WO 2007/091269 A2 | 8/2007 |
| WO | WO 2011/117353 A1 | 9/2011 |

OTHER PUBLICATIONS

Wang Shunqing et al., "Development and validation of vectors containing multiple siRNA expression cassettes for maximizing the efficiency of gene silencing," *BMC Biotechnology, Biomed Central Ltd.*, Dec. 22, 2006, vol. 6, No. 1, p. 50.
Poliseno et al: "370. Multi-Copy,Multi-siRNA Vectors as Versatile Tools for Multiple Gene Knock-Down Applications", *Molecular Therapy, Nature Publishing Group*, Aug. 15, 2005, vol. 11, p. 144.
International Search Report for corresponding PCT Application No. PCT/2013/058603 dated Jul. 29, 2013.
European Search Report of corresponding International Application No. GB 1207291.4 dated Aug. 17, 2012.

* cited by examiner

*Primary Examiner* — Jennifer Pitrak McDonald
(74) *Attorney, Agent, or Firm* — Pepper Hamilton LLP

(57) ABSTRACT

The present invention relates to a method for producing pools of siRNA molecules suitable for RNA interference.

8 Claims, 38 Drawing Sheets

Specification includes a Sequence Listing.

- 1: NEB dsRNA ladder, 2ul = 200ng
- 2: loop1 AGTTG
- 3: loop2 AGTTTG
- 4: loop3 AGTTAG
- 5: loop4 AGTTTTG
- 6: loop5 AGTTTAG
- 7: loop6 AGTGTAG
- 8: NEB dsRNA ladder, 2ul = 200ng
- 9: loop1 AGTTG
- 10: loop2 AGTTTG
- 11: loop3 AGTTAG
- 12: loop4 AGTTTTG
- 13: loop5 AGTTTAG
- 7'14: loop6 AGTGTAG 0.1U T1/ugRNA, 30'
0.1U T1/ugRNA, 30'
0.1U T1/ugRNA, 30'
0.1U T1/ugRNA, 30'
0.1U T1/ugRNA, 30'
0.1U T1/ugRNA, 30'

0.1U T1/ugRNA, 120'
0.1U T1/ugRNA, 120'
0.1U T1/ugRNA, 120'
0.1U T1/ugRNA, 120'
0.1U T1/ugRNA, 120'
0.1U T1/ugRNA, 120'

HIGH COMPLEXITY SIRNA POOLS

CROSS-REFERENCE TO RELATED PATENT APPLICATIONS

This application is a U.S. National Phase Application under 35 U.S.C. § 371 of International Patent Application No. PCT/EP2013/058603, filed Apr. 25, 2013, which claims priority to GB Application No. 1207291.4 and EP Application No. 12165702.7 both filed Apr. 26, 2012, and EP Application No. 12190148.2 filed Oct. 26, 2012, all of which are incorporated herein by reference in their entireties. The International application was published on Oct. 31, 2013 as International Publication No. WO 2013/160393.

SEQUENCE LISTING

The instant application contains a Sequence Listing which has been submitted electronically in ASCII format and is hereby incorporated by reference in its entirety. Said ASCII copy, created on May 25, 2017, is named 10276-003910-US0_SL.txt and is 169,525 bytes in size.

FIELD OF THE INVENTION

The present invention relates to a method for producing pools of siRNA molecules suitable for RNA interference. The methods rely on in vitro transcription and hybridization of template molecules to generate annealed RNA molecules which comprise double stranded sections defining at least part of the siRNA sequences and a single stranded loop sequence being capable of being recognised, cleaved and digested by an RNase. The present invention further relates to nucleic acid molecules and kits thereof wherein the nucleic acid molecules comprise DNA molecules which can be used in the afore described methods in accordance with the invention.

BACKGROUND

RNA interference (RNAi) is a powerful tool for performing loss of function studies in diverse organisms by transiently shutting of gene expression. Various methods have been developed to allow for efficient RNAi.

One of the common approaches is to use small inhibitory (siRNA) molecules which are typically double-stranded RNA molecules of a length of 15 to 30 nucleotides. The sequences of such siRNA molecules are selected so that they match sequences of the mRNA to be silenced by RNAi. The siRNAs are then brought into contact with the organism or cell for which gene silencing studies are to be performed. The siRNA molecules are integrated into the RISC complex a complex enzymatic machinery involving the so-called Ago proteins mediating the separation of the double-stranded siRNA molecules and effecting the hybridization of single stranded siRNA molecules with the target mRNA ultimately leading to the desired transient silencing of the respective mRNA, i.e. gene that is targeted by the siRNAs.

RNAi and siRNAs can be used in a versatile manner. For example, siRNA libraries may be designed to perform screens for loss of function studies addressing not only one, but numerous and, in principle, all genes of a particular cell or organism.

Some of the drawbacks of RNAi and siRNAs, which have been increasingly recognised in recent years, are so-called off-target-effects and efficacy as well as problems relating to the manufacturing of pools of siRNAs, which either allow for silencing of the expression of various genes at the same time, or a single gene by using a multitude of siRNAs being specific for that specific target gene.

In principle, the selectivity of RNAi can be addressed by properly selecting siRNAs. For example, one may select the sequence of an siRNA that determines which sequence of the gene to be silenced will be recognised such that a sequence is selected that should in principle be unique to the target gene and not be found in other sequences. By properly selecting such siRNA sequences, it should be possible to ensure that only the gene of interest is silenced. However, even though it should in principle be possible to select target siRNA sequences such that no other target sequences are recognised by the siRNAs with the consequence that no off-target-effects should occur, such siRNAs are not necessarily effective to the desired degree.

Effectiveness is determined inter alia by the fact that a target sequence may not easily be accessible in the in vivo situation to the siRNA due to interaction with proteins within a cell or the fact that the sequence of the target genes may adopt confirmations that render them non- or at least partially accessible to the siRNA. Due to these facts, an siRNA sequence which according to common selection procedures should not provide any off-target effects, may not prove effective or may also impact the expression of other genes. In view of the aforementioned problems, it may be necessary to design siRNAs with different sequences and to use them simultaneously in order to silence the expression of a single gene. For reasons not understood using numerous siRNA sequences against the same target gene, the danger of off-target effects may be reduced, perhaps by increasing the signal to nose ratio for specific siRNAs over non-specific or non-effective siRNAs.

Manufacturing of siRNAs by e.g. solid phase chemistry can be rather time and cost consuming. Particularly if one wants to produce complex pools of siRNAs either of siRNAs being directed to the same target gene or siRNA pools recognising different target genes can thus become prohibitive from a cost perspective.

Nevertheless such pools of siRNA sequences are of high interest because, as mentioned before, they allow efficient silencing of the expression of a single gene as then not each and every siRNA has to be tested stepwise. Rather, one can quite straigthforwardly silence a gene by using such a pool or one can even silence numerous genes at the same time.

In the light of this background, there is thus continuing interest in methods that allow for provision of pools of siRNAs that allow silencing of either expression of a single gene and/or that allow silencing of expression of numerous genes at the same time. Furthermore, there is a continuing interest in providing new methods for efficiently producing siRNAs and in particular the aforementioned siRNA pools. It is inter alia these problems that the present invention addresses.

OBJECTIVES AND SUMMARY OF THE PRESENT INVENTION

It is one objective of the present invention to provide efficient methods for producing siRNAs. It is in particular an objective of the present invention to provide methods that allow manufacturing of siRNA pools which can either be used to silence the expression of single genes and/or the expression of various genes at the same time. Furthermore, it is an objective of the present invention not only to provide methods but also tools in the form of nucleic acid molecules and kits that can be used for methods of manufacturing siRNAs and in particular pools of siRNAs either for the silencing of a single genes and/or simultaneous silencing of various genes. It is another objective of the present invention to provide pools of siRNAs, which can be used to selectively silence gene expression at reduced off-target effects.

These and other objectives as they will become apparent from the ensuing description are attained by the subject matter of the independent claims. The dependent claims relate to some of the preferred embodiments of the present invention.

The invention as described herein starts from the finding that a new enzymatic approach can be used to produce defined, complex pools of short interfering RNAs (siRNAs) for the gene specific inhibition of gene expression in vitro and in vivo. In the first step of the method, two partly complementary single strand RNAs are generated by in vitro transcription from custom DNA templates. Hybridization of the two single strand RNAs gives rise to a double strand RNA molecule composed of alternating base pairing and non base pairing sections. Using a single strand specific ribonuclease, the non base pairing loop sections are degraded, cleaving the long double strand RNA precursor into a mixture of short double strand RNA molecules corresponding to the base pairing sections of the precursor molecule. Such a single strand specific ribonuclease is preferably RNAse T1.

The inventors of the present invention thus have found that it is possible to produce siRNAs by designing and providing template nucleic acid molecules that upon transcription, hybridization and digestion with selected Rnases, of which RNAse T1 may be preferred, can be used to produce the same siRNAs or pools of different siRNAs which may be directed to the same target genes and/or pools of siRNAs which are directed to different target genes. To this end, the present invention uses template molecules and preferably DNA molecules which upon transcription and hybridization, preferably in vitro transcription and in vitro hybridization, yield hybridized RNA molecules as depicted in FIGS. 1 and 2. The resulting hybridized RNA molecules are characterised by sections of double-stranded RNA comprising at least part of the sequences of the final siRNA molecules and single-stranded loop sequences which can be recognised, cleaved and digested by RNases as mentioned herein, of which RNAse T1 may be preferred. As the RNases as mentioned herein, of which RNAse T1 may be preferred, preferentially recognise, cleave and digest the single-stranded RNA loop section over the double-stranded RNA sections, one ultimately obtains double-stranded siRNA molecules. It is immediately evident to a skilled person that by manufacturing template molecules which upon transcription and hybridization will lead to RNA molecules as depicted in FIGS. 1 and 2, one can produce either siRNAs of the same sequence, pools of siRNAs of different sequences, which can be used to silence expression of a single target gene and/or pools of siRNA molecules of different sequences which can be used to silence the expression of numerous genes, such as e.g. genes defining pathways. The pools of siRNAs, which may de designated as siRNA pools, may also be used for genome wide screens of genes. Such high complexity pools can also be used for treating a disease in a human or animal being. They may also be used to silence the expression of numerous genes, such as e.g. genes defining pathways. The pools of siRNAs, which may de designated as siRNA pools, may also be used for genome wide screens of genes.

As the template DNA molecules may be preferably made from DNA, these template molecules can be integrated into common vector systems and thus serve as a blueprint and storage device of such template molecules. However, manufacturing of template molecules, which may preferably be made of DNA molecules, is far more economical, both in terms of cost and time than direct synthesis of specific siRNA molecules. Once such a template molecule, which may preferably be a DNA molecule has been made and cloned in a vector, it can be stored, propagated and then in vitro transcribed and hybridized, once there is a need for a new batch of siRNA molecules.

By selecting and adjusting the length of the sections in the template molecules which will ultimately correspond to the siRNA molecules, it is possible to produce siRNAs of a length as they are commonly used for RNAi, i.e. typically between 15 to 30 nucleotides. It is thus possible to produce siRNA molecules by selecting the length of the sequences in the template molecule which will correspond to the siRNA molecules that e.g. have already been found to be effective for certain genes in certain organisms. For the case of mammalian organisms and cells, one can thus produce siRNAs e.g. of a length of 21, 22 and 23 nucleotides.

Further, as will be apparent from the ensuing description, by properly selecting the sequences in the template molecule which will correspond to the single-stranded loop sequences and positioning the nucleotides at which the various RNases, of which RNAse T1 may be preferred, will preferentially cleave, it will be possible to produce siRNA molecules having a 3' overhang of e.g. between 1 to 5 nucleotides. Further, it is of course also possible to produce blunt-ended siRNA molecules if desired.

The present invention is illustrated with respect to a template molecule where overall 14 different siRNA sequences, all of which were directed to the same target gene, namely AUKRB, were incorporated into a template molecule, for which the sequences giving rise to the single-stranded loop sequences, were selected to be cleavable and digestible by RNase T1. It is furthermore demonstrated that the resulting pool of 14 siRNA sequences, all of which had a length of 21 nucleotides and a 3' overhang of 2 nucleotides was efficient in silencing the expression of AUKRB.

The present invention furthermore illustrates that complex pools of 15 and 60 siRNAs, which were obtained using the methods described herein, provide better on-target effects for Scyl1 or PolG than established siRNAs and esiRNA pools against these genes. Further, such complex siRNA pools effectively avoid off-target effects as is shown in comparison to siRNAs against PolG and Scyl1, which are known to give off-target effects for Mad2, and in comparison to so called smart pools. It seems reasonable to assume in view of the data presented that the reduced off-target effects result from low concentration of siRNAs, which may be responsible for the off-target effects, in the pools. Interestingly, the pools were shown in a genome wide analysis to not lead to substantial off-target effects on other genes.

The person skilled in the art will of course immediately realise that this concept can be transferred to template molecules for which the siRNA sequences are selected such that different genes other than AUKRB, PolG or Scyl 1 are silenced and that the loop sequences may be modified either to result in siRNAs of different lengths and different 3' overhangs or that loop sequences are selected which are recognised, cleaved and digested by RNases different from RNase T1.

The data presented hereinafter further show for the preferred RNase T1, according to which considerations loop sequences may be selected to allow for efficient cleavage by RNAse T1. In case of RNAse T1, loop sequences may be of about at least 3 nucleotides in length with efficient cleavage being achieved by loop sequences of preferably at least 5, 6, 7, 8, 9, or 10 nucleotides in length. Even though longer loop sequences may be used it seems that loop sequences below about 15 nucleotides in length will be optimal from an economic perspective as well as in avoiding secondary structure formation, which may affect efficiency of cleavage. It seems reasonable to assume that these findings may also apply to other single stranded RNAses than RNAse T1. In the case of RNAse T1, the loop sequences will have to comprise a G after which cleavage takes place. However, the sequences may be preferably selected such that the loop sequence of the sense and antisense strand to not lead to the unusual base paiting of G and T. Even more preferably, loop sequences may thus be made only of G and A allowing e.g. incorporation of modified T and C nucleotides in those sequence portions that will ultimately lead to the siRNA sequences.

The present invention in a first aspect thus relates to a method of preparing double stranded RNA molecules, wherein each strand of said different double stranded molecules has a length of 15 to 30 nucleotides wherein said different double stranded RNA molecules are capable of target-specific RNA interference of at least one target gene, said method comprising at least the steps of
- a. Providing at least one first DNA molecule,
- b. Providing at least one second DNA molecule,
- c. In vitro transcribing said at least one first and at least one second DNA molecules using an RNA polymerase to obtain corresponding at least one first and at least one second RNA molecules,
- d. Hybridizing said at least one first and at least one second RNA molecules of step c. to obtain an double stranded RNA molecule of the general structure depicted in FIG. 1,
- e. Digesting the double stranded RNA molecule obtained in step d. with an RNase, of which RNAse T1 may be preferred, capable of preferentially recognizing, cleaving and digesting the single stranded loop-sequence-elements over the hybridized double stranded sections of the double stranded RNA obtained in step d. thereby removing single stranded RNA loops,
  wherein the sequence of said target-sequence-elements depicted on FIG. 1 of the at least one first DNA molecule is sense to sequences of said at least one target gene of RNA interference, wherein the sequences of said target-sequence-elements$_{rc}$ of the at least one second DNA molecule are the reverse complements of the sequences of the target-sequence-elements of the at least one first DNA molecule, which they hybridize to, and wherein the loop-sequence elements of the at least one first and at least one second DNA molecules are not reverse complements of each other,
  wherein the sequences of the loop-sequence-elements are selected such that double stranded RNA molecules are obtained by recognition, cleavage and digestion of the single stranded loop-sequence elements by an RNase in step e., wherein each strand of said resulting double stranded molecules has a length of 15 to 30 nucleotides and wherein said resulting double stranded RNA molecules are capable of target-specific RNA interference of at least one target gene.

In a preferred embodiment of this first aspect, the present invention relates to a method comprising at least the steps of:
- a. Providing at least one first DNA molecule comprising in the 5'-3' direction as repeating units a nucleic acid sequence with the following elements:

5'-[(target-sequence-element)-(loop-sequence-element)]$_k$-3', with k being an integer >1,
  with the target-sequence-element being a continuous sequence of 15 to 30 desoxyribonucleotides, which is sense to a sequence in said at least one target gene of RNA interference,
  with the loop-sequence-element being a continuous sequence of 3 to preferably 20 desoxyribonucleotides, which does not match a sense or antisense sequence in said at least one target gene of RNA interference,
- b. Providing at least one second. DNA molecule comprising in the 5'-3' direction in a repetitive manner a nucleic acid sequence with the following elements:

5'-[(target-sequence-element)$_{rc}$-(loop-sequence-element)]$_l$-3', with l being an integer >1 and having the same value as k in the first DNA molecule,
  with the target-sequence-element$_{rc}$ being a continuous sequence of 15 to 30 desoxyribonucleotides,
  with the loop-sequence-element being a continuous sequence of 3 to preferably 20 desoxyribonucleotides, which does not match a sense or antisense sequence in said at least one target gene of RNA interference,
  wherein the target-sequence-elements$_{rc}$ counted from the 3' end in the repeating units of said second DNA molecule are the respective reverse complement of the target-sequence-elements counted from the 5' end in the repeating units of said first DNA molecule, and
  wherein the loop-sequence-elements in the repeating units of said second DNA molecule are not reverse complements of the loop-sequence-elements in the repeating units of said first DNA molecule,
- c. in vitro transcribing said at least one first and at least one second DNA molecules using an RNA polymerase to obtain corresponding at least one first and at least one second RNA molecules,
- d. Hybridizing said at least one first and at least one second RNA molecules of step c. to obtain a double stranded RNA molecule of the general structure depicted in FIG. 1,
- e. Digesting the double stranded RNA molecule obtained in step d. with an RNase, of which RNAse T1 may be preferred, capable of preferentially recognizing, cleaving and digesting the single stranded loop-sequence-elements over the hybridized double stranded sections of the double stranded RNA obtained in step d. thereby removing single stranded RNA loops,
  wherein the sequences of the loop-sequence-elements are selected such that double stranded RNA molecules are obtained by recognition, cleavage and digestion of the single stranded loop-sequence elements by an RNase in step e., wherein each strand of said resulting double stranded molecules has a length of 15 to 30 nucleotides, wherein said resulting double stranded RNA molecules are capable of target-specific RNA interference of at least one target gene.

In a second aspect the present invention relates to a method of preparing different double stranded RNA molecules, wherein each strand of said double stranded molecules has a length of 15 to 30 nucleotides, wherein said double stranded RNA molecules are capable of target-specific RNA interference of at least one target gene, said method comprising at least the steps of:

a. Providing at least one DNA molecule,
b. In vitro transcribing said at least one DNA molecules using an RNA polymerase to obtain corresponding at least one first RNA molecule, which upon hybridization provides the general structure depicted in FIG. 2,
c. Digesting the RNA molecule obtained in step b. with an RNase, of which RNAse T1 may be preferred, capable of preferentially recognizing, cleaving and digesting the single stranded loop-sequence-elements over the hybridized double stranded sections of the double stranded RNA obtained in step b. thereby removing single stranded RNA loops,
wherein the sequence of said target-sequence-elements depicted on FIG. 2 of the at least one first DNA molecule is sense to sequences of said at least one target gene of RNA interference, wherein the sequences of said target-sequence-elements$_{rc}$ of the at least one DNA molecule are the reverse complements of the sequences of the target-sequence-elements of the at least one first DNA molecule, which they hybridize to, and wherein the loop-sequence elements of the at least one first and at least one second DNA molecules are not reverse complements of each other,
wherein the sequences of the loop-sequence-elements are selected such that double stranded RNA molecules are obtained by recognition, cleavage and digestion of the single stranded loop-sequence elements by an RNase in step c., wherein each strand of said resulting double stranded molecules has a length of 15 to 30 nucleotides and wherein said resulting double stranded RNA molecules are capable of target-specific RNA interference of at least one target gene.

In a preferred embodiment of the second aspect, the present invention relates to a method comprising at least the steps of:
a. Providing at least one first DNA molecule comprising in the 5'-3' direction as repeating units a nucleic acid sequence with the following elements:
5'-[(target-sequence-element)-(loop-sequence-element)]$_k$-(target-sequence-element)-(loop-sequence-element)$_{hp}$-[(target-sequence-element)$_{rc}$-(loop-sequence-element)]$_l$-3',
with k being an integer >1,
with l being an integer >1 and being the same as l,
with the target-sequence-element being a continuous sequence of 15 to 30 desoxyribonucleotides, which is sense to a sequence in said at least one target gene of RNA interference,
with the loop-sequence-element being a continuous sequence of 3 to preferably 20 desoxyribonucleotides, which does not match a sense or antisense sequence in said at least one target gene of RNA interference, wherein the (loop sequence element)$_{hp}$ is of sufficient length to allow for a hairpin structure enabling a self-hybdrization pattern depicted in FIG. 2, with the target-sequence-element$_{rc}$ being a continuous sequence of 15 to 30 desoxyribonucleotides,
wherein the target-sequence-elements$_{rc}$ counted from the 3' end are the respective reverse complement of the target-sequence-elements counted from the 5' end,
wherein the loop-sequence-elements following the (loop sequence element)$_{hp}$ are not reverse complements of the loop-sequence-elements preceeding the in the repeating units of said second DNA molecule,
b. In vitro transcribing said at least one first DNA molecules using an RNA polymerase to obtain corresponding at least one first RNA molecule, which upon hybridization provides the general structure depicted in FIG. 2,
c. Digesting the double stranded RNA molecule obtained in step b. with an RNase, of which RNAse T1 may be preferred, capable of preferentially recognizing, cleaving and digesting the single stranded loop-sequence-elements over the hybridized double stranded sections of the double stranded RNA obtained in step b. thereby removing single stranded RNA loops,
wherein the sequences of the loop-sequence-elements are selected such that double stranded RNA molecules are obtained by recognition, cleavage and digestion of the single stranded loop-sequence elements by an RNase in step c., wherein each strand of said resulting double stranded molecules has a length of 15 to 30 nucleotides and wherein said resulting double stranded RNA molecules are capable of target-specific RNA interference of at least one target gene.

In a third aspect, the present invention relates to a combination or a kit of at least two DNA molecules, which upon in vitro transcription, hybridization and digestion with an RNase, of which RNAse T1 may be preferred, are capable of providing double stranded RNA molecules, wherein each strand of said different double stranded molecules has a length of 15 to 30 nucleotides and wherein said double stranded RNA molecules are capable of target-specific RNA interference of at least one target gene, wherein said at least two DNA molecules have the sequence elements necessary to obtain an RNA molecule of the general structure depicted in FIG. 1 after in vitro transcription and hybridization,
wherein the sequences of the loop-sequence-elements are selected such that double stranded RNA molecules can be obtained after cleavage and digestion with an RNase, of which RNAse T1 may be preferred, capable of preferentially recognizing and cleaving the single stranded loop-sequence-elements over the hybridized double stranded sections of the double stranded RNA thereby removing single stranded RNA loops.

In a preferred embodiment of the third aspect, the present invention relates to a combination or a kit, obtainable by
a. at least one first DNA molecule comprising in the 5'-3' direction as repeating units a nucleic acid sequence with the following elements:
5'-[(target-sequence-element)-(loop-sequence-element)]$_k$-3', with k being an integer >1,
with the target-sequence-element being a continuous sequence of 15 to 30 desoxyribonucleotides, which is sense to a sequence in said at least one target gene of RNA interference,
with the loop-sequence-element being a continuous sequence of 3 to preferably 20 desoxyribonucleotides, which does not match a sense or antisense sequence in said at least one target gene of RNA interference,
b. at least one second DNA molecule comprising in the 5'-3' direction in a repetitive manner a nucleic acid sequence with the following elements:
5'-[(target-sequence-element)$_{rc}$-(loop-sequence-element)]$_l$-3',
with l being an integer >1 and having the same value as k in the first DNA molecule,
with the target-sequence-element$_{rc}$ being a continuous sequence of 15 to 30 desoxyribonucleotides,
with the loop-sequence-element being a continuous sequence of 3 to preferably 20 desoxyribonucleotides, which does not match a sense or antisense sequence in said at least one target gene of RNA interference, wherein the target-sequence-elements$_{rc}$ counted from the 3' end in the repeating units of said second DNA molecule are the respective reverse complement of the target-sequence-elements counted from the 5' end in the repeating units of said first DNA molecule, and wherein the loop-sequence-elements in the repeating units of said second DNA molecule are not reverse complements of the loop-sequence-elements in the repeating units of said first DNA molecule, wherein said at least one first and second DNA molecules can be in vitro transcribed and hybridized to obtain a double stranded RNA molecule of the general structure depicted in FIG. 1, wherein the sequences of the loop-sequence-elements are selected such that double stranded RNA molecules can be obtained by recognition, cleavage and digestion of the single stranded loop-sequence elements by an RNase, of which RNAse T1 may be preferred, capable of preferentially recognizing, cleaving and digesting the single stranded loop-sequence-elements over the hybridized double stranded sections of the double stranded RNA thereby removing single stranded RNA loops.

In a fourth aspect, the present invention relates to at least one DNA molecule, which upon in vitro transcription, hybridization and digestion with an RNase, of which RNAse T1 may be preferred, is capable of providing double stranded RNA molecules, wherein each strand of said double stranded molecules has a length of 15 to 30 nucleotides and wherein said different double stranded RNA molecules are capable of target-specific RNA interference of at least one target gene, wherein said at least one DNA molecule has the sequence elements necessary to obtain an RNA molecule of the general structure depicted in FIG. 2 after in vitro transcription and hybridization, wherein the sequences of the loop-sequence-elements are selected such that double stranded RNA molecules are obtained after digestion with an RNase, of which RNAse T1 may be preferred, capable of preferentially recognizing, cleaving and digesting the single stranded loop-sequence-elements over the hybridized double stranded sections of the double stranded RNA thereby removing single stranded RNA loops.

In a preferred embodiment of the fourth aspect, the present invention relates to at least one DNA molecule, obtainable by:
a) Providing at least one DNA molecule,
b) In vitro transcribing said at least one DNA molecules using an RNA polymerase to obtain corresponding at least one first RNA molecule, which upon hybridization provides the general structure depicted in FIG. 2,
c) Digesting the RNA molecule obtained in step b. with an RNAse, of which RNAse T1 may be preferred, capable of preferentially recognizing, cleaving and digesting the single stranded loop-sequence-elements over the hybridized double stranded sections of the double stranded RNA obtained in step b. thereby removing single stranded RNA loops, wherein the sequence of said target-sequence-elements depicted on FIG. 2 of the at least one first DNA molecule is sense to sequences of said at least one target gene of RNA interference, wherein the sequences of said target-sequence-elements$_{rc}$ of the at least one DNA molecule are the reverse complements of the sequences of the target-sequence-elements of the at least one first DNA molecule, which they hybridize to, and wherein the loop-sequence elements of the at least one first and at least one second DNA molecules are not reverse complements of each other, wherein the sequences of the loop-sequence-elements are selected such that double stranded RNA molecules are obtained by recognition, cleavage and digestion of the single stranded loop-sequence elements by an RNase, of which RNAse T1 may be preferred, in step c., wherein each strand of said resulting double stranded molecules has a length of 15 to 30 nucleotides and wherein said resulting double stranded RNA molecules are capable of target-specific RNA interference of at least one target gene.

Such combinations, kits and DNA molecules may be provided with
optionally an RNA polymerase,
optionally a buffer for in vitro transcription,
optionally a buffer for hybridization,
optionally an RNase, and
optionally written instructions.

In a fifth aspect the present invention relates to the use of any method as described herein, any kit as described herein or any template molecule for producing siRNA pools.

In a sixth aspect, the invention relates to combinations of at least 5, preferably at least 8 siRNAs against at least one specific gene. Such high complexity siRNA pools may be assumed to provide improved on-target and reduced off-target effects. The siRNAs of such high complexity siRNA pools may be produced by the methods in accordance with the invention, but also by methods known in the state of the art such as by chemical synthesis. Such high complexity pools can be used for treating a disease in a human or animal being. They may also be used to silence the expression of numerous genes, such as e.g. genes defining pathways. The pools of siRNAs, which may de designated as siRNA pools, may also be used for genome wide screens of genes.

FIGURE LEGENDS

Figure 3:
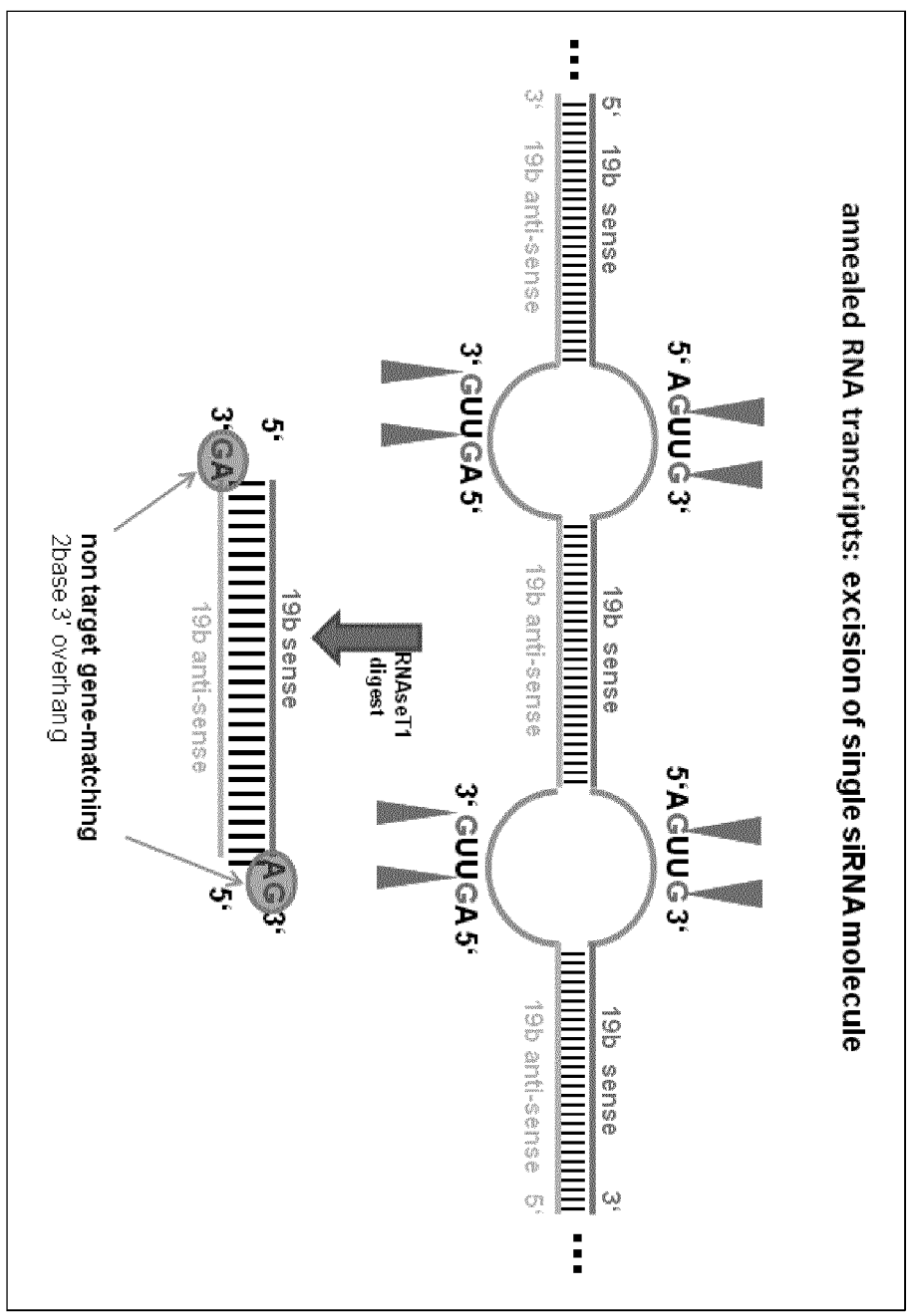

FIG. 3 depicts schematically two annealed RNA molecules as used in Example 1 and the effects of an RNase T1 digest.
(top): target gene specific, base-pairing 19base sense and antisense sequences. Base-pairing highlighted by vertical bars ("IIIIII"). Non base-pairing, non gene-specific constant loop sequence indicated as curved line. 5 base loop sequence indicated above or below loop with Guanine positions, accessible to RNAseT1 highlighted by arrows. Points of RNAseT1 cleavage 3' to accessible Guanines indicated by arrows.
(bottom): 19b sense and antisense sequence remain unaffected by RNAseT1 cleavage. Cleavage by Rnase T1 leads to a 3' overhang of AG resulting in a total of 21 base length for sense and antisense strand. The 3' overhang AG bases are constant and do not have to match the target gene sequence.

Figure 4:
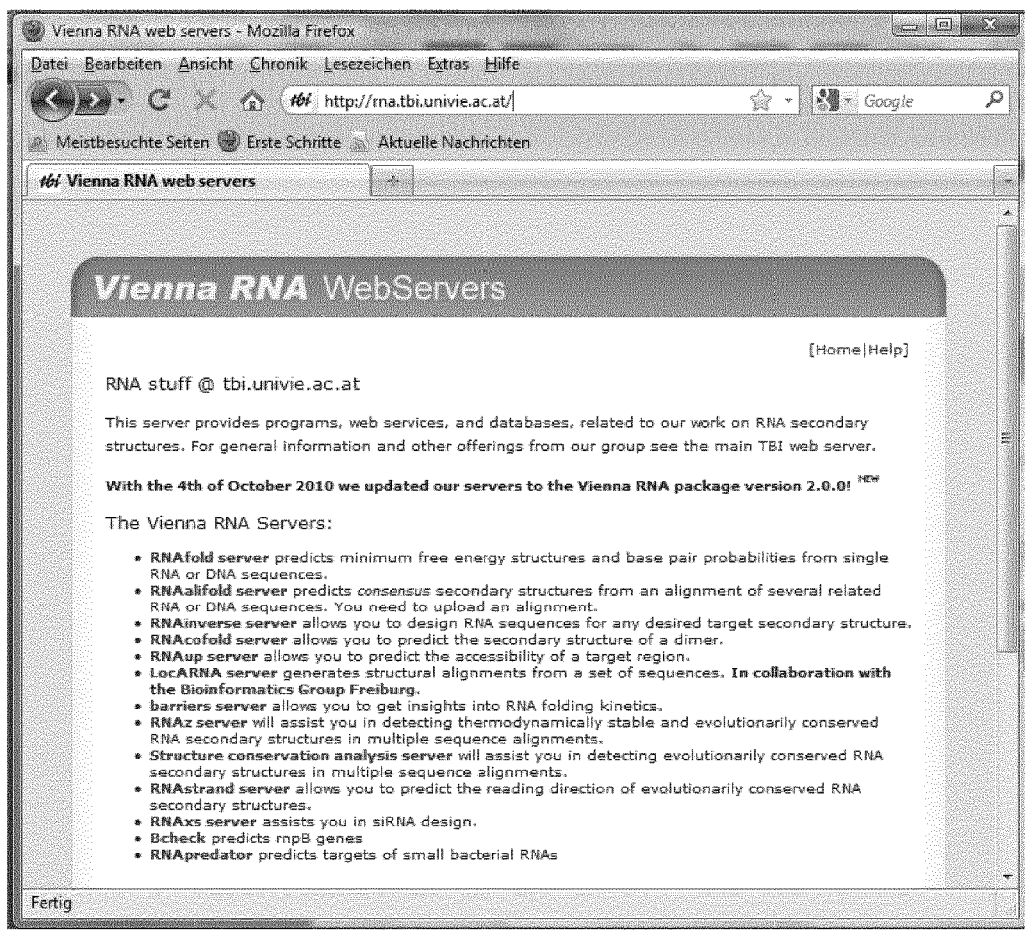
Figure 5:
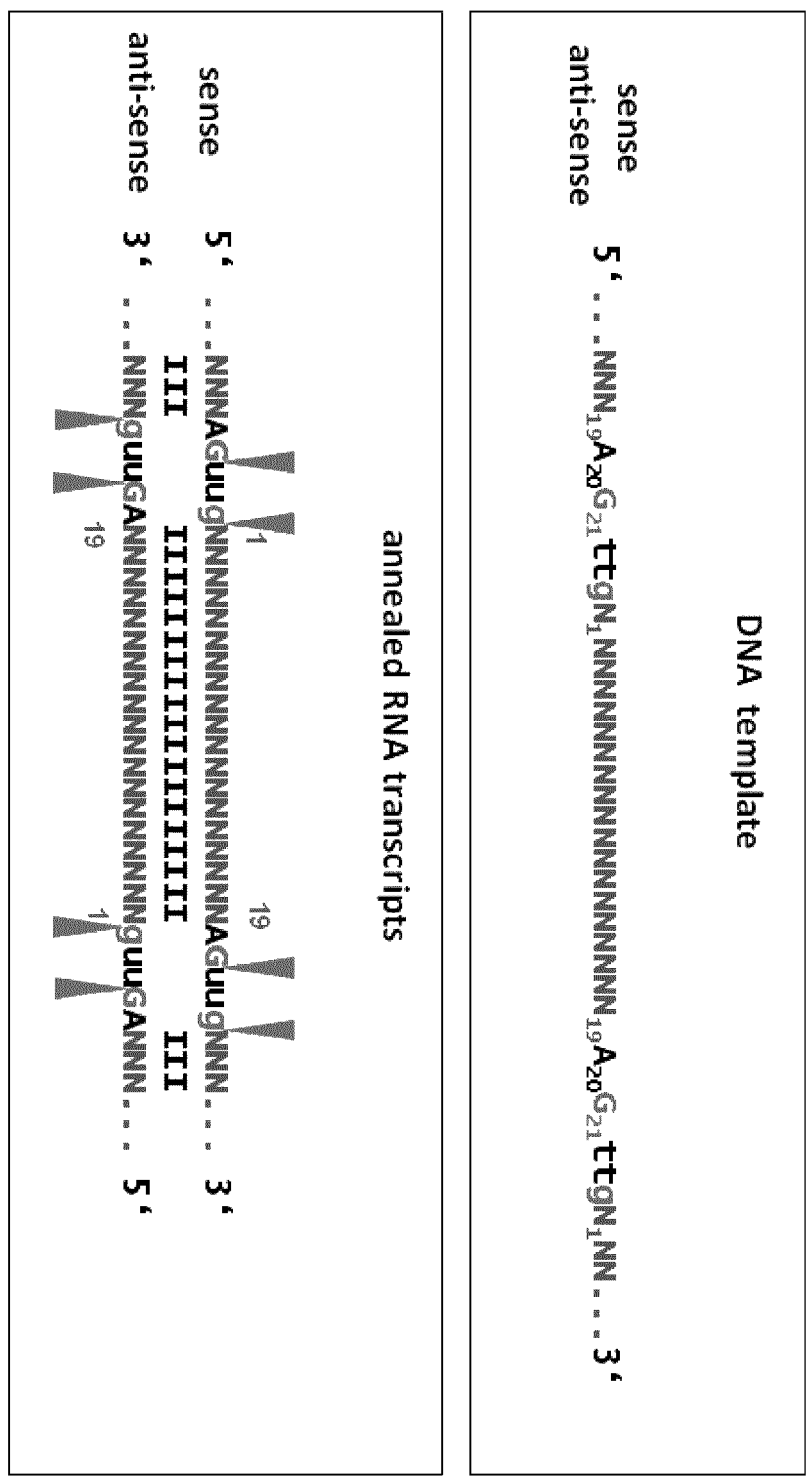

FIG. 4 depicts the homepage and available software suites of the Vienna RNA WebServers FIG. 5 Upper box: Scheme of DNA template for both sense and antisense strand as used in example 1. 19 gene matching, base pairing nucleotides ($N_1$ to $N_{19}$) of siRNA sequence in indicated position in siRNA. 5 base loop sequence AGTTG. Excised loop sequence (ttg) in lower case.

Lower box: annealing of sense and antisense strand transcribed from template as indicated in upper box. Arrowheads indicate positions of RNAseT1 cleavage, 3' of non base pairing G nucleotides. Base-pairing nucleotides indicated by "I" between sense and antisense strand. Mature siRNA after RNAseT1 digest highlighted by blue background color.

Figure 6:
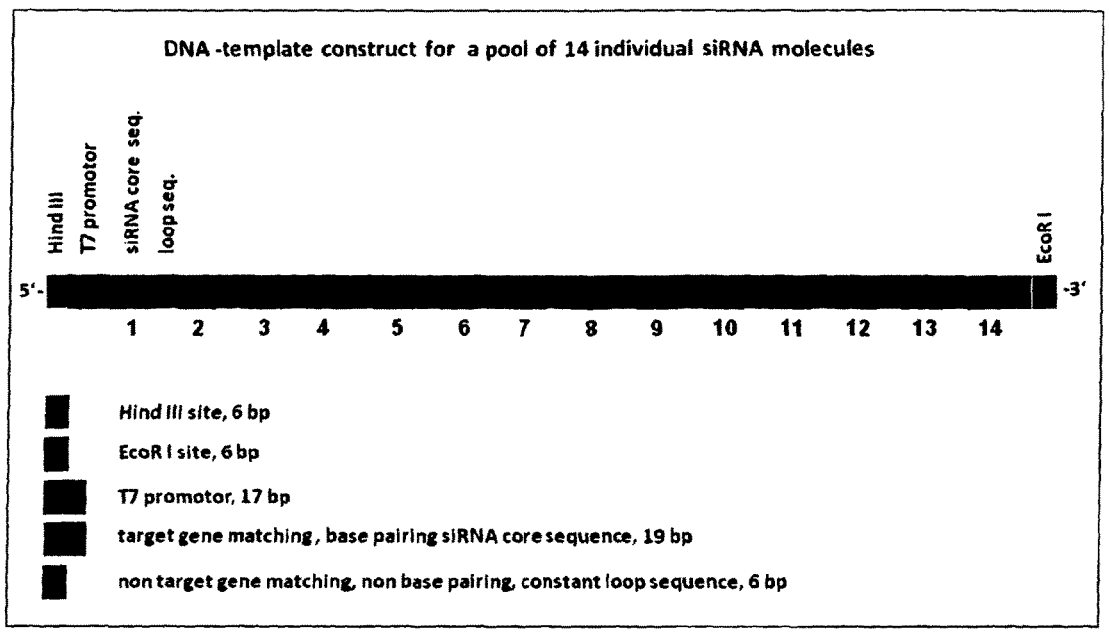
Figure 6:
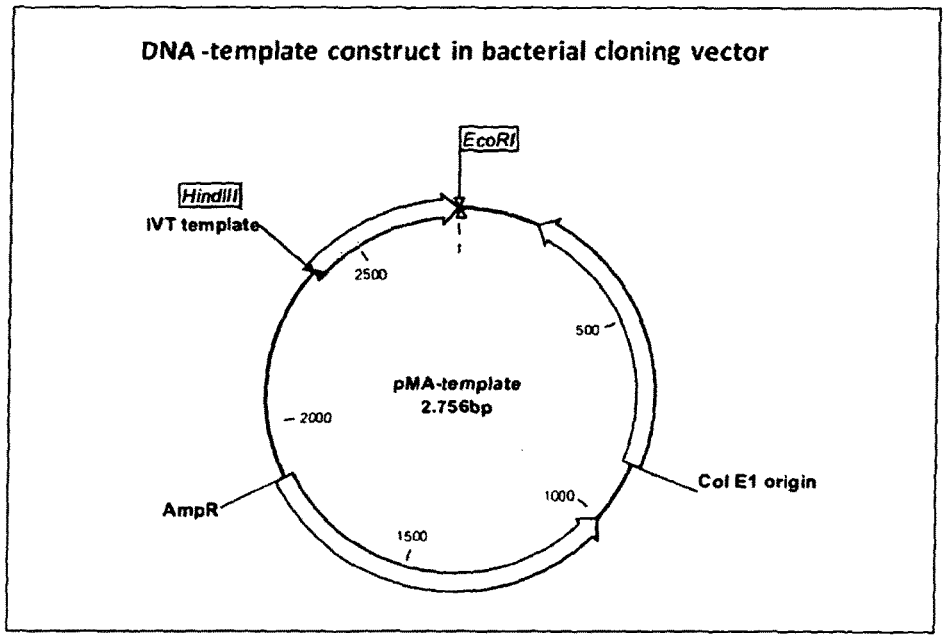

FIG. 6 Upper panel depicts schematically overall structure of template used for producing pools of 14 siRNAs as described in Example 1 and 2.

Lower panel shows template cassette inserted into pMA bacterial cloning vector by EcoRI and HindIII restriction sites as obtained from DNA template provider (e.g. Geneart)

Figure 7:
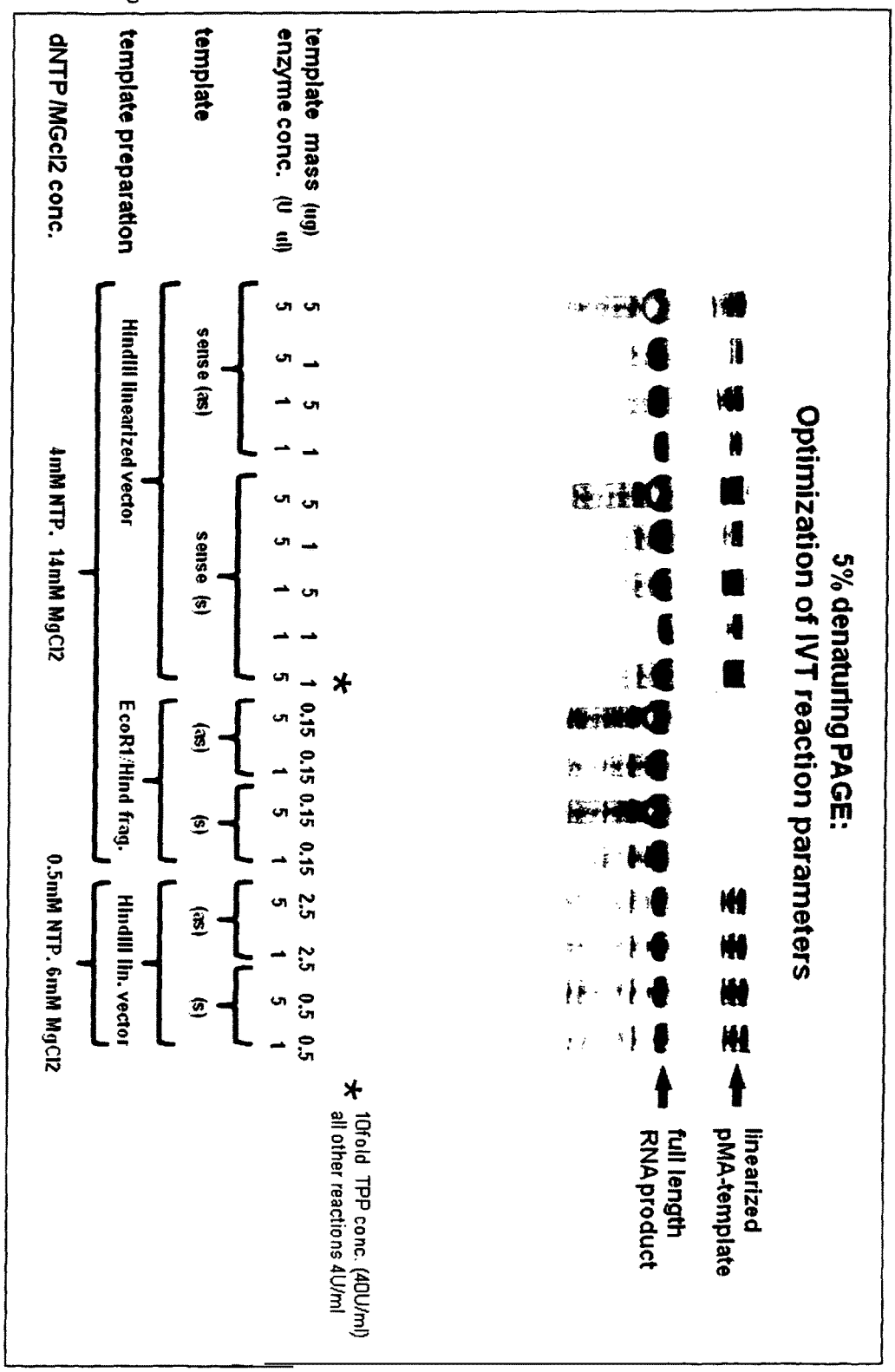

FIG. 7 depicts optimization of in vitro transcription (IVT) of template of Example 1. Each lane of the 5% denaturing PAA gel loaded with 5 µl sample from one IVT reaction with 100 µl (lane 1-9) and 50 ul (lane 10-17) total volume. Parameters varied between reactions as indicated below the gel image were: template mass (0.15-5 µg), enzyme concentration (1 or 5 units RNA pol T7), template (sense or antisense), template preparation (Hind III linearized vector, HindII-EcoRI excised template fragment), dNTP (4 mM vs 0.5 mM) and $MgCl_2$ concentration (14 mM vs 6 mM). T7 RNA polymerase enzyme, 10× reaction buffer and thermostable pyrophosphatase from NEB.

Figure 8:
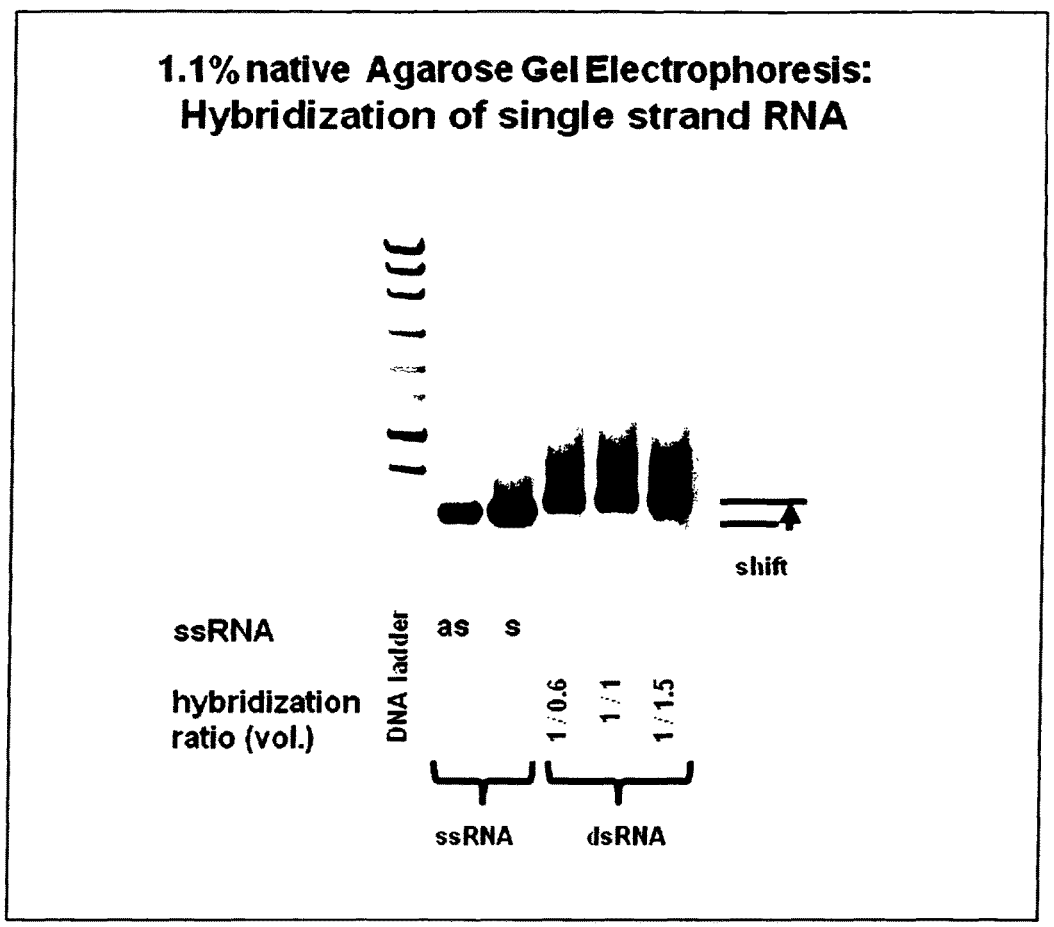

FIG. 8 depicts efficiency of annealing step of single stranded RNA of Example 1. 1 µl per lane of single strand RNA (lane 2 and 3) or hybridization reaction (lane 4 to 6) loaded on 1.1% native agarose gel. Sense (lane 3) and antisense (lane 2) single strand RNA were hybridized in 3 ratios (antisense/sense): 1/0.6, 1/1, 1/1.5. Main band of all hybridization reactions show shift to higher molecular weight as compared to single strand RNA, indicative for formation of double strand RNA.

Figure 9:
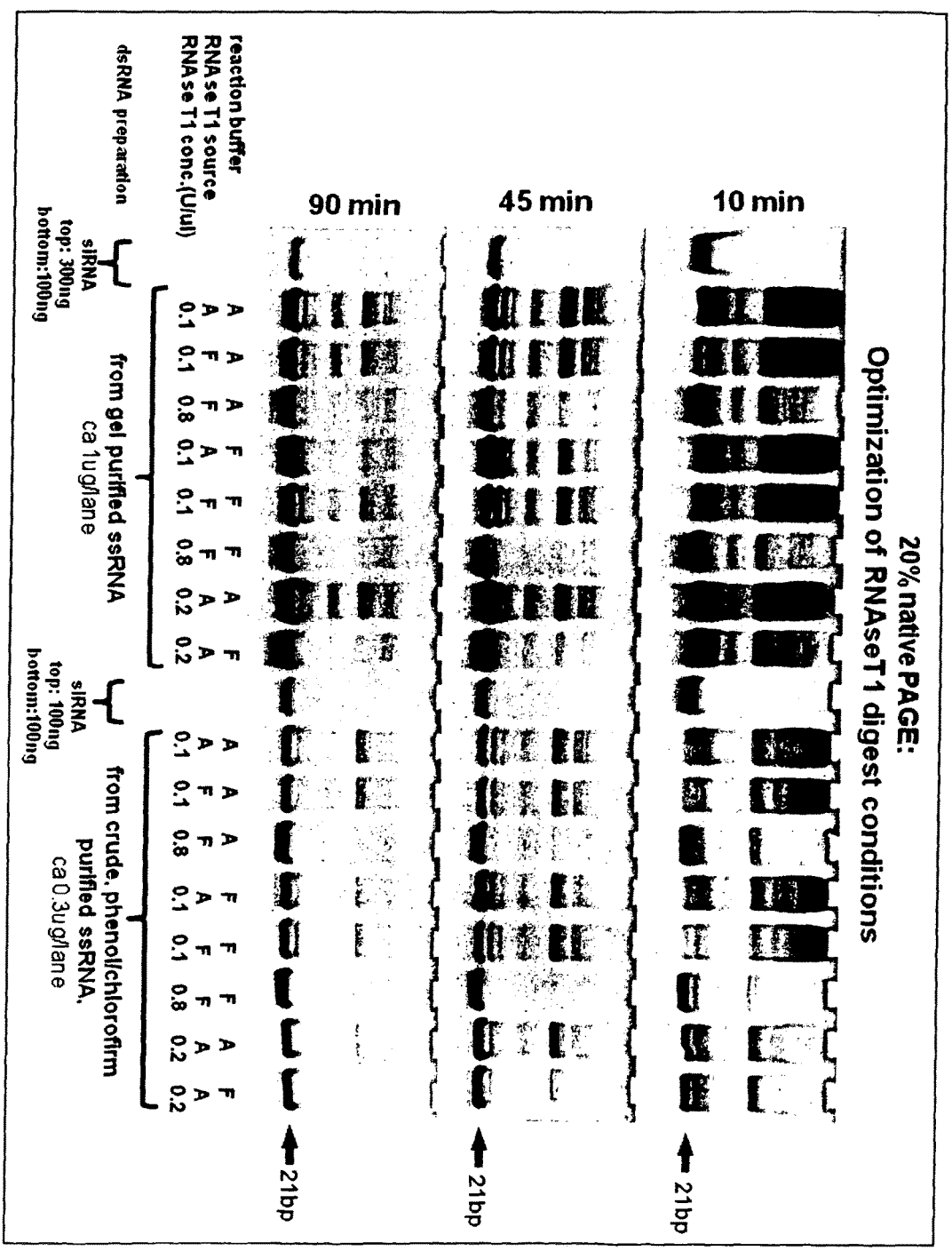

FIG. 9 depicts optimization of RNAse T1 digest of annealed RNA molecules with ATGGT loop sequence as used for example 1. Each lane of 20% native PAA gel loaded with 5 µl sample of 20 ul RNAse T1 cleavage reaction, taken after 10 min (top gel image), 45 min (center gel image) and 90 min (bottom gel image). dsRNA from hybridized gel purified single strand RNA (lane 2-9) or phenol chloroform extracted single strand RNA (lane 11-18) were cleaved under 8 different reaction conditions, varying 3 parameters: reaction buffer (A=Ambion "structure buffer": 10 mM Tris/Cl pH 7.0, 100 mM KCl, 10 mM $MgCl_2$, FF=Fermentas reaction buffer: 50 mM Tris/Cl ph7.4, 2 mM EDTA), RNAse T1 (A=Ambion 1 units/µl, F=Fementas 1000 units/µl) and RNAse T1 concentration (0.1 to 0.8 units/µl). 100 ng and 300 ng of synthetic siRNA were loaded on lane 1 and 10 as standard. Red arrows indicate the position of 21 nucleotide dsRNA fragments, identical to synthetic siRNAs, 0.8 units/µl of RNAse T1 in a $MgCl_2$ free buffer are sufficient to digest 1 µg of dsRNA to 21 bp fragments in 45 min at 37° C.

Figure 10:
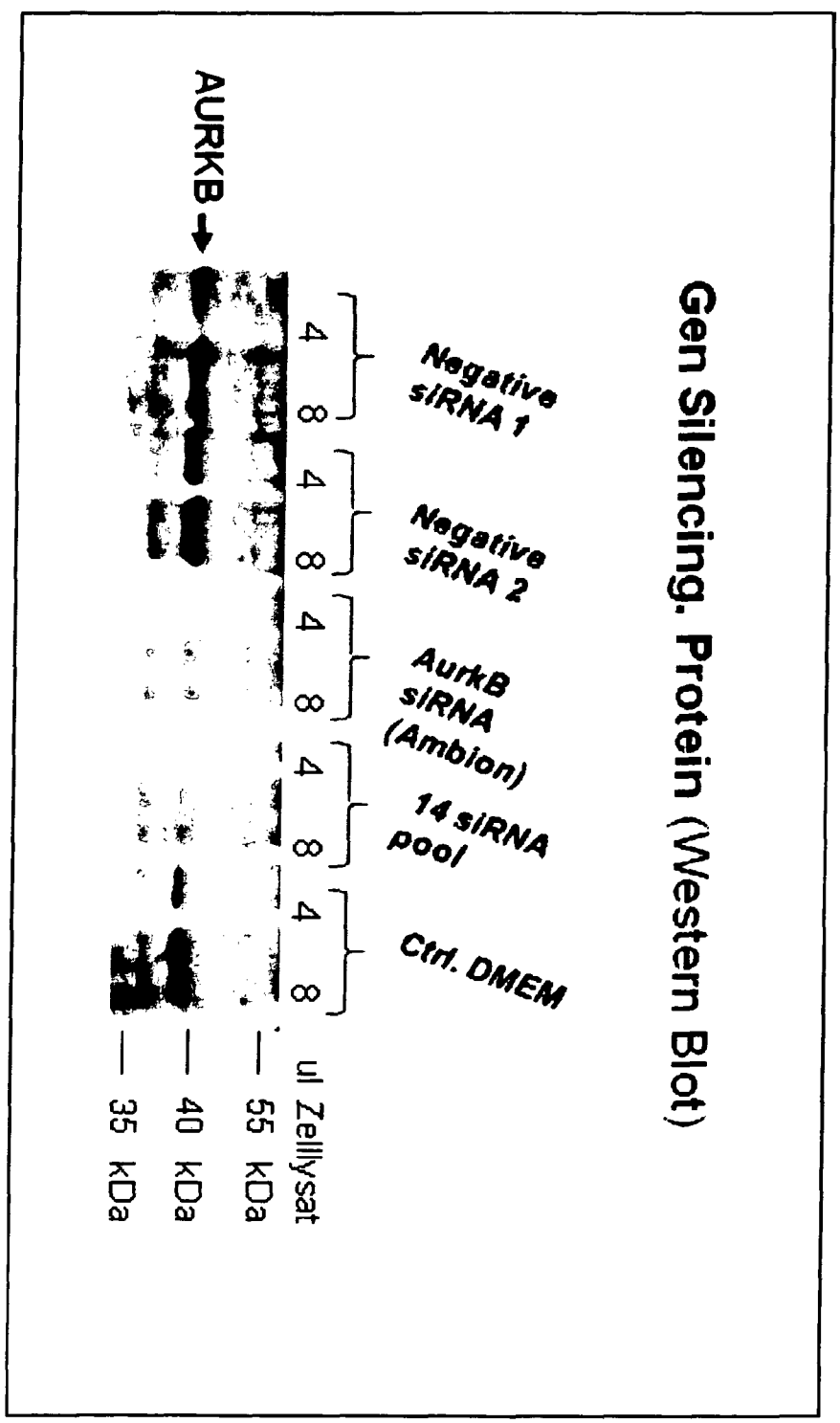

FIG. 10 depicts Western Blot analysis of AURKB protein knock down by a 14 siRNA pool targeting human AURKB, generated from a dsRNA with AGTTG loop sequence elements. Human HeLa cells were transfected with the siRNA pool or synthetic control siRNAs in a final concentration of 10 nM. Each cell lysates, generated 48 h after transfection was loaded on two lanes of a denaturing SDS PAA gel in a volume of 4 µl and 8 µl. The blot was developed with an antibody specific to human AURKB. Little or no change in AURKB protein in negative control siRNA (lane 1-4) transfected cells as compared to medium control (lanes 9, 10). Identical, almost complete reduction of AURKB protein for the validated, positive control siRNA targeting AURKB (synthetic AURKB siRNA, Ambion #s495) (lane 5, 6) and the siRNA pool (lanes 7, 8).

Figure 11:
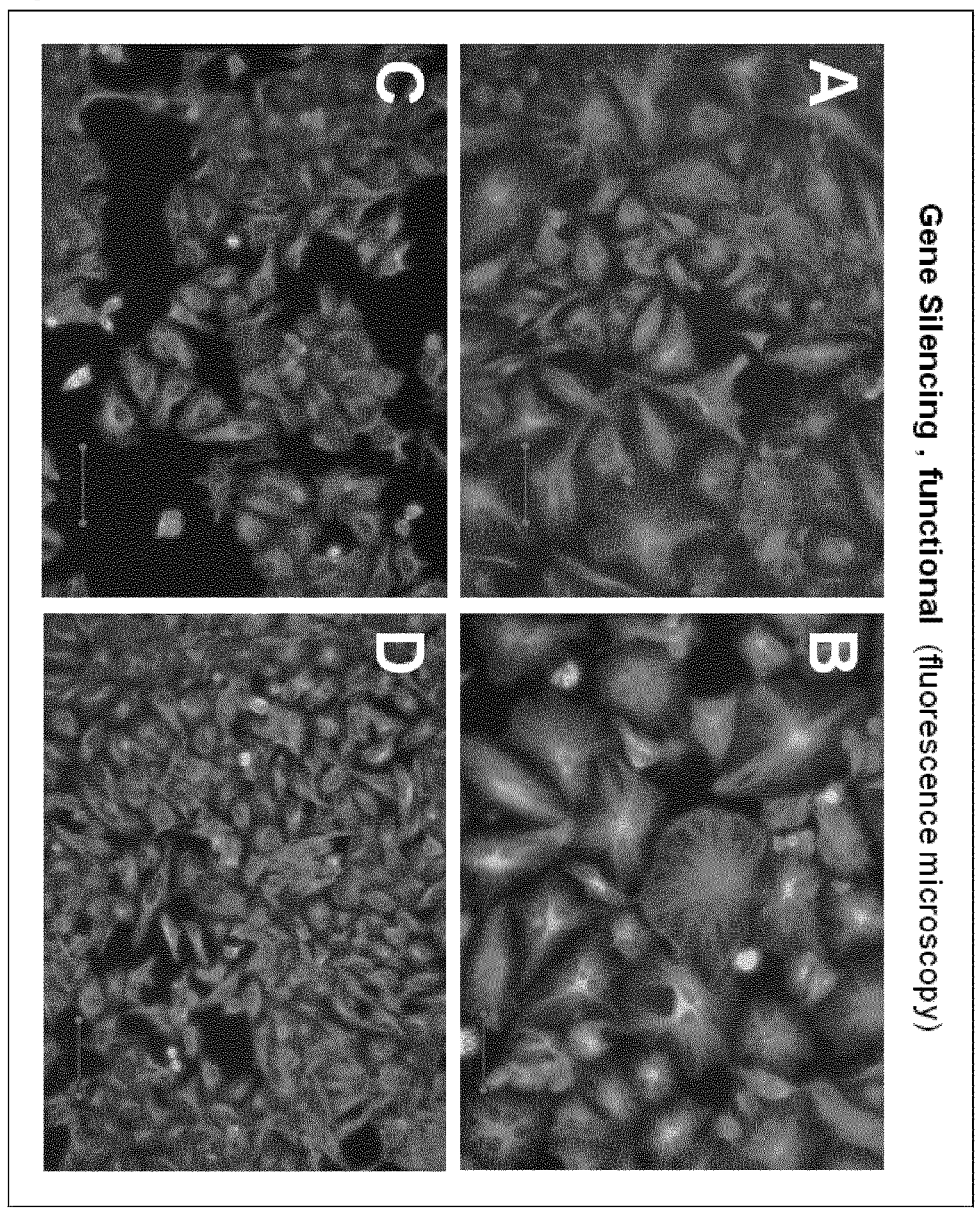

FIG. 11 depicts the functional validation of a 14 siRNA pool targeting human AURKB, generated from a dsRNA with AGTTG loop sequence elements. Human HeLa cells were transfected with the siRNA pool or synthetic control siRNAs in a final concentration of 10 nM. 72 h after transfection, cells were fixed and stained with Dapi for cell nuclei (blue) and an antibody specific to human alpha tubulin (green). Cells were imaged by confocal fluorescence microscopy using a 20× lense. The red sale bar at the lower right of each panel indicates a distance of 100 uM. The 4 panels show cells transfected as follows: A: synthetic AURKB siRNA (Ambion #s495), B: 14 siRNA AURKB pool, C: negative control siRNA (Ambion), D: untransfected cells. Cells with strongly increased cell size and multiple cell nuclei are predominant in panel A and B, indicative for efficient knock down of AURKB.

Figure 12:
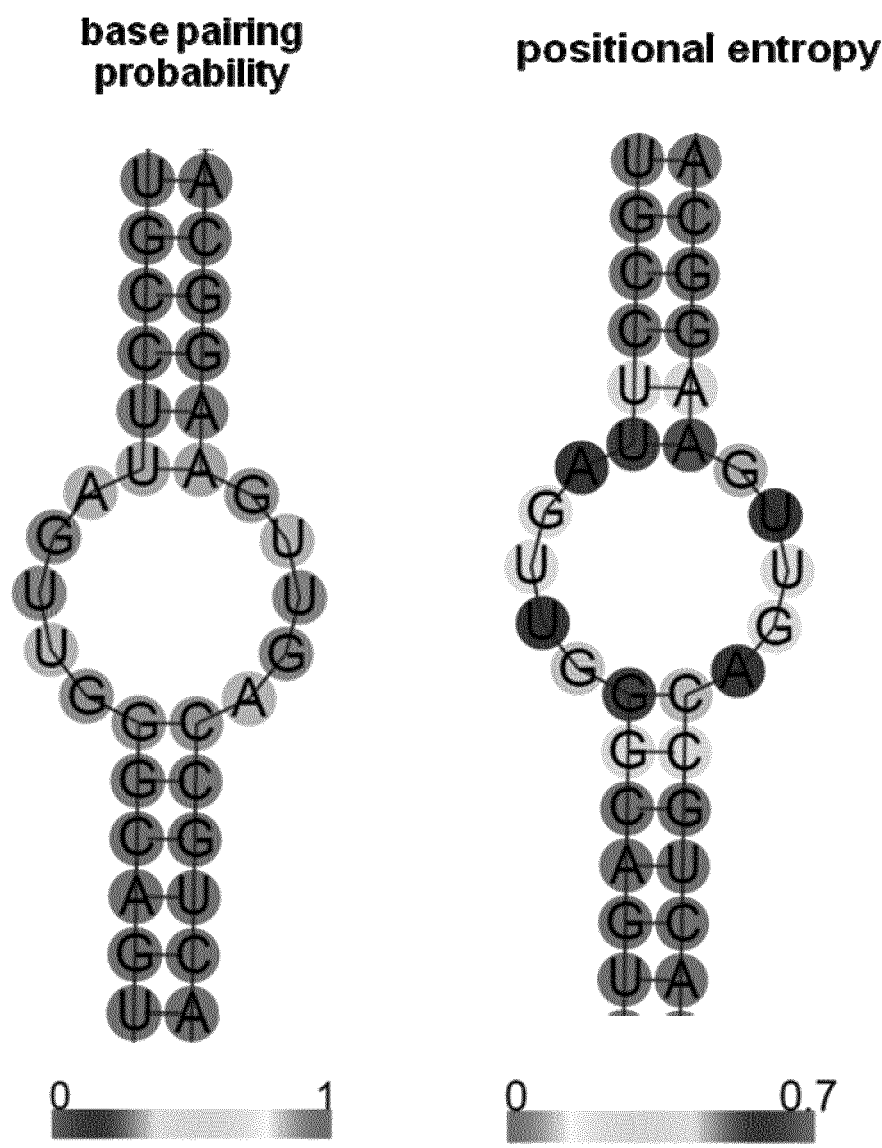

FIG. 12 depicts minimal free energy structure of dsRNA with loop sequence AGTTG (complete sequence as depicted see SEQ ID NO: 547 and SEQ ID NO: 548) as determined by RNAfold. The image shows one of 14 single strand loops with adjacent base pairing dsRNA regions. Color code indicates base pairing probability (left) and positional entropy (right). Base pairing probability is identical to all 14 loops. Positional entropy is constant between the 14 base pairing segments but shows some variability between the loop sequences (not shown).

Figure 13:
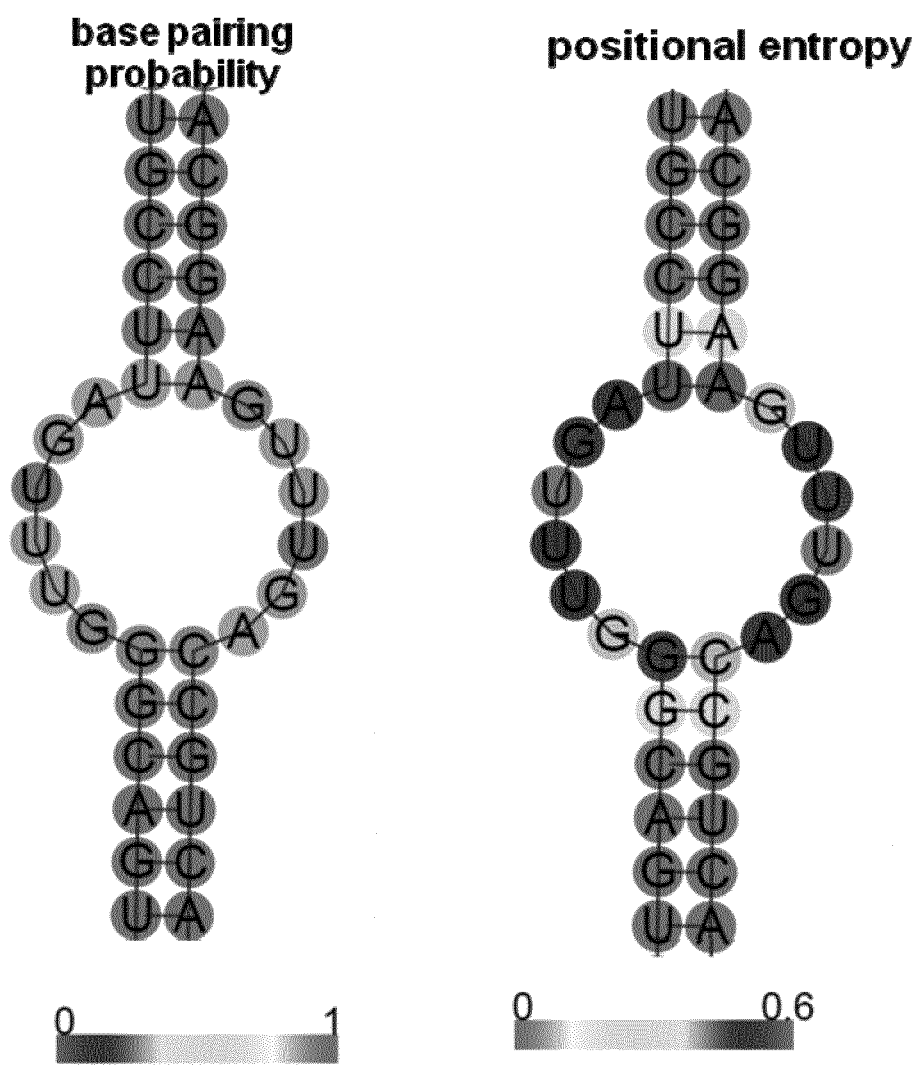

FIG. 13 depicts minimal free energy structure of dsRNA with loop sequence AGTTTG (complete sequence as depicted see SEQ ID NO: 549 and SEQ ID NO: 550) as determined by RNAfold. The image shows one of 14 single strand loops with adjacent base pairing dsRNA regions. Color code indicates base pairing probability (left) and positional entropy (right). Base pairing probability is identical to all 14 loops. Positional entropy is constant between the 14 base pairing segments but shows some variability between the loop sequences (not shown).

Figure 14:
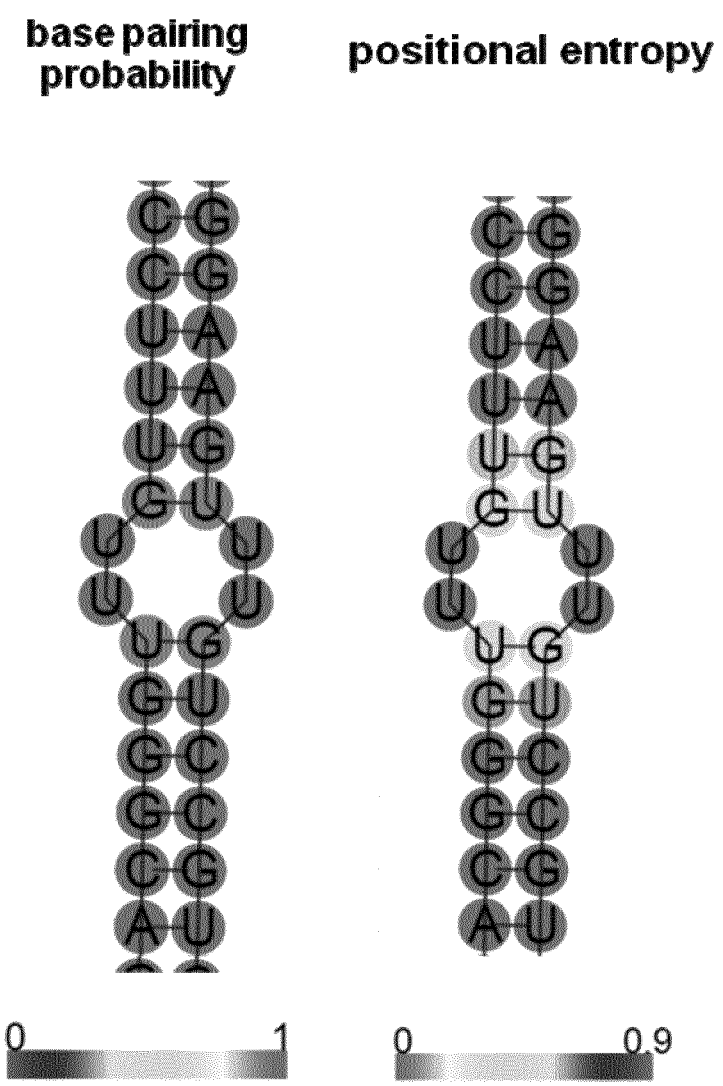

FIG. 14 depicts minimal free energy structure of dsRNA with loop sequence TGTTTG (complete sequence as depicted see SEQ ID NO: 551 and SEQ ID NO: 552) as determined by RNAfold. The image shows one of 14 single strand loops with adjacent base pairing dsRNA regions. Color code indicates base pairing probability (left) and positional entropy (right). Base pairing probability and positional entropy is identical between all 14 segments of the dsRNA (not shown).

Figure 15:
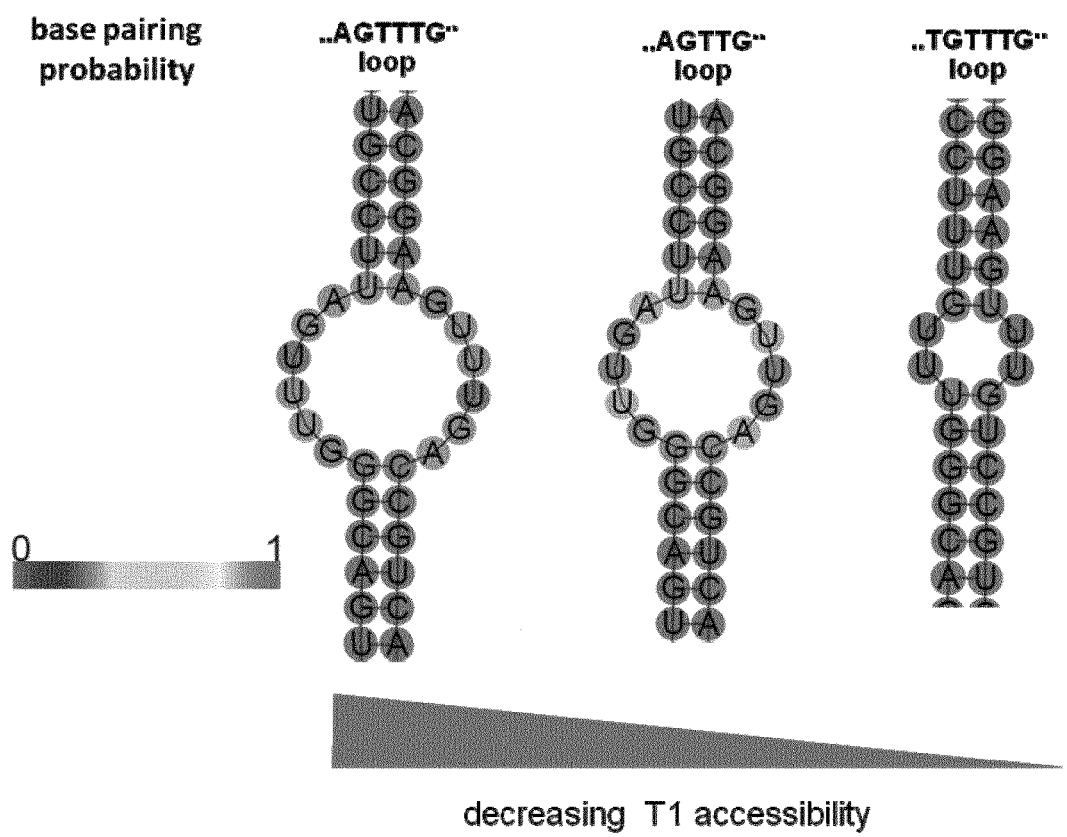

FIG. 15 compares accessibility to RNAse T1 between dsRNAs with three loop sequences AGTTTG, AGTTG and TGTTTG based on RNAfold minimal free energy structure (complete sequences as depicted see SEQ ID NOs: 547-552). The image shows one of 14 single strand loops with adjacent base pairing dsRNA regions. The color code indicates the base pairing probability.

Figure 16:
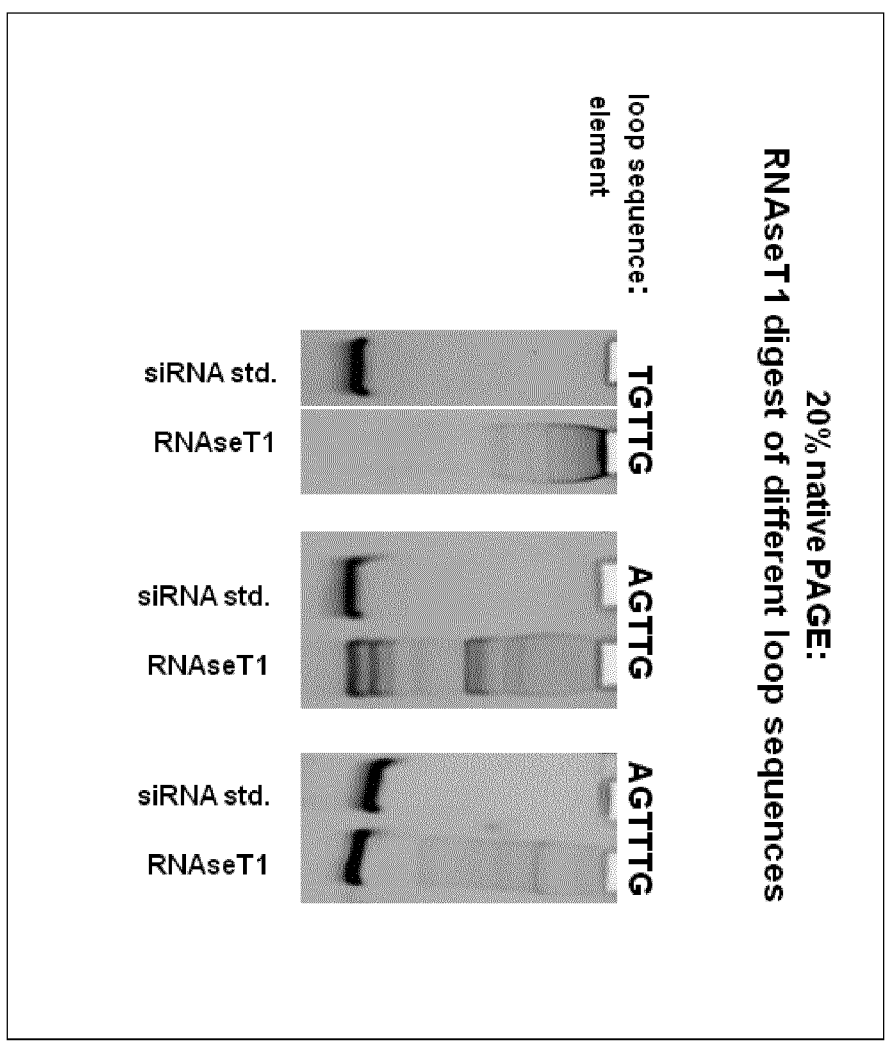

FIG. 16 Comparison of RNAse T1 cleavage efficiency between dsRNAs with the three loop sequence elements AGTTTG, AGTTG and TGTTTG. Equal amounts of dsRNA containing the three loop sequences were digested with equal concentration of RNAse T1 for 10 minutes. Samples were analyzed by 20% native PAGE. Synthetic siRNA was loaded for comparison. DsRNA with AGTTTG loop sequence element was completely digested to 21 base pair dsRNA fragments identical to the siRNA control.

Figure 17:
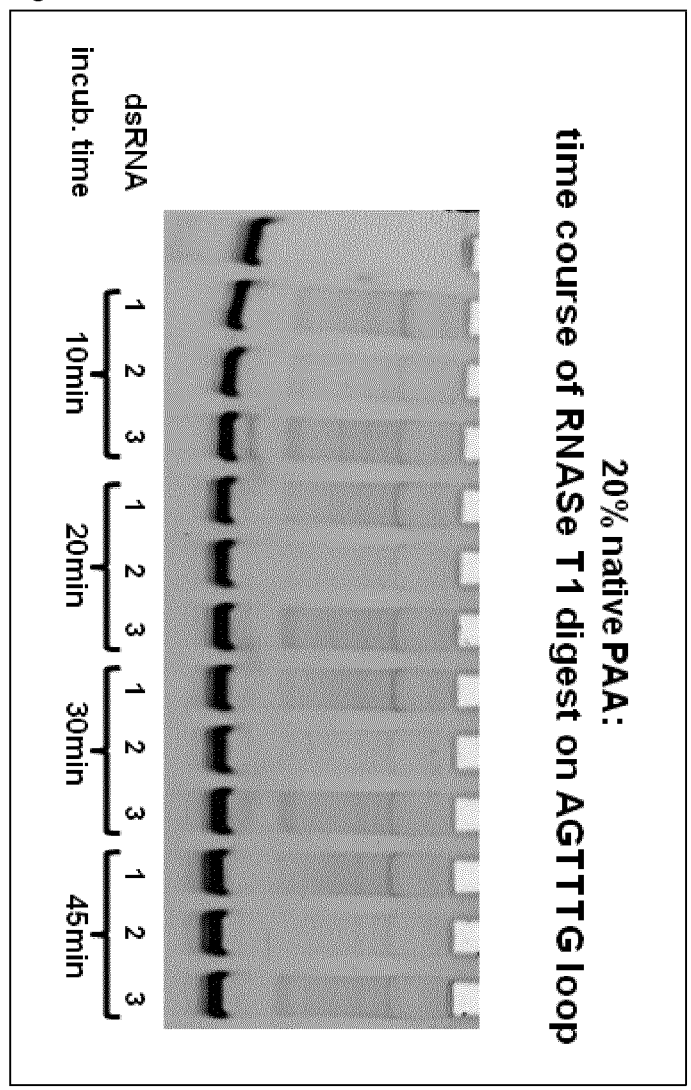

FIG. 17 Time course of RNAse T1 cleavage of dsRNA with AGTTTG loop sequence element. 3 dsRNA preparations (ds RNA 1, 2 and 3) with identical sequence purified by size exclusion chromatography (dsRNA 1 and 2) or phenol chloroform extraction and ethanol precipitation (dsRNA3) were incubated with 1 unit/µl of RNAse T1 at 37° C. Aliquots were taken after 10, 20, 30 and 45 minutes and analyzed by 20% native PAGE. A synthetic siRNA was loaded for comparison (lane 1) (synthetic AURKB siRNA, Ambion #s495). For all three dsRNA samples, completion of the digest was reached after 10 minutes. Lower purity of dsRNA 3 (lanes 4, 7, 10 and 13), did not affect the efficiency of the digest.

Figure 18:
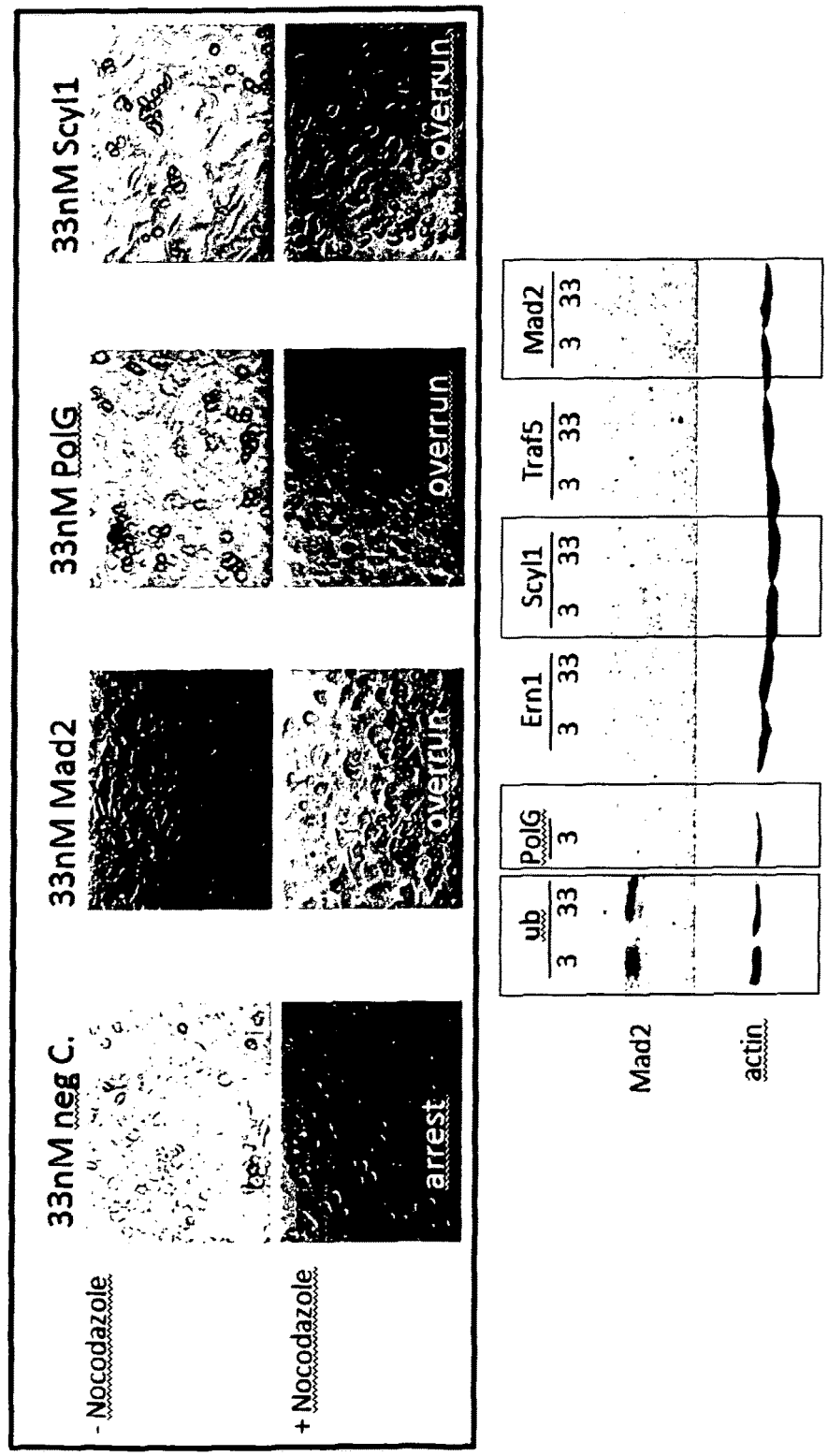

FIG. 18 depicts the off-target effect on Mad2 expression by the siRNAs, "PolG siRNA OT" and "Scyl1 siRNA OT" as compared to a non gene targeting "negative Control" and a "Mad2 siRNA" with on-target silencing of Mad2 as positive control. Upper panel shows arrest or overrun of mitotic arrest in the absence or presence of nocodazole depending on Mad2 expression. Lower panel shows effects of siRNA transfection on Mad2 protein expression as verified by Western Blots. Details are described in Example 3.

Figure 19:
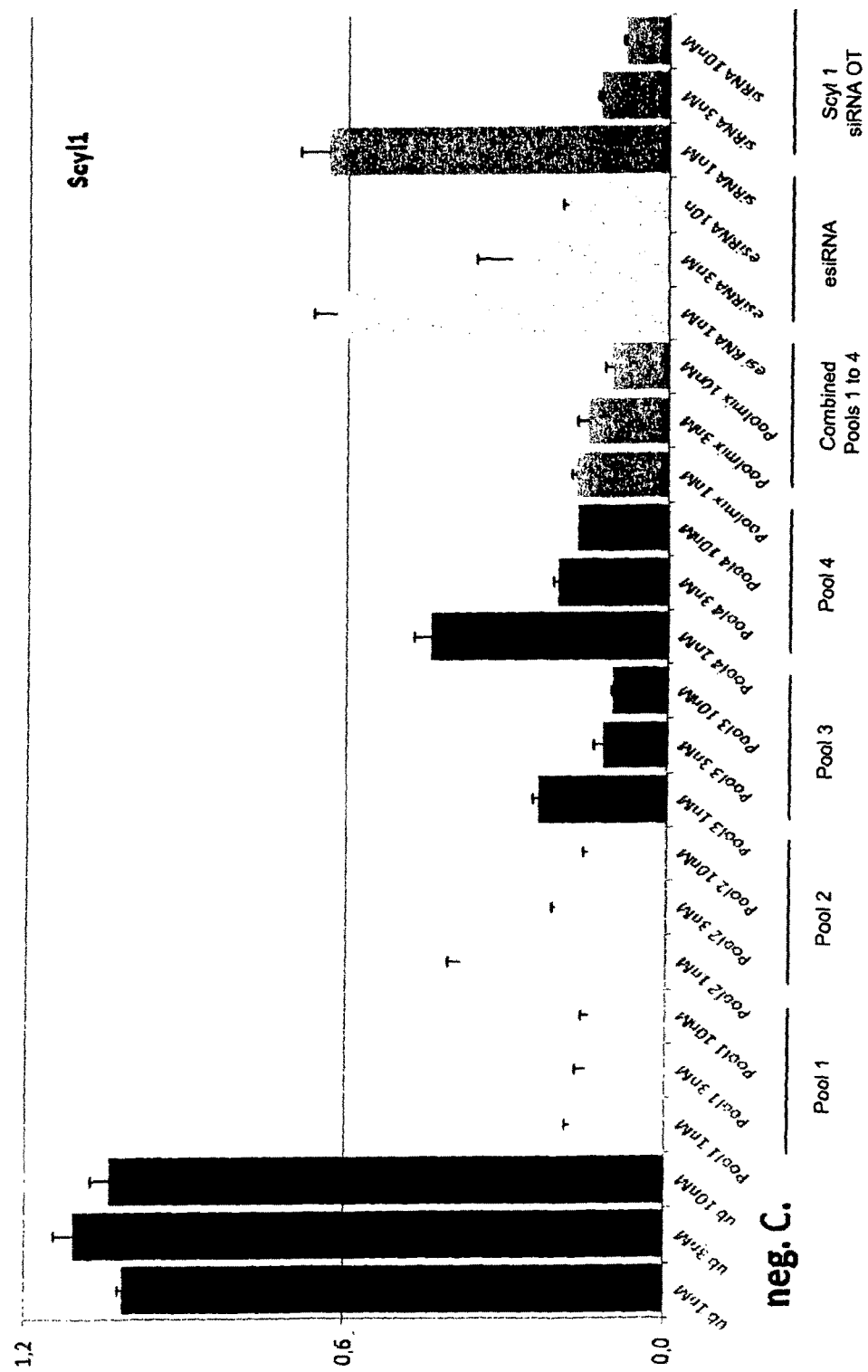

FIG. 19 depicts the improved on-target silencing of Scyl1 by the Pools 1, 2, 3 or 4 and the combined Pools 1 to 4 for Scyl1 as compared to the esiRNA for Scyl1 and "Scyl1 siRNA OT" as determined by RT-PCR. Scyl1 expression is indicated as % remaining Scyl1 mRNA as compared to a "negative Control" treated sample. Details are described in Example 3.

Figure 20:
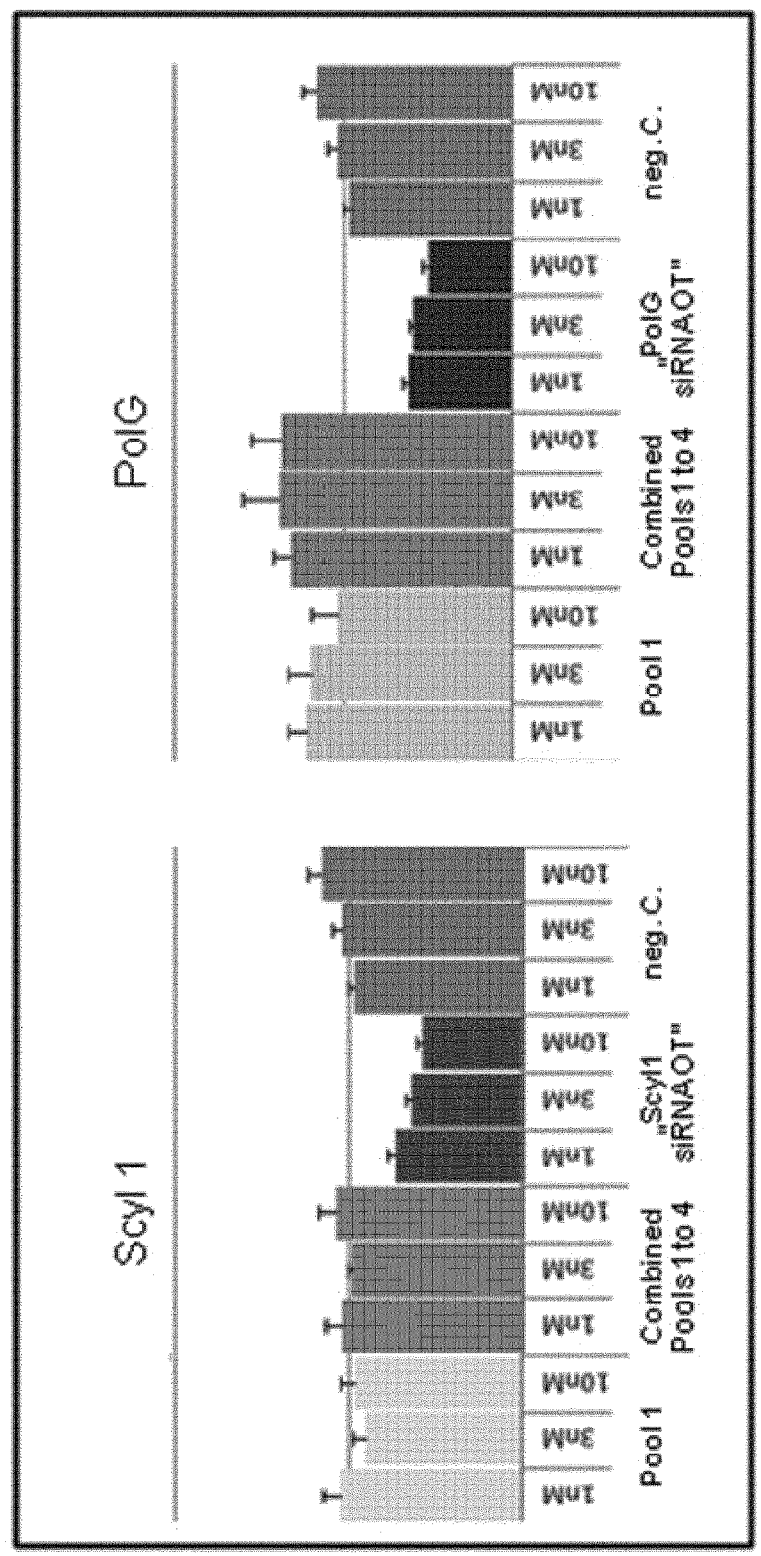

FIG. 20 depicts the reduced off-target effect on Mad2 expression by Pool 1 and the combined Pools 1 to 4 for Scyl1 as compared to "Scyl1 siRNA OT" as positive control and the non gene targeting siRNA "negative control" (neg. C), of Pool 1 for PolG, of combined Pools 1 to 4 for PolG and of the siRNA "PolG siRNA OT" on Mad2 at 1 nM, 3 nM or 10 nM. Effects on Mad2 expression were determined by Luciferase assay. Details are described in Example 3.

Figure 21:
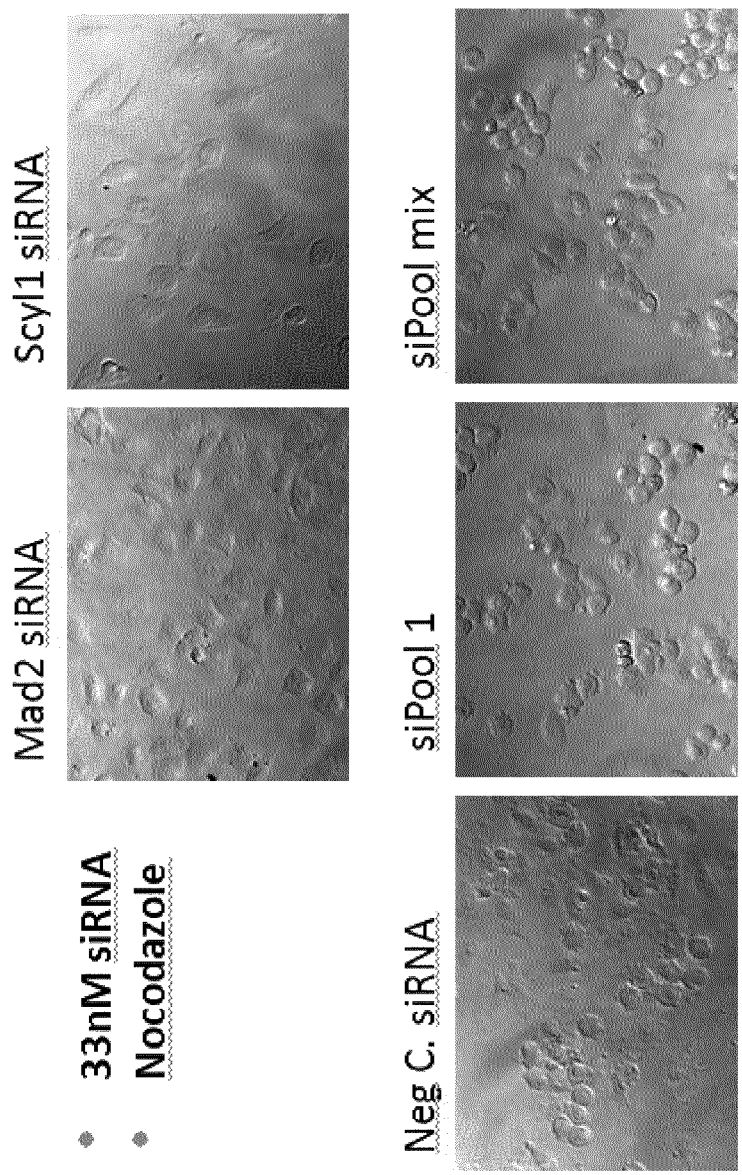

FIG. 21 depicts the reduced off-target effects on Mad2 as determined by a cellular assay. To this end, HeLa cells were transfected with 33 nM of either "Mad2 siRNA", "negative Control siRNA", Pool 1 for Scyl1, the combined Pools 1 to 4 for Scyl1 and "Scyl1 siRNA OT". If nodocazole was added, an overrun was observed for "Mad2 siRNA" and "Scyl1 siRNA OT", but not for "negative Control siRNA" (neg. C. siRNA), Pool1 for Scyl1 or for the combined Pools 1 to 4 for Scyl1. Details are described in Example 3.

Figure 22:
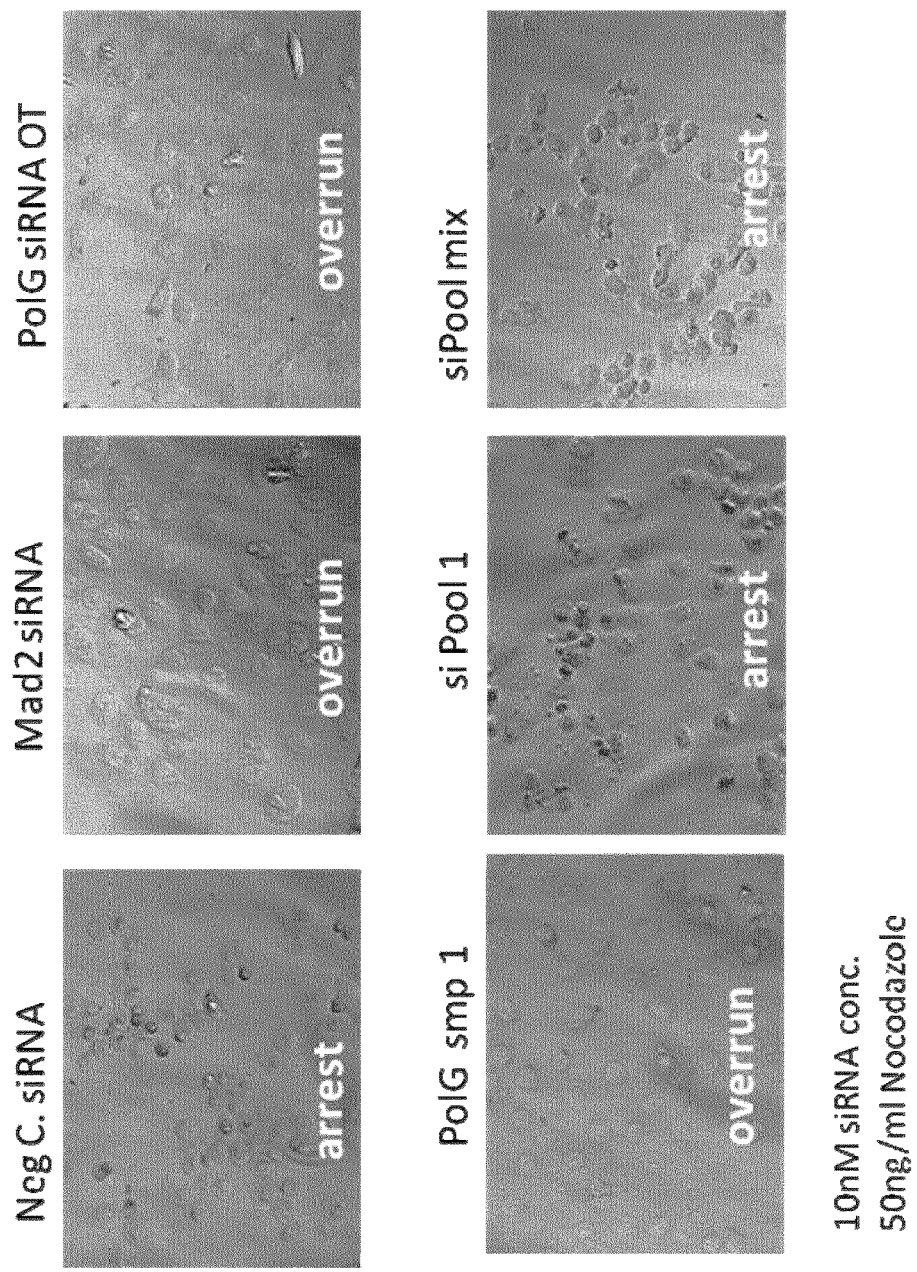

FIG. 22 depicts off-target effects on Mad2 as determined by a cellular assay. To this end, HeLa cells were transfected with 10 nM of either "Mad2 siRNA", "negative Control siRNA", Pool 1 for PolG, the combined Pools 1 to 4 for PolG, smart pool 1 (smp 1) for PolG and "PolG siRNA OT". If nocodazol was added, an overrun was observed for "Mad2 siRNA" and "PolG siRNA OT", but not for "negative Control siRNA", Pool1 for PolG or for the combined Pools 1 to 4 for PolG. Details are described in Example 3.

Figure 23:
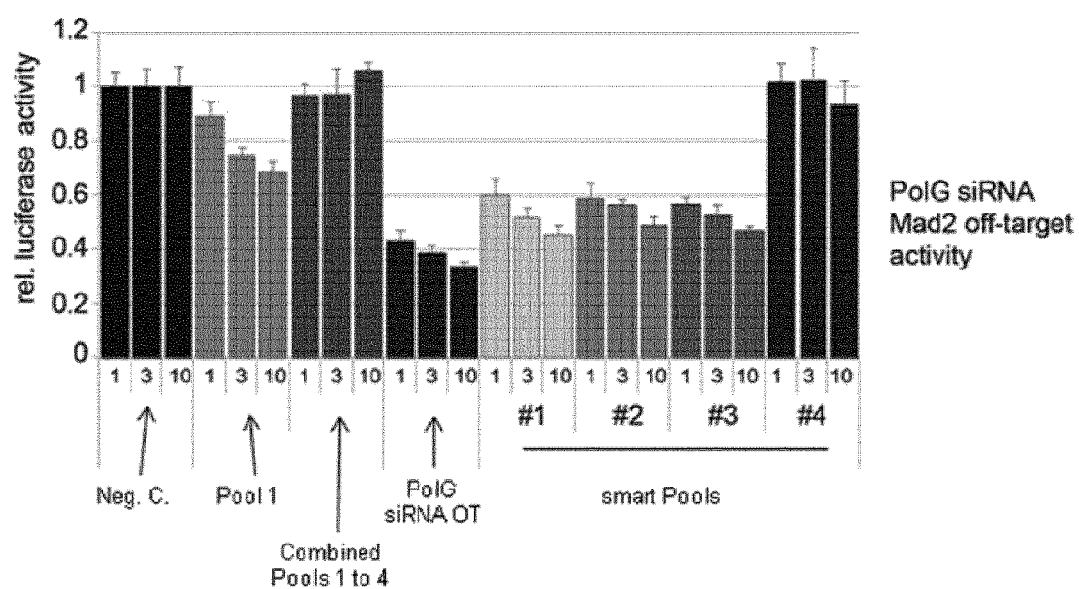

FIG. 23 depicts off-target effects on Mad2 as determined with a luciferase assay by Pool 1 for PolG and combined Pools 1 to 4 for PolG vs. the off-target effects of "PolG siRNA OT" and smart pools #1, #2, #3 and #4 (smp 1, smp 2, smp 3 and smp 4) for PolG. Each pool or individual siRNA was transfected in 3 concentrations, 1,3 and 10 nM as indicated below the bars. Details are described in Example 3.

Figure 24:
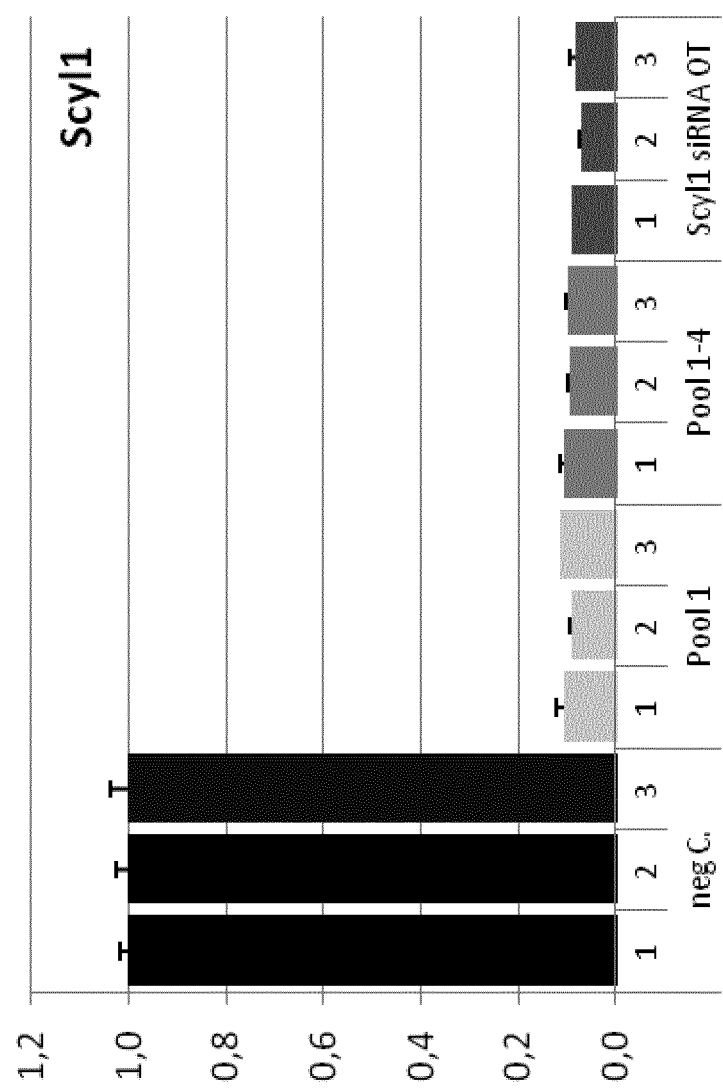

FIG. 24 depicts on-target effects of the Pools 1, the combined Pools 1 to 4 for Scyl1 and "Scyl1 siRNA OT on Scyl1 expression as determined by RT-PCR. Details are described in Example 4.

Figure 25:
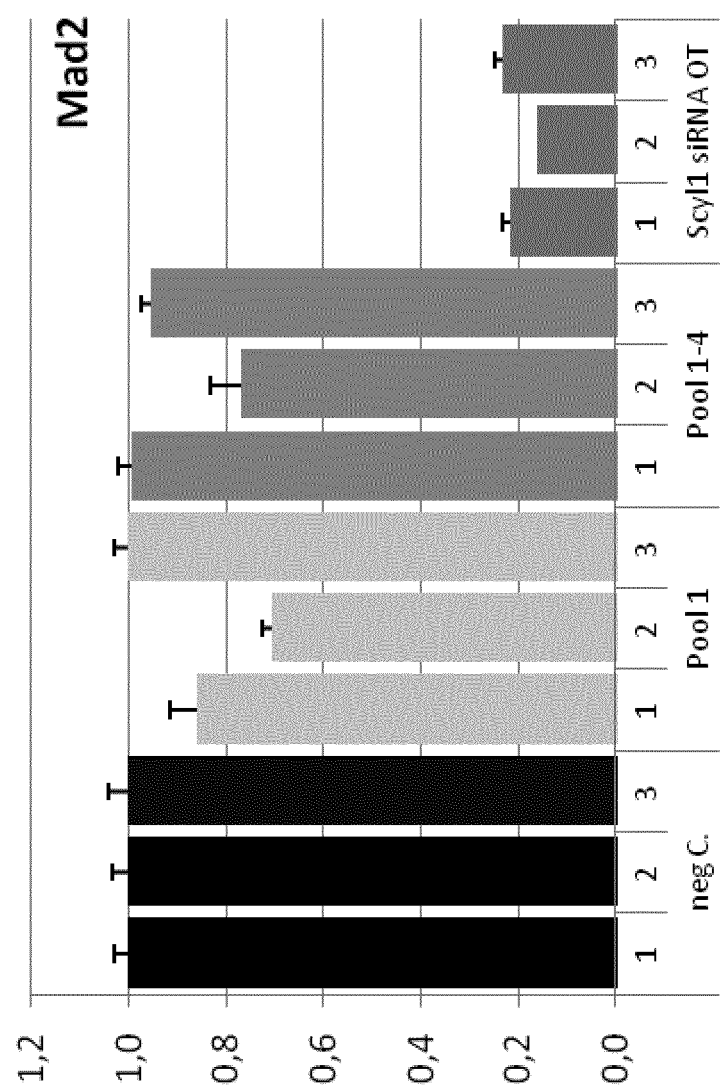

FIG. 25 depicts the reduced off-target effect on Mad2 expression by Pool 1 (see Table 7) and the combined Pools 1 to 4 for Scyl1 as compared to "Scyl1 siRNA OT" as positive control. Details are described in Example 4.

Figure 26:
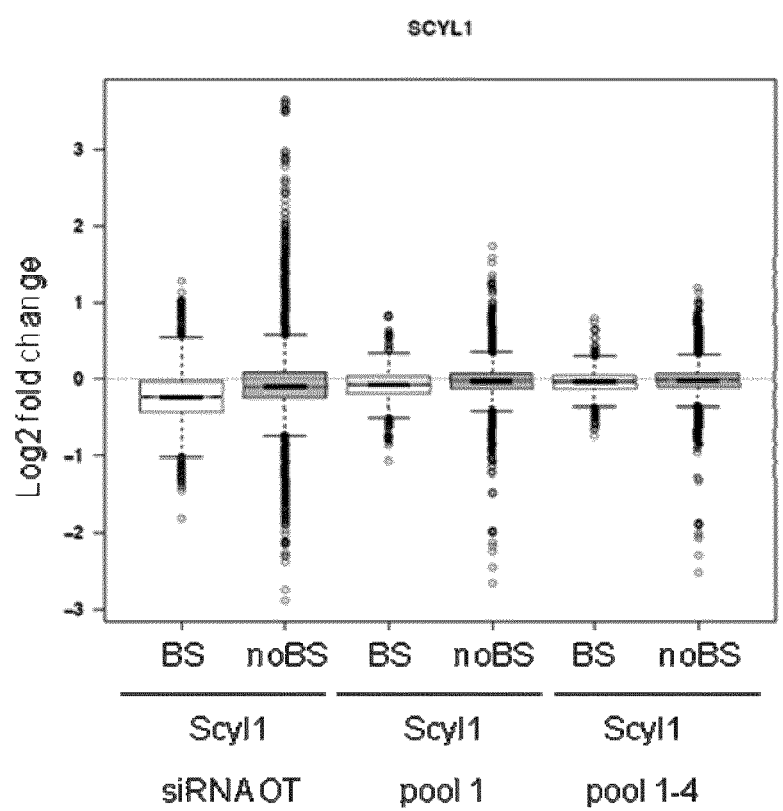

FIG. 26 depicts the Logarithmic fold changes (base 2) of transcripts without (noBS) or with one or more potential binding site(s) for "Scyl1 siRNA OT" (BS). The two leftmost boxes show log 2 fold changes of the samples treated with the single siRNA versus untransfected control samples, the central two boxes fold changes for the complex siRNA pool 1 and the two rightmost boxes for the complex siRNA pool 1 to 4. The boxes represent the interquartile range (IQR) consisting of the central 50% of the data. The whiskers indicate the maximum and minimum of the data defined as 1.5 times the interquartile range. Data values larger than the maximum and smaller than the minimum are drawn as outliers (black circles). Notches roughly indicate the 95% confidence interval of the median (+/−1.58 IQR/sqrt(n)). Details are described in Example 4.

Figure 27:
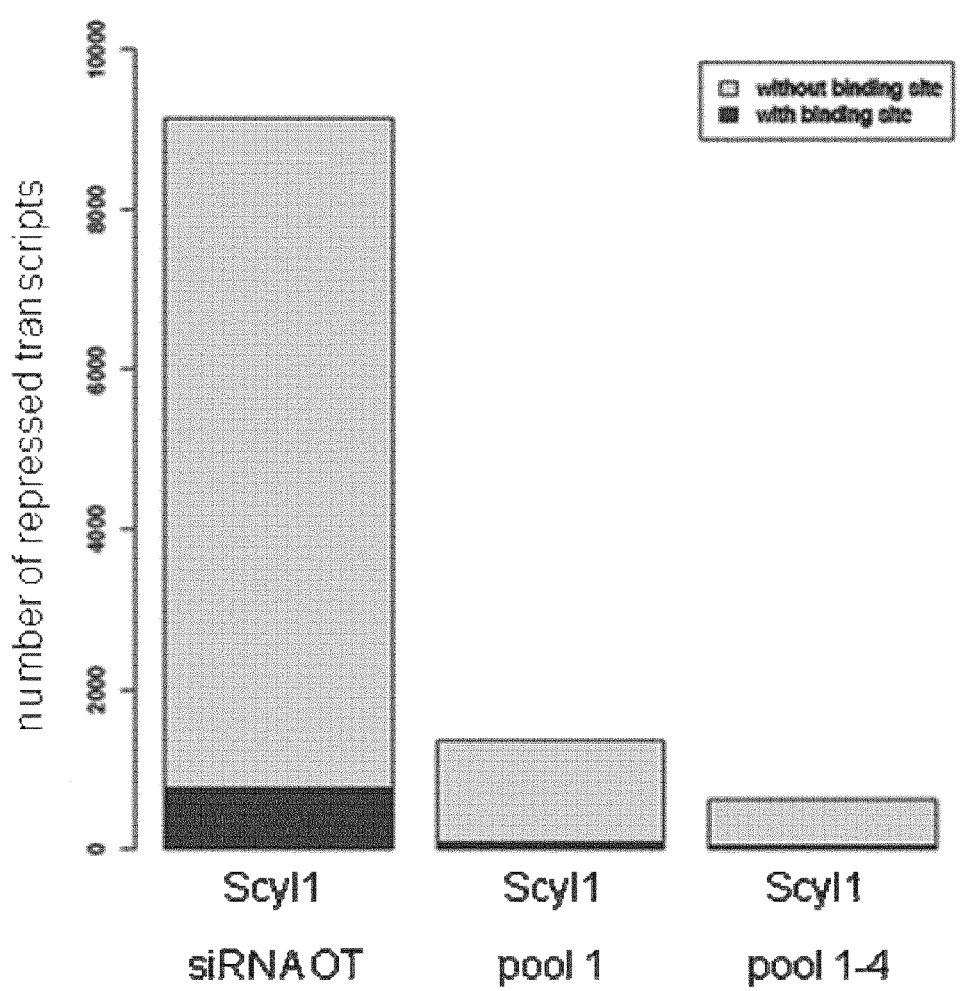

FIG. 27 depicts the number of repressed transcripts in the individual experiments. Transcripts with a potential binding site (seed sequence) to the "Scyl1 siRNA-OT" are represented in the dark grey fraction of the bar, the remaining transcripts in the light grey fraction of the bar. Transcripts differentially expressed at a q-value level of 0.001 were considered. Details are described in Example 4.

Figure 28:
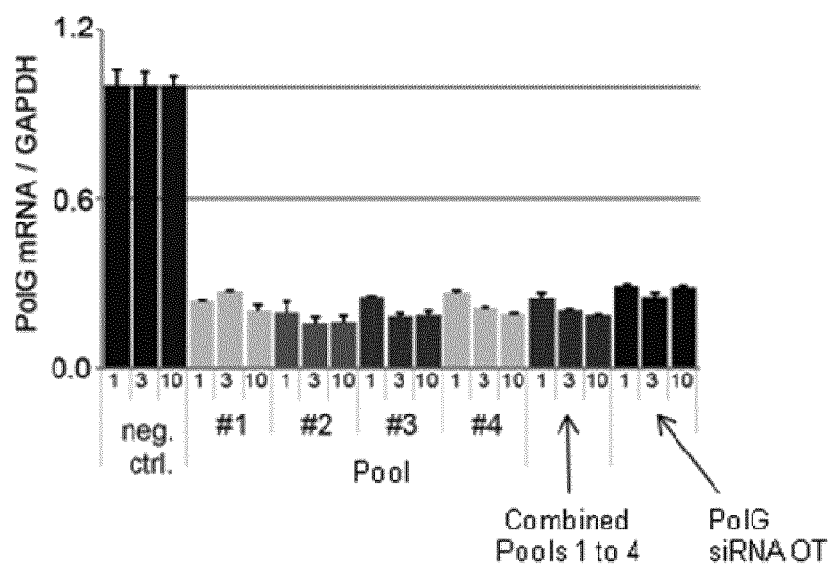

FIG. 28 depicts on-target activity of different complex siRNA pools (siPools) on PolG. Hela cells were transfected with 1, 3 or 10 nM concentrations of siPools containing 15 siRNAs (pools #1-4), a combination of all 15 siRNA-siPools resulting in a siPool containing 60 different siRNAs (pool 60) or specific siRNA "PolG si RNA OT" directed against PolG. PolG mRNA levels were measured by qPCR and normalized to GAPDH. Relative expression levels were calculated based on transfection of an unspecific control siRNA (neg. ctrl.).

Figure 29:
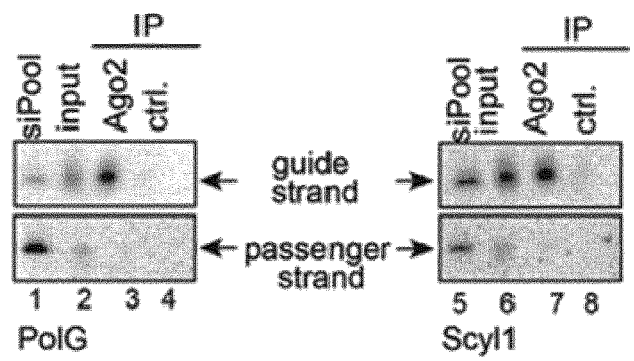
Figure 29:
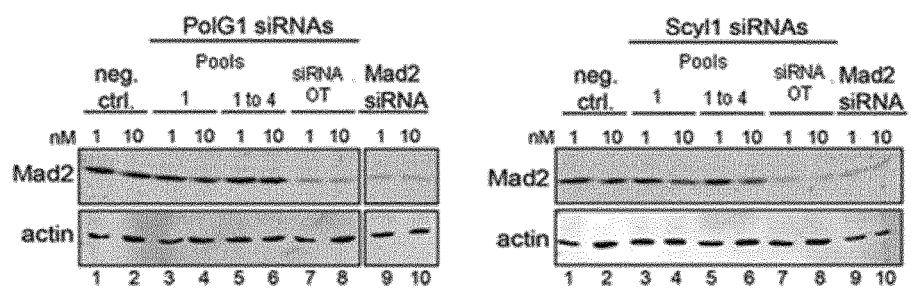
Figure 29:
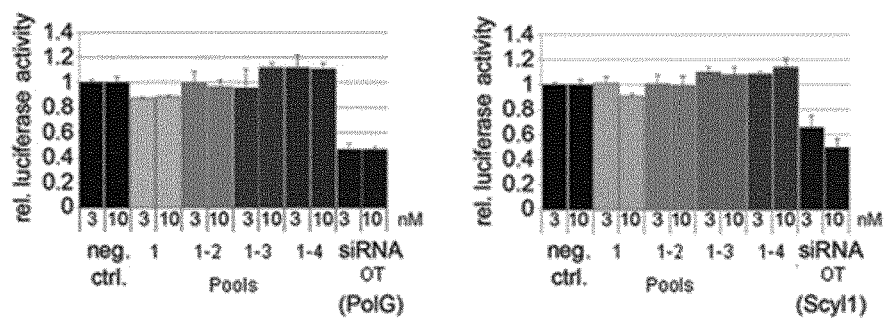

FIG. 29 depicts off-target activity of different complex siRNA pools (siPools). (A) Hela cells were transfected with 10 nM of combined pools 1 to 4 for PolG or Scyl1. To validate that the specific off-T siRNAs are present in the pools, Ago2 was immunoprecipitated from the lysates and passenger and guide strands of PolG off-T (left) or Scyl1 off-T (right) siRNAs was analyzed by Northern blotting. As positive controls, 3 pmol of total siPools and 2.5% input material were used. (B) Hela cells were transfected with 1 or 10 nM Pool 1 combined Pools 1 to 4 or specific off-T siRNAs directed against PolG (PolG siRNA OT) or Scyl1 (Scyl1 siRNA OT) Mad2 protein levels were analyzed by western blotting 48 h after transfection. A specific Mad2 siRNA served as a positive control (lanes 9 and 10). Actin expression levels were used as loading controls (lower panels). (C) Hela cells were transfected with 3 or 10 nM siRNA off-T or Pools 1, 1-2, 1-3 or 1-4 different siRNAs directed against PolG or Scyl1. Off-target activity was analyzed using Mad2 3'UTR controlling firefly-luciferase activity. Relative luciferase activity was calculated using the ratio of firefly/renilla luciferase and via normalization to the corresponding ratios of the empty control vector.

Figure 30:
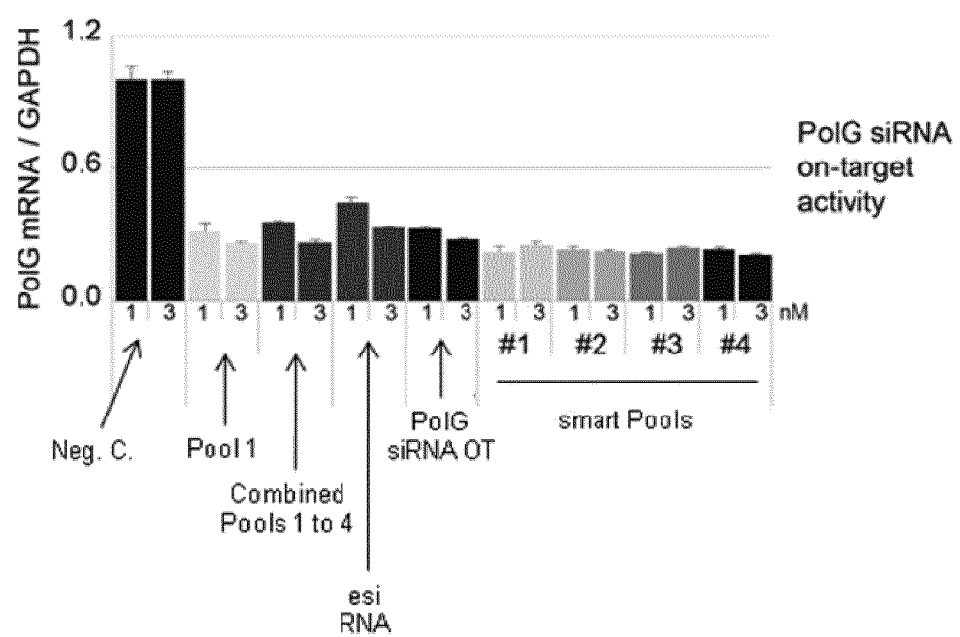

FIG. 30 depicts comparison of complex siRNA pools (siPools) with other available RNAi reagents. qPCR analysis of on-target activities of various siRNA reagents for PolG. Hela cells were transfected with 1 or 3 nM Pool 1, combined Pools 1 to 4, PolG siRNA OT, esiRNAs and four different smart pools directed against PolG. mRNA levels were normalized to GAPDH and relative expression levels were calculated using a negative control siRNA. Smart pool #4 served as a Mad2 off-target negative control.

Figure 31:
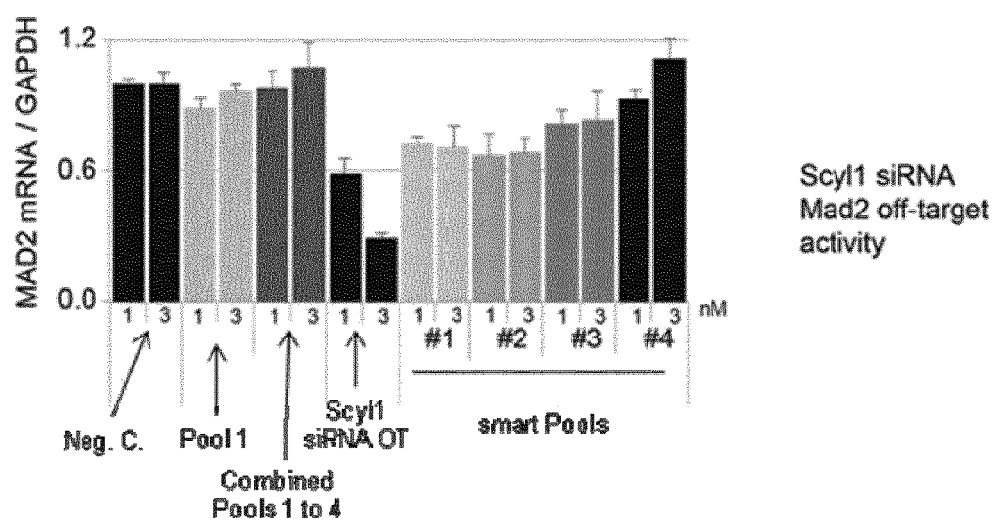

FIG. 31 depicts comparison of complex siRNA pools (siPools) with other available RNAi reagents. qPCR analysis of off-target effect on MAD2 of various siRNA reagents for SCYL1. Hela cells were transfected with 1 or 3 nM Pool 1, combined Pools 1 to 4, Scyl1 siRNA OT, and four different smart pools directed against Scyl1. MAD2 mRNA levels were normalized to GAPDH and relative expression levels were calculated using a negative control siRNA. Smart pool #4 served as a Mad2 off-target negative control.

Figure 32:
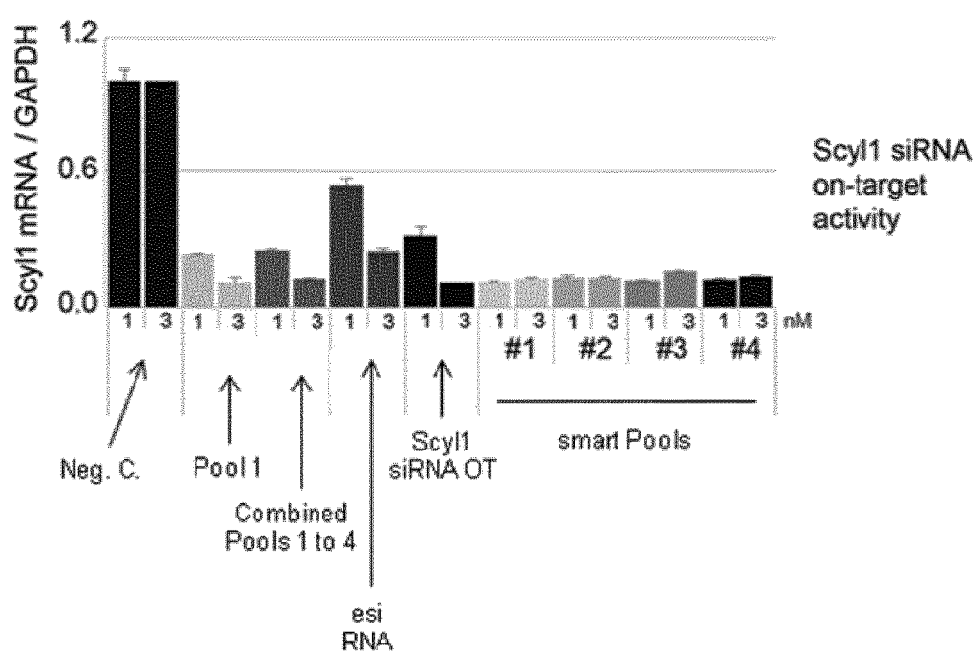

FIG. 32 depicts comparison of complex siRNA pools (siPools) with other available RNAi reagents. qPCR analysis of on-target silencing activities of various siRNA reagents for SCYL1. Hela cells were transfected with 1 or 3 nM Pool 1, combined Pools 1 to 4, Scyl1 siRNA OT, esiRNAs and four different smart pools directed against Scyl1. mRNA levels were normalized to GAPDH and relative expression levels were calculated using a negative control siRNA. Smart pool #4 served as a Mad2 off-target negative control.

Figure 33:
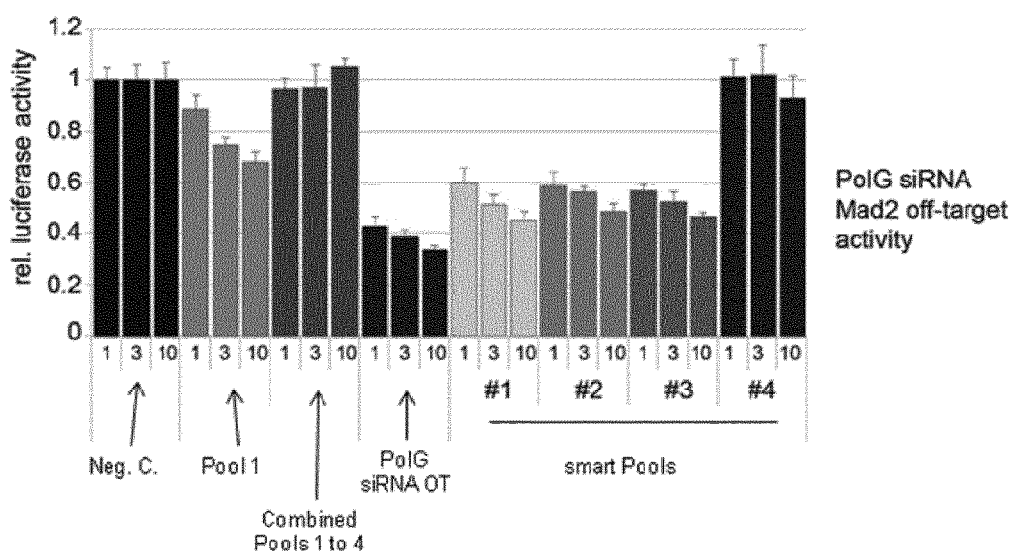

FIG. 33 depicts comparison of complex siRNA pools (siPools) with other available RNAi reagents. Hela cells were transfected with 1 or 3 nM Pool 1, combined Pools 1 to 4, PolG siRNA OT, and four different smart pools directed against PolG. Off-target activity was analyzed using a reporter system based on firefly-luciferase activity controlled by the Mad2 3' UTR. Relative luciferase activity was calculated using the ratio of firefly/renilla luciferase and via normalization to the corresponding ratios of the empty control vector. Smart pool #4 served as a Mad2 off-target negative control.

Figure 34:
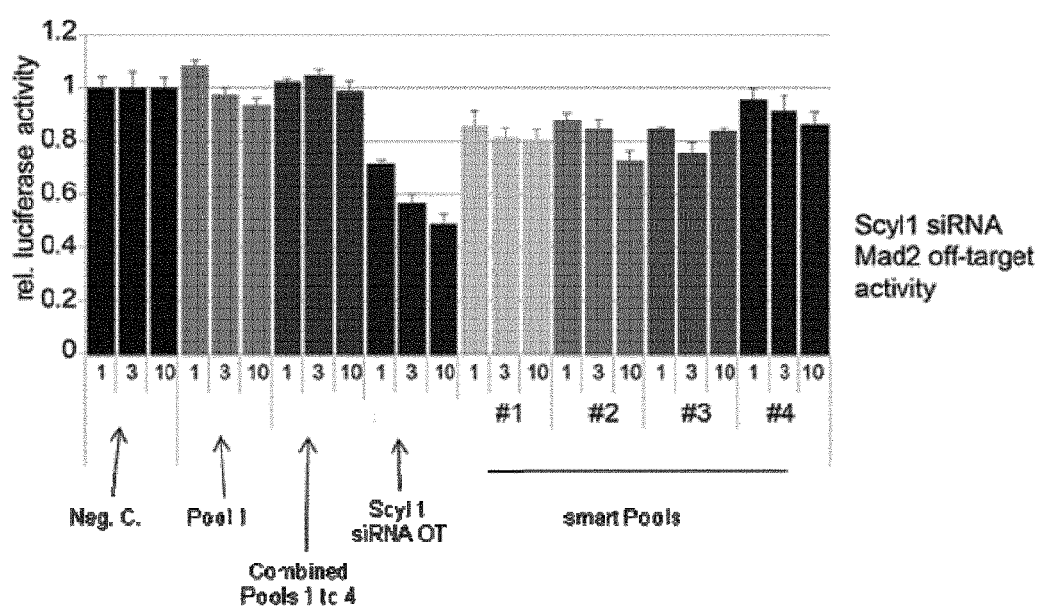

FIG. 34 depicts comparison of complex siRNA pools (siPools) with other available RNAi reagents. Hela cells were transfected with 1 or 3 nM Pool 1, combined Pools 1 to 4, Scyl1 siRNA OT, and four different smart pools directed against Scyl1 Off-target activity was analyzed using a reporter system based on firefly-luciferase activity controlled by the Mad2 3' UTR. Relative luciferase activity was calculated using the ratio of firefly/renilla luciferase and via normalization to the corresponding ratios of the empty control vector. Smart pool #4 served as a Mad2 off-target negative control.

Figure 35A:
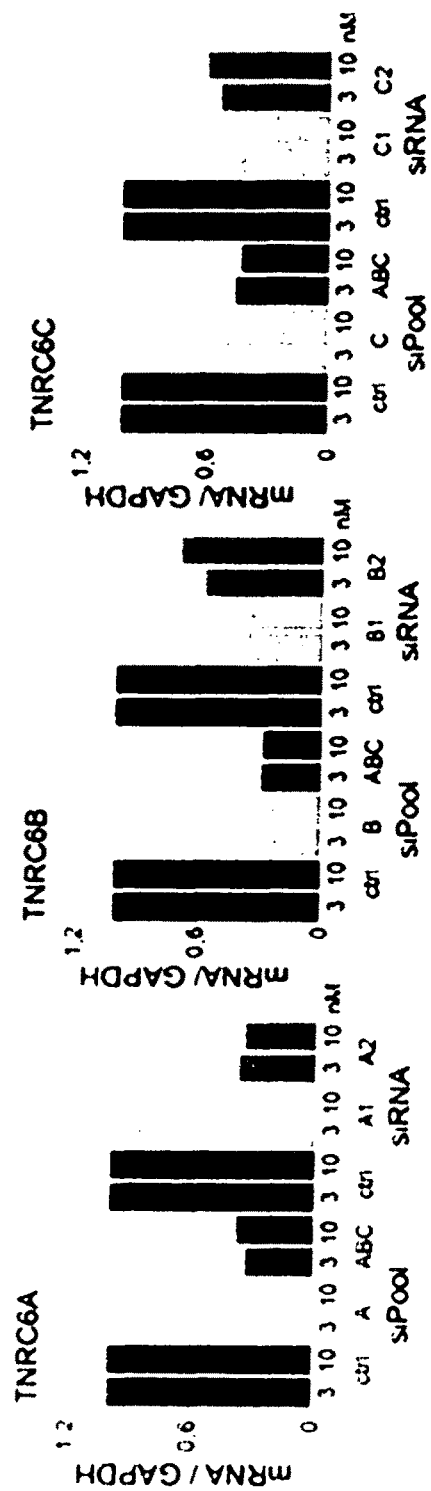
Figure 35:
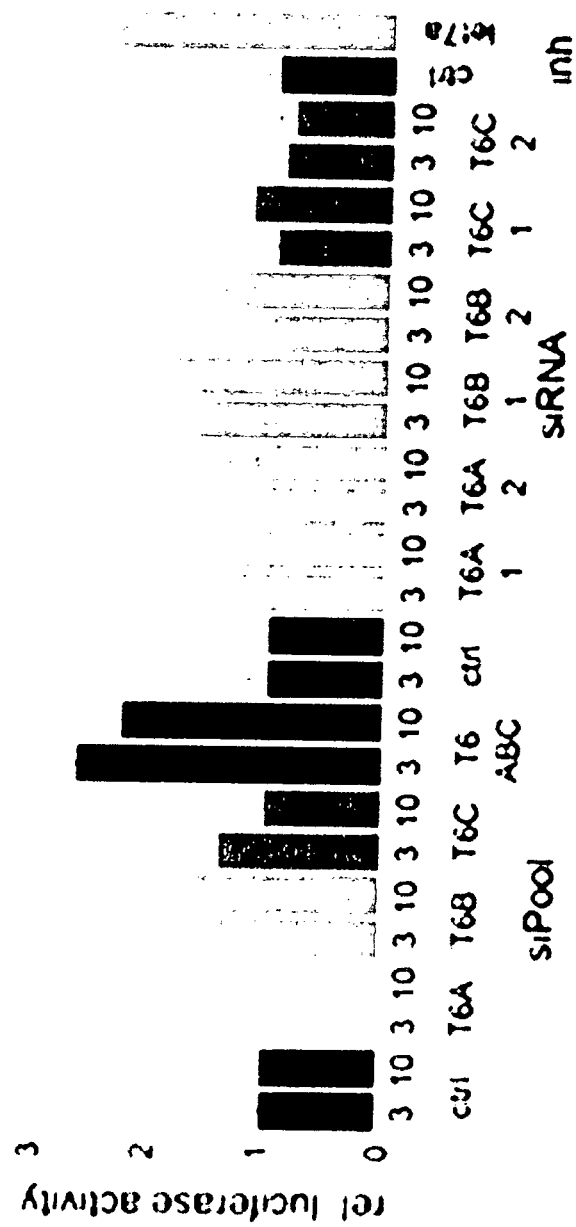

FIG. 35 depicts silencing of the three members of the TNRC6 gene family by combinations of sipools and individual siRNAs in HeLa cells. A) TNRC6A (left), TNRC6B (center) and TNRC6C (right) were silenced by 3 and 10 nM of siPool and siRNA. SiPools were either specific to the individual TNRC6 gene (A, B or C) or a mixture of all three pools (ABC). Two individual siRNAs were tested against each gene (A1, A2, B1, B2, C1, C2). Gene silencing was quantified by RT-PCR and normalized to GAPDH mRNA and a negative control siRNA. B) Quantification of TNRC6 gene family silencing by a functional luciferase assay. Firefly luciferase was expressed from a reporter construct containing LET7 miRNA binding sites repressing Luciferase expression in Hela cells. Simultaneous silencing of all three members of the TNRC6 gene family became obvious in a de-repression of luciferase expression. Each siRNA or siRNA pool were transfected in Hela cells in concentrations of 3 and 10 nM. siRNA pools targeting individual TNRC6 genes (T6A, T6B, T6C) or all three TNRC6 genes (T6ABC) were compared to the effect of individual siRNAs (T6A1,-2, T6B1,-2, T6C1,-2). Luciferase activity was measured in a dual luciferase assay and normalized to negative control siRNA transfected samples.

Figure 36:
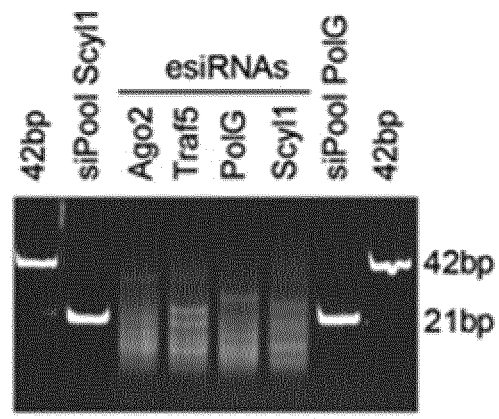

FIG. 36 depicts a siRNA pools and esiRNAs analyzed on a 20% native PAA TBE gel. Approximately 300 ng of 42 bp dsRNA markers, siPools targeting SCYL1 and POLG and esiRNAs (Sigma) targeting the genes AGO2, TRAF5, POLG and SCYL1 were loaded as indicated above the gel image.

FIG. 37 depicts enzymatic cleavage of dsRNA with different loop sequences by RNaseT1 under limiting conditions. Long dsRNA with 15siRNAs targeting human AURKB were generated from DNA templates containing 6 different loop sequence elements: 1) AGTTG, 2) AGTTTG, 3) AGTTAG, 4) AGTTTTG, 5) AGTTTAG, 6)AGTGTAG. DsRNAs were digested with 0.1 unit of RNaseT1/ug dsRNA for 30 (lanes 1-7) and 120 minutes (lanes 9-14) resulting in a partial digest of the dsRNA.dsRNA fragments were resolved on a native 20% PAA TBE gel. 200 ng dsRNA marker (NEB) with a smallest fragment of 21 bp (red arrow) was loaded on lane 1 and 8.

DETAILED DESCRIPTION OF THE INVENTION

Figure 1:
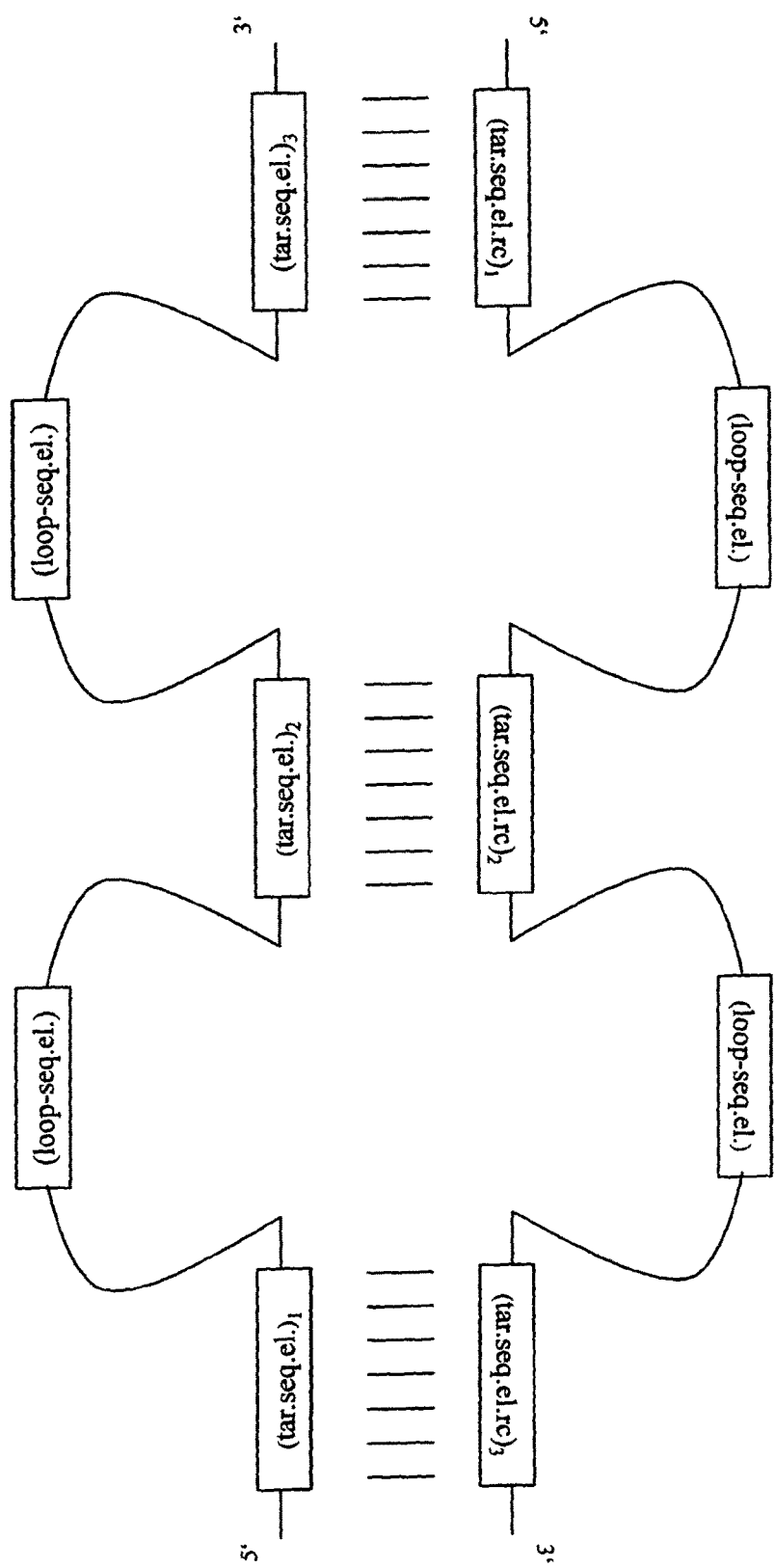
FIG. 1 depicts schematically hybridized RNA molecules for use in methods in accordance with the invention. "targ.seq.el" stands for target sequence element, "loop.seq.el." stands for loop sequence element.
Figure 2:
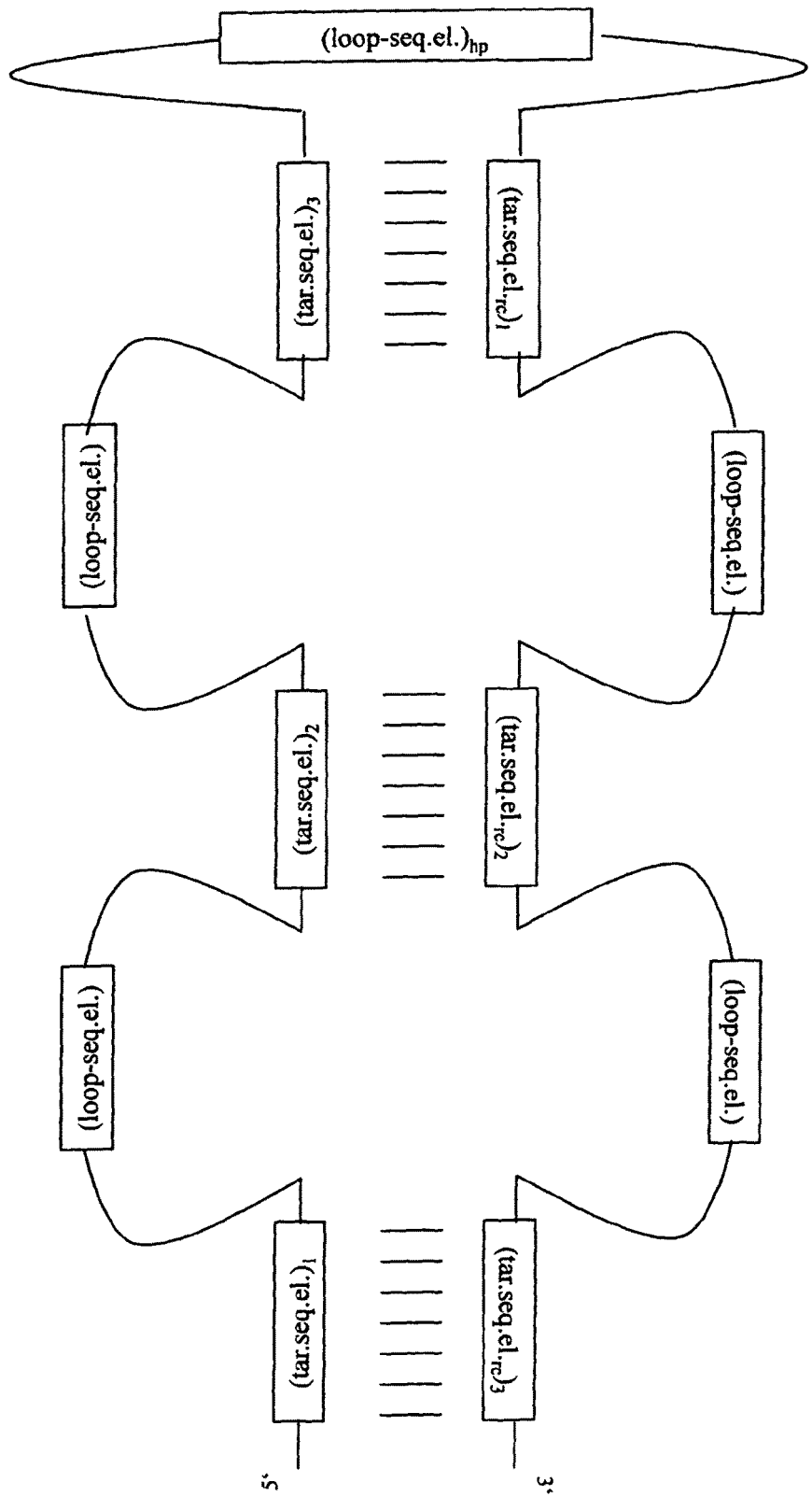
FIG. 2 depicts schematically a self-hybridized RNA molecule for use in methods in accordance with the invention. "targ.seq.el" stands for target sequence element, "loop.seq.el." stands for loop sequence element. "rc" stands for reverse complement. "(loop.seq.el.)$_{hp}$" stands for hairpin loop sequence element.

As already mentioned, the present invention is based on the concept of transcribing and hybridising template molecules which will give rise to annealed RNA molecules of the general structure depicted in FIGS. 1 and 2. Even though the present invention for the sake of understanding is illustrated primarily with respect to molecules of FIG. 1 and FIG. 2, the invention is not limited to these specific embodiments. Rather, the invention is directed to any method whereby in vitro transcription and hybridization RNA molecules are produced, which are characterised by double-stranded sections at least partially defining the siRNA to be produced and intermittent single-stranded loop sequences which are preferentially recognised, cleaved and digested by RNases over the double-stranded sections defining the siRNas to be produced. By the steps of transcribing such template molecules, hybridising them and digesting them with an RNase, of which RNAse T1 may be preferred, ultimately a multitude of siRNA molecules can be produced which for the purposes of the present invention are described as siRNA pools. The invention has been described by using such template molecules by in vitro transcription, hybridization and digestion with RNase T1 to produce an siRNA pool for the gene silencing of AUKRB, Scyl 1 and PolG. As has been pointed out and will be described in further detail below, the skilled person will immediately understand that the invention is neither limited to the production of siRNAs for these specific target gene nor to the use of RNase T1. Nevertheless, the invention will be explained primarily with respect to the specific constructs disclosed herein as this should facilitate an understanding of the invention.

Before the present invention is described in further detail, the following definitions are provided:

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun e.g. "a" or "an", "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, and preferably ±5%.

If technical terms such as RNAi and siRNA are not defined otherwise, they are used in their common technical sense. A suitable source for the understanding of such technical terms may be Günter Kahl, The Dictionary of Gene Technology, $2^{nd}$ edition, 2001, Wiley VCH.

If the term "RNase T1" is used hereinafter this should apply to all forms and variants of RNase T1, e.g. those that have been optimised by mutation, as long these forms and variants provide for the same activity and specificity as RNase T1. The RNase T1, which was used in the experiments described hereinafter, has the sequence of MMYSKLLTLTTLLLPTALALPSLVERACDYTCGSNC-YSSSDVSTAQAAGYQLHEDGETVG SNSYPHKYNNY-EGFDFSVSSPYYEWPILSSGDVYSGGSPGADRVVFN-ENNQLAGVITHTG ASGNNFVECT
(SEQ ID No.: 546) and was obtained from Fermentas (Thermo).

The term "siRNA pool" as used as described herein refers to a multitude of siRNA molecules which can be produced in accordance with the methods of the present invention. These siRNA molecules may either all have the same sequence, may have different sequences being directed to the same target gene or may have different sequences being directed to different target genes.

The term siRNA molecule is used to describe double-stranded RNA molecules wherein each strand of said double-stranded RNA molecules has a length of 15 to 30 nucleotides and wherein said double-stranded RNA molecules by way of the selected sequences are capable of RNAi of at least one target gene. As will become apparent from the ensuing description, the term siRNA molecules comprise blunt ended siRNA molecules as well as siRNA molecules with a 3' overhang.

The terms "high complexity siRNA pool", "complex siRNA pools" or "siPools" are used hereinafter to refer particularly to a combination of at least 5 and preferably at least 8 siRNAs, all being targeted against at least one gene, preferably against one gene. Even more preferably, such a high complexity siRNA pool may comprise at least 10, at least 11, at least 12, at least 13 or at least 14, preferably at least 15, at least 20, at least 25, at least 30, at least 40, at least 50, at least 60, at least 70, at least 80, at least 90 or at least 100 siRNAs, all being targeted against at least one gene, preferably against one. The siRNAs of such high complexity siRNA pools may be produced by the methods in accordance with the invention, but also by methods known in the state of the art such as by chemical synthesis. Hig complexity pools against different genes can thus be obtained by mixing high complexity pools against one gene, which according to the above considerations comprise at least at least 5, preferably at least 8 siRNAs and even more preferably at least 10, at least 11, at least 12, at least 13 or at least 14, preferably at least 15, at least 20, at least 25, at least 30, at least 40, at least 50, at least 60, at least 70, at least 80, at least 90 or at least 100 siRNAs against one gene. Such high complexity pools can be used for treating a disease in a human or animal being.

The terms DNA, RNA etc. are used in their common sense. It is to be understood that where the present invention, for example, mentions DNA molecules, this does not necessarily exclude that such DNA molecules are modified DNA molecules having e.g. modifications or unusual bases. However, such modifications have to be selected so that the properties of these DNA molecules, such as the ability to be replicated, in vitro transcribed and hybridized are not affected. It is preferred that DNA molecules comprise the naturally occurring bases and have a phosphate backbone.

The term siRNA molecule as pointed out above must refer to a double-stranded RNA molecule. However, as the siRNA molecules are produced by in vitro transcription, hybridization and digestion with an RNase, of which RNAse T1 may be preferred, the RNA molecules can be made from nucleotides that are modified to increase protease resistance. Again, such modifications must be selected so that the in vitro transcribed RNA molecule can still be recognised, cleaved and digested by RNases, of which RNAse T1 may be preferred, as described herein. Even though it is understood that RNAs comprise U instead of T, the ensuing description where it refers to specific sequences may not reflect this. Thus, the person skilled in the art will understand that when a sequence is mentioned to be an RNA and where the sequence is indicated to comprise T, this actually refers to U. It is preferred to have siRNA molecules which do not comprise any non-natural modifications meaning that the siRNA molecules should use the common RNA nucleotides being A, U, C, G being connected by phosphate bonds.

As mentioned herein, the invention contemplates for loops sequences to be cleaved by e.g. RNase T1 loop sequence which only consist of A and G. This will allow to make siRNAs by in vitro transcription, which can incorporate modified T and C. Examples of such modified nucleotides are sugar modifications as 2'-Fluoro-2'-deoxy, 2'-Amino-2'-deoxy, 2'-Azido-2'-deoxy or 2'-O-methylcytidin or uridine.

As already mentioned above, the present invention in a first aspect relates to a method of preparing double stranded RNA molecules, wherein each strand of said different double stranded molecules has a length of 15 to 30 nucleotides wherein said different double stranded RNA molecules are capable of target-specific RNA interference of at least one target gene, said method comprising at least the steps of:
  a. Providing at least one first DNA molecule,
  b. Providing at least one second DNA molecule,
  c. In vitro transcribing said at least one first and at least one second DNA molecules using an RNA polymerase to obtain corresponding at least one first and at least one second RNA molecules,
  d. Hybridizing said at least one first and at least one second RNA molecules of step c. to obtain an double stranded RNA molecule of the general structure depicted in FIG. 1,
  e. Digesting the double stranded RNA molecule obtained in step d. with an RNase, of which RNAse T1 may be preferred, capable of preferentially recognizing, cleaving and digesting the single stranded loop-sequence-elements over the hybridized double stranded sections of the double stranded RNA obtained in step d. thereby removing single stranded RNA loops, wherein the sequence of said target-sequence-elements depicted on FIG. 1 of the at least one first DNA molecule is sense to sequences of said at least one target gene of RNA interference, wherein the sequences of said target-sequence-elements$_{rc}$ of the at least one second DNA molecule are the reverse complements of the sequences of the target-sequence-elements of the at least one first DNA molecule, which they hybridize to, and wherein the loop-sequence elements of the at least one first and at least one second DNA molecules are not reverse complements of each other, wherein the sequences of the loop-sequence-elements are selected such that double stranded RNA molecules are obtained by recognition, cleavage and digestion of the single stranded loop-sequence elements by an RNase in step e., wherein each strand of said resulting double stranded molecules has a length of 15 to 30 nucleotides and wherein said resulting double stranded RNA molecules are capable of target-specific RNA interference of at least one target gene.

In a preferred embodiment of this first aspect, the present invention relates to a method comprising at least the steps of:

a. Providing at least one first DNA molecule comprising in the 5'-3' direction as repeating units a nucleic acid sequence with the following elements:

5'-[(target-sequence-element)-(loop-sequence-element)]$_k$-3', with k being an integer >1, with the target-sequence-element being a continuous sequence of 15 to 30 desoxyribonucleotides, which is sense to a sequence in said at least one target gene of RNA interference, with the loop-sequence-element being a continuous sequence of 3 to preferably 20 desoxyribonucleotides, which does not match a sense or antisense sequence in said at least one target gene of RNA interference, b. Providing at least one second DNA molecule comprising in the 5'-3' direction in a repetitive manner a nucleic acid sequence with the following elements:

5'-[(target-sequence-element)$_{rc}$-(loop-sequence-element)]$_l$-3', with l being an integer >1 and having the same value as k in the first DNA molecule, with the target-sequence-element$_{rc}$ being a continuous sequence of 15 to 30 desoxyribonucleotides, with the loop-sequence-element being a continuous sequence of 3 to 20 preferably desoxyribonucleotides, which does not match a sense or antisense sequence in said at least one target gene of RNA interference, wherein the target-sequence-elements$_{rc}$ counted from the 3' end in the repeating units of said second DNA molecule are the respective reverse complement of the target-sequence-elements counted from the 5' end in the repeating units of said first DNA molecule, and wherein the loop-sequence-elements in the repeating units of said second DNA molecule are not reverse complements of the loop-sequence-elements in the repeating units of said first DNA molecule, c. In vitro transcribing said at least one first and at least one second DNA molecules using an RNA polymerase to obtain corresponding at least one first and at least one second RNA molecules, d. Hybridizing said at least one first and at least one second RNA molecules of step c. to obtain a double stranded RNA molecule of the general structure depicted in FIG. 1, e. Digesting the double stranded RNA molecule obtained in step d. with an RNase, of which RNAse T1 may be preferred, capable of preferentially recognizing, cleaving and digesting the single stranded loop-sequence-elements over the hybridized double stranded sections of the double stranded RNA obtained in step d. thereby removing single stranded RNA loops, wherein the sequences of the loop-sequence-elements are selected such that double stranded RNA molecules are obtained by recognition, cleavage and digestion of the single stranded loop-sequence elements by an RNase, of which RNAse T1 may be preferred, in step e., wherein each strand of said resulting double stranded molecules has a length of 15 to 30 nucleotides, wherein said resulting double stranded RNA molecules are capable of target-specific RNA interference of at least one target gene.

FIG. 1 shows a hybridized RNA molecule that is obtained upon in vitro transcription and hybridization of the at least one first DNA and at least one second DNA molecule mentioned for the above mentioned first aspect of the present invention as well as its preferred embodiment. As one can see, the first and the second DNA molecules consist of target sequence elements as well as loop sequence elements.

The target sequence elements are selected such that they comprise at least a substantial part of the sequence of the siRNA molecules to be produced. Thus, the target sequence elements comprise a sequence that matches part of a sequence of the target gene(s) that is (are) to be silenced by the siRNA molecules. For the sake of nomenclature, the target sequence element in the at least one first DNA molecule should correspond to the sense sequence of the target gene to be ultimately targeted by the siRNA molecules. This follows from the understanding that one strand of the siRNA corresponds to the sequence of a cDNA of a gene which is understood to refer to the sense sequence. The sequence of at least one first DNA molecule corresponds to the cDNA sequence and thus to the sense sequence. As a consequence, the target sequence elements of the second DNA molecule will comprise a sequence corresponding to the antisense sequence of the target gene. Given that the at least one first and at least one second DNA molecule upon transcription and hybridization should form double-stranded RNA section of the target sequence elements, the target sequence elements of the at least one first and the at least one second molecule will have to be selected both in terms of sequence and order such that the first target sequence element of the first DNA sequence counted from the 5' end can hybridize to the sequence of the first target sequence element of the second DNA molecule counted from the 3' end. Similarly, the second target sequence element of the first DNA molecule counted from the 5' end must be selected so that it can hybridize with the target sequence element for the second target sequence element of the second DNA molecule counted from the 3' end. As a consequence, the first target sequence element of the second DNA molecule counted from the 3' end will be the reverse complement of the first target sequence element of the first DNA molecule counted from the 5' end. Similarly, the second target sequence element counted from the 3' end of the second DNA molecule will be the reverse complement of the second target sequence element of the first DNA molecule counted from the 5' end, etc. This relationship is depicted in FIG. 1.

Further, the various target sequence elements of the first and the second DNA molecule which upon transcription and hybridization of these DNA molecules form double-stranded RNA sections are intermitted by single-stranded loop sequence elements. These loop sequence elements must be selected such that they upon in vitro transcription and hybridization of the two DNA molecules do not form double-stranded sections, but instead single-stranded loop sections such that they can be recognised, cleaved and digested by an RNase over double-stranded target sequence elements.

Even though this is not depicted in FIG. 1, the invention also envisages embodiments where the first target sequence element, as counted from the 5' end, is preceded by a loop sequence element and where the last target sequence element, as counted from the 5' end, is followed by a sequence element.

It is also evident to the skilled person that different loop sequences may be used. Such different loop sequence elements may be selected that they are recognised, cleaved and digested by different RNases. However, they may also be selected that they are all recognised, cleaved and digested by the same RNase, of which RNAse T1 may be preferred, albeit at different positions. A further explanation as to how the loop sequence elements will have to be selected with respect to the RNasese to be used will be given below. However, the skilled person will understand that the loop sequence elements of the first DNA molecule and the second DNA molecules cannot be the reverse complements of each other as in this case they would not form a single-stranded loop sequence.

As is immediately evident from FIG. 1, the concept laid out for the first aspect of the invention cannot only be realised by the use of two different DNA molecules, which upon in vitro transcription and hybridization form the general structure depicted in FIG. 1, but can also be realised by single DNA molecules that in addition to the target sequence elements and the loop sequence elements comprise an additional loop sequence element, which is designated for the purposes of the present invention as a hairpin loop sequence element that allows upon in vitro transcription of such a DNA molecule the 3' end to fall back to the 5'end and to form the general structure depicted in FIG. 2. However, the considerations to be applied for the selection of the target sequence elements and the loop sequence element as pointed out above for the first aspect of the invention equally apply. Thus, it must be ensured that the first target sequence element counted from the 3' end is the reverse complement of the first target sequence element counted from the 5' end. Further, the second target sequence element counted from the 3' end must be the reverse complement of the second target sequence element counted from the 5' end, etc. Again the sequences of the loop sequence elements shall be selected to be not reverse complements of each other.

In a second aspect the present invention thus relates to a method of preparing different double stranded RNA molecules, wherein each strand of said double stranded molecules has a length of 15 to 30 nucleotides, wherein said double stranded RNA molecules are capable of target-specific RNA interference of at least one target gene, said method comprising at least the steps of:

a. Providing at least one DNA molecule,
b. In vitro transcribing said at least one DNA molecules using an RNA polymerase to obtain corresponding at least one first RNA molecule, which upon hybridization provides the general structure depicted in FIG. 2,
c. Digesting the RNA molecule obtained in step b. with an RNase, of which RNAse T1 may be preferred, capable of preferentially recognizing, cleaving and digesting the single stranded loop-sequence-elements over the hybridized double stranded sections of the double stranded RNA obtained in step b. thereby removing single stranded RNA loops,
   wherein the sequence of said target-sequence-elements depicted on FIG. 2 of the at least one first DNA molecule is sense to sequences of said at least one target gene of RNA interference, wherein the sequences of said target-sequence-elements$_{rc}$ of the at least one DNA molecule are the reverse complements of the sequences of the target-sequence-elements of the at least one first DNA molecule, which they hybridize to, and wherein the loop-sequence elements of the at least one first and at least one second DNA molecules are not reverse complements of each other,
   wherein the sequences of the loop-sequence-elements are selected such that double stranded RNA molecules are obtained by recognition, cleavage and digestion of the single stranded loop-sequence elements by an RNase, of which RNAse T1 may be preferred, in step c., wherein each strand of said resulting double stranded molecules has a length of 15 to 30 nucleotides and wherein said resulting double stranded RNA molecules are capable of target-specific RNA interference of at least one target gene.

In a preferred embodiment of this second aspect, the present invention relates to a method comprising at least the steps of:

a. Providing at least one first DNA molecule comprising in the 5'-3' direction as repeating units a nucleic acid sequence with the following elements:
   5'-[(target-sequence-element)-(loop-sequence-element)]$_k$-(target-sequence-element)-(loop-sequence-element)$_{hp}$-[(target-sequence-element)$_{rc}$-(loop-sequence-element)]$_l$-3',
   with k being an integer >1,
   with l being an integer >1 and being the same as l,
   with the target-sequence-element being a continuous sequence of 15 to 30 desoxyribonucleotides, which is sense to a sequence in said at least one target gene of RNA interference,
   with the loop-sequence-element being a continuous sequence of 3 to preferably 20 desoxyribonucleotides, which does not match a sense or antisense sequence in said at least one target gene of RNA interference, wherein the (loop sequence element)$_{hp}$ is of sufficient length to allow for a hairpin structure enabling a self-hybdrization pattern depicted in FIG. 2, with the target-sequence-element$_{rc}$ being a continuous sequence of 15 to 30 desoxyribonucleotides,
   wherein the target-sequence-elements$_{rc}$ counted from the 3' end are the respective reverse complement of the target-sequence-elements counted from the 5' end,
   wherein the loop-sequence-elements following the (loop sequence element)$_{hp}$ are not reverse complements of the loop-sequence-elements preceeding the in the repeating units of said second DNA molecule, b. In vitro transcribing said at least one first DNA molecules using an RNA polymerase to obtain corresponding at least one first RNA molecule, which upon hybridization provides the general structure depicted in FIG. 2, c. Digesting the double stranded RNA molecule obtained in step b. with an RNase, of which RNAse T1 may be preferred, capable of preferentially recognizing, cleaving and digesting the single stranded loop-sequence-elements over the hybridized double stranded sections of the double stranded RNA obtained in step b. thereby removing single stranded RNA loops, wherein the sequences of the loop-sequence-elements are selected such that double stranded RNA molecules are obtained by recognition, cleavage and digestion of the single stranded loop-sequence elements by an RNase, of which RNAse T1 may be preferred, in step c., wherein each strand of said resulting double stranded molecules has a length of 15 to 30 nucleotides and wherein said resulting double stranded RNA molecules are capable of target-specific RNA interference of at least one target gene.

As for the first aspect of the invention and even though this is not depicted in FIG. 2, the invention for the second aspect also envisages embodiments where the first target sequence element, as counted from the 5' end, is preceded by a loop sequence element and where the last target sequence element, as counted from the 5' end, is followed by a sequence element.

It is furthermore contemplated also for the second aspect that different loop sequence may be used. Such different loop sequence elements may be selected that they are recognised, cleaved and digested by different RNases. However, they may also be selected that they are all recognised, cleaved and digested by the same RNase, albeit at different positions. A further explanation as to how the loop sequence elements will have to be selected with respect to the RNasese to be used will be given below. However, the skilled person will understand that the loop sequence elements of the first DNA molecule and the second DNA molecules cannot be the reverse complements of each other as in this case they would not form a single-stranded loop sequence.

As regards the hairpin loop sequence element of FIG. 2, the only restriction is that the sequence must be of sufficient length to allow a self-hybridization as depicted in FIG. 2.

For both, the first and second aspect of the invention, the number of target sequence elements which define the number of an siRNAs that will be produced by methods in accordance with either the first or the second aspect of the invention can vary. Thus, the number of target sequence elements ultimately giving rise to a number of siRNA molecules may be at least 2, at least 3, at least 4, at least 5, at least 6, at least 7, at least 8, at least 9, at least 10, at least 11, at least 12, at least 13, at least 14, at least 15, at least 20, at least 30, at least 40, at least 50, at least 60, at least 70, at least 80, at least 90 or at least 100. However, in view of the overall length of the resulting hybridized RNA molecules as depicted in FIG. 1 or FIG. 2, it seems reasonable that the number of target sequence elements should not exceed more than 100 target sequence elements with an overall number of up to 50 to 60 target sequence elements being reasonable.

Consequently, the integer of k and l for both the first and second aspect of the invention can be at least 2, at least 3, at least 4, at least 5, at least 6, at least 7, at least 8, at least 9, at least 10, at least 11, at least 12, at least 13, at least 14, at least 15, at least 20, at least 30, at least 40, at least 50, at least 60, at least 70, at least 80, at least 90 or at least 100. However, in view of the overall length of the resulting hybridized RNA molecules as depicted in FIG. 1 or FIG. 2, it seems reasonable that the integer of k and l for both the first and second aspect of the invention should not exceed more than 100 target with values of up to 50 to 60 being preferred upper limits.

In order to obtain high complexity siRNA pools, the number of target sequence elements may be at least 5, 6, 7, preferably at least 8, 9, 10, 11, 12, 13, 14, more preferably at least 15, 16, 17, 18, 19, 20, 25, 30, 40, 50, 60, 70, 90 or at least 100 sequence elements. It seems that efficient gene silencing and reduced off-target effects as described below can be achieved with a high complexity siRNA pool having at least 8 to 10 such as 11, 12, 13, 14, or 15 siRNAs and thus at least 8 to 10 target such as 11, 12, 13, 14, or 15 sequence elements (if the high complexity siRNA pool is produced by methods in accordance with the invention). A high complexity siRNA pool having at least about 11 to at least about 15 siRNAs and thus at least about 11 to at least about 15 target sequence elements (if the high complexity siRNA pool is produced by methods in accordance with the invention) seems to give substantially no off-target effect. A high complexity siRNA pool having at least about 40 to at least about 60 siRNAs and thus at least about 40 to at least about 60 target sequence elements (if the high complexity siRNA pool is produced by methods in accordance with the invention) seems to give no off-target effect at all.

As has been mentioned above, methods in accordance with the first and second aspect of the present invention and their preferred embodiments can be used to produce different pools of siRNA molecules.

If the sequences of the target sequence elements are the same, the resulting pool with the methods in accordance with the first and second aspect of the present invention and their preferred embodiments will provide an efficient means of producing a pool comprising the same siRNAs. However, if the sequences of the target sequence elements are not the same, two different scenarios can be envisaged.

If the sequences of the target sequence elements are not the same, but are selected such that the resulting siRNAs are all directed to the same target sequence, the methods in accordance with the present invention will allow production of pools of siRNAs all of which are directed to the same target gene. The advantages of such pools and embodiments of the present invention where the target sequence elements are not the same but are directed to the same target genes include that one can efficiently produce a plethora of siRNA sequences. This pool of sequences can then be used to silence the expression of a gene and it can be assumed that at least some of the siRNAs will be effective. As has been noted above, complex siRNA pools, even where all siRNAs are directed to the same target gene can show reduced off-target effects as it seems that those siRNAs which work well with respect to a particular target gene seem to suppress off-target effects by other siRNAs being directed against the same gene.

High complexity siRNA pools in accordance with the invention comprise at least 5, preferably at least 8 siRNAs, all being targeted against at least one gene of interest. The siRNAs of such high complexity siRNA pools may be produced by the methods in accordance with the invention, but also by methods known in the state of the art such as by chemical synthesis. The invention contemplates to combine different high complexity siRNA pools, with each pool being directed against on target gene of interest to achieve a combination which can be used to simultaneously silence multiple genes and by simultaneously reducing off-target effects.

In a second scenario, the sequences of the target sequence elements are not the same and can be moreover directed to different target genes. The resulting siRNA pool will in this respect be an siRNA pool allowing gene silencing of various target genes. This approach can be used to effectively provide combinations of siRNAs which can be used to e.g. silence gene expression of various homologues of a gene family and/or to e.g. silence gene expression of various genes all which belong to cellular pathways such signal transduction pathways. In this second scenario, one can also create high complexity siRNA pools for silencing e.g. gene homologues or e.g. members of a signal transduction pathway by selecting at least 8 target sequence elements for one homologue or member of the signal transduction pathway, and selecting further at least 8 additional target sequence elements against another homologue or member of the signal transduction pathway, etc. Depending on how many siRNAs for each separate gene will be present in the resulting pool, high complexity pools against different target genes may be obtained with such high complexity pools comprising at least five, preferably at least 8 to 10 such as at least 11, 12, 13, 14, or at least 15 siRNAs against each single gene.

It is thus to be understood that the aforementioned number of target sequence elements, which can be present may not only relate to the number of target sequence element of identical sequence being present but also to target sequence elements of different sequences being present. In one particular aspect the aforementioned number may thus relate to the number of different target sequence elements all of which are being directed to a single target gene or all of which are directed to different target genes.

As will become apparent from the ensuing description, the loop sequence elements can be chosen such that the resulting siRNA molecules upon recognition, cleavage and digestion (after transcription and hybridization of the template molecules) by the RNAse(s) are blunt ended. However, the loop sequence elements may also be configured to give rise to siRNA molecules with a 3' overhang. As will be set out below, the length of the 3' overhang may be determined by the position of the base/nucleotide that is recognised, cleaved and digested by the RNase, of which RNAse T1 may be preferred. Thus, the length of the target sequence of the resulting siRNAs depending on the specific scenario may be determined by this target sequence element alone, e.g. if blunt-ended sequences are desired or by the target sequence elements plus some of the nucleotides of the loop sequence elements, namely those that precede the cleavage site of the RNAs. Therefore, no strict limitations are given on the length of the target sequence element.

However, the length of the target sequence elements should be selected such that taking the additional bases that may be added from the loop sequence element into account, the resulting siRNA molecules have a length of 15 to 30 nucleotides. Preferably, the resulting siRNA molecules have a length of 17 to 25, 18 to 24, 19 to 23, or 20, 21, or 22 nucleotides with siRNA molecules having a length of 21 nucleotides being preferred. Where the siRNA molecules should have a 3' overhang, the target sequence elements and the loop sequence elements may be designed to give an overhang of 1 to 5, 1 to 4, 1 to 3 or 1 to 2 nucleotides.

Depending on the number of nucleotides resulting from the loop sequence elements, the length of the target sequence element will thus typically have a continuous sequence of 17 to 23, 17 to 22, 17 to 21, 18, 19 or 20 nucleotides.

In all of the embodiments discussed herein it can be particularly preferred that siRNAs have a length of 21 to 23 nucleotides including a 3' overhang of 1 to 2 nucleotides.

As pointed out above, the loop sequence elements may be the same throughout the hybridized molecules as depicted in FIG. 1 and FIG. 2. If exactly the same sequences are used for all loop sequence elements, the loop sequence elements will be recognised by the same RNAs and will give rise to siRNAs of the same length and 3' overhang assuming of course that the target sequence elements would then have the same length. However, the loop sequence elements may be selected such that they are all recognised by the same RNase, of which RNAse T1 may be preferred, but that the specific sequences are selected that this specific RNase cleaves at different positions. This would give rise to siRNAs with different overhangs and lengths, again assuming that the target sequence element as such would have the same length. Furthermore, the loop sequence elements may differ not only with respect to the position at which they are cleaved by the same RNase, of which RNAse T1 may be preferred, but also as to the RNase that is capable of recognising, cleaving and digesting them.

Using these different embodiments, the methods in accordance with the invention, as well as the kits and DNA molecules as described below, can be optimised to provide efficient means for producing siRNAs that have been identified to be particularly suitable for silencing either of single or numerous target genes. Thus, if e.g. certain siRNAs are known to efficiently silence the expression of a particular gene and if these siRNAs differ e.g. by their length and overhangs, these siRNAs can be implemented into the DNA molecules being used according to the first and second aspects of the invention and their preferred embodiments by e.g. modifying the loop sequences accordingly.

As pointed out, the loop sequences are selected such that upon transcription and hybridization these sequence elements form single-stranded, unpaired RNA loops which can preferentially be recognised, cleaved and digested over double-stranded target sequence element sections by an RNase. Typically such RNases will be sequence-specific for the respective single-stranded loop sequence elements in double-stranded RNA molecules and not act, at least not substantially, on the hybridized double-stranded section of the RNA molecules.

RNases may be selected from the group consisting of RNase T1, RNase Ba, ST, C2, RNase U2, RNase PhyM, RNase A, RNase CL3, and RNase T2. The sequences which are to be recognised, cleaved and digested by these various RNases can be deduced to some extent from prior art teaching. In the following, only some of the most preferred sequences are thus mentioned for the afore-mentioned Rnases. The person skilled in the art, based on the information provided in the context of the present invention will be in a position to readily modify these sequences or identify further sequences, which are suitable for the loop sequence elements.

If in the following it is stated in the context of the loop sequences for RNase T1 or any other RNase mentioned herein that X and Y being selected such that there is no hybridization of two molecules consisting just of the loop-sequence-element, this is to be understood that hybridization does not occur to an extent that double stranded or other secondary structure elements form which would prevent the respective RNase from acting on the loop sequences. Further, the loop sequences must be selected such that the loop sequences of the sense and antisense strand molecules as described hereinafter do not hybridize to an extent that double stranded or other secondary structure elements form, which would prevent the respective RNase from acting on the loop sequences.

Next to the specific RNase T1 loop sequences discussed in the following, the experiments described hereinafter allow the following conclusion for loop sequences being cleavable by RNase T1. It seems that the optimal minimal length of a loop sequence being cleavably by RNase T1 is 5 to 6 nucleotides. Loop sequences with longer sequences may be used, but the improvement in cleavage efficiency does not seem to be substantial. It seems reasonable that the overall length of the loop sequences should not substantially exceed the length of the siRNA defining target sequences. Further, it seems reasonable that the overall length of the sequence element may optimally not exceed 15 nucleotides with reasonable overall loop sequence length being 5, 6, 7, 8, 9, 10, 11, or 12 nucleotides. The integer of m in the below mentioned examples of loop sequences for RNase T1 may thus be 1 or 2 and the integer of n may thus be 1, 2, 3, 4, 5, 6, 7, 8 or 9. Even though a G may be present in the below described position $(Y)_n$, thereby creating an additional cleavage site it seems best that a loop sequence element should comprise preferably on two G.

Further, it seems that the loop sequence element should have optimally a sequence, which minimizes the occurrence of unusual G-T base pairs in the loop sequence elements upon hybridization of the sense and antisense strand. Thus a loop sequence comprising A and G only may be most preferred. This would also allow to incorporate modified T and C in the siRNA target sequences.

In the case of a loop sequence element cleavable by RNase T1, the loop-sequence-element may have the sequence 5'-$(X)_m$-G-$(Y)_n$-G-3',
  with X being A, T or C and m being an integer of 0 to 4 or 1 to 4 such as 0, 1, 2, 3, or 4,
  with Y being A, T or C and n being an integer of 0 to 17 or 2 to 17, such as 0, 1, 2, 3, 4, 5, 6, 7, 8, 9, 10, 11, 12, 13, 14, 15, 16, or 17, and
  with X and Y being selected such that there is no hybridization of two molecules consisting just of the loop-sequence-element.

In a preferred embodiment and in the case of a loop sequence element cleavable by RNase T1, the loop-sequence-element may have the sequence 5'-$(X)_m$-G-$(Y)_n$-G-3',
  with X being A or C and m being an integer of 1 to 2,
  with Y being A, T or C and n being an integer of 2 to 10, such as 2, 3, 4, 5, 6, 7, 8, 9, or 10, and
  with X and Y being selected such that there is no hybridization of two molecules consisting just of the loop-sequence-element.

In a further preferred embodiment and in the case of a loop sequence element cleavable by RNase T1, the loop-sequence-element may have the sequence 5'-$(X)_m$-G-$(Y)_n$-G-3',
  with X being A and m being an integer of 1,
  with Y being A, T or C and n being an integer of 2 to 5, such as 2, 3, 4, or 5, and
  with X and Y being selected such that there is no hybridization of two molecules consisting just of the loop-sequence-element.

In a further preferred embodiment and in the case of a loop sequence element cleavable by RNase T1, the loop-sequence-element may have the sequence 5'-$(X)_m$-G-$(Y)_n$-G-3',
  with X being A and m being an integer of 1,
  with Y being T and n being an integer of 2, 3, or 4, and
  with X and Y being selected such that there is no hybridization of two molecules consisting just of the loop-sequence-element.

In an even more preferred embodiment and in the case of a loop sequence element cleavable by RNase T1, the loop-sequence-element may have the sequence 5-$(X)_m$-G-$(Y)_n$-G-3',
  with X being A and m being an integer of 1, or 2,
  with Y being A and n being an integer of 2, 3, 4, or 5, and
  with X and Y being selected such that there is no hybridization of two molecules consisting just of the loop-sequence-element.

In one of the most preferred embodiment and in the case of a loop sequence element cleavable by RNase T1, the loop-sequence-element may have the sequence 5'-$(X)_m$-G-$(Y)_n$-G-3',
  with X being A and m being an integer of 1,
  with Y being A and n being an integer of 2, 3, or 4, and
  with X and Y being selected such that there is no hybridization of two molecules consisting just of the loop-sequence-element.

A particularly preferred sequence for RNase T1 is AGTTG, AGTTTG, or AGTGTAG. Even more preferred sequences of RNAse T1 are AGAAG and AGAAAG.

In view of the information presented in Heinemann et al. (1985), *Pure & Appl. Chem.*, 57(3), 417-422, it seems justified to assume that RNase Ba, ST, C2 will act similarly on loop sequences described for RNase T1.

In the case of a loop sequence element cleavable by RNase U2, the loop-sequence-element may have the sequence 5'-$(X)_m$-A-$(Y)_n$-A-3',
  with X being T, G or C and m being an integer of 1 to 4, such as 1, 2, 3, or 4,
  with Y being T, G or C and n being an integer of 2 to 17, such as 2, 3, 4, 5, 6, 7, 8, 9, 10, 11, 12, 13, 14, 15, 16, or 17, and
  with X and Y being selected such that there is no hybridization of two molecules consisting just of the loop-sequence-element.

In the case of a loop sequence element cleavable by RNase PhyM, the loop-sequence-element may (i) have the sequence 5'-$(X)_m$-A-$(Y)_n$-A-3',
  with X being T, G or C and m being an integer of 1 to 4, such as 1, 2, 3, or 4,
  with Y being T, G or C and n being an integer of 2 to 17, such as 2, 3, 4, 5, 6, 7, 8, 9, 10, 11, 12, 13, 14, 15, 16, or 17, and
  with X and Y being selected such that there is no hybridization of two molecules consisting just of the loop-sequence-element,
or (ii) have the sequence
  with X being A, G or C and m being an integer of 1 to 4,
  with Y being A, G or C and n being an integer of 2 to 17, and
  with X and Y being selected such that there is no hybridization of two molecules consisting just of the loop-sequence-element.

In all loop sequences for RNase PhyM it may be contemplated that $(X)_m$ and $(Y)_n$ do not contain any A or T if the loops sequences comprises A or T as the nucleotides where the RNase acts.

In the case of a loop sequence element cleavable by RNase A, the loop-sequence-element may (i) have the sequence 5'-$(X)_m$-C-$(Y)_n$-C-3', with X being A, T, or G and m being an integer of 1 to 4, such as 1, 2, 3, or 4, with Y being A, T, or G and n being an integer of 2 to 17, such as 2, 3, 4, 5, 6, 7, 8, 9, 10, 11, 12, 13, 14, 15, 16, or 17, and with X and Y being selected such that there is no hybridization of two molecules consisting just of the loop-sequence-element, or (ii) have the sequence 5'-(X)$_m$-T-(Y)$_n$-T-3', with X being A, G or C and m being an integer of 1 to 4, such as 1, 2, 3, or 4, with Y being A, G or C and n being an integer of 2 to 17, such as 2, 3, 4, 5, 6, 7, 8, 9, 10, 11, 12, 13, 14, 15, 16, or 17, and with X and Y being selected such that there is no hybridization of two molecules consisting just of the loop-sequence-element.

In the case of a loop sequence element cleavable by RNase CL3, the loop-sequence-element may have the sequence 5'-(X)$_m$-C-(Y)$_n$-C-3', with X being A, T, or G and m being an integer of 1 to 4, such as 1, 2, 3, or 4, with Y being A, T, or G and n being an integer of 2 to 17, such as 2, 3, 4, 5, 6, 7, 8, 9, 10, 11, 12, 13, 14, 15, 16, or 17, and with X and Y being selected such that there is no hybridization of two molecules consisting just of the loop-sequence-element.

In the case of a loop sequence element cleavable by RNase T2, the loop-sequence-element may have the sequence 5'-(X)$_m$-A-(Y)$_n$-A-3', with X being T, C, or G and m being an integer of 1 to 4, such as 1, 2, 3, or 4, with Y being T, C, or G and n being an integer of 2 to 17, such as 2, 3, 4, 5, 6, 7, 8, 9, 10, 11, 12, 13, 14, 15, 16, or 17, and with X and Y being selected such that there is no hybridization of two molecules consisting just of the loop-sequence-element.

The above mentioned sequence are of exemplary nature. It is to be understood that the loop-sequence elements can be selected such that in said hybridized RNA molecule, they are cleaved by an RNase after the first, second, third, fourth or fifth position of the 5'-end of the single stranded loop-sequence-element. This can allow to produce the afore-mentioned 3' overhangs.

As is obvious from the aforementioned loop sequence elements for the various RNases, the length of the loop depending on the number of the nucleotides X and Y can differ. There are no strict rules as to what is the optimal length of such a loop sequence element in order to be most efficiently recognisable, cleavable and digestible by the respective RNases. In general, the loop should have a length between 3 to 20 nucleotides, with lengths of 3 to 15, 3 to 10, 3 to 9, 3 to 8 nucleotides and in particular lengths of 4, 5, 6, 7 nucleotides being preferred.

In order to determine an optimized loop length and sequence, the skilled person will understand that this sequences should be non-gene specific. Even if gene specific sequences are used, the loop will usually not give rise to siRNAs as it is single stranded and cut at all e.g. G-positions in case of RNase T1. However, even for unusual situations (e.g. comparetively long loop sequences) one can avoid that the loop sequence give themselves rise to undesired siRNAs by properly considering the sepcific sequences. For optimization, one can refer e.g. to established databases and software programmes which allow structure prediction of various loop sequence structures. For example, the Vienna RNA WebServer at RNA.tbi.univie.ac.at offers various programes which inter alia allow prediction of minimum free energy structures, base pair probabilities and secondary structure predictions from single RNA or DNA sequences or allow prediction of the secondary structure of double stranded RNAs. This web service also provides programmes for assisting in siRNA design. In this respect, reference is made to the software suits RNAfold server, RNAcofold server and RNAxs server (see also FIG. 4). Other software programs for designing siRNAs are available e.g. at dharmacon.com/designcenter/DesignCenterPage.aspx, or ecom.mwgdna.com/register/index.tcl?return_url=%2fservices %2 fwebgist%2fsirna_desig n%3fuser_id%3d740967. These latter software programs have been used for designing siRNAs of the Examples.

It has further been found that the minimum free energy structure prediction provided by the RNAfold server provides a suitable guiding parameter for determining both the exact sequence identity as well as the sequence length of the loop sequence elements being recognised, cleaved and digested by e.g. RNase T1. For example, the minimum free energy structure, calculated by RNAfold (see above) for loop sequence structures AGTTG and AGTTTG predicts a low base pairing probability for both loops, suggesting a better accessibility of the desired G-nucleotides to RNAse T1 for the larger, 6 nucleotide loop sequence, AGTTTG than for the smaller, 5 nucleotide sequence AGTTG. For the 6 nucleotide TGTTTG loop sequence structure however, RNAfold predicts a high base pairing probability due to 4 non canonical GU base pairing positions, reducing the effective single strand loop region to the two, central T nucleotides. These data indicate that, considering the length of the effective single strand loop region a measure for the accessibility of the desired G nucleotides to RNAseT1, the AGTTTG loop sequence structure should be optimized for RNAse T1 digest, followed by AGTTG and, worst of all 3, TGTTTG. This is moreover confirmed by the experimental data set out hereinafter in Example 2.

The afor-mentioned software programmes can also be used to determine which hairpin loop sequence element as depicted FIG. 2 are suitable to allow self-annealing.

As mentioned above, the present invention in a third aspect relates to a combination or a kit of at least two DNA molecules, which upon in vitro transcription, hybridization and digestion with an RNase are capable of providing double stranded RNA molecules, wherein each strand of said different double stranded molecules has a length of 15 to 30 nucleotides and wherein said double stranded RNA molecules are capable of target-specific RNA interference of at least one target gene, wherein said at least two DNA molecules have the sequence elements necessary to obtain an RNA molecule of the general structure depicted in FIG. 1 after in vitro transcription and hybridization, wherein the sequences of the loop-sequence-elements are selected such that double stranded RNA molecules can be obtained after cleavage and digestion with an RNase capable of preferentially recognizing and cleaving the single stranded loop-sequence-elements over the hybridized double stranded sections of the double stranded RNA thereby removing single stranded RNA loops.

In a preferred embodiment of this third aspect, the present invention relates to a combination, obtainable by:

a. Providing at least one first DNA molecule comprising in the 5'-3' direction as repeating units a nucleic acid sequence with the following elements:

5'-[(target-sequence-element)-(loop-sequence-element)]$_k$-3', with k being an integer >1,
    with the target-sequence-element being a continuous sequence of 15 to 30 desoxyribonucleotides, which is sense to a sequence in said at least one target gene of RNA interference,
    with the loop-sequence-element being a continuous sequence of 3 to preferably 20 desoxyribonucleotides, which does not match a sense or antisense sequence in said at least one target gene of RNA interference,
b. Providing at least one second DNA molecule comprising in the 5'-3' direction in a repetitive manner a nucleic acid sequence with the following elements:
    5'-[(target-sequence-element)$_{rc}$-(loop-sequence-element)]$_l$-3',
    with l being an integer >1 and having the same value as k in the first DNA molecule,
    with the target-sequence-element$_{rc}$ being a continuous sequence of 15 to 30 desoxyribonucleotides,
    with the loop-sequence-element being a continuos sequence of 3 to preferably 20 desoxyribonucleotides, which does not match a sense or antisense sequence in said at least one target gene of RNA interference,
    wherein the target-sequence-elements$_{rc}$ counted from the 3' end in the repeating units of said second DNA molecule are the respective reverse complement of the target-sequence-elements counted from the 5' end in the repeating units of said first DNA molecule, and
    wherein the loop-sequence-elements in the repeating units of said second DNA molecule are not reverse complements of the loop-sequence-elements in the repeating units of said first DNA molecule,
c. In vitro transcribing said at least one first and at least one second DNA molecules using an RNA polymerase to obtain corresponding at least one first and at least one second RNA molecules,
d. Hybridizing said at least one first and at least one second RNA molecules of step c. to obtain a double stranded RNA molecule of the general structure depicted in FIG. 1,
e. Digesting the double stranded RNA molecule obtained in step d. with an RNase, of which RNase T1 may be preferred, capable of preferentially recognizing and cleaving the single stranded loop-sequence-elements over the hybridized double stranded sections of the double stranded RNA obtained in step d. thereby removing single stranded RNA loops,
wherein the sequences of the loop-sequence-elements are selected such that double stranded RNA molecules are obtained by recognition, cleavage and digestion of the single stranded loop-sequence elements by an RNase, of which RNase T1 may be preferred, in step e. thereby removing single stranded RNA loops, wherein each strand of said resulting double stranded molecules has a length of 15 to 30 nucleotides, wherein said resulting double stranded RNA molecules are capable of target-specific RNA interference of at least one target gene RNA.

In a fourth aspect the present invention relates to at least one DNA molecule, which upon in vitro transcription, hybridization and digestion with an RNase, of which RNase T1 may be preferred, is capable of providing double stranded RNA molecules, wherein each strand of said double stranded molecules has a length of 15 to 30 nucleotides and wherein said different double stranded RNA molecules are capable of target-specific RNA interference of at least one target gene, wherein said at least one DNA molecule has the sequence elements necessary to obtain an RNA molecule of the general structure depicted in FIG. 2 after in vitro transcription and hybridization, wherein the sequences of the loop-sequence-elements are selected such that double stranded RNA molecules are obtained after digestion with an RNase, of which RNase T1 may be preferred, capable of preferentially recognizing, cleaving and digesting the single stranded loop-sequence-elements over the hybridized double stranded sections of the double stranded RNA thereby removing single stranded RNA loops.

In a preferred embodiment of this fourth aspect, the present invention relates to at least one DNA molecule, obtainable by:
    a. Providing at least one DNA molecule,
    b. In vitro transcribing said at least one DNA molecules using an RNA polymerase to obtain corresponding at least one first RNA molecule, which upon hybridization provides the general structure depicted in FIG. 2,
    c. Digesting the RNA molecule obtained in step b. with an RNase, of which RNase T1 may be preferred, capable of preferentially recognizing, cleaving and digesting the single stranded loop-sequence-elements over the hybridized double stranded sections of the double stranded RNA obtained in step b. thereby removing single stranded RNA loops,
    wherein the sequence of said target-sequence-elements depicted on FIG. 2 of the at least one first DNA molecule is sense to sequences of said at least one target gene of RNA interference, wherein the sequences of said target-sequence-elements$_{rc}$ of the at least one DNA molecule are the reverse complements of the sequences of the target-sequence-elements of the at least one first DNA molecule, which they hybridize to, and wherein the loop-sequence elements of the at least one first and at least one second DNA molecules are not reverse complements of each other, wherein the sequences of the loop-sequence-elements are selected such that double stranded RNA molecules are obtained by recognition, cleavage and digestion of the single stranded loop-sequence elements by an RNase, of which RNase T1 may be preferred, in step c., wherein each strand of said resulting double stranded molecules has a length of 15 to 30 nucleotides and wherein said resulting double stranded RNA molecules are capable of target-specific RNA interference of at least one target gene.

As regards the structure and elements of the DNA molecules to be used for the third and fourth aspects as well as their preferred embodiments, reference is made to the same considerations as laid out above for the methods forming the first and second aspects as well as the preferred embodiments thereof. Thus the considerations mentioned for the number of targets sequence elements, the number of loop sequence elements, their positioning, etc.

It is to be understood that such combinations, kits and DNA molecules may be provided in a form where they additionally comprise components that will allow performing the methods in accordance with the invention. These components include inter alia an RNA polymerase, a buffer for in vitro transcription, nucleotides for in vitro transcription, means for purifying and isolating the in vitro transcribed RNA molecules, a buffer for hybridization, an RNase, means for purifying and isolating the obtained siRNAs and written instructions for performing methods in accordance with the invention.

In a fifth aspect the present invention relates to the use of any method as described herein, any kit as described herein or any template molecule for producing siRNA pools.

It is to be understood that the various steps of the methods, kits etc. in accordance with the invention such as in vitro transcription, hybridization, RNase digest etc. can be performed as it is know to the skilled person from standard textbooks. The skilled person thus will be able to readily determine how to clone the template molecule in vectors for propagation, which promoter and termination sequences have to be used, and how hybridization can be performed. The same applies to purification steps of the in vitro transcribed RNAs or the siRNAs after the RNase digest.

As mentioned above, the present invention relates in a sixth aspect to combinations of at least 8 siRNAs against at least one specific gene, e.g. to high complexity pools. Such high complexity siRNA pools may be assumed to provide improved on-target and reduced off-target effects. These findings are based on the experiments described hereinafter for the genes Scyl1 and PolG. For these genes, known siRNAs exist, which are known to efficiently silence expression of Scyl1 and PolG but to give off-target effects for Mad2. By comparing for both genes high complexity siRNA pools having 15 siRNAs with the known siRNAs, esiRNAs and smart pools it was observed that the high complexity siRNA pools provide better on-target and reduced off-target effects. In both cases, siRNA pools having 15 siRNAs showed almost a slight to no off-target effect if compared to a negative control siRNA for which no off-target effects are known. If the complexity of the pool was raised to 60 siRNAs, no off-target effect at all was observed. While these high complexity siRNA pools were produced with the methods in accordance with the invention, it is clear that they can be produced by other means such as chemical synthesis, albeit less efficiently.

The data suggest that high complexity siRNA pools of at least 8 to 10 siRNAs provide generally efficient on- and reduced off-target effects. The off-target effects may be further reduced by having up to about 11, 12, 13, 14, or 15 siRNAs. If a complete reduction of off-target effects is to be achieved, the number of siRNAs may be increased to about at least 20, 30, 40, 50, 60, 70, 80, 90 or about at least 100. The siRNAs of high complexity siRNA pools may be produced by the methods in accordance with the invention, but also by methods known in the state of the art such as by chemical synthesis.

Of course, high complexity siRNA pools for specific genes such as different homologues of a gene family or different members of a signal transduction pathway can be separately prepared and then combined to obtain an siRNA pool that can then be used to simultaneously silence a number of genes without getting substantial off-target effects.

As regards the specific steps that need to be undertaken for performing the present invention, some general exemplary teaching is provide in the following. Specific exemplary embodiments are then mentioned in the example section.

Design of Templates for In Vitro Transcription

DNA templates for in vitro transcription can be generated by gene synthesis as offered by multiple commercial providers (i.e. Geneart). For each siRNA pool, which is produced according to the first or third aspect of the invention at least two template DNA constructs are required: one for the sense RNA strand and one for the antisense RNA strand.

If siRNA pools are produced according to the second or fourth aspect of the invention at least one template DNA constructs is required, which however has to also implement the sequences for the sense and antisense RNA strand. Such a single DNA template will in addition comprise a hairpin look sequence element ((loop-seq.el)$_{hp}$ of FIG. 2). The invention will however be discussed for the first or third aspect of the invention. The considerations mentioned in this context apply mutatis mutandis to the second and fourth aspect.

The templates are composed of the following, minimal parts (see FIGS. 1 and 3): 1. A minimal RNA polymerase promoter sequence (for instance the viral 19base T7 promoter sequence) at the 5' end of the template construct. 2. variable, target gene specific sequence fragments reverse complementary between the sense and antisense template constructs (target sequence elements corresponding to (tar.seq.el.) and (targ.seq.el$_{rc}$) of FIG. 1). 3. Non gene specific loop sequences, non reverse complementary between the sense and antisense template constructs (corresponding to (loop-seq-el.) of FIG. 1). Variable, gene specific, reverse complementary and non gene specific, non reverse complementary loop sections are alternating, which may start and end with a loop section. For convenient and cost efficient production of the template DNA, the minimal template described above can be cloned into a suitable bacterial high cloning plasmids using e.g. two different, terminal restriction sites for linearization or excision from the plasmid backbone. The plasmid should not contain the RNA promoter used in template.

The variable, gene specific, reverse complementary sequence sections can be selected from the cDNA sequence of the targeted gene applying any of the published siRNA selection algorithms or custom selection criteria (see e.g. Vienna RNA WebServer at rna.tbi.unvie.ac.at (see. FIG. 4), particularly the RNAxs Server; other tools include the siDesign Center (Dharmacon/Thermo: dharmacon.com / designcenter/DesignCenterPage.aspx) and the online siMAX™ Design Tool (Eurofins MWG: eurofinsdna.com/products-services/sirna/sirna-design.html). To trigger an RNAi response, they should have a length between 19 and 28 base pairs even though the synthesis method would also allow the use of shorter and longer sequence sections.

Non gene specific, non reverse complementary loop sections must be optimized for minimal base pairing between the product sense and antisense RNA strands to allow the recognition and cleavage by a single strand specific ribonuclease such as RNAseT1. Loop sections as short as 5 base pairs containing guanine nucleotide residues at specific positions were found to be sufficient for efficient and specific cleavage by RNAseT1. Longer loop sections are functional and possibly superior for RNAseT1 or other single strand specific ribonucleases. For example one may use RNAfold Server and RNAcofold Server of the Vienna RNA WebServer (see. FIG. 4) to identify optimal loop sequence elements based on their minimal free energy and base pairing propensity. Reference is made to the above explanations in this context.

The use of RNAseT1 which shows a high specificity for cleaving 3' of guanine ribonucleotide residues allows the generation of siRNA fragments with 3' overhangs as described in FIG. 5. To that end, guanine residues must be placed at specific positions in the loop section. Blunt ends can be generated by placing guanine residues at the 3' and 5' terminal positions of the loop sections.

DNA Template Preparation

DNA templates for in vitro transcription designed as described above can be generated by gene synthesis as offered by multiple commercial providers (i.e. Geneart). DNA templates, cloned in plasmid vectors must be either linearized by restriction digest at the 3' end of the template construct (opposite end of the T7 promoter). Alternatively, the template can be excised by restriction digest and purified by preparative agarose gel electrophoresis and gel extraction.

In Vitro Transcription

The transcription of sense and antisense RNA strands in separate in vitro transcription reactions allows an individual quality control, purification and quantification of both strands for a precise use of equal amounts of both strands in the downstream annealing reaction (see below). Alternatively, both strands could be generated in one single in vitro transcription reaction using a mixture of sense and antisense DNA template.

Suitable viral RNA polymerases as RNAs polymerase T3 and T7 are offered by multiple commercial reagent providers or can be generated from bacterial expression clones and protein purification by established protocols. Optimal reaction conditions are described in multiple publications. High yields of RNA, exceeding concentrations of 1 µg/µl can be obtained from comparably cheap reagents, making in vitro transcription an extremely cost effective way of RNA synthesis. To remove residual non incorporated nucleotides and buffer components, in transcriptions reactions can be purified by size exclusion chromatography, using gel filtration resins of suitable pore size (G25 or 50, S200-400). The obtained purified RNA product can be quantified by spectrophotometry and visualized by denaturing polyacrylamide gel electrophoresis for quality control. For efficient downstream single strand RNA annealing, the full length RNA transcript should be the main product of the reaction (>90% of total RNA).

Hybridization/Single Strand RNA Annealing

Equal amounts of both single strand RNAs are hybridized in 1× annealing buffer (30 mM Hepes pH 7.4, 100 mM KAc, 2 mM MgAc) by a melting and annealing program in a conventional PCR cycler. For efficient and precise annealing of both strands, the reaction is first heated for 2 min to 98° C. and then slowly cooled to 4° C. As RNA is susceptible to hydrolysis at high temperatures, the cooling process can be started with a faster cooling step from 98° C. to 80° C. (1° C./s), followed by a slow cooling step in the range from 80° C. to 55° C. (0.1° C./s) for optimal hybridization. The mixture can then be rapidly cooled to 4° C. (1° C./s) and kept on ice for downstream use. As both strands share perfect base pair match over the 19b coding sections, single strand annealing is a robust process with multiple possible annealing programs.

Ribonuclease Digest

As RNAsT1 has a high specificity for guanosine residues in single stranded RNA, a range of enzyme and substrate concentrations as well as multiple buffer constitutions are possible. The concentration of RNAseT1, required for a complete digest of the long dsRNA substrate is dependent on the size and sequence of the single strand loops, which determine the accessibility of the guanosine residues. 3 loop sequences were tested (5' to 3' direction): 1): AGTTG, 2): AGTTTG, 3): TGTTTG. For loop 1) with 5 nucleotides, 12 ug of dsRNA were completely digested to 21mer dsRNA fragments by 40 units of RNAsT1 in 45 minutes. For the 6 nucleotide loop 2) the same amount of dsRNA was completely digested to 21 mer-dsRNA fragments under identical conditions in 10 minutes. The loop sequence 3), where 4 G-T base pairing reduces the single strand region to 2 nucleotides and masks the guanosine residue, no satisfactory conditions were found (see for detail below), the results well matching the base probability prediction of the RNAcofold Server programe of the Vienna RNA WebServer and thus accessibility by RNase T1. The length of the fragments, generated by RNAseT1 from the above described long dsRNA precursor was identical to commercial 21-mer siRNAs as determined by 20% PAA electrophoresis. The increased length are due to the 2 5'-overangs, left from the loop section (see FIG. 3). Very high concentrations of RNAseT1 (>10 fold of conditions described above) also cause a digest of the double strand RNA. However, there seems to be a sufficiently large window of suitable saturating enzyme concentrations that yield the same, complete digest with little or no detectable smaller degradation products (<21b).

siRNA Purification

Even under saturating enzyme conditions as described above, there are small amounts of larger dsRNA fragments only detectable by PAA gel electrophoresis (20%) and sensitive detection methods. Those larger fragments however can trigger an interferon response in higher vertebrate cells (as human, mouse, or other cell) leading to apoptosis and cell death. It is therefore advisable, that all dsRNA fragments larger 30 bp are completely removed. For low throughput and proof of concept experiments as described below, this can be achieved by preparative PAA gel electrophoresis, excision of the respective dsRNA bands followed by elution and precipitation of the 21mer dsRNA fragments and optionally size exclusion chromatography. For high throughput experiments the same effect can be achieved by ion pair reverse phase chromatography.

siRNA Pool Transfection and Demonstration of Functionality

Standard human tissue culture cells (HeLa, A549 or other cells) can be seeded in multititer plates at suitable, subconfluent densities. For Hela or A549, 1000 cells/well are e.g. suitable for 384 well format. RNAseT1 generated siRNA pools as well as standard, commercial siRNAs as controls are transfected in a final concentration of 10 nM using a standard commercial transfection reagent as Oligofectamine RNAiMax (Invitrogen). For a 384 well format with cells seeded in 30 µl of complete medium, 0.06 µl/well of Oligofectamine RNAiMax should show efficient transfection. The complex of dsRNA and reagent, formed according to the instructions of the reagent provider, can then be added to the cell suspension at the time point of cell seeding or on the adherent cells 24 h post seeding. The gene silencing effect of the tested dsRNA can be assessed by phenotypic analysis, RT-PCR measuring specific mRNA concentration or western blotting, measuring specific protein concentration. In all cases, the gene specific effect of a gene targeting high complexity pool or siRNA is compared to a negative control siRNA. As proof of concept, a RNAseT1 generated, complex siRNA pool of 14siRNAs targeting AURKB was compared to an experimentally validated, highly active commercial siRNA (AMbion/life technology) against AURKB (see below). The gene specific, phenotypic effect of AURKB knock down as assessed by phenotypic analysis was most clear and pronounced in the cells, transfected by the AURKB complex siRNA pool.

Cell Culture and Transfections

Hela cells were cultivated in Dulbeco's modified eagles medium substituted with 10% FCS and Penicillin/Streptomycin. siRNA transfections were done using Lipofectamine RNAiMax (Life Technologies) according to the manufacturer's protocol. Cells were harvested 24 h or 48 h after transfection.

qPCR and Western Blot

RNA was isolated 24 h after transfection followed by cDNA synthesis and qPCR. The following Primers were used:

```
PolG forward:
                                (SEQ ID No.: 344)
5'-TTCCAGGACCTGATGCAGTA-3'

PolG reverse:
                                (SEQ ID No.: 345)
5'-ACAGGCAGGTAGGAGACACC-3'

Scyl1 forward:
                                (SEQ ID No.: 333)
5'-CTGGAGGAAGTGGAGAAGGA-3'

Scyl1 reverse:
                                (SEQ ID No.: 334)
5'-TCAGCTTGGAGGTGAGTGAG-3'

Mad2 forward:
                                (SEQ ID No.: 338)
5'-AGATGACAGTGCACCCAGAG-3'

Mad2 reverse:
                                (SEQ ID No.: 339)
5'-TCCAACAGTGGCAGAAATGT-3'

GAPDH forward:
                                (SEQ ID No.: 335)
5'-ATGGGTGTGAACCATGAGAA-3'

GAPDH reverse:
                                (SEQ ID No.: 336)
5'-GTGCTAAGCAGTTGGTGGTG-3'.
```

For Western blot analysis, cells were harvested and lysed in NET buffer (50 mM Tris pH 7.4, 150 mM NaCl, 5 mM EDTA, 0.5% NP40, 10% glycerol) 48 h after transfection. Proteins were separated by SDS-PAGE followed by semi-dry electro blotting. The following antibodies were used: polyclonal anti-Mad2 (Bethyl Laboratories) at a dilution of 1:5000 and a monoclonal mouse anti beta-actin antibody (clone AC15 from Abcam) at a dilution of 1:5000 in TBS-Tween with 5% milk-powder. Fluorescently labeled IRDye 800 CW antibodies were used as secondary antibodies (Li-COR). Western blots were imaged with an Odyssey Fluorescence scanner (Li-COR).

Dual Luciferase Assay

To generate the off-target reporter construct, a modified pMIR dual luciferase reporter plasmid (Beitzinger et al., (2007), *RNA Biol*, 4 was used. The 3'UTR of Mad2 was amplified by PCR and cloned into the corresponding SacI and PmeI sites of pMIR. The following primers were used:

```
Mad2-forward:
                                (SEQ ID No.: 346)
5'-GATCGAGCTCGGATGACATGAGGAAAATAA-3'

Mad2-reverse:
                                (SEQ ID No.: 347)
5'-GATCGTTTAAACAAGACAAATTTAAAACAAACTTA-3'
```

Hela cells were transfected in 96 well plates with 1, 3 or 10 nM siRNA concentrations and 20 ng pMIR Mad2 3'UTR plasmid using Lipofectamine 2000 (Life Technologies). Cells were harvested and lysed in passive lysis buffer (Promega) 24 h after transfection. Firefly/renilla luminescence ratios were normalized to corresponding ratios of the empty pMIR plasmid.

Co-Immunoprecipitation and Northern Blotting

Hela cells were transfected with 10 nM siPools and lysed in NET buffer (50 mM Tris pH 7.4, 150 mM NaCl, 5 mM EDTA, 0.5% NP40, 10% glycerol) 48 h after transfection. Lysates were used for Ago2-siRNA co-immunoprecipitation. Protein-G sepharose beads (GE) were pre-incubated with monoclonal anti-Ago2 (11A9) antibody (Rudel et al., (2008), *RNA*, 14, 1244-1253). Lysates were incubated with the Ago2 antibody-coupled beads for 4 h at 4° C. Immunoprecipitations were subsequently washed with NET buffer followed by proteinase K digestion and phenol/chloroform extraction of bound RNAs. Northern blot was performed as described earlier (Pall et al., *Nat Protoc* (2008), 3, 1077-1084). As probes for siRNA detection, antisense DNA oligos for the corresponding off-T siRNAs were used:

```
PolG Pool #1 siRNA off-T guide:
                                (SEQ ID No.: 348)
5'-GGGTGAAGCGCTGGATATT-3'

PolG Pool #1 siRNA off-T passenger:
                                (SEQ ID No.: 349)
5'-AATATCCAGCGCTTCACCC-3'

Scyl1 Pool #1 siRNA off-T guide:
                                (SEQ ID No.: 350)
5'-GCCTCATCCACAACAATGT-3'

Scyl1 Pool #1 siRNA off-T passenger:
                                (SEQ ID No.: 351)
5'-ACATTGTTGTGGATGAGGC-3'
```

EXAMPLES

Example 1

Preparation of siRNA Pool Comprising 14 siRNAs Against AURKB

Template Design 21 base pair siRNA sequences targeting human AURKB were obtained from different commercial siRNA providers. AUKRB exists as a long and short isoform. The nucleic acid sequence of the long isoform has SEQ ID No. 57 (Genbank accession no. NM_004217.3), the amino acid sequence of the long isoform has SEQ ID No. 58 (Genbank accession no. NP_004208.2). The nucleic acid sequence of the short isoform has SEQ ID No. 59 (Genbank accession no. NM_001256834.1), the amino acid sequence of the short isoform has SEQ ID No. 60 (Genbank accession no. NP 001243763). The following 14 sequences, all which target both isoforms, were chosen:

TABLE 1

| Complete sequence | | | | |
|---|---|---|---|---|
| siRNA# | sense | SEQ ID No.: | Reverse complement antisense | SEQ ID No.: |
| 1 | AAGGCAAGUUU GGAAACGUTT | 1 | ACGUUUCCAAA CUUGCCUUTG | 15 |
| 2 | GAUGCUCUAAU GUACUGCCTT | 2 | GGCAGUACAUU AGAGCAUCTG | 16 |
| 3 | GAAGAGCUGCA CAUUUGACTT | 3 | GUCAAAUGUGC AGCUCUUCTG | 17 |
| 4 | UCUUAACGCGG CACUUCACTT | 4 | GUGAAGUGCCG CGUUAAGATG | 18 |

TABLE 1-continued

Complete sequence

| siRNA# | sense | SEQ ID No.: | Reverse complement antisense | SEQ ID No.: |
|---|---|---|---|---|
| 5 | UCGUCAAGGUGGACCUAAATT | 5 | UUUAGGUCCACCUUGACGAUG | 19 |
| 6 | CCAAACUGCUCAGGCAUAAUT | 6 | UUAUGCCUGAGCAGUUUGGAG | 20 |
| 7 | GGUGAUGGAGAAUAGCAGUTT | 7 | ACUGCUAUUCUCCAUCACCTT | 21 |
| 8 | CCUGCGUCUCUACAACUAUTT | 8 | AUAGUUGUAGAGACGCAGGAT | 22 |
| 9 | GUCCCAGAUAGAGAAGGAGTT | 9 | CUCCUUCUCUAUCUGGGACTT | 23 |
| 10 | GGUCCUCUUCAAGUCCCAGTT | 10 | CUGGGACUUGAAGAGGACCTT | 24 |
| 11 | CCAACAUCCUGCGUCUCUAUT | 11 | UAGAGACGCAGGAUGUUGGGA | 25 |
| 12 | GACAAUGUGUGGCACCCUGTT | 12 | CAGGGUGCCACACAUUGUCTT | 26 |
| 13 | GCAGAGAGAUCGAAAUCCATT | 13 | UGGAUUUCGAUCUCUCUGCGC | 27 |
| 14 | GCCAGAAAAUCUGCUCUUATT | 14 | UAAGAGCAGAUUUUCUGGCTT | 28 |

For each of those sequences, the two 3' overhang nucleotides were removed to obtain the following 19b core sequences resulting in the target sequence elements ((tar.se-q.el.) in FIG. 1) for SEQ ID Nos.: 29 to 42 and the reverse complement target sequence elements ((tar.seq.el._{rc}) in FIG. 1) for SEQ ID Nos.: 43 to 56.

TABLE 2

19 bp core sequence without 3' overhang

| siRNA# | sense | SEQ ID No.: | Reverse complement antisense | SEQ ID No.: |
|---|---|---|---|---|
| 1 | AAGGCAAGUUUGGAAACGU | 29 | ACGUUUCCAAACUUGCCUU | 43 |
| 2 | GAUGCUCUAAUGUACUGCC | 30 | GGCAGUACAUUAGAGCAUC | 44 |
| 3 | GAAGAGCUGCACAUUUGAC | 31 | GUCAAAUGUGCAGCUCUUC | 45 |
| 4 | UCUUAACGCGGCACUUCAC | 32 | GUGAAGUGCCGCGUUAAGA | 46 |
| 5 | UCGUCAAGGUGGACCUAAA | 33 | UUUAGGUCCACCUUGACGA | 47 |
| 6 | CCAAACUGCUCAGGCAUAA | 34 | UUAUGCCUGAGCAGUUUGG | 48 |
| 7 | GGUGAUGGAGAAUAGCAGU | 35 | ACUGCUAUUCUCCAUCACC | 49 |
| 8 | CCUGCGUCUCUACAACUAU | 36 | AUAGUUGUAGAGACGCAGG | 50 |
| 9 | GUCCCAGAUAGAGAAGGAG | 37 | CUCCUUCUCUAUCUGGGAC | 51 |

TABLE 2-continued 19 bp core sequence without 3' overhang

| siRNA# | sense | SEQ ID No.: | Reverse complement antisense | SEQ ID No.: |
|---|---|---|---|---|
| 10 | GGUCCUCUUCAAGUCCCAG | 38 | CUGGGACUUGAAGAGGACC | 52 |
| 11 | CCAACAUCCUGCGUCUCUA | 39 | UAGAGACGCAGGAUGUUGG | 53 |
| 12 | GACAAUGUGUGGCACCCUG | 40 | CAGGGUGCCACACAUUGUC | 54 |
| 13 | GCAGAGAGAUCGAAAUCCA | 41 | UGGAUUUCGAUCUCUCUGC | 55 |
| 14 | GCCAGAAAAUCUGCUCUUA | 42 | UAAGAGCAGAUUUUCUGGC | 56 |

Sense and antisense core sequences of all 14 constructs of Table 2 were concatenated to two continuous sequences, in which each siRNA sequence was separated from adjacent sequences by an identical loop sequence of 5 bases (FIG. 3).

The 5 base loop sequence 5'-AGTTG-3' was selected for the following features:
Complete mismatch with its own reverse complement sequence, showing minimal binding free energy in RNA folding prediction (Vienna RNAfold server, rna.tbi.univie.ac.at/cgi-bin/RNAfold.cgi)
Guanin base ("G") at position 2 and 5 for RNAseT1 cleavage 3' of second loop nucleotide and 5' of first siRNA nucleotide.

FIG. 5 shows the general sequence structure of the DNA template (upper box) and the in vitro transcribed RNAs (lower box) for a single siRNA target sequence element flanked by non base pairing loop sequence elements. Positions giving rise to final siRNA product are in capital letters, excised loop sequence (tttg) in lower case. Arrowheads indicate positions of RNAseT1 cleavage, 3' of non base pairing G nucleotides. Base-pairing nucleotides indicated by "|" between sense and antisense strand. Mature siRNA after RNAseT1 digest is highlighted by blue background color.

For in vitro transcription of the construct, the minimal T7 RNA polymerase promoter sequence 5'-TAATACGACT-CACTATAGG-3' (SEQ ID NO: 553) was placed 5' of the concatenated siRNA-loop sequence for both sense and antisense constructs. For cloning into suitable vector sequences, a HindIII restriction site (5'-AAGCTT-3') was placed 5' of the T7 RNA polymerase promotor and a EcoRI site (5'-GAATTC-3') 3' of the terminal siRNA sequence (FIG. 3). The resulting template is shown in FIG. 6.

Template Preparation

The final template sequences, submitted for Gene Synthesis, were as follows:

```
Sense Template (SEQ ID No. 61):
AAGCTTTAATACGACTCACTATAGGAGTTGGCCAGAAAATCTGCTC
TTAAGTTGGCAGAGAGATCGAAATCCAAGTTGGACAATGTGTGGCA
CCCTGAGTTGCCAACATCCTGCGTCTCTAAGTTGGGTCCTCTTCAA
GTCCCAGAGTTGGTCCCAGATAGAGAAGGAGAGTTGCCTGCGTCTC
TACAACTATAGTTGGGTGATGGAGAATAGCAGTAGTTGCCAAACTG
CTCAGGCATAAAGTTGTCGTCAAGGTGGACCTAAAAGTTGTCTTAA
CGCGGCACTTCACAGTTGGAAGAGCTGCACATTTGACAGTTGGATG
CTCTAATGTACTGCCAGTTGAAGGCAAGTTTGGAAACGTAGAATTC Antisense Template (SEQ ID No. 62):
AAGCTTTAATACGACTCACTATAGGAGTTGACGTTTCCAAACTTGC
CTTAGTTGGGCAGTACATTAGAGCATCAGTTGGTCAAATGTGCAGC
```

```
                        -continued
TCTTCAGTTGGTGAAGTGCCGCGTTAAGAAGTTGTTTAGGTCCACC
TTGACGAAGTTGTTATGCCTGAGCAGTTTGGAGTTGACTGCTATTC
TCCATCACCAGTTGATAGTTGTAGAGACGCAGGAGTTGCTCCTTCT
CTATCTGGGACAGTTGCTGGGACTTGAAGAGGACCAGTTGTAGAGA
CGCAGGATGTTGGAGTTGCAGGGTGCCACACATTGTCAGTTGTGGA
TTTCGATCTCTCTGCAGTTGTAAGAGCAGATTTTCTGGCAGAATTC
```

Sense and antisense RNA templates were then obtained as plasmid DNA, cloned into Genearts standard pMA cloning vector using the HindIII (5') and EcoRI(3') restriction site. In detail, 100 ul of template vector preparation were subjected to a HindIII/EcoRI double digest under standard conditions indicated by the reagent provider (New England Biolabs). The 400base insert fragments were separated from the vector by agarose gel electrophoresis and recovered from the gel using a commercial Gel Extraction kit (Qiagen). Purified template DNA was eluted in nuclease free water.

In Vitro Transcription and RNA Purification

Sense and antisense RNA strands were transcribed from the corresponding purified DNA templates by a commercial T7 RNA polymerase according to the instructions of the provider (NEB). The enzyme concentration was set to 5 U/ul (10 ul of NEB enzyme in 100 ul reaction) which is presumably close to saturation. This concentration was used to transcribe 50 ng/µl linearized pMA vector (3 kb) or 3 µg/ul excised template (400 bp). These conditions may not be saturating. For maximal RNA yield, nucleotide concentrations was elevated to 4 mM (per nucleotide). The transcription reaction was terminated by the addition of RNAse free DNAse (Ambion/life technology)) to remove the DNA template. For downstream processing steps, ssRNA from reactions with identical template were pooled. The obtained full length single strand RNA was separated from non-incorporated nucleotides and short RNA fragments by preparative denaturing 6% PAGE. The bands containing the full length single strand RNA were excised from the gel, eluted over night at 4° C. in 1× annealing buffer with 0.1 mM EDTA and precipitated with 300 mM NaAc pH 5.4 and 2.5 volumes of cold 100% EtOH. After washing with 70% EtOH, the single strand RNAs were resuspended in 50 ul 1× annealing buffer. Concentrations of the purified single strand RNAs as determined by spectrophotometry were 0.7 µg/µl for the sensen strand and 1.1 ug/ul for the antisense strand. For analytical purpose, RNA obtained from IVT reactions was also purified from buffer components by phenol chloroform extraction and/or gel filtration chromatographic using S300HR spin columns (Amersham/GE). Quality and concentration of the purified RNA was assessed by polyacrylamide gel-electrophoresis on a denaturing 5% TBE gel with 8M urea. Some of the results of the in vitro transcription are depicted in FIG. 7.

During preliminary optimization it was found that in vitro transcription for 4 h at 37° C. gave reasonable high yield (~1 µg/µ RNA with >90% full length RNA) 1 and purity. It was observed that long incubation (as over night) increase yield but also degradation products. It seems that an incubation between 4 or 8 hours may be optimal.

Hybridization/Single Strand Annealing RNAse T1 Digest

Equal amounts of sense and antisense RNA strands were annealed in a final, total concentration of 0.65 ug/ul in 1× annealing buffer (30 mM Hepes pH 7.4, 100 mM K Ac, 2 mM MgAc)). For efficient and reproducible hybridization of the RNA strands, the annealing reaction was performed in a thermocycler applying a custom program. Briefly, after an initial 2 minute melting step at 98° C., samples were slowly cooled to 4° C. using a faster ramp speed of –1° C./s for the range from 98 to 80° C. to protect RNA integrity and a slow ramp speed of –1° C./s between 80 and 55° C. for optimal hybridization.

For analytical purpose, different ratios of sense and antisense single strand RNA were hybridized under conditions described above and analyzed by 1.1% agarose gel electrophoresis. For all ratios, the hybridization gave rise to a major band with a shift up in molecular weight as compared to the bands of the single strand RNAs, indicating that at least a large fraction of the single strand RNA had successfully hybridized to their corresponding double strand molecules. Some results of the annealing step are depicted in FIG. 8.

RNAse T1 Digest and siRNA Purification

Annealed double strands RNA of 341 base pair length were digested to a pool of 14 different 21 base pair siRNAs by use of RNAseT1, a ribonuclease cleaving single strand RNA 3' of Guanosine ribonucleotide residues. Commercial RNAseT1 (Fermentas/Thermo) was applied in a concentration of 0.5 units enzyme/ul to digest 13 ug of RNA in a volume of 80 ul. Reaction buffer conditions were chosen as suggested by the enzyme provider (50 mMTris/HCL pH 7.5, 2 mM EDTA.). The reaction was incubated for 45 min at 37° C. and directly loaded on a preparative 20% PAA gel to separate the siRNAs from residual longer dsRNA species. The band, corresponding to the 21mer siRNA fragments was visualized by UV-shadowing, cut out of the gel and eluted over night in RNA gel elution buffer (1× annealing buffer, 0.1 mM EDTA). To obtain a 10 uM siRNA solution, the eluted RNA was precipitated in 2.5 volumes of ethanol and re-dissolved in the corresponding volume of 1× annealing buffer.

For analytical purpose, 4 µg of dsRNAs purified by different methods as described above were digested with RNAseT1 enzyme preparations from two providers (highly purified enzyme from Ambion/Life Technologies, 1 unit/µl; recombinant enzyme from Fermentas/Thermo 1000 units/µl) in concentrations ranging from 0.1 to 0.8 units/µl using two different buffer systems (Ambions "structure buffer": 10 mM Tris/Cl pH 7.0, 100 mM KCl, 10 mM MgCl$^2$; Fermentas reaction buffer: 50 mM Tril/Cl pH 7.5, 2 mM EDTA). Of the 20 µl reactions, 6 µl aliquots were taken after 10, 45 and 90 minutes of incubation at 37° C. and analyzed by 20% native PAGE. The results, some of which are shown in FIG. 9, indicated that neither the source of the enzyme nor the purity of the dsRNA substrate affected the quality and efficiency of the digest. Critical parameters were the concentration of the enzyme and dsRNA substrate, the buffer conditions and the duration of the reaction. Of the two buffers compared, the "structure buffer" from Ambion showed a reproducibly reduced enzyme processivity, presumably due to the presence of 10 mM $MgCl_2$ which had been shown to inhibit RNAseT1 activity. 0.8 units/ul of RNAseT1 in absence of $MgCl_2$ cleaved 1 µg gel purified dsRNA substrate in 45 minutes to 21 base pair dsRNA fragments with only trace amounts of dsRNA longer or shorter than 21 base pairs. None of the tested conditions lead to complete digest of the long dsRNA substrate to 21 base pair fragments within 10 minutes. For an incubation time of 90 minutes, a concentration of 0.2 units/µl of RNAseT1 in absence $MgCl_2$ was sufficient to cleave 1 µg of substrate RNA to 21 base pair fragments.

Transfection and Demonstration of Functionality

HeLa cells were seeded in 384 well multi-titer plates in 30 ul/well of DMEM supplemented with 10% FCS and a cell seeding density of 1000 cells/well. 24 h post seeding, cells were transfected with the enzymatically produced pool of 14 different siRNAs targeting human AURKB, a standard, commercial siRNA targeting human AURKB (Ambion/life technology, siRNA ID s495) and two negative control siRNAs targeting no human gene. The sense sequence of siRNA ID s495 has SEQ ID No. 63, the antisense sequence of siRNA ID s495 has SEQ ID No. 64. The sense sequence of the first negative control siRNA has SEQ ID No. 65, the antisense sequence of the first negative control siRNA has SEQ ID No. 66. The sense sequence of the second negative control siRNA has SEQ ID No. 67, the antisense sequence of the second negative control siRNA has SEQ ID No. 68. As transfection reagent, Lipofectamine RNAiMax (Invitrogen/life technology) was used in a concentration of 0.06 µl/well following the instructions of the provider. Final siRNA concentration in the cell culture medium was 10 nM.

Gene specific inhibition of gene expression was demonstrated by western blotting against human AURKB using standard methods (see FIG. 10) The 14 siRNA pool targeting AURKB showed equal, almost complete degradation of AURKB protein as the validated AURKB siRNA. Both negative control siRNAs showed no reduction of AURKB protein as compared to the non transfected medium control. Phenotypic response was analyzed by light microscopy (see FIG. 11. The 14 siRNA pool targeting AURKB showed an at least equal or even stronger AURKB phenotype than the validated AURKB siRNA, obvious in a strongly decreased cell number and dramatically increased cell size with multiple cell nuclei. Cells transfected with a negative control siRNA showed reduced cell number but no increased cell size as compared to non transfected cells.

Example 2

Testing Different Loop Sequence Elements for RNaseT1 Cleavage

The same siRNA pool was then generated, however with an AGTTTG or TGTTTG loop sequence element instead of the AGTTG loop sequence element of Example 1. The minimal free energy (MFE) structure prediction as performed by RNAfold indicates that the AGTTTG loop sequence element should have the largest single strand RNA region granting best RNAseT1 accessibility to both guanosine ribonucleotide residues within the loop sequence element (FIGS. 12 and 15). The AGTTG loop sequence element is predicted to have the second best RNAseT1 accessibility followed by the TGTTTG loop sequences, which, due to guanosine-thymidine base pairing shows the shortest stretch of accessible single strand RNA(see FIGS. 13, 14 and 15).

As shown in FIG. 16, the cleavage efficiency of the three different loop sequence elements shows good correlation with the length of the predicted single strand RNA region within the loop sequence: For 3 different dsRNA preparation with different purification methods applied, the AGTTTG loop sequence with 6 non base pairing ribonucleotides reaches complete cleavage by RNAseT1 to 21mer dsRNA fragment within an incubation time of 10 minutes at 37° C. in absence of $MgCl_2$(FIGS. 16 and 17).

Under identical reaction conditions, an equal amount of long dsRNA substrate with AGTTG loop sequence elements is only partially cleaved to a range of different dsRNA fragment sizes (FIG. 16). An optimization of the reaction conditions for the cleavage of the AGTTG loop sequence elements is shown in FIG. 9. The dsRNA substrate with TGTTTG loop sequence elements, predicted to have only 2 non baise pairing ribonucleotide residues is largely resistant to RNAseT1 cleavage under identical reaction conditions (FIG. 16).

Example 3

Testing Complex siRNA Pools for Off-Target Effects

The following experiment describes the improvement of using complex siRNA pools on off-target effects. In order to determine off-target effects of siRNAs, it was crucial to identify siRNAs, which in addition to silencing an on-target gene are known to give an off-target effect on an identified off target gene. Sigoillot et al., *Nat. Methods,* 9(4), 363-366 (2012) describe a genome wide RNAi screen for new factors of the spindle assembly checkpoint in which they identify multiple siRNAs by off target effect based phenotypes. Amongst others, siRNAs targeting the genes Scyl1, PolG, Ern1 and Traf5. were shown to suppress the expression of the gene Mad2 by an off-target effect.

In order to determine the efficiency of complex siRNA pools in achieving optimal on-target gene silencing with minimal off target effects, complex siRNA pools were generated for PolG and Scyl1. For each gene, four complex siRNA pools (labeled as Pool 1, Pool 2, Pool 3 and Pool 4) were generated with each Pool comprising 15 siRNAs. For both PolG and Scyl1, Pool 1 comprised as one of the 15 siRNAs an siRNA which is known from Sigoillot et al., vide supra to give an off-target effect on Mad2. Further, for both PolG and Scyl1, Pools 1 to 4 were combined to give a Pool of 60 siRNAs.

For both PolG and Scyl1, the effects of Pools 1 and 4 and of the combined Pool comprising all 60 siRNAs were determined vs. the siRNAs for PolG and Scyl1 being known to give an off-target effect for Mad2. In addition, Pools 1 and 4 and the combined Pool comprising all 60 siRNAs were determined vs. pools comprising 4 siRNAs against PolG with one of the four siRNAs being the known siRNA for PolG or Scyl1 which is known to give an off-target effect for Mad2. These pools of four siRNAs are designated herein as "smart pools" and are described in more detail hereinafter.

The off-target effects on Mad2 were either determined by a Luciferase assay or by a cellular assay which are also described in more detail hereinafter.

Materials and Methods

Generation of Complex siRNA Pools for PolG

The complex siRNA pools for PolG were generated as described above in Example 1. Thus, DNA templates were prepared comprising the 15 target sequence elements for the ultimate siRNAs being interrupted by the loop sequence element 5'-AGTTTG-3' giving rise to a construct as schematically depicted in FIGS. 5 and 6. These DNA templates were cloned into the pMA cloning vector using the HindIII (5') and EcoRI (3') site, in vitro transcribed from the T7 RNA polymerase promoter, digested with RNAse T1 and the resulting complex siRNA was purified as described above.

The sequence for the siRNAs were chosen using the on-line siRNA design platform provided by Thermo "siDesign-Center". SiRNAs were designed against the coding sequence as well as the 3'UTR of POLG. For each pool of 15 siRNAs, siRNA sequences were selected to have a maximum of 7 nucleotide overlap.

The chosen target sequence elements were as follows:

TABLE 3

PolG Pool 1

19 bp core sequence without 3' overhang for PolG Pool 1

| siRNA# | sense | SEQ ID No.: | Reverse complement antisense | SEQ ID No.: |
|---|---|---|---|---|
| 1 | CGAGCAAATCTTCGGGCAA | 69 | TTGCCCGAAGATTTGCTCG | 84 |
| 2 | GCGTCGAGCACCTGCAGAA | 70 | TTCTGCAGGTGCTCGACGC | 85 |
| 3 | GCCAGAAGTCCCAGAGGAA | 71 | TTCCTCTGGGACTTCTGGC | 86 |
| 4 | CTAAGAAGGTGAAGAAGGA | 72 | TCCTTCTTCACCTTCTTAG | 87 |
| 5 | AGGAGGAGTTTCAACAAGA | 73 | TCTTGTTGAAACTCCTCCT | 88 |
| 6 | CCACAGAGCTCCTGCCCAA | 74 | TTGGGCAGGAGCTCTGTGG | 89 |
| 7 | GCTTACTAATGCAGTTTAA | 75 | TTAAACTGCATTAGTAAGC | 90 |
| 8 | CAGGAAGAGTTTATGACCA | 76 | TGGTCATAAACTCTTCCTG | 91 |
| 9 | GATAATTGAACTCACCAAA | 77 | TTTGGTGAGTTCAATTATC | 92 |
| 10 | GGTGTGGACTACAGGACAA | 78 | TTGTCCTGTAGTCCACACC | 93 |
| 11 | CATTGTTGCTTGTTGGGTA | 79 | TACCCAACAAGCAACAATG | 94 |
| 12 | GGGTGAAGCGCTGGATATT | 80 | AATATCCAGCGCTTCACCC | 95 |
| 13 | CTGATGCAGTGCCCTAGAA | 81 | TTCTAGGGCACTGCATCAG | 96 |
| 14 | GGAAAGAATTAATGCTCTA | 82 | TAGAGCATTAATTCTTTCC | 97 |
| 15 | GCCCCAAAGTTCACATTAA | 83 | TTAATGTGAACTTTGGGGC | 98 |

The above 19b core sequences result in the target sequence elements ((tar.seq.el.) in FIG. 1) for SEQ ID Nos.: 69 to 83 and the reverse complement target sequence elements ((tar.seq.el._{rc}) in FIG. 1) for SEQ ID Nos.: 84 to 98.

SEQ ID Nos.: 80 and 95 refer to the siRNA sequence described in Sigoillot et al., vide supra as being specific for the target PolG and giving an off-target effect for Mad2.

TABLE 4

PolG Pool 2

19 bp core sequence without 3' overhang for PolG Pool 2

| siRNA# | sense | SEQ ID No.: | Reverse complement antisense | SEQ ID No.: |
|---|---|---|---|---|
| 1 | CGGCACAACCCATTGGACA | 99 | TGTCCAATGGGTTGTGCCG | 114 |
| 2 | CCACAAAGCAAGGCCAGAA | 100 | TTCTGGCCTTGCTTTGTGG | 115 |
| 3 | GAGTCAGAAATGTTCAATA | 101 | TATTGAACATTTCTGACTC | 116 |
| 4 | CCATGAAGGACATTCGTGA | 102 | TCACGAATGTCCTTCATGG | 117 |
| 5 | GAGAGAGGTACAAAGAAGA | 103 | TCTTCTTTGTACCTCTCTC | 118 |
| 6 | GAAGAAGGAACCAGCCACA | 104 | TGTGGCTGGTTCCTTCTTC | 119 |
| 7 | CCATATGGCAAACGGTAGA | 105 | TCTACCGTTTGCCATATGG | 120 |
| 8 | CGGTAGAAGAACTGGATTA | 106 | TAATCCAGTTCTTCTACCG | 121 |
| 9 | CAAGGAAGTCACAGTGGAA | 107 | TTCCACTGTGACTTCCTTG | 122 |
| 10 | AAGATTCCTTCTAACTGAA | 108 | TTCAGTTAGAAGGAATCTT | 123 |
| 11 | GAATTCAGTGGGTTCAGAA | 109 | TTCTGAACCCACTGAATTC | 124 |
| 12 | GCAGAAGCCCCAAAGTTCA | 110 | TGAACTTTGGGGCTTCTGC | 125 |
| 13 | GCTCTGATGCAGTGCCCTA | 111 | TAGGGCACTGCATCAGAGC | 126 |
| 14 | AATTAATGCTCTAACGTGA | 112 | TCACGTTAGAGCATTAATT | 127 |
| 15 | CGTGATAAACCTGCTCCAA | 113 | TTGGAGCAGGTTTATCACG | 128 |

The above 19b core sequences result in the target sequence elements ((tar.seq.el.) in FIG. 1) for SEQ ID Nos.: 99 to 113 and the reverse complement target sequence elements ((tar.seq.el.$_{rc}$) in FIG. 1) for SEQ ID Nos.: 114 to 128.

TABLE 5

PolG Pool 3

19 bp core sequence without 3' overhang for PolG Pool 3

| siRNA# | sense | SEQ ID No.: | Reverse complement antisense | SEQ ID No.: |
|---|---|---|---|---|
| 1 | GCAGAGGTGCACAGACTTT | 129 | AAAGTCTGTGCACCTCTGC | 144 |
| 2 | GTGAGAACTTCCAGGACCT | 130 | AGGTCCTGGAAGTTCTCAC | 145 |
| 3 | GAGATGAAGAAGTCGTTGA | 131 | TCAACGACTTCTTCATCTC | 146 |
| 4 | CAGGAGAGAGGTACAAAGA | 132 | TCTTTGTACCTCTCTCCTG | 147 |
| 5 | AAGCTAAGAAGGTGAAGAA | 133 | TTCTTCACCTTCTTAGCTT | 148 |
| 6 | GCAGTGAGGAGGAGGAGTT | 134 | AACTCCTCCTCCTCACTGC | 149 |
| 7 | TAGAAGAACTGGATTACTT | 135 | AAGTAATCCAGTTCTTCTA | 150 |
| 8 | GGTAATAGCTGTAATGTGG | 136 | CCACATTACAGCTATTACC | 151 |
| 9 | GGGCATCAGCCGTGAGCAT | 137 | ATGCTCACGGCTGATGCCC | 152 |
| 10 | TGCGCAAGGTCCAGAGAGA | 138 | TCTCTCTGGACCTTGCGCA | 153 |
| 11 | AGAGAGAAACTGCAAGGAA | 139 | TTCCTTGCAGTTTCTCTCT | 154 |
| 12 | GCAGTTGAATTCAGTGGGT | 140 | ACCCACTGAATTCAACTGC | 155 |
| 13 | GACTACAGGACAAGGGGCA | 141 | TGCCCCTTGTCCTGTAGTC | 156 |
| 14 | GTTCACATTAACTCAGGCA | 142 | TGCCTGAGTTAATGTGAAC | 157 |
| 15 | AATGCTCTAACGTGATAAA | 143 | TTTATCACGTTAGAGCATT | 158 |

The above 19b core sequences result in the target sequence elements ((tar.seq.el.) in FIG. 1) for SEQ ID Nos.: 129 to 143 and the reverse complement target sequence elements ((tar.seq.el.$_{rc}$) in FIG. 1) for SEQ ID Nos.: 144 to 158.

TABLE 6

PolG Pool 4

19 bp core sequence without 3' overhang for PolG Pool 4

| siRNA# | sense | SEQ ID No.: | Reverse complement antisense | SEQ ID No.: |
|---|---|---|---|---|
| 1 | GAGAAGGAGCCTCGAGAAC | 159 | GTTCTCGAGGCTCCTTCTC | 174 |
| 2 | TGAAGAAGTCGTTGATGGA | 160 | TCCATCAACGACTTCTTCA | 175 |
| 3 | AAGAAAGCTAAGAAGGTGA | 161 | TCACCTTCTTAGCTTTCTT | 176 |
| 4 | GTGAGGAGGAGGAGTTTCA | 162 | TGAAACTCCTCCTCCTCAC | 177 |
| 5 | ATGGCAAACGGTAGAAGAA | 163 | TTCTTCTACCGTTTGCCAT | 178 |
| 6 | CTTACAACGACGTGGACAT | 164 | ATGTCCACGTCGTTGTAAG | 179 |
| 7 | CTGAGAAGGCCCAGCAGAT | 165 | ATCTGCTGGGCCTTCTCAG | 180 |
| 8 | CGCAAGGTCCAGAGAGAAA | 166 | TTTCTCTCTGGACCTTGCG | 181 |
| 9 | AGGAAGTCACAGTGGAAGA | 167 | TCTTCCACTGTGACTTCCT | 182 |

TABLE 6-continued

PolG Pool 4

19 bp core sequence without 3' overhang for PolG Pool 4

| siRNA# | sense | SEQ ID No.: | Reverse complement antisense | SEQ ID No.: |
|---|---|---|---|---|
| 10 | GGAAGAAGTGGGAGGTGGT | 168 | ACCACCTCCCACTTCTTCC | 183 |
| 11 | GCTCCCAAACTCAGGCTTT | 169 | AAAGCCTGAGTTTGGGAGC | 184 |
| 12 | GGGCATTGTTGCTTGTTGG | 170 | CCAACAAGCAACAATGCCC | 185 |
| 13 | CATTAACTCAGGCATTTCA | 171 | TGAAATGCCTGAGTTAATG | 186 |
| 14 | CTAGAAGGGGAAAGAATTA | 172 | TAATTCTTTCCCCTTCTAG | 187 |
| 15 | TTAATGCTCTAACGTGATA | 173 | TATCACGTTAGAGCATTAA | 188 |

The above 19b core sequences result in the target sequence elements ((tar.seq.el.) in FIG. 1) for SEQ ID Nos.: 159 to 173 and the reverse complement target sequence elements ((tar.seq.el.,) in FIG. 1) for SEQ ID Nos.: 174 to 188.

Sense and antisense core sequences of all 15 constructs of Table 3 to 6 were concatenated to two continuous sequences, in which each siRNA sequence was separated from adjacent sequences by an identical loop sequence of 5 bases (see FIG. 3).

The 5 base loop sequence 5'-AGTTTG-3' was selected for the following features:
  Complete mismatch with its own reverse complement sequence, showing minimal binding free energy in RNA folding prediction (Vienna RNAfold server, rna.tbi.univie.ac.at/cgi-bin/RNAfold.cgi)
  Guanin base ("G") at position 2 and 5 for RNAseT1 cleavage 3' of second loop nucleotide and 5' of first siRNA nucleotide.

For in vitro transcription of the construct, the minimal T7 RNA polymerase promoter sequence 5'-TAATACGACTCACTATAGG-3' (SEQ ID NO: 553) was placed 5' of the concatenated siRNA-loop sequence for both sense and antisense constructs. For cloning into suitable vector sequences, a HindIII restriction site (5'-AAGCTT-3') was placed 5' of the T7 RNA polymerase promotor and a EcoRI site (5'-GAATTC-3') 3' of the terminal siRNA sequence (FIG. 3). DNA templates were then synthesized, cloned, in vitro transribed, digested with RNAse I and purified as described above in Example 1.

Generation of Complex siRNA Pools for Scyl1

The complex siRNA pools for Scyl1 were generated as described above for PolG. Thus, DNA templates were prepared comprising the 15 target sequence elements for the ultimate siRNAs being interrupted by the loop sequence element 5'-AGTTTG-3' giving rise to a construct as schematically depicted in FIGS. 5 and 6. These DNA templates were cloned into the pMA cloning vector using the HindIII (5') and EcoRI (3') site, in vitro transcribed from the T7 RNA polymerase promoter, digested with RNAse T1 and the resulting complex siRNA was purified as described above.

The sequence for the siRNAs were chosen using the on-line siRNA design platform provided by Thermo "siDesign-Center". SiRNAs were designed against the coding sequence as well as the 3'UTR of SCYL1. For each pool of 15 siRNAs, siRNA sequences were selected to have a maximum of 7 nucleotide overlap.

The chosen target sequence elements were as follows:

TABLE 7

Scyl1 Pool 1

19 bp core sequence without 3' overhang for Scyl1 Pool 1

| siRNA# | Sense | SEQ ID No.: | Reverse complement antisense | SEQ ID No.: |
|---|---|---|---|---|
| 1 | CGTTGGGAATATACCTCAA | 189 | TTGAGGTATATTCCCAACG | 204 |
| 2 | GCAGAGTGGTCAGAGAGAA | 190 | TTCTCTCTGACCACTCTGC | 205 |
| 3 | GCAAGAGCCTGGACGCATT | 191 | AATGCGTCCAGGCTCTTGC | 206 |
| 4 | GAGGATTTCTGTCGGCACA | 192 | TGTGCCGACAGAAATCCTC | 207 |
| 5 | GAGTATCAGCAGAAGATCA | 193 | TGATCTTCTGCTGATACTC | 208 |
| 6 | GTACATGGCTTCCTGGACA | 194 | TGTCCAGGAAGCCATGTAC | 209 |
| 7 | GGCTACAGGCCAAGGATGA | 195 | TCATCCTTGGCCTGTAGCC | 210 |
| 8 | GCTCTGCGGTCTCACTGTA | 196 | TACAGTGAGACCGCAGAGC | 211 |
| 9 | GGAGCTTCCTGTCCAAATT | 197 | AATTTGGACAGGAAGCTCC | 212 |
| 10 | GGAGAAGGATGTCCATGCA | 198 | TGCATGGACATCCTTCTCC | 213 |

TABLE 7-continued

Scyl1 Pool 1

19 bp core sequence without 3' overhang for Scyl1 Pool 1

| siRNA# | Sense | SEQ ID No.: | Reverse complement antisense | SEQ ID No.: |
|---|---|---|---|---|
| 11 | GACCACAAATCCTCCAAAT | 199 | ATTTGGAGGATTTGTGGTC | 214 |
| 12 | GCCTCATCCACAACAATGT | 200 | ACATTGTTGTGGATGAGGC | 215 |
| 13 | GCCATCTCACGTGTACATA | 201 | TATGTACACGTGAGATGGC | 216 |
| 14 | GAGCCACAATAAATTCTAT | 202 | ATAGAATTTATTGTGGCTC | 217 |
| 15 | GTCGACAGGTCAAGGCTGA | 203 | TCAGCCTTGACCTGTCGAC | 218 |

The above 19b core sequences result in the target sequence elements ((tar.seq.el.) in FIG. 1) for SEQ ID Nos.: 189 to 203 and the reverse complement target sequence elements ((tar.seq.el.$_{rc}$) in FIG. 1) for SEQ ID Nos.: 204 to 218.

SEQ ID Nos.: 200 and 215 refer to the siRNA sequence described in Sigoillot et al., vide supra as being specific for the target Scyl1 and giving an off-target effect for Mad2.

TABLE 8

Scyl1 Pool 2

19 bp core sequence without 3' overhang for Scyl1 Pool 2

| siRNA# | sense | SEQ ID No.: | Reverse complement antisense | SEQ ID No.: |
|---|---|---|---|---|
| 1 | TCGATGGACTGGAGACAGA | 219 | TCTGTCTCCAGTCCATCGA | 234 |
| 2 | GGCAGAGTGGTCAGAGAGA | 220 | TCTCTCTGACCACTCTGCC | 235 |
| 3 | CAGCAGACATGTGGCGCTT | 221 | AAGCGCCACATGTCTGCTG | 236 |
| 4 | GTGAGCTGGTGGGAGCAAA | 222 | TTTGCTCCCACCAGCTCAC | 237 |
| 5 | CAGCCCGCTTCCTGCAGAA | 223 | TTCTGCAGGAAGCGGGCTG | 238 |
| 6 | GAGGAGTATCAGCAGAAGA | 224 | TCTTCTGCTGATACTCCTC | 239 |
| 7 | CAAAGCTGAACGAGGCCAA | 225 | TTGGCCTCGTTCAGCTTTG | 240 |
| 8 | TTGCACGGCTACAGGCCAA | 226 | TTGGCCTGTAGCCGTGCAA | 241 |
| 9 | CACTGTAGATCCTGAGAAA | 227 | TTTCTCAGGATCTACAGTG | 242 |
| 10 | TGGAGGAAGTGGAGAAGGA | 228 | TCCTTCTCCACTTCCTCCA | 243 |
| 11 | AGACGCAGGAGGAGGACAA | 229 | TTGTCCTCCTCCTGCGTCT | 244 |
| 12 | CGACTGGAGCAGCTGGGAA | 230 | TTCCCAGCTGCTCCAGTCG | 245 |
| 13 | CCGAGAGGAAGGTGGCCAA | 231 | TTGGCCACCTTCCTCTCGG | 246 |
| 14 | CATCTCACGTGTACATAAT | 232 | ATTATGTACACGTGAGATG | 247 |
| 15 | CATAATCAGAGCCACAATA | 233 | TATTGTGGCTCTGATTATG | 248 |

The above 19b core sequences result in the target sequence elements ((tar.seq.el.) in FIG. 1) for SEQ ID Nos.: 219 to 233 and the reverse complement target sequence elements ((tar.seq.el.$_{rc}$) in FIG. 1) for SEQ ID Nos.: 234 to 248.

TABLE 9

Scyl1 Pool 3

19 bp core sequence without 3' overhang for Scyl1 Pool 3

| siRNA# | sense | SEQ ID No.: | Reverse complement antisense | SEQ ID No.: |
|---|---|---|---|---|
| 1 | CCGTGTCCATCTTCGTCTA | 249 | TAGACGAAGATGGACACGG | 264 |
| 2 | CTTCAAAACTCTACGGCAC | 250 | GTGCCGTAGAGTTTTGAAG | 265 |
| 3 | TGGCTTACATCGATGGACT | 251 | AGTCCATCGATGTAAGCCA | 266 |
| 4 | CCCTCAGCTTCCTGGTCAA | 252 | TTGACCAGGAAGCTGAGGG | 267 |
| 5 | GTGGCAGAGTGGTCAGAGA | 253 | TCTCTGACCACTCTGCCAC | 268 |
| 6 | TCAAAGAGCCAGCCGAGAA | 254 | TTCTCGGCTGGCTCTTTGA | 269 |
| 7 | AGGAGTATCAGCAGAAGAT | 255 | ATCTTCTGCTGATACTCCT | 270 |
| 8 | CTGTGGTGGTCAAGATGTT | 256 | AACATCTTGACCACCACAG | 271 |
| 9 | TCAATGTGGAGCTGATGAA | 257 | TTCATCAGCTCCACATTGA | 272 |
| 10 | CTGAGAAATCCGTGCGAGA | 258 | TCTCGCACGGATTTCTCAG | 273 |
| 11 | CAGGAGGAGGACAAGGACA | 259 | TGTCCTTGTCCTCCTCCTG | 274 |
| 12 | TGACAGATGGGACGACGAA | 260 | TTCGTCGTCCCATCTGTCA | 275 |
| 13 | CCAAGTGAGCCGTGCTAGT | 261 | ACTAGCACGGCTCACTTGG | 276 |
| 14 | CCAGGCCATCTCACGTGTA | 262 | TACACGTGAGATGGCCTGG | 277 |
| 15 | GTACATAATCAGAGCCACA | 263 | TGTGGCTCTGATTATGTAC | 278 |

The above 19b core sequences result in the target sequence elements ((tar.seq.el.) in FIG. 1) for SEQ ID Nos.: 249 to 263 and the reverse complement target sequence elements ((tar.seq.el.$_{rc}$) in FIG. 1) for SEQ ID Nos.: 264 to 278.

TABLE 10

Scyl1 Pool 4

19 bp core sequence without 3' overhang for Scyl1 Pool 4

| siRNA# | sense | SEQ ID No.: | Reverse complement antisense | SEQ ID No.: |
|---|---|---|---|---|
| 1 | CATCGATGGACTGGAGACA | 279 | TGTCTCCAGTCCATCGATG | 294 |
| 2 | TGAAGGAGCTGGAGATCTC | 280 | GAGATCTCCAGCTCCTTCA | 295 |
| 3 | GCTACACCAGATCGTGAAA | 281 | TTTCACGATCTGGTGTAGC | 296 |
| 4 | GCAGCCTCATCCACAACAA | 282 | TTGTTGTGGATGAGGCTGC | 297 |
| 5 | CTGGTGGCTTCATGAGCAA | 283 | TTGCTCATGAAGCCACCAG | 298 |
| 6 | ACGCATTCCCTGAGGATTT | 284 | AAATCCTCAGGGAATGCGT | 299 |
| 7 | AGTATCAGCAGAAGATCAT | 285 | ATGATCTTCTGCTGATACT | 300 |
| 8 | GGCTCCTACCTCAGTGCTA | 286 | TAGCACTGAGGTAGGAGCC | 301 |
| 9 | CTGTAGATCCTGAGAAATC | 287 | GATTTCTCAGGATCTACAG | 302 |
| 10 | AGGAAGTGGAGAAGGATGT | 288 | ACATCCTTCTCCACTTCCT | 303 |
| 11 | GGACAAGGACACAGCAGAG | 289 | CTCTGCTGTGTCCTTGTCC | 304 |
| 12 | ACAGATGGGACGACGAAGA | 290 | TCTTCGTCGTCCCATCTGT | 305 |
| 13 | GCCCCACAGATGTATTTAT | 291 | ATAAATACATCTGTGGGGC | 306 |

TABLE 10-continued

Scyl1 Pool 4

19 bp core sequence without 3' overhang for Scyl1 Pool 4

| siRNA# | sense | SEQ ID No.: | Reverse complement antisense | SEQ ID No.: |
|---|---|---|---|---|
| 14 | AGGCCATCTCACGTGTACA | 292 | TGTACACGTGAGATGGCCT | 307 |
| 15 | TAATCAGAGCCACAATAAA | 293 | TTTATTGTGGCTCTGATTA | 308 |

The above 19b core sequences result in the target sequence elements ((tar.seq.el.) in FIG. 1) for SEQ ID Nos.: 279 to 293 and the reverse complement target sequence elements ((tar.seq.el.$_{rc}$) in FIG. 1) for SEQ ID Nos.: 294 to 308.

Sense and antisense core sequences of all 15 constructs of Table 7 to 10 were concatenated to two continuous sequences, in which each siRNA sequence was separated from adjacent sequences by an identical loop sequence of 5 bases (see FIG. 3).

The 5 base loop sequence 5'-AGTTTG-3' (SEQ ID No.: 309) was selected for the following features :
  Complete mismatch with its own reverse complement sequence, showing minimal binding free energy in RNA folding prediction (Vienna RNAfold server, rna.tbi.univie.ac.at/cgi-bin/RNAfold.cgi)
  Guanin base ("G") at position 2 and 5 for RNAseT1 cleavage 3' of second loop nucleotide and 5' of first siRNA nucleotide.

For in vitro transcription of the construct, the minimal T7 RNA polymerase promoter sequence 5'-TAATACGACT-CACTATAGG-3' (SEQ ID No.: 310) was placed 5' of the concatenated siRNA-loop sequence for both sense and antisense constructs. For cloning into suitable vector sequences, a HindIII restriction site (5'-AAGCTT-3') (SEQ ID No.: 311) was placed 5' of the T7 RNA polymerase promoter and a EcoRI site (5'-GAATTC-3') (SEQ ID No.: 312) 3' of the terminal siRNA sequence (FIG. 3). DNA templates were then synthesized, cloned, in vitro transcribed, digested with RNAse TI and purified as described above in Example 1.

Generation of Control siRNAs

The siRNA described in Sigoillot et al., vide supra as having PolG as a target and giving off-target effects on Mad2 had the following sense sequence 5'-GGGU GAA GCGCUGGAUAUUTT (SEQ ID No.: 313) and the following reverse complement antisense-sequence: 5'-AAUAUC-CAGCGCUUCACCCTT (SEQ ID No.: 314). This siRNA was labeled "PolG siRNA OT". This siRNA was obtained from Eurogentec.

The siRNA described in Sigoillot et al., vide supra as having Scyl1 as a target and giving off-target effects on Mad2 had the following sense-sequence 5'-GCCUCAUC-CACAACAAUGUTT (SEQ ID No.: 315) and the following reverse complement antisense-sequence: 5'-ACAUUGUU-GUGGAUGAGGCTT (SEQ ID No.: 316). This siRNA was labeled "Scyl1 siRNA OT". This siRNA was obtained from Eurogentec.

Further, a negative control siRNA was designed, which should have no effect on PolG, Scyl1 or Mad2. This siRNA had the following sense-sequence: 5'-UUGUCUUG-CAUUCGACUAATT (SEQ ID No.: 317) and the following reverse complement antisense-sequence 5'-UUAGUC-GAAUGCAAGACAATT (SEQ ID No.: 318). This siRNA was labeled "negative Control" (neg.C.).

Further, an siRNA which should have Mad2 as a target and which should have no effect on PolG or Scyl1. This siRNA had the following sense-sequence: 5'-GGAAC AACUGAAAGAUUGGTT (SEQ ID No.: 319) and the following reverse complement antisense-sequence: 5'-CCA AUCUUUCAGUUGUUCCTT (SEQ ID No.: 320). This siRNA was labeled "Mad2 siRNA1".

Generation of Smart Pool siRNAs

Smart pool siRNAs are merchandized as providing better on-target vs. off-target effects by the vendor Thermo Fisher. Smart pools consist of 4 different siRNAs for one target gene. To allow for comparison of complex siRNA pools in accordance with the inventions vs. the smart pool approach, the 4 siRNAs comprising the smart pool for POLG were purchased as individual siRNAs from Thermo Fisher. Of these 4 siRNAs 3 were combined in all possible combinations with the siRNA being known has having PolG as a target and giving an off-target effect on Mad2 This resulted in four different smart pools for PolG comprising four siRNAs.

The first siRNA of the smart pools for PolG had the following sense-sequence: 5'-GGUAUCGGCUGUCG-GAUGA (SEQ ID No.: 321) and the following reverse complement antisense-sequence 5'-UCAUCCGACAGC-CGAUACC (SEQ ID No.: 322). The second siRNA of the smart pools for PolG had the following sense-sequence: 5'-AGUGGGACCUGCAAGAAUU (SEQ ID No.: 323) and the following reverse complement antisense-sequence 5'-AAUUCUUGCAGGUCCCACU (SEQ ID No.: 324). The third siRNA of the smart pools for PolG had the following sense-sequence: 5'-UCACAAGGAUGGUAA UAGC (SEQ ID No.: 325) and the following reverse complement antisense-sequence 5'-GCUAUUACCAUC-CUUGUGA (SEQ ID No.: 326). The fourth siRNA of the smart pools for PolG had the following sense-sequence: 5'-GCUUACUAAUGCAGUUUAA (SEQ ID No.: 327) and the following reverse complement antisense-sequence 5'-UUAAACUGCAUUAGUAAGC (SEQ ID No.: 328). The siRNAs were obtained from Thermo Fisher. These four siRNAs were mixed in all combinations with the siRNA being known has having PolG as a target and giving an off-target effect on Mad2 (SEQ ID No.: 313 and 314, see above) except for Smart Pool 4 giving rise to Smart Pools 1 to 4 (smp 1 to 4) for PolG each smart pool comprising four siRNAs.

The first siRNA of the smart pools for Scyl1 had the following sense-sequence: 5'-UUUCUCAGGAUCUACA-GUGAG-3' (SEQ ID No.: 340). The second siRNA of the smart pools for Scyl1 had the following sense-sequence: 5'-UUGAGGUAUAUUCCCAACGGG-3' (SEQ ID No.: 341). The third siRNA of the smart pools for Scyl1 had the following sense-sequence: 5'-UUGGUUUCUACAAA GCGGUUG-3' (SEQ ID No.: 342). The fourth siRNA of the smart pools for Scyl1 had the following sense-sequence:

5'-UUGUACAAUAAAUACAUCUGU-3' (SEQ ID No.: 343). The siRNAs were obtained from Thermo Fisher. These four siRNAs were mixed in all combinations with the siRNA being known has having Scyl1 as a target and giving an off-target effect on Mad2 (SEQ ID No.: 315 and 316, see below) except for Smart Pool 4 giving rise to Smart Pools 1 to 4 (smp 1 to 4) for Scyl1 each smart pool comprising four siRNAs.

Generation of esiRNAs

EsiRNAs were obtained from Sigma. This esiRNA represents the RNAseIII digested dsRNA of a fragment of the human POLG gene with the following sequence:

(SEQ ID No.: 329)
GGAAGAAGTGGGAGGTGGTTGCTGAACGGGCATGGAAGGGGGGCACAG

AGTCAGAAATGTTCAATAAGCTTGAGAGCATTGCTACGTCTGACATAC

CACGTACCCCGGTGCTGGGCTGCTGCATCAGCCGAGCCCTGGAGCCCT

CGGCTGTCCAGGAAGAGTTTATGACCAGCCGTGTGAATTGGGTGGTAC

AGAGCTCTGCTGTTGACTACTTACACCTCATGCTTGTGGCCATGAAGT

GGCTGTTTGAAGAGT.

This SCYL1 esiRNA represents the RNAseIII digested dsRNA of a fragment of the human SCYL1 gene with the following sequence:

(SEQ ID No.: 330)
CAGCCGAGAAGCAAAAATTCTTCCAGGAGCTGAGCAAGAGCCTGGAC

GCATTCCCTGAGGATTTCTGTCGGCACAAGGTGCTGCCCCAGCTGCT

GACCGCCTTCGAGTTCGGCAATGCTGGGGCCGTTGTCCTCACGCCCC

TCTTCAAGGTGGGCAAGTTCCTGAGCGCTGAGGAGTATCAGCAGAAG

ATCATCCCTGTGGTGGTCAAGATGTTCTCATCCACTGACCGGGCCAT

GCGCATCCGCCTCCTGCAGCAGATGGAGCAGTTCATCCAGTACCTTG

ACGAGCCAACAGTCAACACCCAGATCTTCCCCCACGTCGTACATGGC

TTCCTGGACACCAACCCTGCCATCCGGGAGCAGACGGTCAAGTCCAT

GCTGCTCCTGGCCCCAAAGCTGAACGAGGCCAACCTCAATGTGGAGC

TGA

Determination of on-Target Gene Silencing Activity of siRNAs

The on-target silencing activity of complex siRNA pools, smart pools, esiRNAs and control siRNAs on PolG or Scyl1 were determined using Reverse-Transcription PCR (RT-PCR). Hela cells were seeded and cultivated in DMEM substituted with 10% FCS and Penicillin/Streptomycine (PenStrep). SiRNAs, complex siRNA pools, esiRNAs and smart pools were transfected in concentrations of 1, 3 or as indicated using LipofectamineRNAiMAX (Life Technologies). Cells were harvested for RNA extraction and RT-PCR 48 h after transfection. Gene knock down was calculated using the delta CT method with GAPDH serving as house keeper gene. The following primer pairs were applied:

POLG forward:
(SEQ ID No.: 331)
TTCCAGGACCTGATGCAGTA,

POLG reverse:
(SEQ ID No.: 332)
ACAGGCAGGTAGGAGACACC

SCYL1 forward:
(SEQ ID No.: 333)
CTGGAGGAAGTGGAGAAGGA

SCYL1 reverse:
(SEQ ID No.: 334)
TCAGCTTGGAGGTGAGTGAG

GAPDH forward:
(SEQ ID No.: 335)
ATGGGTGTGAACCATGAGAA

GAPDH reverse:
(SEQ ID No.: 336)
GTGCTAAGCAGTTGGTGGTG

Determination of Off-Target Effect on Mad2 by Luciferase Assay

Off-targets effects on Mad2 were quantified with a dual luciferase approach using the vector pmir-RL-TK (Beitzinger et al, 2007). To that end, the complete 3'UTR of MAD2 with the sequence GGATGACATGAGGAAAATAATGT-AATTGTAATTTTGAAATGTGGTTTTCCTGAAATCAA-GTCATCTATAGTTGATATGTTTTATTTCATTGGTTAA-TTTTTACATGGAGAAAACCAAAATGATACTTACTG-AACTGTGTGTAATTGTTCCTTTTATTTTTTTGGTAC-CTATTTGACTTACCATGGAGTTAACATCATGAATTT-A TTGCACATTGTTCAAAAGGAACCAGGAGGTT-TT-TTTGTCAACATTGTGATGTATATTCCTTTGAAGATA-GTAACTGTAGATGGAAAAACTTGTGCTATAAAGCT-AGATGCTTTCCTAAATCAGATGTTTTGGTCAAGTA-GTTTGACTCAGTATAGGTAGGGAGATATTTAAGTA-TAAAATACAACAAAGGAAGTCTAAATATTCAGAAT-CTTTGTTAAGGTCCTGAAAGTAACTCATAATCTAT-AAACAATGAAATATTGCTGTATAGCTCC TTTTGAC-CTTCATTTCATGTATAGTTTTCCCTATTGAATCAGT-TTCCAATTATTTGACTTTAATTTAT GTAACTTGAAC-CTATGAAGCAATGGATATTTGTACTGTTTAATGTT-CTGTGATACAGAACTCTTAAAA ATGTTTTTTCATGT-GTTTTATAAAATCAAGTTTTAAGTGAAAGTGAGGA-AATAAAGTTAAGTTTGTTT TAAATTTGTCTT (SEQ ID No.: 337) was cloned in the 3' end of the firefly luciferase gene. A Renilla luciferase gene was present in the dual luciferase vector (Beitzinger et al., RNA Biol. (2007), 4(2): 76-84) for internal normalization. 20 ng of dual luciferase vector along with different concentrations of siRNA were transfected in Hela cells, seeded in 96-well dishes in DMEM with 10% FCS and PenStrep. Firefly and Renilla Luciferase activity were measured 24 h post transfection Determination of Off-Target Effect on MAD2 by Cellular Assay Mad2 is an integral part of mitotic spindle check points. Wrongly assembled chromosomes inhibit mitosis on the metaphase level to give the cell time correctly distribute the chromosomes on daughter cells. The mitotic interruption can be induced by spindle poisons such as nodocazole. However, Mad2 is essential for this interruption induced by spindle poisons. If Mad2 expression is down-regulated by e.g. RNAi, mitosis will continue even in the presence of spindle poisons such as nodocazole. Interruption of mitosis can be determined visually by rounded and slightly elevated cells. Thus, if Mad2 expression is downregulated, cells will continue to proliferate even in the presence of nodocazole which is labeled herein as "overrun".

Hela cells were seeded in DMEM with 10% FCS and PenStrep on glass cover slips and transfected with 10 nM siRNA. 30 h after transfection, 50 ng/ml Nocodazol was added to arrest cells in mitosis. 48 h post transfection, cells were fixed with 1% paraformaldehyde in PBS and imaged by phase contrast microscopy.

Determination of Off-Target Effect on MAD2 by Western Blotting

Hela cells were seeded and grown in DMEM substituted with 10% FCS and PenStrep on 6-well dishes. SiRNAs were transfected in a final concentration of 3 and 33 nM using Lipofectamine RNAiMax (Life Technologies) as transfection reagent. 48 h after transfection, cells were harvested and lysed. The denatured proteins were resolved on 10% SDS PAGE and transferred to a ECL Hybond membrane (GE Healthcare) on a semi-dry blotting device. The blot membrane was incubated over night at 4° C. with an affinity purified primary rabbit anti human MAD2 antibody (Bethyl Laboratories Inc.) at a dilution of 1:5000 and a monoclonal mouse anti beta actin antibody (clone AC15 from Abcam) at a dilution of 1:5000 in TBS-Tween with 5% milk-powder. As secondary antibodies fluorescently labeled polyclonal goat anti rabbit or goat anti mouse antibodies (anti-rabbit IgG (H+L) IRDye 800 CW, anti-mouse IgG (H+L) IRDye 800 CW, Li-COR) were incubated for 2 h at room temperature in a dilution of 1 to 10000 in TBS-Tween with 5% milk powder. The blot was imaged in two wavelength with a Odyssey Fluorescence scanner (Li-COR)

Results

Off-target Effects on Mad2 by siRNAs for Scyl1 and PolG

HeLa cell were transfected with the siRNAs "negative Control", "PolG siRNA OT", "Scyl1 siRNA OT" or "Mad2 siRNA". Expression of Mad 2 and actin as a control was determined by Western Blotting. The siRNAs "PolG siRNA OT", "Scyl1 siRNA" and "Mad2 siRNA" led to decreased Mad2 expression (see FIG. 18, lower panel). In addition, cell density, size and morphology were visually inspected either in the absence or presence of 50 ng/ml nocodazole. For cells transfected with the siRNAs "PolG siRNA OT", "Scyl1 siRNA OT" and "Mad2 siRNA", an overrun of the mitotic arrest was observed in the presence of nocodazole. For the negative control, a uniform mitotic arrest was observed (see FIG. 18, upper panel). This data confirms that the siRNAs"PolG siRNA OT" and "Scyl1 siRNA OT" have a strong off-target effect on Mad2 expression.

on-target Effects on Scyl1 by Complex siRNA Pools for Scyl1

HeLa cell were transfected with siRNA "negative control", Pools 1 to 4 for Scyl1 (see Tables 7 to 10) separately as well as all combined pools 1 to 4 for Scyl1, esiRNA for Scyl1 and the siRNA "Scyl1 siRNA OT" at 1 nM, 3 nM or 10 nM. Effects on Scyl1 expression were determined by qPCR as described above (see FIG. 19).

on-target Effects by High Complexity siRNA Pools/or PolG

HeLa cell were transfected with siRNA "negative control", Pools 1 to 4 for PolG (see Tables 3 to 6) separately as well as all combined pools 1 to 4 for PolG and the siRNA "PolG siRNA OT" at 1 nM, 3 nM or 10 nM. Effects on PolG expression were determined by RT-PCR as described above in Experiment 3 (see FIG. 28).

Off-target Effects on Mad2 by Complex siRNA Pools for Scyl1 or PolG

HeLa cells were transfected with siRNA "negative control", with Pool 1 for Scyl1 (see Table 7) separately as well as with combined Pools 1 to 4 for Scyl1, with Pool 1 for PolG (see Table 3) separately as well as with combined Pools 1 to 4 for PolG and with the siRNA "Scyl1 siRNA OT" or with the siRNA "PolG siRNA OT) at 1 nM, 3 nM or 10 nM. Effects on Mad2 expression were determined by Luciferase assay as described above (see FIG. 20).

Both, the complex siRNA Pool 1 and the combined complex siRNA Pools 1 to 4 for Scyl1 and PolG give strongly reduced off-target effects on Mad2 even though these pools comprise "Scyl1 siRNA OT" and "PolG siRNA OT", respectively. Pool 1 for Scyl1 comprised as one of the 15 siRNAs the "Scyl1 siRNA OT" (see siRNA #12 (SEQ ID No.: 200) of Table 7 and sequence of "Scyl1 siRNA OT" (SEQ ID NO:316). Pool 1 for PolG comprised as one of the 15 siRNAs the "PolG siRNA OT" (see siRNA #12 (SEQ ID No.: 80) of Table 3 and sequence of "PolG siRNA OT" (SEQ ID NO:313).

The off-target effects were also determined by the cellular assay. To this end, HeLa cells were transfected with 33 nM of either "Mad2 siRNA", "negative Control siRNA", Pool 1 for Scyl1, the combined Pools 1 to 4 for Scyl1 and "Scyl1 siRNA OT". If 50 ng/ml nodocazole was added, an overrun of the mitotic arrest was observed for "Mad2 siRNA" and "Scyl1 siRNA OT", but not for "negative Control siRNA", Pool1 for Scyl1 or for the combined Pools 1 to 4 for Scyl1 (see FIG. 21).

The same was observed for PolG. Thus, HeLa cells were transfected with 33 nM of either "Mad2 siRNA", "negative Control siRNA", Pool 1 for PolG, the combined Pools 1 to 4 for PolG and "PolG siRNA OT". If 50 ng/ml nodocazole was added, an overrun of the mitotic arrest was observed for "Mad2 siRNA" and "PolG siRNA OT", but not for "negative Control siRNA", Pool 1 for PolG or for the combined Pools 1 to 4 for PolG (see FIG. 22).

Off-target Effects on Mad2 by Complex siRNA Pools for PolG Vs. Smart Pools

The off-target effects on Mad2 by Pool 1 for PolG and combined Pools 1 to 4 for PolG was compared with the off-target effects of "PolG siRNA OT" and Smart Pools 1, 2, 3 and 4 (smp 1, smp 2, smp 3 and smp 4) for PolG. See above for construction of smart pools for PolG. Off-target effects were determined by the RT-PCR or Luciferase assay and by a phenotypic assay. Results are depicted in FIG. 23 for the PCR assay, in FIG. 33 for Luciferase assay and in FIG. 22 for the phenotypic assay. The on-target effects of the same pools as well as of esiRNA of an independent experiment are depicted in FIG. 30 as determined by PCR.

Off-target Effects on Mad2 by Complex siRNA Pools for Scyl1 Vs. Smart Pools

The off-target effects on Mad2 by Pool 1 for Scyl1 and combined Pools 1 to 4 for Scyl1 were compared with the off-target effects of "Scyl1 siRNA OT" and Smart Pools 1, 2, 3 and 4 (smp 1, smp 2, smp 3 and smp 4) for Scyl1. See above for construction of smart pools for Scyl1. Off-target effects were determined by the RT-PCR, the Luciferase assay and by a phenotypic assay. Results are depicted in FIG. 31 for the PCR assay and in FIG. 34 for the Luciferase assay. The on-target effects of the same pools as well as of esiRNA of an independent experiment are depicted in FIG. 32 as determined by RT-PCR.

Taken together, the data demonstrate that while on-target silencing of complex siRNA pools matches at least the efficiency of other available RNAi reagents, only complex siRNA pools eliminated off-target effects.

Experiment 4

Global Off-target Effects by Complex siRNA Pools for Scyl1

Next, the off-target by complex siRNA pools for Scyl1 and a control siRNA on Scyl1 were determined on a global basis by gene expression array analysis.

Materials and Methods
Determination of Expression Data

Hela cells were seeded and cultivated in DMEM substituted with 10% FCS and Penicillin/Streptomycine (Pen-Strep). SiRNAs, and complex siRNA pools were transfected in concentrations of 3 nM using Lipofectamine RNAiMAX (Life Technologies). Each transfection was performed in triplicates to allow statistical analysis of the results. Untransfected cells served as a control. Cells were harvested for RNA extraction 48 h after transfection. Global RNA expression was analyzed on a Human Gene 1.0 ST array from Affymetrix.

Normalization of raw intensity values from CEL files was performed using variance stabilization (VSN, Huber, 2002) and the median polish was used to summarize individual probes to an expression level per gene or transcript. Genes were defined using a custom chip description file based on ensemble gene identifiers and transcripts were defined with a custom chip description file based on ensemble transcript identifiers (Dai et al., *Nucleic Acids Res.* (2005), 10(33), 175)). The normalized data on the gene level was used for plotting the gene expression levels of Scyl1 and Mad2, for all other analyses, the normalized data on transcript level was used, since this data allows for distinguishing between transcripts with different 3'-UTRs of the same gene.

Non- and low expressed transcripts were filtered out before testing for differential expression by requiring at least one expression value of the 12 samples to be above the 40th percentile of all expression values. In addition, the 20% of transcripts with lowest interquartile-range, representing constantly expressed genes, were removed. This procedure resulted in 68,580 transcripts for differential expression testing and log 2 fold change estimation. Differential gene expression between cells treated with one or more siRNAs and untreated cells was estimated using limma (Smyth G K. *Stat Appl Genet Mol Biol*. (2004) 3, Article 3)). Because a large number of tests were performed for differential expression, false positive findings were controlled with the false discovery rate (FDR) (Benjamini et al., *Journal of the Royal Statistical Society*, Series B (Methodological) (1995), 57(1), 289-300).

Instead of multiple testing adjusted p-values, so-called q-values are reported which indicate the largest FDR at which the gene/transcript could be considered significant. Genes/transcripts with a q-value below 0.001 were considered significant differentially expressed. All log 2 fold changes reported are in the form of siRNA experiment versus control. Analyses were performed within the statistical programming environment R (R development core team (2011), R: A Language and Environment for Statistical Computing, Vienna, Austria, R: Foundation for Statistical Computing) and using Bioconductor (Gentleman et al., *Genome Biol*. (2004), 5(10), R80) packages.

Sequence Analysis

Human 3'-UTR sequences were retrieved from ensemble version 68 for the transcripts represented on the microarray. The siRNA seed sequences (nucleotides 2 to 8 of the siRNA) was searched for in the 3'-UTRs of the transcripts and matches were reported for the individual seed sequences.

The on-target silencing activity of complex siRNA pools and control siRNAs on Scyl1 and the off-target activity on Mad2 were determined using Reverse-Transcription PCR (RT-PCR). Gene knock down was calculated using the delta CT method with GAPDH serving as house keeper gene.

The following primer pairs were applied:

```
SCYL1 forward:
                            (SEQ ID No.: 333)
CTGGAGGAAGTGGAGAAGGA SCYL1 reverse:
                            (SEQ ID No.: 334)
TCAGCTTGGAGGTGAGTGAG GAPDH forward:
                            (SEQ ID No.: 335)
ATGGGTGTGAACCATGAGAA GAPDH reverse:
                            (SEQ ID No.: 336)
GTGCTAAGCAGTTGGTGGTG Mad2 forward:
                            (SEQ ID No.: 338)
AGATGACAGTGCACCCAGAG Mad2 reverse:
                            (SEQ ID No.: 339)
TCCAACAGTGGCAGAAATGT
```

Results
Off-target Effects on Mad2 1 by Complex siRNA Pools for Scyl1 or PolG Hela cells were transfected with Pool 1 for Scyl1 (see Table 7) separately as well as with combined Pools 1 to 4 for Scyl1 and with the siRNA "Scyl1 siRNA OT" each at 3 nM. On-target effects on Scyl1 (see FIG. 24) and off-target effects on Mad2 (see FIG. 25) were verified by qRT-PCR. The transfection of complex siRNA Pools as well as "Scyl1 siRNA OT" shows efficient on target effects on Scyl1 expression (FIG. 24). But only "Scyl1 siRNA OT" results in strong off-target effects on Mad2 expression (FIG. 25).

Reduced off-target effects of complex siRNA were further determined by global gene expression analysis. Both the complex siRNA Pool 1 as well as the combined Pools 1 to 4 showed lower amounts of regulated transcripts in comparison to the single "Scyl1 siRNA OT" (FIG. 26). The number of regulated transcripts both with (BS) or without a binding site (noBS) for "Scyl1 siRNA OT" reveals that the use of complex siRNA pools results in a reduced number or regulated transcripts which could be considered as reduced off-target activity. This is shown by the reduced spreading of the regulated transcripts (FIG. 26). In addition to that the reduced off-target activity of the complex siRNA pools is depicted by the increased amounts of repressed transcripts with (BS) and without (noBS) one or more seed sequence matches for "Scyl1 siRNA OT" after transfection of the single siRNA "Scyl1 siRNA OT" compared the transfection of complex siRNA pools (FIG. 26). The reduced number of repressed transcripts is in addition to that also shown by the down shift of the boxes representing the interquartile range (IQR) consisting of the central 50% of the data.

Experiment 5

Off-target Effects by High Complexity siRNA Pools for PolG

Further experiments were conducted to confirm the off-target effects observed for complex siRNA pools for PolG and Scyl1 (see Experiment 3). To ensure that the off-target siRNAs had indeed entered the RNAi mechanism, the 60 siRNA-containing pools (Pools 1 to 4) against PolG or Scyl1 (see Experiment 3) were transfected into HeLa cells and Ago2 was immunoprecipitated from the cell lysates (FIG. 29A). The off target siRNAs were analyzed by Northern blotting using probes against the guide (upper panel) or the passenger strand (lower panel). The guide strand was readily detectable in Ago2 complexes indicating that siRNAs are efficiently processed and loaded by Ago2.

To further solidify the results of Experiment 3, Mad2 protein reduction by PolG and Scyl1 siRNA off target effects was analyzed (FIG. 29B). HeLa cells were transfected with siRNAs against PolG (left panel, Pool 1, combined Pools 1 to 4, neg. C., and single "PolG siRNA OT") or Scyl1 (right panel, Pool 1, combined Pools 1 to 4, neg. C., and single "Scyl1 siRNA OT"). Cells were analyzed and protein extracts were analyzed by western blotting against Mad2. In accordance with the results on Mad2 mRNA levels, it was found that both off target siRNAs as well as the control siRNA directed against Mad2 strongly reduce Mad2 protein levels (left and right panels, lanes 7-10). However, when the same off-target siRNAs are placed into complex siRNA pools, the Mad2 protein depletion is strongly reduced (left and right panels, lanes 3-6).

Finally, we generated luciferase reporters containing miRNA-like binding sites for the PolG off-target siRNA or the Scyl1 off-target siRNA (FIG. 29C). The single off-target siRNAs were transfected into HeLa cells and a reduction of the luciferase activity was observed (left and right panels, siRNA off-T). However, when the siRNAs were part of complex siRNA pools (Pool 1, combined Pools 1 and 2, combined Pools 1 to 3, and combined Pools 1 to 4), the reduction of the luciferase activity was abolished. Furthermore, we analyzed the complexity requirements of the pools for off-target elimination. While the Scyl1 off target effect was already eliminated when 15 siRNAs were used, the effects of the PolG pools were slightly stronger in pools with higher complexity (left panel, compare Pool 1 with combined Pools 1 and 2).

Experiment 6

Simultaneous Knock Down of Redundant Gene Family Members

The convenient production procedure as well as the efficient knock down prompted us to ask whether we can knock down redundant gene family members using one siPool. For our analysis, we chose the human TNRC6 protein family comprising TNRC6A, B and C. These proteins are downstream factors of Ago proteins and are essential for miRNA-guided gene silencing. We generated complex siRNA pools against the individual TNRC6 proteins (FIG. 35C, siPool A, B and C) and also combined them to one siPool (siPool ABC).

The sequence for the siRNAs were chosen by selecting for siRNAs with a T residue in position 1 and G or C residues in position 19. Overall GC content was between 7 and 12 GC residues of the 19mer antisense strand sequence. Furthermore positions 2,10 and 18 of the antisense strand were preferred to be A/T, A and G/C respectively. SiRNAs were designed against the coding sequence as well as the 3'UTR of TNRC6 A, B and C. For each pool of 30 siRNAs, siRNA sequences were selected to have a maximum of 7 nucleotide overlap.

The chosen target sequence elements were as follows:

TABLE 11

Pool A 19 bp core sequence without 3' overhang for Pool A

| siRNA# | sense | SEQ ID No.: | Reverse complement antisense | SEQ ID No.: |
|---|---|---|---|---|
| 1 | GCAGGGATTTAGTGCAAGA | 352 | TCTTGCACTAAATCCCTGC | 382 |
| 2 | GCCTCGGTATCCTCGTGAA | 353 | TTCACGAGGATACCGAGGC | 383 |
| 3 | GCAGTGCTTTAACAAATCA | 354 | TGATTTGTTAAAGCACTGC | 384 |
| 4 | GGACCTGTGTCTTCTACAA | 355 | TTGTAGAAGACACAGGTCC | 385 |
| 5 | GAGTTGGCTTCAGAATGTA | 356 | TACATTCTGAAGCCAACTC | 386 |
| 6 | GCACTGGACTTGGTTCCCA | 357 | TGGGAACCAAGTCCAGTGC | 387 |
| 7 | GGATGCTCCTGAAAGCAAA | 358 | TTTGCTTTCAGGAGCATCC | 388 |
| 8 | GGCCAGTATTAGAGAACAA | 359 | TTGTTCTCTAATACTGGCC | 389 |
| 9 | GGAAACTTGTGAATCTGAA | 360 | TTCAGATTCACAAGTTTCC | 390 |
| 10 | GGAGGCTCTTATGGTACTA | 361 | TAGTACCATAAGAGCCTCC | 391 |
| 11 | GACAAATGTTCAGGCCCTA | 362 | TAGGGCCTGAACATTTGTC | 392 |
| 12 | GGCACTAACTTTCAAGTTA | 363 | TAACTTGAAAGTTAGTGCC | 393 |
| 13 | GCAGCAAACTCCCAGAGTA | 364 | TACTCTGGGAGTTTGCTGC | 394 |
| 14 | GGCGCAAATTCTGGAGGAA | 365 | TTCCTCCAGAATTTGCGCC | 395 |
| 15 | GGAACAAACTGCCTAGCAA | 366 | TTGCTAGGCAGTTTGTTCC | 396 |
| 16 | GGATCAGGGTTCTGCCACA | 367 | TGTGGCAGAACCCTGATCC | 397 |
| 17 | GGAGAGCGATGGTAGTACA | 368 | TGTACTACCATCGCTCTCC | 398 |
| 18 | GAAGATGATTCTGCTGCTA | 369 | TAGCAGCAGAATCATCTTC | 399 |

TABLE 11-continued

Pool A 19 bp core sequence without 3' overhang for Pool A

| siRNA# | sense | SEQ ID No.: | Reverse complement antisense | SEQ ID No.: |
|---|---|---|---|---|
| 19 | GGAGAAACTTCAAGGAATA | 370 | TATTCCTTGAAGTTTCTCC | 400 |
| 20 | CGTTTCCGGTTGGAACGAA | 371 | TTCGTTCCAACCGGAAACG | 401 |
| 21 | GGATAATGGTACTTCAGCA | 372 | TGCTGAAGTACCATTATCC | 402 |
| 22 | GGAACCCATTGCTGCGGCA | 373 | TGCCGCAGCAATGGGTTCC | 403 |
| 23 | GATATGCCATTGCCTGGAA | 374 | TTCCAGGCAATGGCATATC | 404 |
| 24 | GCCACCATATACAAAGAAA | 375 | TTTCTTTGTATATGGTGGC | 405 |
| 25 | CGAAGGGTCTGAGTGGCAA | 376 | TTGCCACTCAGACCCTTCG | 406 |
| 26 | GATGAAAGGTGGAAACAAA | 377 | TTTGTTTCCACCTTTCATC | 407 |
| 27 | GGAGGAATGTTACAAGACA | 378 | TGTCTTGTAACATTCCTCC | 408 |
| 28 | GGCCTCAGATTTCCAAAGA | 379 | TCTTTGGAAATCTGAGGCC | 409 |
| 29 | GCAGCAGCCTCCAGCACAA | 380 | TTGTGCTGGAGGCTGCTGC | 410 |
| 30 | GGCTTGAACTCAAACTTGA | 381 | TCAAGTTTGAGTTCAAGCC | 411 |

The above 19b core sequences result in the target 30 sequence elements ((tar.seq.el.) in FIG. 1) for SEQ ID Nos.: 352 to 381 and the reverse complement target sequence elements ((tar.seq.el.$_{rc}$) in FIG. 1) for SEQ ID Nos.: 382 to 411.

TABLE 12

Pool B 19 bp core sequence without 3' overhang for Pool B

| siRNA# | sense | SEQ ID No.: | Reverse complement antisense | SEQ ID No.: |
|---|---|---|---|---|
| 1 | GCATCAGATTCCAAATCTA | 412 | TAGATTTGGAATCTGATGC | 442 |
| 2 | GGAGGAGTCTGGAACACCA | 413 | TGGTGTTCCAGACTCCTCC | 443 |
| 3 | GGCAGTGCTTCCTCCCACA | 414 | TGTGGGAGGAAGCACTGCC | 444 |
| 4 | GGATGAATCCTCTTGCCAA | 415 | TTGGCAAGAGGATTCATCC | 445 |
| 5 | CCGTCCACCTAATTCCAAA | 416 | TTTGGAATTAGGTGGACGG | 446 |
| 6 | CCAGTTATCTCCTCAACAA | 417 | TTGTTGAGGAGATAACTGG | 447 |
| 7 | CCCAGACCTTCAAACCAAA | 418 | TTTGGTTTGAAGGTCTGGG | 448 |
| 8 | GGATATGGTTCTGGCTTCA | 419 | TGAAGCCAGAACCATATCC | 449 |
| 9 | GGAACCGAGTCTCGCTTTA | 420 | TAAAGCGAGACTCGGTTCC | 450 |
| 10 | GCTGCCCTCTGTAGCCACA | 421 | TGTGGCTACAGAGGGCAGC | 451 |
| 11 | GGAAGCCAATATGCACAAA | 422 | TTTGTGCATATTGGCTTCC | 452 |
| 12 | GATAGCTGGTTACCTGCCA | 423 | TGGCAGGTAACCAGCTATC | 453 |
| 13 | CCTGCCAAATCTCCACCAA | 424 | TTGGTGGAGATTTGGCAGG | 454 |
| 14 | GGAGTGCCATGGAAAGGTA | 425 | TACCTTTCCATGGCACTCC | 455 |
| 15 | GCTGCGGGATAACACCACA | 426 | TGTGGTGTTATCCCGCAGC | 456 |

TABLE 12-continued

Pool B

19 bp core sequence without 3' overhang for Pool B

| siRNA# | sense | SEQ ID No.: | Reverse complement antisense | SEQ ID No.: |
|---|---|---|---|---|
| 16 | GGGTCTAATTCTTCCCTCA | 427 | TGAGGGAAGAATTAGACCC | 457 |
| 17 | CAGCAAAGTTCCCTGATTA | 428 | TAATCAGGGAACTTTGCTG | 458 |
| 18 | CAGATCCCATAGGACACAA | 429 | TTGTGTCCTATGGGATCTG | 459 |
| 19 | CCACTCATCTCTCCAACAA | 430 | TTGTTGGAGAGATGAGTGG | 460 |
| 20 | GGGTCAACCTTGAGAACGA | 431 | TCGTTCTCAAGGTTGACCC | 461 |
| 21 | GCCCACTGCTGACATTCCA | 432 | TGGAATGTCAGCAGTGGGC | 462 |
| 22 | GACATTCCATCTGAATCTA | 433 | TAGATTCAGATGGAATGTC | 463 |
| 23 | GCACTGCCCTGATCCGATA | 434 | TATCGGATCAGGGCAGTGC | 464 |
| 24 | GCACATGTGTGTGTTGGGA | 435 | TCCCAACACACACATGTGC | 465 |
| 25 | GTTTGCCACTGATGATGAA | 436 | TTCATCATCAGTGGCAAAC | 466 |
| 26 | CAGCCGCTTTCTGGCACAA | 437 | TTGTGCCAGAAAGCGGCTG | 467 |
| 27 | CCAGTCAGATCCCGTGGGA | 438 | TCCCACGGGATCTGACTGG | 468 |
| 28 | CGATCTTGCTGGCGCTTCA | 439 | TGAAGCGCCAGCAAGATCG | 469 |
| 29 | GGGCAGCCCTGCTCCTTTA | 440 | TAAAGGAGCAGGGCTGCCC | 470 |
| 30 | GGAGGAGGGTCGGATTCAA | 441 | TTGAATCCGACCCTCCTCC | 471 |

The above 19b core sequences result in the target sequence elements ((tar.seq.el.) in FIG. 1) for SEQ ID Nos.: 412 to 441 and the reverse complement target sequence elements ((tar.seq.el.$_{rc}$) in FIG. 1) for SEQ ID Nos.: 442 to 471.

TABLE 13

Pool C

19 bp core sequence without 3' overhang for Pool C

| siRNA# | sense | SEQ ID No.: | Reverse complement antisense | SEQ ID No.: |
|---|---|---|---|---|
| 1 | GGCCTGTACTTGGACATGA | 472 | TCATGTCCAAGTACAGGCC | 502 |
| 2 | GAAACTTGCTGCCACAAGA | 473 | TCTTGTGGCAGCAAGTTTC | 503 |
| 3 | GAATGTGTCTTTCAGCGCA | 474 | TGCGCTGAAAGACACATTC | 504 |
| 4 | GCAGACAAATGGACTGCCA | 475 | TGGCAGTCCATTTGTCTGC | 505 |
| 5 | GGGCAGTGCTGAAGGAATA | 476 | TATTCCTTCAGCACTGCCC | 506 |
| 6 | CGTACAGCCTGGTGGTGAA | 477 | TTCACCACCAGGCTGTACG | 507 |
| 7 | GCGGCATCTTCTGGAACTA | 478 | TAGTTCCAGAAGATGCCGC | 508 |
| 8 | GAATGATCTTGACCCAAGA | 479 | TCTTGGGTCAAGATCATTC | 509 |
| 9 | CCCTAGGTCTGAAAGGAAA | 480 | TTTCCTTTCAGACCTAGGG | 510 |
| 10 | GGGTCTGGTTGGAATGACA | 481 | TGTCATTCCAACCAGACCC | 511 |
| 11 | CGGTACCGGTCAAACAGAA | 482 | TTCTGTTTGACCGGTACCG | 512 |
| 12 | GTAAACATGTGGGATAGAA | 483 | TTCTATCCCACATGTTTAC | 513 |
| 13 | GGTGGATAATGGCACAGCA | 484 | TGCTGTGCCATTATCCACC | 514 |

TABLE 13 -continued

Pool C 19 bp core sequence without 3' overhang for Pool C

| siRNA# | sense | SEQ ID No.: | Reverse complement antisense | SEQ ID No.: |
|---|---|---|---|---|
| 14 | GAATAATGCTGCTTCCCAA | 485 | TTGGGAAGCAGCATTATTC | 515 |
| 15 | GAAAGCACCTCCTCCTGCA | 486 | TGCAGGAGGAGGTGCTTTC | 516 |
| 16 | GATGAGGCCTGGATCATGA | 487 | TCATGATCCAGGCCTCATC | 517 |
| 17 | GAGGAGGCCTTGAAGAGTA | 488 | TACTCTTCAAGGCCTCCTC | 518 |
| 18 | GCCCGCCAATCTCCAAAGA | 489 | TCTTTGGAGATTGGCGGGC | 519 |
| 19 | GCAGCAAGTTGCGCGCACA | 490 | TGTGCGCGCAACTTGCTGC | 520 |
| 20 | CCGGTGGCTTGTCGGTGAA | 491 | TTCACCGACAAGCCACCGG | 521 |
| 21 | GCATGGTGCTATCCCTGGA | 492 | TCCAGGGATAGCACCATGC | 522 |
| 22 | GGTACGATTTAATCCAGAA | 493 | TTCTGGATTAAATCGTACC | 523 |
| 23 | CCTCAAGAGTGGAGGTAAA | 494 | TTTACCTCCACTCTTGAGG | 524 |
| 24 | GAGGCCACCTCCAGGGTTA | 495 | TAACCCTGGAGGTGGCCTC | 525 |
| 25 | GCTGGCTCGTTCTTCGAAA | 496 | TTTCGAAGAACGAGCCAGC | 526 |
| 26 | GGCCTCTTATCACATTCCA | 497 | TGGAATGTGATAAGAGGCC | 527 |
| 27 | CCACCTGAATCTGACTCAA | 498 | TTGAGTCAGATTCAGGTGG | 528 |
| 28 | GCAATGCTGTGGTCCGGTA | 499 | TACCGGACCACAGCATTGC | 529 |
| 29 | GCCCAGAAGTCTCTGCACA | 500 | TGTGCAGAGACTTCTGGGC | 530 |
| 30 | CGAGTTCGCTGGTGAAGAA | 501 | TTCTTCACCAGCGAACTCG | 531 |

The above 19b core sequences result in the target sequence elements ((tar.seq.el.) in FIG. 1) for SEQ ID Nos.: 472 to 501 and the reverse complement target sequence elements ((tar.seq.el.$_{rc}$) in FIG. 1) for SEQ ID Nos.: 502 to 531.

This sequences were incorporated into a construct using the RNase T1 loop sequence AGTTTG as described in Example 3.

The negative control siRNA (ctrl.) had the sense sequence 5'-UUGUCUUGCAUUCGACUAAUT-3' (SEQ ID No.: 532) and the following reverse complement antisense-sequence: 5'-UUAGUCGAAUGCAAGACAAUT-3' (SEQ ID No.: 533).

The first control siRNA for TNRC6A (siRNA A1) had the sense sequence 5'-UAAUGCCAAGCGAGCUACAUT-3' (SEQ ID No.: 534) and the following reverse complement antisense-sequence: 5'-UGUAGCUCGCUUGGCAUUA-UT-3' (SEQ ID No.: 535).

The second control siRNA for TNRC6A (siRNA A2) had the sense sequence 5'-UAUAGUACUGCACUGA-AUAUT-3 (SEQ ID No.: 536) and the following reverse complement antisense-sequence: 5'-UAUUCAGUGCA-GUACUAUAUT-3' (SEQ ID No.: 537).

The first control siRNA for TNRC6B (siRNA B1) had the sense sequence 5'-GGAGUGCCAUGGAAAGGUAUT-3' (SEQ ID No.: 538) and the following reverse complement antisense-sequence: 5'-UACCUUUCCAUGGCACUC-CUT-3' (SEQ ID No.: 539).

The second control siRNA for TNRC6B (siRNA B2) had the sense sequence 5'-GGAAGUUGUUGCUAAGAAAUT- 3' (SEQ ID No.: 540) and the following reverse complement antisense-sequence: 5'-UUUCUUAGCAACAACUUC-CUT-3' (SEQ ID No.: 541).

The first control siRNA for TNRC6C (siRNA CD had the sense sequence 5'-CAAUGGCGUUGGUAAUAUCUT-3' (SEQ ID No.: 542) and the following reverse complement antisense-sequence: 5'-GAUAUUACCAACGCCAUU-GUT-3' (SEQ ID No.: 543).

The second control siRNA for TNRC6C (siRNA C2) had the sense sequence 5'-CAAUAUGAAUCUUGAUCAGUT-3' (SEQ ID No.: 544) and the following reverse complement antisense-sequence: 5'-CUGAUCAAGAUUCAUAUU-GUT-3' (SEQ ID No.: 545).

All siPools knocked down their individual on-targets. Single siRNAs knocked down the TNRC6 genes as well but showed rather variable efficiencies (FIG. 35A). Strikingly, the siPool ABC targeting all TNRC6 genes indeed reduced the mRNA levels of each family member efficiently. We next tested the consequences of TNRC6 gene knock down using a miRNA reporter assays based on a luciferase gene controlled by the HMGA2 3' UTR (FIG. 35D). This 3' UTR contains seven let-7a binding sites and is repressed by the miRNA machinery (Mayr et al., (2007) Science 315, 1576-1579. Inhibition of let-7a by antisense inhibitors leads to a relief of repression (right bar) indicating that the reporter system is indeed under the control of let-7a. Knock down of TNRC6A or B either by the siPools or by individual siRNAs relieved repression and led to an increase of luciferase activity of about 1.5-1.8 fold (FIG. 35B). Knock down of TNRC6C alone had only a minor effect on luciferase activity. Of note, TNRC6C expression is much weaker in the HEK 293 cells that have been used (FIG. 35E). Knock down of all three family members simultaneously by the siPool ABC released repression by 2.3 to 2.5 fold, a similar range observed by the antisense inhibitor against let-7a. In summary, siPools can be used for efficient knock down of redundant gene family members and Furthermore, the siPool ABC against all TNRC6 genes is a valuable control for experiments aiming at identification of miRNA target genes.

Experiment 7 siPools do not Cause Measurable Interferon Responses

Since siPools and esiRNAs derive from longer dsRNA precursors and such precursors might cause an interferon response, we tested the expression of interferon response genes after siRNA transfection. We used complex siRNA pools (siPools) and esiRNAs against four different targets (PolG, Scyl 1, Traf5 and Ago2) and analyzed them on an agarose gel. While siPools show distinct 21 nt long bands, all purchased esiRNAs were characterized by an RNA smear ranging from 15 to more than 40 nts (FIG. 36). For interferon response experiments, we changed the cell line to MCF7 cells, which are more sensitive compared to other cell lines such as HeLa cells. All four target genes were efficiently knocked down by the siPools, while the esiRNA-mediated knock down was slightly less efficient (data not shown). We next analyzed the expression of the interferon response genes IFNB1 and OAS1 upon knock down. While siPools did not cause expression of IFNB1 or OAS1, two esiRNAs led to a strong (Scyl1, PolG) and another one (Traf5) to a medium to low interferon response (data not shown). This effect was esiRNA concentration dependent suggesting that indeed the longer RNA species within the esiRNAs cause this effect. The esiRNA against Ago2 did not cause a significant interferon response (data not shown). Similar results were obtained, when the interferon response genes IL6 and STAT1 were measured (data not shown). Together, the data suggest that due to a limited accuracy of RNase III digestion, esiRNAs contain longer by-products that cause off target effects. This is not observed for siPools.

Experiment 8

Testing of Further Loop Sequences

The following loop sequences were incorporated into the construct for the siRNA pool for AUKS:

```
Loop sequence 1:
AGTTG

Loop sequence 2:
AGTTTG

Loop sequence 3:
AGTTAG

Loop sequence 4:
AGTTTTG

Loop sequence 5:
AGTTTAG

Loop sequence 6:
AGTGTAG
```

Constructs with the loops sequence were in vitro transcribed and digested with RNase T1 under different conditions. The varied parameters included RNase T1 concentration (0.1 to 10 U RNase T1/µg dsRNA), incubation time (5 to 120 min), and MgCl$_2$ concentration (100 mM).

The following conclusions can be drawn from these experiments:

At high concentrations 10 U RNase T1/µg dsRNA vs 0.1 RNase T1/µg dsRNA and long incubation time (20 min vs 5 min) at these concentrations, siRNAs start to loose 3#-overhangs. A concentration of 0.1 to 5 U RNase T1/µg ds RNA at incubation times of 5 to 120 min seems to result in complete digest with no loss of 3'-overhangs.

Inclusion of MgCl$_2$ does not alter specificity of digest, but reduces efficiency.

Regardless of loop sequences, no siRNAs shorter than 21 nt are observed at optimized digest conditions. No significant improvement is observed when increasing length from e.g. AGTTG to AGTTTG. However, when reducing number of T-G hydrogen bonds by replacing e.g. T with A, improvement of the digest is observed: FIG. 37 depicts a digest at 0.1 U RNase T1/µg dsRNA and 30 or 120 min incubation, i.e. at conditions where the digest is substantially complete. One can conclude from these data that the loop sequences AGTTTAG and AGTGTAG work better than e.g. AGTTG, AGTTTG or AGTTTTG. AGTTAG works better than AGTTTG and AGTTTAG works better than AGTTTTG.

Some embodiments of the invention relate to:
1. Method of preparing double stranded RNA molecules, wherein each strand of said different double stranded molecules has a length of 15 to 30 nucleotides wherein said different double stranded RNA molecules are capable of target-specific RNA interference of at least one target gene, said method comprising at least the steps of:
   a. Providing at least one first DNA molecule,
   b. Providing at least one second DNA molecule,
   c. In vitro transcribing said at least one first and at least one second DNA molecules using an RNA polymerase to obtain corresponding at least one first and at least one second RNA molecules,
   d. Hybridizing said at least one first and at least one second RNA molecules of step c. to obtain an double stranded RNA molecule of the general structure depicted in FIG. 1,
   e. Digesting the double stranded RNA molecule obtained in step d. with an RNase, of which RNase T1 may be preferred, capable of preferentially recognizing, cleaving and digesting the single stranded loop-sequence-elements over the hybridized double stranded sections of the double stranded RNA obtained in step d. thereby removing single stranded RNA loops, wherein the sequence of said target-sequence-elements depicted on FIG. 1 of the at least one first DNA molecule is sense to sequences of said at least one target gene of RNA interference, wherein the sequences of said target-sequence-elements$_{rc}$ of the at least one second DNA molecule are the reverse complements of the sequences of the target-sequence-elements of the at least one first DNA molecule, which they hybridize to, and wherein the loop-sequence elements of the at least one first and at least one second DNA molecules are not reverse complements of each other,
      wherein the sequences of the loop-sequence-elements are selected such that double stranded RNA molecules are obtained by recognition, cleavage and digestion of the single stranded loop-sequence elements by an RNase, of which RNase T1 may be preferred, in step e., wherein each strand of said resulting double stranded molecules has a length of 15 to 30 nucleotides and wherein said resulting double stranded RNA molecules are capable of target-specific RNA interference of at least one target gene.

2. Method according to 1, said method comprising at least the steps of:
   a. Providing at least one first DNA molecule comprising in the 5'-3' direction as repeating units a nucleic acid sequence with the following elements:
      5'-[(target-sequence-element)-(loop-sequence-element)]$_k$-3',
      with k being an integer >1,
      with the target-sequence-element being a continuous sequence of 15 to 30 desoxyribonucleotides, which is sense to a sequence in said at least one target gene of RNA interference,
      with the loop-sequence-element being a continuous sequence of 3 to preferably 20 desoxyribonucleotides, which does not match a sense or antisense sequence in said at least one target gene of RNA interference,
   b. Providing at least one second DNA molecule comprising in the 5'-3' direction in a repetitive manner a nucleic acid sequence with the following elements:
      5'-[(target-sequence-element)$_{rc}$-(loop-sequence-element)]$_l$-3',
      with l being an integer >1 and having the same value as k in the first DNA molecule,
      with the target-sequence-element, being a continuous sequence of 15 to 30 desoxyribonucleotides,
      with the loop-sequence-element being a continuous sequence of 3 to preferably 20 desoxyribonucleotides, which does not match a sense or antisense sequence in said at least one target gene of RNA interference, wherein the target-sequence-elements$_{rc}$ counted from the 3' end in the repeating units of said second DNA molecule are the respective reverse complement of the target-sequence-elements counted from the 5' end in the repeating units of said first DNA molecule, and
      wherein the loop-sequence-elements in the repeating units of said second DNA molecule are not reverse complements of the loop-sequence-elements in the repeating units of said first DNA molecule,
   c. In vitro transcribing said at least one first and at least one second DNA molecules using an RNA polymerase to obtain corresponding at least one first and at least one second RNA molecules,
   d. Hybridizing said at least one first and at least one second RNA molecules of step c. to obtain a double stranded RNA molecule of the general structure depicted in FIG. 1,
   e. Digesting the double stranded RNA molecule obtained in step d. with an RNase, of which RNase T1 may be preferred, capable of preferentially recognizing, cleaving and digesting the single stranded loop-sequence-elements over the hybridized double stranded sections of the double stranded RNA obtained in step d. thereby removing single stranded RNA loops, wherein the sequences of the loop-sequence-elements are selected such that double stranded RNA molecules are obtained by recognition, cleavage and digestion of the single stranded loop-sequence elements by an RNase, of which RNase T1 may be preferred, in step e., wherein each strand of said resulting double stranded molecules has a length of 15 to 30 nucleotides, wherein said resulting double stranded RNA molecules are capable of target-specific RNA interference of at least one target gene.

3. Method of preparing different double stranded RNA molecules, wherein each strand of said double stranded molecules has a length of 15 to 30 nucleotides, wherein said double stranded RNA molecules are capable of target-specific RNA interference of at least one target gene, said method comprising at least the steps of:
   a. Providing at least one DNA molecule,
   b. In vitro transcribing said at least one DNA molecules using an RNA polymerase to obtain corresponding at least one first RNA molecule, which upon hybridization provides the general structure depicted in FIG. 2,
   c. Digesting the RNA molecule obtained in step b. with an RNase, of which RNase T1 may be preferred, capable of preferentially recognizing, cleaving and digesting the single stranded loop-sequence-elements over the hybridized double stranded sections of the double stranded RNA obtained in step b. thereby removing single stranded RNA loops,
      wherein the sequence of said target-sequence-elements depicted on FIG. 2 of the at least one first DNA molecule is sense to sequences of said at least one target gene of RNA interference, wherein the sequences of said target-sequence-elements$_{rc}$ of the at least one DNA molecule are the reverse complements of the sequences of the target-sequence-elements of the at least one first DNA molecule, which they hybridize to, and wherein the loop-sequence elements of the at least one first and at least one second DNA molecules are not reverse complements of each other,
      wherein the sequences of the loop-sequence-elements are selected such that double stranded RNA molecules are obtained by recognition, cleavage and digestion of the single stranded loop-sequence elements by an RNase, of which RNase T1 may be preferred, in step c., wherein each strand of said resulting double stranded molecules has a length of 15 to 30 nucleotides and wherein said resulting double stranded RNA molecules are capable of target-specific RNA interference of at least one target gene.

4. Method according to 3, said method comprising at least the steps of:
   a. Providing at least one first DNA molecule comprising in the 5'-3' direction as repeating units a nucleic acid sequence with the following elements:
      5'-[(target-sequence-element)-(loop-sequence-element)]$_k$-(target-sequence-element)-(loop-sequence-element)$_{hp}$-[(target-sequence-element)$_{rc}$-(loop-sequence-element)]$_l$-3',
      with k being an integer >1,
      with l being an integer >1 and being the same as 1,
      with the target-sequence-element being a continuous sequence of 15 to 30 desoxyribonucleotides, which is sense to a sequence in said at least one target gene of RNA interference,
      with the loop-sequence-element being a continuous sequence of 3 to preferably 20 desoxyribonucleotides, which does not match a sense or antisense sequence in said at least one target gene of RNA interference, wherein the (loop sequence element)$_{hp}$ is of sufficient length to allow for a hairpin structure enabling a self-hybdrization pattern depicted in FIG.

2, with the target-sequence-element$_{rc}$ being a continuous sequence of 15 to 30 desoxyribonucleotides, wherein the target-sequence-elements$_{rc}$ counted from the 3' end are the respective reverse complement of the target-sequence-elements counted from the 5' end, wherein the loop-sequence-elements following the (loop sequence element)$_{hp}$ are not reverse complements of the loop-sequence-elements preceeding the in the repeating units of said second DNA molecule, b. In vitro transcribing said at least one first DNA molecules using an RNA polymerase to obtain corresponding at least one first RNA molecule, which upon hybridization provides the general structure depicted in FIG. 2, c. Digesting the double stranded RNA molecule obtained in step b. with an RNase, of which RNase T1 may be preferred, capable of preferentially recognizing, cleaving and digesting the single stranded loop-sequence-elements over the hybridized double stranded sections of the double stranded RNA obtained in step b. thereby removing single stranded RNA loops, wherein the sequences of the loop-sequence-elements are selected such that double stranded RNA molecules are obtained by recognition, cleavage and digestion of the single stranded loop-sequence elements by an RNase, of which RNase T1 may be preferred, in step c., wherein each strand of said resulting double stranded molecules has a length of 15 to 30 nucleotides and wherein said resulting double stranded RNA molecules are capable of target-specific RNA interference of at least one target gene.

5. Method according to any of 1, 2, 3 or 4, wherein the number of target-sequence-elements is at least 2, at least 3, at least 4, at least 5, at least 6, at least 7, at least 8, at least 9, at least 10, at least 11, at least 12, at least 13, at least 14 or at least 15, wherein the sequence of said target-sequence-elements of the at least one first DNA molecule as depicted in FIG. 1 or of the at least one DNA molecule as depicted in FIG. 2 is sense to sequences of said at least one target gene of RNA interference, wherein the sequences of said target-sequence-elements$_{rc}$ of the at least one second DNA molecule as depicted in FIG. 1 or of the at least one DNA molecule as depicted in FIG. 2 are the reverse complements of the sequences of the target-sequence-elements of the at least one first DNA molecules depicted in FIG. 1 or of the at least one DNA molecule as depicted in FIG. 2, which they hybridize to, wherein the loop-sequence elements of the at least one first DNA molecules are not reverse complements of each other, and, in case of the at least one DNA molecule as depicted in FIG. 2 the (loop sequence element)$_{hp}$ is of sufficient length to allow for a hairpin structure enabling a self-hybdrization pattern depicted in FIG. 2.

6. Method according to any of 1, 2, 3, or 4, wherein the sequences of said target-sequence elements are the same.

7. Method according to any of 1, 2, 3, or 4, wherein the sequences of said target-sequence elements are not the same.

8. Method according to 7, wherein the sequences of said target-sequence elements are not the same and result in different double stranded RNA molecules, wherein each strand of said double stranded molecules has a length of 15 to 30 nucleotides, wherein said different double stranded RNA molecules are capable of target-specific RNA interference of the same gene.

9. Method according to 7, wherein the sequences of said target-sequence elements are not the same and result in different double stranded RNA molecules, wherein each strand of said double stranded molecules has a length of 15 to 30 nucleotides, wherein said different double stranded RNA molecules are capable of target-specific RNA interference of at least two different target genes.

10. Method according to any of 1, 2, 3, 4, 5, 6, 7, 8 or 9 wherein the loop-sequence elements are the same.

11. Method according to any of 1, 2, 3, 4, 5, 6, 7, 8 or 9 wherein the loop-sequence elements are not the same.

12. Method according to any of 1, 2, 3, 4, 5, 6, 7, 8, 9, 10 or 11, wherein each strand of said different double stranded molecules has a length of 17 to 25 nucleotides.

13. Method according to 12, wherein each strand of said different double stranded molecules has a length of 18 to 24 nucleotides.

14. Method according to 13, wherein each strand of said different double stranded molecules has a length of 19 to 23 nucleotides.

15. Method according to 14, wherein each strand of said different double stranded molecules has a length of 20, 21, or 22 nucleotides.

16. Method according to 15, wherein each strand of said different double stranded molecules has a length of 21 nucleotides.

17. Method according to any of 1, 2, 3, 4, 5, 6, 7, 8, 9, 10, 11, 12, 13, 14, 15 or 16, wherein each strand of said different double stranded molecules has a 3'-overhang from 1 to 5 nucleotides.

18. Method according to 17, wherein each strand of said different double stranded molecules has a 3'-overhang from 1 to 4 nucleotides.

19. Method according to 18, wherein each strand of said different double stranded molecules has a 3'-overhang of 1 to 3 nucleotides.

20. Method according to 19, wherein each strand of said different double stranded molecules has a 3'-overhang of 1 to 2 nucleotides.

21. Method according to any of 1, 2, 3, 4, 5, 6, 7, 8, 9, 10, 11, 12, 13, 14, 15, 16, 17, 18, 19 or 20, wherein the target-sequence-elements have a continuous sequence of 17 to 23 nucleotides.

22. Method according to 21, wherein the target-sequence-elements have a continuous sequence of 17 to 22 nucleotides.

23. Method according to 22, wherein the target-sequence-elements have a continuous sequence of 17 to 21 nucleotides.

24. Method according to 23, wherein the target-sequence-elements have a continuous sequence of 18, 19, or 20 nucleotides.

25. Method according to 24, wherein the target-sequence-elements have a continuous sequence of 19 nucleotides.

26. Method according to any of 1, 2, 3, 4, 5, 6, 7, 8, 9, 10, 11, 12, 13, 14, 15, 16, 17, 18, 19, 20, 21, 22, 23, 24 or 25, wherein the loop-sequence-elements are selected such that in said hybridized RNA molecule, they are cleaved and digested by an RNase, of which RNase T1 may be preferred, which is sequence specific for single stranded RNA loops in double stranded RNA molecules, but which does not act on the hybridized double stranded sections of the RNA molecule.

27. Method according to claim 26, wherein the RNase is selected from the group consisting of RNase T1, RNase Ba, ST, C2, RNase U2, RNase PhyM, RNase A, RNase CL3, and, RNase T2.

28. Method according to any of 1, 2, 3, 4, 5, 6, 7, 8, 9, 10, 11, 12, 13, 14, 15, 16, 17, 18, 19, 20, 21, 22, 23, 24, 25, 26 or 27, wherein the loop-sequence-element is cleavable by RNase T1 and has the sequence 5'-$(X)_m$-G-$(Y)_n$-G-3', with X being A, T or C and m being an integer of 1 to 4, such as 1, 2, 3, or 4,
with Y being A, T or C and n being an integer of 2 to 17 such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

29. Method according to 28, wherein the loop-sequence-element is cleavable by RNase T1 and has the sequence 5'-$(X)_m$-G-$(Y)_n$-G-3',
with X being A or C and m being an integer of 1 to 2,
with Y being A, T or C and n being an integer of 2 to 10, such as 2, 3, 4, 5, 6, 7, 8, 9, or 10, and
with X and Y being selected such that there is no hybridization of two molecules consisting just of the loop-sequence-element.

30. Method according to 29, wherein the loop-sequence-element is cleavable by RNase T1 and has the sequence 5'-$(X)_m$-G-$(Y)_n$-G-3',
with X being A and m being an integer of 1,
with Y being A, T or C and n being an integer of 2 to 5, such as 2, 3, 4, or 5, and
with X and Y being selected such that there is no hybridization of two molecules consisting just of the loop-sequence-element.

31. Method according to 30, wherein the loop-sequence-element is cleavable by RNase T1 and has the sequence 5'-$(X)_m$-G-$(Y)_n$-G-3',
with X being A and m being an integer of 1,
with Y being T and n being an integer of 2 to 4, such as 2, 3, or 4, and
with X and Y being selected such that there is no hybridization of two molecules consisting just of the loop-sequence-element.

32. Method according to 29, wherein the loop-sequence-element is cleavable by RNase T1 and has the sequence 5'-$(X)_m$-G-$(Y)_n$-G-3',
with X being A and m being an integer of 1, or 2,
with Y being A and n being an integer of 2, 3, 4, or 5, and
with X and Y being selected such that there is no hybridization of two molecules consisting just of the loop-sequence-element.

33. Method according to 32, wherein the loop-sequence-element is cleavable by RNase T1 and has the sequence 5'-$(X)_m$-G-$(Y)_n$-G-3',
with X being A and m being an integer of 1,
with Y being A and n being an integer of 2, 3, or 4, and
with X and Y being selected such that there is no hybridization of two molecules consisting just of the loop-sequence-element.

34. Method according to any of 1, 2, 3, 4, 5, 6, 7, 8, 9, 10, 11, 12, 13, 14, 15, 16, 17, 18, 19, 20, 21, 22, 23, 24, 25, 26 or 27, wherein the loop-sequence-element is cleavable by RNase U2 and has the sequence 5'-$(X)_m$-A-$(Y)_n$-A-3',
with X being T, G or C and m being an integer of 1 to 4, such as 1, 2, 3, or 4,
with Y being T, G or C and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

35. Method according to any of 1, 2, 3, 4, 5, 6, 7, 8, 9, 10, 11, 12, 13, 14, 15, 16, 17, 18, 19, 20, 21, 22, 23, 24, 25, 26 or 27, wherein the loop-sequence-element is cleavable by RNase PhyM and (i) has the sequence 5'-$(X)_m$-A-$(Y)_n$-A-3',
with X being T, G or C and m being an integer of 1 to 4, such as 1, 2, 3, or 4,
with Y being T, G or C and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element,
or (ii) has the sequence 5'-$(X)_m$-T-$(Y)_n$-T-3',
with X being A, G or C and m being an integer of 1 to 4, such as 1, 2, 3, or 4,
with Y being A, G or C and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

36. Method according to any of 1, 2, 3, 4, 5, 6, 7, 8, 9, 10, 11, 12, 13, 14, 15, 16, 17, 18, 19, 20, 21, 22, 23, 24, 25, 26 or 27, wherein the loop-sequence-element is cleavable by RNase A and (i) has the sequence 5'-$(X)_m$-C-$(Y)_n$-C-3',
with X being A, T, or G and m being an integer of 1 to 4, such as 1, 2, 3, or 4,
with Y being A, T, or G and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element,
or (ii) has the sequence 5'-$(X)_m$-T-$(Y)_n$-T-3',
with X being A, G or C and m being an integer of 1 to 4, such as 1, 2, 3, or 4,
with Y being A, G or C and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

37. Method according to any of 1, 2, 3, 4, 5, 6, 7, 8, 9, 10, 11, 12, 13, 14, 15, 16, 17, 18, 19, 20, 21, 22, 23, 24, 25, 26 or 27, wherein the loop-sequence-element is cleavable by RNase CL3 and has the sequence 5'-$(X)_1$-C-$(Y)_n$-C-3',
with X being A, T, or G and m being an integer of 1 to 4, such as 1, 2, 3, or 4,
with Y being A, T, or G and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

38. Method according to any of 1, 2, 3, 4, 5, 6, 7, 8, 9, 10, 11, 12, 13, 14, 15, 16, 17, 18, 19, 20, 21, 22, 23, 24, 25, 26 or 27, wherein the loop-sequence-element is cleavable by RNase T2 and has the sequence 5'-$(X)_1$-A-$(Y)_n$-A-3',
with X being T, C, or G and m being an integer of 1 to 4, such as 1, 2, 3, or 4,
with Y being T, C, or G and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

39. Method according to any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38, wherein the loop-sequence elements are selected such that in said hybridized RNA molecule, they are cleaved by an RNase after the first, second, third, fourth or fifth position of the 5'-end of the single stranded loop-sequence-element.

40. Method according to any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein multiple DNA molecules are used, wherein each DNA molecule comprises target-sequence elements that allow for RNA interference of 1 specific gene and wherein the different DNA molecules allow of RNA interference of different genes.

41. A combination or a kit of at least two DNA molecules, which upon in vitro transcription, hybridization and digestion with an RNase, of which RNase T1 may be preferred, are capable of providing double stranded RNA molecules, wherein each strand of said different double stranded molecules has a length of 15 to 30 nucleotides and wherein said double stranded RNA molecules are capable of target-specific RNA interference of at least one target gene, wherein said at least two DNA molecules have the sequence elements necessary to obtain an RNA molecule of the general structure depicted in FIG. 1 after in vitro transcription and hybridization, wherein the sequences of the loop-sequence-elements are selected such that double stranded RNA molecules can be obtained after cleavage and digestion with an RNase, of which RNase T1 may be preferred, capable of preferentially recognizing and cleaving the single stranded loop-sequence-elements over the hybridized double stranded sections of the double stranded RNA thereby removing single stranded RNA loops.

42. A combination or a kit according to 41, obtainable by
a. at least one first DNA molecule comprising in the 5'-3' direction as repeating units a nucleic acid sequence with the following elements:
5'-[(target-sequence-element)-(loop-sequence-element)]$_k$-3',
with k being an integer >1,
with the target-sequence-element being a continuous sequence of 15 to 30 desoxyribonucleotides, which is sense to a sequence in said at least one target gene of RNA interference,
with the loop-sequence-element being a continuous sequence of 3 to preferably 20 desoxyribonucleotides, which does not match a sense or antisense sequence in said at least one target gene of RNA interference
b. at least one second DNA molecule comprising in the 5'-3' direction in a repetitive manner a nucleic acid sequence with the following elements:
5'-[(target-sequence-element)$_{rc}$-(loop-sequence-element)]$_l$-3',
with l being an integer >1 and having the same value as k in the first DNA molecule,
with the target-sequence-element$_{rc}$ being a continuous sequence of 15 to 30 desoxyribonucleotides,
with the loop-sequence-element being a continuous sequence of 3 to preferably 20 desoxyribonucleotides, which does not match a sense or antisense sequence in said at least one target gene of RNA interference, wherein the target-sequence-elements$_{rc}$ counted from the 3' end in the repeating units of said second DNA molecule are the respective reverse complement of the target-sequence-elements counted from the 5' end in the repeating units of said first DNA molecule, and wherein the loop-sequence-elements in the repeating units of said second DNA molecule are not reverse complements of the loop-sequence-elements in the repeating units of said first DNA molecule, wherein said at least one first and second DNA molecules can be in vitro transcribed and hybridized to obtain a double stranded RNA molecule of the general structure depicted in FIG. 1, wherein the sequences of the loop-sequence-elements are selected such that double stranded RNA molecules can be obtained by recognition, cleavage and digestion of the single stranded loop-sequence elements by an RNase, of which RNase T1 may be preferred, capable of preferentially recognizing, cleaving and digesting the single stranded loop-sequence-elements over the hybridized double stranded sections of the double stranded RNA thereby removing single stranded RNA loops.

43. At least one DNA molecule, which upon in vitro transcription, hybridization and digestion with an RNase, of which RNase T1 may be preferred, is capable of providing double stranded RNA molecules, wherein each strand of said double stranded molecules has a length of 15 to 30 nucleotides and wherein said different double stranded RNA molecules are capable of target-specific RNA interference of at least one target gene, wherein said at least one DNA molecule has the sequence elements necessary to obtain an RNA molecule of the general structure depicted in FIG. 2 after in vitro transcription and hybridization, wherein the sequences of the loop-sequence-elements are selected such that double stranded RNA molecules are obtained after digestion with an RNase, of which RNase T1 may be preferred, capable of preferentially recognizing, cleaving and digesting the single stranded loop-sequence-elements over the hybridized double stranded sections of the double stranded RNA thereby removing single stranded RNA loops.

44. At least one DNA molecule according to 43, obtainable by:
a. Providing at least one DNA molecule,
b. In vitro transcribing said at least one DNA molecules using an RNA polymerase to obtain corresponding at least one first RNA molecule, which upon hybridization provides the general structure depicted in FIG. 2,
c. Digesting the RNA molecule obtained in step b. with an RNase, of which RNase T1 may be preferred, capable of preferentially recognizing, cleaving and digesting the single stranded loop-sequence-elements over the hybridized double stranded sections of the double stranded RNA obtained in step b. thereby removing single stranded RNA loops, wherein the sequence of said target-sequence-elements depicted on FIG. 2 of the at least one first DNA molecule is sense to sequences of said at least one target gene of RNA interference, wherein the sequences of said target-sequence-elements$_{rc}$ of the at least one DNA molecule are the reverse complements of the sequences of the target-sequence-elements of the at least one first DNA molecule, which they hybridize to, and wherein the loop-sequence elements of the at least one first and at least one second DNA molecules are not reverse complements of each other,
wherein the sequences of the loop-sequence-elements are selected such that double stranded RNA molecules are obtained by recognition, cleavage and digestion of the single stranded loop-sequence elements by an RNase, of which RNase T1 may be preferred, in step c., wherein each strand of said resulting double stranded molecules has a length of 15 to 30 nucleotides and wherein said resulting double stranded RNA molecules are capable of target-specific RNA interference of at least one target gene.

45. A combination or a kit of at least two DNA molecules according to any of 41 to 42 or at least one DNA molecule according to any of 43 to 44, wherein the number of target-sequence-elements is at least 2, at least 3, at least 4, at least 5, at least 6, at least 7, at least 8, at least 9, at least 10, at least 11, at least 12, at least 13, at least 14 or at least 15, wherein the sequence of said target-sequence-elements of the at least one first DNA molecule as depicted in FIG. 1 or of the at least one DNA molecule as depicted in FIG. 2 is sense to sequences of said at least one target gene of RNA interference, wherein the sequences of said target-sequence-elements$_{rc}$ of the at least one second DNA molecule as depicted in FIG. 1 or of the at least one DNA molecule as depicted in FIG. 2 are the reverse complements of the sequences of the target-sequence-elements of the at least one first DNA molecules depicted in FIG. 1 or of the at least one DNA molecule as depicted in FIG. 2, which they hybridize to, wherein the loop-sequence elements of the at least one first DNA molecules are not reverse complements of each other, and, in case of the at least one DNA molecule as depicted in FIG. 2 the (loop sequence element)$_{hp}$ is of sufficient length to allow for a hairpin structure enabling a self-hybdrization pattern depicted in FIG. 2.

46. A combination or a kit of at least two DNA molecules according to any of 41, 42, and 45 and or at least one DNA molecule according to any of 43, 44, and 44, wherein the sequences of said target-sequence elements are the same.

47. A combination or a kit of at least two DNA molecules according to any of 41, 42, and 45 and or at least one DNA molecule according to any of 43, 44, and 45, wherein the sequences of said target-sequence elements are not the same.

48. A combination or a kit of at least two DNA molecules according to 47 and or at least one DNA molecule according to 47, wherein the sequences of said target-sequence elements are not the same and different double stranded RNA molecules can be obtained, wherein each strand of said double stranded molecules has a length of 15 to 30 nucleotides, wherein said different double stranded RNA molecules are capable of target-specific RNA interference of the same gene.

49. A combination or a kit of at least two DNA molecules according to 47, and or at least one DNA molecule according to 47, wherein the sequences of said target-sequence elements are not the same and different double stranded RNA molecules can be obtained, wherein each strand of said double stranded molecules has a length of 15 to 30 nucleotides, wherein said different double stranded RNA molecules are capable of target-specific RNA interference of at least two different target genes.

50. A combination or a kit of at least two DNA molecules according to any of 41, 42, and 45, 46, 47, 48, 49 or at least one DNA molecule according to any of 43, 44, and 45, 46, 47, 48, 49, wherein the loop-sequence elements are the same.

51. A combination or a kit of at least two DNA molecules according to any of 41, 42, and 45, 46, 47, 48, 49 or at least one DNA molecule according to any of 43, 44, and 45, 46, 47, 48, 49, wherein the loop-sequence elements are not the same.

52. A combination or a kit of at least two DNA molecules according to any of 41, 42, and 45, 46, 47, 48, 49, 50, 51 or at least one DNA molecule according to any of 43, 44, and 45, 46, 47, 48, 49, 50, or 51 wherein each strand of said different double stranded molecules has a length of 17 to 25 nucleotides after digestion with said RNase.

53. A combination or a kit of at least two DNA molecules according to 51 or at least one DNA molecule according to 51, wherein each strand of said different double stranded molecules has a length of 18 to 24 nucleotides with said RNase.

54. A combination or a kit of at least two DNA molecules according to 53 or at least one DNA molecule according to 53, wherein each strand of said different double stranded molecules has a length of 19 to 23 nucleotides with said RNase.

55. A combination or a kit of at least two DNA molecules according to 54 or at least one DNA molecule according to 54, wherein each strand of said different double stranded molecules has a length of 20, 21, or 22 nucleotides with said RNase.

56. A combination or a kit of at least two DNA molecules according to 55 or at least one DNA molecule according to 55, wherein each strand of said different double stranded molecules has a length of 21 nucleotides with said RNase.

57. A combination or a kit of at least two DNA molecules according to any of 41, 42, and 445, 46, 47, 48, 49, 50, 51, 52, 53, 54, 55, 56 or at least one DNA molecule according to any of 43, 44, and 45, 46, 47, 48, 49, 50, 51, 52, 53, 54, 55, or 56, wherein each strand of said different double stranded molecules has a 3'-overhang from 1 to 5 nucleotides with said RNase.

58. A combination or a kit of at least two DNA molecules according to 57 or at least one DNA molecule according to 57, wherein each strand of said different double stranded molecules has a 3'-overhang from 1 to 4 nucleotides with said RNase.

59. A combination or a kit of at least two DNA molecules according to 58 or at least one DNA molecule according to 58, wherein each strand of said different double stranded molecules has a 3'-overhang of 1 to 3 nucleotides with said RNase.

60. A combination or a kit of at least two DNA molecules according to 59 or at least one DNA molecule according to 59, wherein each strand of said different double stranded molecules has a 3'-overhang of 1 to 2 nucleotide with said RNase s.

61. A combination or a kit of at least two DNA molecules according to any of 41, 42, and 45, 46, 47, 48, 49, 50, 51, 52, 53, 54, 55, 56, 57, 58, 59, 60 or at least one DNA molecule according to any of 43, 44, and 45, 46, 47, 48, 49, 50, 51, 52, 53, 54, 55, 56, 57, 58, 59, or 60, wherein the target-sequence-elements have a continuous sequence of 17 to 23 nucleotides.

62. A combination or a kit of at least two DNA molecules according to 61 or at least one DNA molecule according to 61, wherein the target-sequence-elements have a continuous sequence of 17 to 22 nucleotides.

63. A combination or a kit of at least two DNA molecules according to 62 or at least one DNA molecule according to 62, wherein the target-sequence-elements have a continuous sequence of 17 to 21 nucleotides.

64. A combination or a kit of at least two DNA molecules according to 63 or at least one DNA molecule according to 63, wherein the target-sequence-elements have a continuous sequence of 18, 19, or 20 nucleotides.

65. A combination or a kit of at least two DNA molecules according to 64 or at least one DNA molecule according to 64, wherein the target-sequence-elements have a continuous sequence of 19 nucleotides.

66. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65 or at least one DNA molecule according to any of 43, 44, and 45, 46, 47, 48, 49, 50, 51, 52, 53, 54, 55, 56, 57, 58, 59, 60, 61, 62, 63, 64 or 65 wherein the loop-sequence-elements are selected such that in said hybridized RNA molecule, they can be cleaved and digested by an RNase, of which RNase T1 may be preferred, which is sequence specific for single stranded RNA loops in double stranded RNA molecules, but which does not act on the hybridized double stranded sections of the RNA molecule.

67. A combination or a kit of at least two DNA molecules according to 66 or at least one DNA molecule according to 66, wherein the RNase is selected from the group consisting of RNase T1, RNase Ba, ST, C2, RNase U2, RNase PhyM, RNase A, RNase CL3, and, RNase T2.

68. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65, 66, 67, or at least one DNA molecule according to any of 43, 44, and 45, 46, 47, 48, 49, 50, 51, 52, 53, 54, 55, 56, 57, 58, 59, 60, 61, 62, 63, 64, 65, 66, or 67, wherein the loop-sequence-element is cleavable by RNase T1 and has the sequence 5'-$(X)_m$-G-$(Y)_n$-G-3',
   with X being A, T or C and m being an integer of 1 to 4, such as 1, 2, 3, or 4,
   with Y being A, T or C and n being an integer of 2 to 17, such as 2, 3, 4, 5, 6, 7, 8, 9, 10, 11, 12, 13, 14, 15, 16, or 17, and
   with X and Y being selected such that there is no hybridization of two molecules consisting just of the loop-sequence-element.

69. A combination or a kit of at least two DNA molecules according to 67 or at least one DNA molecule according to 67, wherein the loop-sequence-element is cleavable by RNase T1 and has the sequence 5'-$(X)_m$-G-$(Y)_n$-G-3',
   with X being A or C and m being an integer of 1 to 2,
   with Y being A, T or C and n being an integer of 2 to 10, such as 2, 3, 4, 5, 6, 7, 8, 9, or 10, and
   with X and Y being selected such that there is no hybridization of two molecules consisting just of the loop-sequence-element.

70. A combination or a kit of at least two DNA molecules according to 69 or at least one DNA molecule according to 69, wherein the loop-sequence-element is cleavable by RNase T1 and has the sequence 5'-$(X)_m$-G-$(Y)_n$-G-3',
   with X being A and m being an integer of 1,
   with Y being A, T or C and n being an integer of 2 to 5, such as 2, 3, 4, or 5, and
   with X and Y being selected such that there is no hybridization of two molecules consisting just of the loop-sequence-element.

71. A combination or a kit of at least two DNA molecules according to 70 or at least one DNA molecule according to 70, wherein the loop-sequence-element is cleavable by RNase T1 and has the sequence 5'-$(X)_m$-G-$(Y)_n$-G-3',
   with X being A and m being an integer of 1,
   with Y being T and n being an integer of 2 to 4, such as 2, 3, or 4, and
   with X and Y being selected such that there is no hybridization of two molecules consisting just of the loop-sequence-element.

72. A combination or a kit of at least two DNA molecules according to 69 or at least one DNA molecule according to 69, wherein the loop-sequence-element is cleavable by RNase T1 and has the sequence 5'-$(X)_m$-G-$(Y)_n$-G-3',
   with X being A and m being an integer of 1, or 2,
   with Y being A and n being an integer of 2, 3, 4, or 5, and
   with X and Y being selected such that there is no hybridization of two molecules consisting just of the loop-sequence-element.

73. A combination or a kit of at least two DNA molecules according to 72 or at least one DNA molecule according to 72, wherein the loop-sequence-element is cleavable by RNase T1 and has the sequence 5'-$(X)_m$-G-$(Y)_n$'-G-3',
   with X being A and m being an integer of 1,
   with Y being A and n being an integer of 2, 3, or 4, and
   with X and Y being selected such that there is no hybridization of two molecules consisting just of the loop-sequence-element.

74. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65, 66, 67, or at least one DNA molecule according to any of 43, 44, and 45, 46, 47, 48, 49, 50, 51, 52, 53, 54, 55, 56, 57, 58, 59, 60, 61, 62, 63, 64, 65, 66, or 67, wherein the loop-sequence-element is cleavable by RNase U2 and has the sequence 5'-$(X)_m$-A-$(Y)_n$-A-3',
   with X being T, G or C and m being an integer of 1 to 4, such as 1, 3, 4, or 4,
   with Y being T, G or C and n being an integer of 2 to 17, such as 2, 3, 4, 5, 6, 7, 8, 9, 10, 11, 12, 13, 14, 15, 16, or 17, and
   with X and Y being selected such that there is no hybridization of two molecules consisting just of the loop-sequence-element.

75. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65, 66, 67, or at least one DNA molecule according to any of 43, 44, and 45, 46, 47, 48, 49, 50, 51, 52, 53, 54, 55, 56, 57, 58, 59, 60, 61, 62, 63, 64, 65, 66, or 67, wherein the loop-sequence-element is cleavable by RNase PhyM and
   (i) has the sequence 5'-$(X)_m$-A-$(Y)_n$-A-3',
   with X being T, G or C and m being an integer of 1 to 4, such as 1, 2, 3, or 4,
   with Y being T, G or C and n being an integer of 2 to 17, such as 2, 3, 4, 5, 6, 7, 8, 9, 10, 11, 12, 13, 14, 15, 16, or 17, and
   with X and Y being selected such that there is no hybridization of two molecules consisting just of the loop-sequence-element,
   or (ii) has the sequence 5'-$(X)_m$-T-$(Y)_n$-T-3',
   with X being A, G or C and m being an integer of 1 to 4,
   with Y being A, G or C and n being an integer of 2 to 17, and
   with X and Y being selected such that there is no hybridization of two molecules consisting just of the loop-sequence-element.

76. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65, 66, 67, or at least one DNA molecule according to any of 43, 44, and 45, 46, 47, 48, 49, 50, 51, 52, 53, 54, 55, 56, 57, 58, 59, 60, 61, 62, 63, 64, 65, 66, or 67, wherein the loop-sequence-element is cleavable by RNase A and (i) has the sequence 5'-(X)$_m$-C-(Y)$_n$-C-3',
with X being A, T, or G and m being an integer of 1 to 4 such as 1, 2, 3, or 4,
with Y being A, T, or G and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element,
or (ii) has the sequence 5'-(X)$_m$-T-(Y)$_n$-T-3',
with X being A, G or C and m being an integer of 1 to 4,
with Y being A, G or C and n being an integer of 2 to 17, and
with X and Y being selected such that there is no hybridization of two molecules consisting just of the loop-sequence-element.

77. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65, 66, 67, or at least one DNA molecule according to any of 43, 44, and 45, 46, 47, 48, 49, 50, 51, 52, 53, 54, 55, 56, 57, 58, 59, 60, 61, 62, 63, 64, 65, 66, or 67, wherein the loop-sequence-element is cleavable by RNase CL3 and has the sequence 5'-(X)$_m$-C-(Y)$_n$-C-3',
with X being A, T, or G and m being an integer of 1 to 4, such as 1, 2, 3, or 4,
with Y being A, T, or G and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

78. A combination or a kit of at least two DNA molecules according to any of 41, 42, and 45, 46, 47, 48, 49, 50, 51, 52, 53, 54, 55, 56, 57, 58, 59, 60, 61, 62, 63, 64, 65, 66, 67, or at least one DNA molecule according to any of 43, 44, and 45, 46, 47, 48, 49, 50, 51, 52, 53, 54, 55, 56, 57, 58, 59, 60, 61, 62, 63, 64, 65, 66, or 67, wherein the loop-sequence-element is cleavable by RNase T2 and has the sequence 5'-(X)$_m$-A-(Y)$_n$-A-3',
with X being T, C, or G and m being an integer of 1 to 4, such as 1, 2, 3, or 4,
with Y being T, C, or G and n being an integer of 2 to 17, such as 2, 3, 4, 5, 6, 7, 8, 9, 10, 11, 12, 13, 14, 15, 16, or 17, and
with X and Y being selected such that there is no hybridization of two molecules consisting just of the loop-sequence-element.

79. A combination or a kit of at least two DNA molecules according to any of 39, 40, and 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 or at least one DNA molecule according to any of 41, 42, and 43, 44, 45, 46, 47, 50, 51, 52, 53, 54, 55, 56, 57, 58, 59, 60, 61, 62, 63, 64, 65, 66, 67, 68, 69, 70, 71, 72, 73, 74, 75, 76, 77, or 78, wherein the loop-sequence elements are selected such that in said hybridized RNA molecule, they are cleaved by an RNase after the first, second, third, fourth or fifth position of the 5'-end of the single stranded loop-sequence-element.

80. A combination or a kit of at least two DNA molecules according to any of 39, 40, and 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or at least one DNA molecule according to any of 41, 42, and 43, 44, 45, 46, 47, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 wherein multiple DNA molecules are used, wherein each DNA molecule comprises target-sequence elements that allow for RNA interference of one specific gene and wherein the different DNA molecules allow of RNA interference of different genes.

81. A combination or a kit of at least two DNA molecules according to any of 39, 40, and 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 or at least one DNA molecule according to any of 41, 42, and 43, 44, 45, 46, 47, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 further comprising:
a. optionally an RNA polymerase,
b. optionally a buffer for in vitro transcription,
c. optionally a buffer for hybridization,
d. optionally an RNase, and
e. optionally written instructions.

82. Use of a method of any of 1 to 40 or a kit or DNA molecule of any 41 to 81 for producing siRNA pools.

83. Use of 82 for producing siRNA pools to silence different genes.

84. Use of 83, wherein the different genes are different homologues of a gene family or different members of a cellular pathway.

85. A combination of at least 5 siRNAs being directed against all being directed against at least one gene.

86. A combination of 67 having at least 8, 9, 10, 11, 12, 13, 14, 15, 16, 17, 18, 19, 20, 21, 22, 23, 24, 25, 30, 40, 50, 60, 70, 80, 90 or at least 100 siRNAs being directed against at least one gene.

87. A combination of 85 or 86 having at least 8, 9, 10, 11, 12, 13, 14, 15, 16, 17, 18, 19, 20, 21, 22, 23, 24, 25, 30, 40, 50, 60, 70, 80, 90 or at least 100 siRNAs being directed against at least one other gene.

88. A combination of 85, 86 or 87, wherein the different genes are different homologues of a gene family or different members of a cellular pathway.

89. A combination of any of 85, 86, 87, or 89 wherein the siRNAs are obtainable by a method of any of 1 to 40.

90. A combination of any of 85, 86, 87, 88, or 89 for use in treating a disease in a human or animal being 91. Method of silencing gene expression by RNAi comprising at least the step of: applying a combination of siRNAs according to any of 85, 86, 87, 88 or 89.

92. Method according to 91,
wherein said combination of siRNAs is selected to allow silencing expression of a single gene.

93. Method according to 92,
wherein said combination of siRNAs is selected to allow silencing expression of more than one, preferably at least 2, 3, 4, 5, 6, 7, 8, 9, or at least 10 genes.

94. Method according to 93,
wherein said combination comprises at least 5, preferably at least 8, 9, 10, 11, 12, 13, 14, 15, 16, 17, 18, 19, 20, 21, 22, 23, 24, 25, 30, 40, 50, 60, 70, 80, 90 or at least 100 siRNAs per gene to be silenced.

95. Method according to any of 91, 92, 93, or 94 for treating a human or animal being suffering from a disease.

96. Method according to any of 91, 92, 93, or 94,
wherein said cell is not in direct contact with the human or animal body.

The invention claimed is:

1. A method of preparing different double stranded RNA molecules, wherein each strand of said different double stranded molecules has a length of 15 to 30 nucleotides wherein said different double stranded RNA molecules are capable of target specific RNA interference of at least one target gene, said method comprising at least the steps of:
   (a) providing at least one first DNA molecule comprising in the 5'-3' direction as repeating units a nucleic acid sequence with the following elements:
      5'-[(target-sequence-element)-(loop-sequence-element)]$_k$3', with k being an integer >1, with each target-sequence-element being a continuous sequence of 15 to 30 deoxyribonucleotides, the sequence of which is identical to a sequence in said at least one target gene, with each loop-sequence-element being a continuous sequence of 5 to 14 deoxyribonucleotides, which is not complementary to the said at least one target gene,
   (b) providing at least one second DNA molecule comprising in the 5'-3' direction in a repetitive manner a nucleic acid sequence with the following elements:
      5'-[(target-sequence-element)$_{rc}$-(loop-sequence-element)]$_l$-3', with l being an integer >1 and having the same value as k in the first DNA molecule, with each target-sequence-elementrc being a continuous sequence of 15 to 30 deoxyribonucleotides, with each loop-sequence-element being a continuous sequence of 5 to 14 deoxyribonucleotides, which is not complementary to the said at least one target gene, wherein the target-sequence-elements rc in order from the 3' end in the repeating units of said second DNA molecule are the respective reverse complement of the target sequence-elements in order from the 5' end in the repeating units of said first DNA molecule, and wherein the loop-sequence-elements in the repeating units of said second DNA molecule are not reverse complements of the loop-sequence-elements in the repeating units of said first DNA molecule,
   (c) in vitro transcribing said at least one first and at least one second DNA molecules using an RNA polymerase to obtain at least one first and at least one second RNA molecules,
   (d) hybridizing said at least one first and at least one second RNA molecules of step (c) to obtain a double stranded RNA molecule comprising single stranded loop-sequence-elements,
   (e) digesting the double stranded RNA molecule obtained in step d. with RNase T1 capable of preferentially recognizing, cleaving, and digesting the single stranded loop-sequence-elements thereby removing single stranded RNA loops to provide short double stranded RNA molecules wherein each strand of each of said short double stranded RNA molecules has a length of 15 to 30 nucleotides, wherein said resulting double stranded RNA molecules are capable of target-specific RNA interference of at least one target gene;
   and wherein each loop-sequence-element is cleavable by RNase T1 and has a sequence selected from the group consisting of 5'-AGTTG-3' and 5'-AGTTTG-3' such that there is no hybridization of two molecules consisting just of the loop-sequence-element.

2. The method according to claim 1, wherein said different double stranded RNA molecules are capable of target specific RNA interference of the same gene.

3. The method according to claim 1, wherein said different double stranded RNA molecules are capable of target specific RNA interference of at least two different target genes.

4. The method according to claim 1, wherein the loop-sequence elements are the same.

5. The method according to claim 1, wherein the loop-sequence elements are not the same.

6. The method according to claim 1, wherein each strand of said different double stranded molecules has a length of 17 to 25 nucleotides.

7. The method according to claim 1, wherein each strand of said different double stranded molecules has a 3'-overhang of 2 nucleotides.

8. The method according to claim 1, wherein the target-sequence-elements have a continuous sequence of 17 to 23 nucleotides.

* * * * *

SEQUENCE LISTING

<160> NUMBER OF SEQ ID NOS: 553

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 1
aaggcaaguu uggaaacgut t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 2
gaugcucuaa uguacugcct t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 3
gaagagcugc acauugact t                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 4
ucuuaacgcg gcacuucact t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 5
ucgucaaggu ggaccuaaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 6
ccaaacugcu caggcauaat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 7
ggugauggag aauagcagut t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 8
ccugcgucuc uacaacuaut t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 9
gucccagaua gagaaggagt t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 10
gguccucuuc aagucccagt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 11
ccaacauccu gcgucucuat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 12
gacaaugugu ggcacccugt t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 13
gcagagagau cgaaauccat t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, complete sequence

<400> SEQUENCE: 14
gccagaaaau cugcucuuat t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 15
acguuuccaa acuugccuut g                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 16
ggcaguacau uagagcauct g                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 17
gucaaaugug cagcucuuct g                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 18
gugaagugcc gcguuaagat g                                              21

```
<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 19
uuuaggucca ccuugacgat g                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 20
uuaugccuga gcaguuugga g                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 21
acugcuauuc uccaucacct t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 22
auaguuguag agacgcagga t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 23
cuccuucucu aucugggact t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 24
cugggacuug aagaggacct t                                              21

<210> SEQ ID NO 25
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 25
uagagacgca ggauguuggg a                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 26
cagggugcca cacauuguct t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 27
uggauuucga ucucucugcg c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, reverse complement antisense, complete sequence

<400> SEQUENCE: 28
uaagagcaga uuuucuggct t                                              21

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 29
aaggcaaguu uggaaacgu                                                 19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 30
gaugcucuaa uguacugcc                                                 19

<210> SEQ ID NO 31
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 31
gaagagcugc acauuugac                                                   19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 32
ucuuaacgcg gcacuucac                                                   19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 33
ucgucaaggu ggaccuaaa                                                   19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 34
ccaaacugcu caggcauaa                                                   19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 35
ggugauggag aauagcagu                                                   19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 36
ccugcgucuc uacaacuau                                                   19

<210> SEQ ID NO 37
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 37
gucccagaua gagaaggag                                                  19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 38
gguccucuuc aagucccag                                                  19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 39
ccaacauccu gcgucucua                                                  19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 40 gacaugugu ggcacccug                                                   19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 41
gcagagagau cgaaaucca                                                  19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 42
gccagaaaau cugcucuua                                                  19

<210> SEQ ID NO 43
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      siRNA, reverse complement antisense, 19 bp core sequence without
      3' overhang

<400> SEQUENCE: 43 acguuccaa acugccuu                                                       19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 44
ggcaguacau uagagcauc                                                     19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 45
gucaaaugug cagcucuuc                                                     19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 46
gugaagugcc gcguuaaga                                                     19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 47
uuuaggucca ccuugacga                                                     19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 48
uuaugccuga gcaguuugg                                                     19
```

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 49
acugcuauuc uccaucacc                                              19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 50
auaguuguag agacgcagg                                              19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 51
cuccuucucu aucugggac                                              19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 52
cugggacuug aagaggacc                                              19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 53
uagagacgca ggauguugg                                              19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 54
cagggugcca cacauuguc                                                19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 55
uggauuucga ucucucugc                                                19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 56
uaagagcaga uuuucuggc                                                19

<210> SEQ ID NO 57
<211> LENGTH: 1314
<212> TYPE: DNA
<213> ORGANISM: Homo sapiens

<400> SEQUENCE: 57
cggggcggga gatttgaaaa gtccttggcc agggcgcggc gtggcagatt cagttgtttg      60
cgggcggccg ggagagtagc agtgccttgg accccagctc tcctccccct ttctctctaa     120
ggatggccca gaaggagaac tcctacccct ggccctacgg ccgacagacg gctccatctg    180
gcctgagcac cctgccccag cgagtcctcc ggaaagagcc tgtcacccca tctgcacttg    240
tcctcatgag ccgctccaat gtccagccca cagctgcccc tggccagaag gtgatggaga    300
atagcagtgg gacacccgac atcttaacgc ggcacttcac aattgatgac tttgagattg    360
ggcgtcctct gggcaaaggc aagtttggaa acgtgtactt ggctcgggag aagaaaagcc    420
atttcatcgt ggcgctcaag gtcctcttca gtcccagat agagaaggag ggcgtggagc     480
atcagctgcg cagagagatc gaaatccagg cccacctgca ccatcccaac atcctgcgtc    540
tctacaacta tttttatgac cggaggagga tctacttgat tctagagtat gccccccgcg    600
gggagctcta caaggagctg cagaagagct gcacatttga cgagcagcga acagccacga    660
tcatggagga gttggcagat gctctaatgt actgccatgg gaagaaggtg attcacagag    720
acataaagcc agaaaatctg ctcttagggc tcaaggagag gctgaagatt gctgacttcg    780
gctggtctgt gcatgcgccc tccctgagga ggaagacaat gtgtggcacc ctggactacc    840 tgccccaga gatgattgag gggcgcatgc acaatgagaa ggtggatctg tggtgcattg     900
gagtgctttg ctatgagctg ctggtgggga cccaccctt tgagagtgca tcacacaacg    960
agacctatcg ccgcatcgtc aaggtggacc taaagttccc cgcttccgtg cccatgggag   1020
cccaggacct catctccaaa ctgctcaggc ataacccctc ggaacggctg cccctggccc   1080
aggtctcagc ccacccttgg gtccgggcca actctcggag ggtgctgcct ccctctgccc   1140

```
ttcaatctgt cgcctgatgg tccctgtcat tcactcgggt gcgtgtgttt gtatgtctgt    1200
gtatgtatag gggaaagaag ggatccctaa ctgttcccct atctgttttc tacctcctcc    1260
tttgtttaat aaaggctgaa gcttttgta ctcatgaaaa aaaaaaaaaa aaaa           1314
```

<210> SEQ ID NO 58
<211> LENGTH: 344
<212> TYPE: PRT
<213> ORGANISM: Homo sapiens

<400> SEQUENCE: 58

```
Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
    130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Met Gly Ala Gln Asp Leu Ile
    290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340
```

<210> SEQ ID NO 59
<211> LENGTH: 1224
<212> TYPE: DNA
<213> ORGANISM: Homo sapiens

<400> SEQUENCE: 59

```
cggggcggga gatttgaaaa gtccttggcc agggcgcggc gtggcagatt cagttgtttg      60
cgggcggccg ggagagtagc agtgccttgg accccaggct ccatctgcc tgagcaccct     120
gccccagcga gtcctccgga aagagcctgt cacccatct gcacttgtcc tcatgagccg     180
ctccaatgtc cagcccacag ctgccctgg ccagaaggtg atggagaata gcagtgggac     240
acccgacatc ttaacgcggc acttcacaat tgatgacttt gagattgggc gtcctctggg     300
caaaggcaag tttggaaacg tgtacttggc tcgggagaag aaaagccatt tcatcgtggc     360
gctcaaggtc ctcttcaagt cccagataga aaggagggc gtggagcatc agctgcgcag     420
agagatcgaa atccaggccc acctgcacca tcccaacatc ctgcgtctct acaactattt     480
ttatgaccgg aggaggatct acttgattct agagtatgcc cccgcgggg agctctacaa     540
ggagctgcag aagagctgca catttgacga gcagcgaaca gccacgatca tggaggagtt     600
ggcagatgct ctaatgtact gccatgggaa gaaggtgatt cacagagaca taaagccaga     660
aaatctgctc ttagggctca agggagagct gaagattgct gacttcggct ggtctgtgca     720
tgccgcctcc ctgaggagga gacaatgtg tggcaccctg gactacctgc cccagagat     780
gattgagggg cgcatgcaca atgagaaggt ggatctgtgg tgcattggag tgctttgcta     840
tgagctgctg gtggggaacc cacccttga gagtgcatca cacaacgaga cctatcgccg     900
catcgtcaag gtggacctaa agttccccgc ttccgtgccc atgggagccc aggacctcat     960
ctccaaactg ctcaggcata cccctcgga acggctgccc ctggcccagg tctcagccca    1020
cccttgggtc cgggccaact ctcggagggt gctgcctccc tctgcccttc aatctgtcgc    1080
ctgatggtcc ctgtcattca ctcgggtgcg tgtgtttgta tgtctgtgta tgtataggg   1140
aaagaaggga tccctaactg ttcccttatc tgttttctac ctcctccttt gtttaataaa    1200
ggctgaagct ttttgtactc atga                                           1224
```

<210> SEQ ID NO 60
<211> LENGTH: 303
<212> TYPE: PRT
<213> ORGANISM: Homo sapiens

<400> SEQUENCE: 60

```
Met Ser Arg Ser Asn Val Gln Pro Thr Ala Ala Pro Gly Gln Lys Val
1               5                   10                  15
Met Glu Asn Ser Ser Gly Thr Pro Asp Ile Leu Thr Arg His Phe Thr
                20                  25                  30
Ile Asp Asp Phe Glu Ile Gly Arg Pro Leu Gly Lys Gly Lys Phe Gly
            35                  40                  45
Asn Val Tyr Leu Ala Arg Glu Lys Lys Ser His Phe Ile Val Ala Leu
        50                  55                  60
Lys Val Leu Phe Lys Ser Gln Ile Glu Lys Glu Gly Val Glu His Gln
65                  70                  75                  80
Leu Arg Arg Glu Ile Glu Ile Gln Ala His Leu His His Pro Asn Ile
                85                  90                  95
Leu Arg Leu Tyr Asn Tyr Phe Tyr Asp Arg Arg Arg Ile Tyr Leu Ile
                100                 105                 110
```

Leu Glu Tyr Ala Pro Arg Gly Glu Leu Tyr Lys Leu Gln Lys Ser
         115                 120                 125

Cys Thr Phe Asp Glu Gln Arg Thr Ala Thr Ile Met Glu Glu Leu Ala
         130                 135                 140

Asp Ala Leu Met Tyr Cys His Gly Lys Lys Val Ile His Arg Asp Ile
145                 150                 155                 160

Lys Pro Glu Asn Leu Leu Leu Gly Leu Lys Gly Glu Leu Lys Ile Ala
                 165                 170                 175

Asp Phe Gly Trp Ser Val His Ala Pro Ser Leu Arg Arg Lys Thr Met
         180                 185                 190

Cys Gly Thr Leu Asp Tyr Leu Pro Pro Glu Met Ile Glu Gly Arg Met
         195                 200                 205

His Asn Glu Lys Val Asp Leu Trp Cys Ile Gly Val Leu Cys Tyr Glu
         210                 215                 220

Leu Leu Val Gly Asn Pro Pro Phe Glu Ser Ala Ser His Asn Glu Thr
225                 230                 235                 240

Tyr Arg Arg Ile Val Lys Val Asp Leu Lys Phe Pro Ala Ser Val Pro
                 245                 250                 255

Met Gly Ala Gln Asp Leu Ile Ser Lys Leu Leu Arg His Asn Pro Ser
         260                 265                 270

Glu Arg Leu Pro Leu Ala Gln Val Ser Ala His Pro Trp Val Arg Ala
         275                 280                 285

Asn Ser Arg Arg Val Leu Pro Pro Ser Ala Leu Gln Ser Val Ala
         290                 295                 300

<210> SEQ ID NO 61
<211> LENGTH: 368
<212> TYPE: DNA
<213> ORGANISM: Artificial Sequence
<220> FEATURE:
<223> OTHER INFORMATION: Description of Artificial Sequence: Synthetic
      sense template

<400> SEQUENCE: 61
aagctttaat acgactcact ataggagttg gccagaaaat ctgctcttaa gttggcagag    60
agatcgaaat ccaagttgga caatgtgtgg caccctgagt tgccaacatc ctgcgtctct   120
aagttgggtc ctcttcaagt cccagagttg gtcccagata gagaaggaga gttgcctgcg   180
tctctacaac tatagttggg tgatggagaa tagcagtagt tgccaaactg ctcaggcata   240
aagttgtcgt caaggtggac ctaaaagttg tcttaacgcg gcacttcaca gttggaagag   300
ctgcacattt gacagttgga tgctctaatg tactgccagt tgaaggcaag tttggaaacg   360
tagaattc                                                           368

<210> SEQ ID NO 62
<211> LENGTH: 368
<212> TYPE: DNA
<213> ORGANISM: Artificial Sequence
<220> FEATURE:
<223> OTHER INFORMATION: Description of Artificial Sequence: Synthetic
      antisense template

<400> SEQUENCE: 62
aagctttaat acgactcact ataggagttg acgtttccaa acttgcctta gttgggcagt    60
acattagagc atcagttggt caaatgtgca gctcttcagt tggtgaagtg ccgcgttaag   120
aagttgttta ggtccacctt gacgaagttg ttatgcctga gcagtttgga gttgactgct   180

```
attctccatc accagttgat agttgtagag acgcaggagt tgctccttct ctatctggga      240
cagttgctgg gacttgaaga ggaccagttg tagagacgca ggatgttgga gttgcagggt      300
gccacacatt gtcagttgtg gatttcgatc tctctgcagt tgtaagagca gattttctgg      360
cagaattc                                                               368
```

```
<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA ID s495, sense

<400> SEQUENCE: 63
ggugauggag aauagcagut t                                                21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA ID s495, antisense

<400> SEQUENCE: 64
acugcuauuc uccaucacct t                                                21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, first negative control

<400> SEQUENCE: 65
aguacugcuu acgauacggt t                                                21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, antisense, first negative control

<400> SEQUENCE: 66
ccguaucgua agcaguacut t                                                21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, sense, second negative control

<400> SEQUENCE: 67
uucuccgaac gugucacgut t                                                21

<210> SEQ ID NO 68
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      siRNA, antisense, second negative control

<400> SEQUENCE: 68
acgugacacg uucggagaat t                                              21

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 69
cgagcaaatc ttcgggcaa                                                 19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 70
gcgtcgagca cctgcagaa                                                 19

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 71
gccagaagtc ccagaggaa                                                 19

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 72
ctaagaaggt gaagaagga                                                 19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 73
aggaggagtt tcaacaaga                                                 19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued siRNA, sense, 19 bp core sequence without 3' overhang

<400> SEQUENCE: 74
ccacagagct cctgcccaa                                                   19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 75
gcttactaat gcagtttaa                                                   19

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 76
caggaagagt ttatgacca                                                   19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 77
gataattgaa ctcaccaaa                                                   19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 78
ggtgtggact acaggacaa                                                   19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 79
cattgttgct tgttgggta                                                   19

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

```
<400> SEQUENCE: 80
gggtgaagcg ctggatatt                                                  19

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 81
ctgatgcagt gccctagaa                                                  19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 82
ggaaagaatt aatgctcta                                                  19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 83
gccccaaagt tcacattaa                                                  19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 84
ttgcccgaag atttgctcg                                                  19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 85
ttctgcaggt gctcgacgc                                                  19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
``` siRNA, reverse complement antisense, 19 bp core sequence without
3' overhang

<400> SEQUENCE: 86
ttcctctggg acttctggc                                                19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 87
tccttcttca ccttcttag                                                19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 88
tcttgttgaa actcctcct                                                19

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 89
ttgggcagga gctctgtgg                                                19

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 90
ttaaactgca ttagtaagc                                                19

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 91
tggtcataaa ctcttcctg                                                19

<210> SEQ ID NO 92

```
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 92
tttggtgagt tcaattatc                                              19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 93
ttgtcctgta gtccacacc                                              19

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 94
tacccaacaa gcaacaatg                                              19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 95
aatatccagc gcttcaccc                                              19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 96
ttctagggca ctgcatcag                                              19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 97
```
tagagcatta attctttcc                                                19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 98
ttaatgtgaa ctttggggc                                                19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 99
cggcacaacc cattggaca                                                19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 100
ccacaaagca aggccagaa                                                19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 101
gagtcagaaa tgttcaata                                                19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 102
ccatgaagga cattcgtga                                                19

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 103
gagagaggta caaagaaga                                          19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 104
gaagaaggaa ccagccaca                                          19

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 105
ccatatggca aacggtaga                                          19

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 106
cggtagaaga actggatta                                          19

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 107
caaggaagtc acagtggaa                                          19

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 108
aagattcctt ctaactgaa                                          19

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 109
gaattcagtg ggttcagaa                                               19

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 110
gcagaagccc caaagttca                                               19

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 111
gctctgatgc agtgccta                                                19

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 112
aattaatgct ctaacgtga                                               19

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 113
cgtgataaac ctgctccaa                                               19

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 114
tgtccaatgg gttgtgccg                                               19

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 115
ttctggcctt gctttgtgg					19

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 116
tattgaacat ttctgactc					19

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 117
tcacgaatgt ccttcatgg					19

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 118
tcttctttgt acctctctc					19

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 119
tgtggctggt tccttcttc					19

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 120
tctaccgttt gccatatgg					19

<210> SEQ ID NO 121
<211> LENGTH: 19
<212> TYPE: DNA
<213> ORGANISM: Artificial Sequence
<220> FEATURE:

```
<223> OTHER INFORMATION: Description of Artificial Sequence: Synthetic
      siRNA, reverse complement antisense, 19 bp core sequence without
      3' overhang

<400> SEQUENCE: 121
taatccagtt cttctaccg                                              19

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 122
ttccactgtg acttccttg                                              19

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 123
ttcagttaga aggaatctt                                              19

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 124
ttctgaaccc actgaattc                                              19

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 125
tgaactttgg ggcttctgc                                              19

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 126
tagggcactg catcagagc                                              19
```

```
<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 127
tcacgttaga gcattaatt                                                  19

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 128
ttggagcagg tttatcacg                                                  19

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 129
gcagaggtgc acagacttt                                                  19

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 130
gtgagaactt ccaggacct                                                  19

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 131
gagatgaaga agtcgttga                                                  19

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 132
caggagagag gtacaaaga                                                  19
```

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 133
aagctaagaa ggtgaagaa                                            19

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 134
gcagtgagga ggaggagtt                                            19

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 135
tagaagaact ggattactt                                            19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 136
ggtaatagct gtaatgtgg                                            19

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 137
gggcatcagc cgtgagcat                                            19

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 138
tgcgcaaggt ccagagaga                                            19

```
<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 139
agagagaaac tgcaaggaa                                                19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 140
gcagttgaat tcagtgggt                                                19

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 141
gactacagga caaggggca                                                19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 142
gttcacatta actcaggca                                                19

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 143
aatgctctaa cgtgataaa                                                19

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 144
aaagtctgtg cacctctgc                                                19
```

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without 3' overhang

<400> SEQUENCE: 145
aggtcctgga agttctcac                                              19

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without 3' overhang

<400> SEQUENCE: 146
tcaacgactt cttcatctc                                              19

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without 3' overhang

<400> SEQUENCE: 147
tctttgtacc tctctcctg                                              19

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without 3' overhang

<400> SEQUENCE: 148
ttcttcacct tcttagctt                                              19

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without 3' overhang

<400> SEQUENCE: 149
aactcctcct cctcactgc                                              19

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without 3' overhang

```
<400> SEQUENCE: 150
aagtaatcca gttcttcta                                                19

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 151
ccacattaca gctattacc                                                19

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 152
atgctcacgg ctgatgccc                                                19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 153
tctctctgga ccttgcgca                                                19

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 154
ttccttgcag tttctctct                                                19

<210> SEQ ID NO 155
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 155
acccactgaa ttcaactgc                                                19

<210> SEQ ID NO 156
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      siRNA, reverse complement antisense, 19 bp core sequence without
      3' overhang

<400> SEQUENCE: 156 tgcccttgt cctgtagtc                                                    19

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 157
tgcctgagtt aatgtgaac                                                   19

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 158
tttatcacgt tagagcatt                                                   19

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 159
gagaaggagc ctcgagaac                                                   19

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 160
tgaagaagtc gttgatgga                                                   19

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 161
aagaaagcta agaaggtga                                                   19

<210> SEQ ID NO 162
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 162
gtgaggagga ggagtttca                                                       19

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 163
atggcaaacg gtagaagaa                                                       19

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 164
cttacaacga cgtggacat                                                       19

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 165
ctgagaaggc ccagcagat                                                       19

<210> SEQ ID NO 166
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 166
cgcaaggtcc agagagaaa                                                       19

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 167
aggaagtcac agtggaaga                                                       19

<210> SEQ ID NO 168
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 168
ggaagaagtg ggaggtggt                                            19

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 169
gctcccaaac tcaggcttt                                            19

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 170
gggcattgtt gcttgttgg                                            19

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 171
cattaactca ggcatttca                                            19

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 172
ctagaagggg aaagaatta                                            19

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 173
ttaatgctct aacgtgata                                            19

<210> SEQ ID NO 174
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      siRNA, reverse complement antisense, 19 bp core sequence without
      3' overhang

<400> SEQUENCE: 174
gttctcgagg ctccttctc                                                    19

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 175
tccatcaacg acttcttca                                                    19

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 176
tcaccttctt agctttctt                                                    19

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 177
tgaaactcct cctcctcac                                                    19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 178
ttcttctacc gtttgccat                                                    19

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 179
atgtccacgt cgttgtaag                                                    19
```

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 180
atctgctggg ccttctcag                                              19

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 181
tttctctctg gaccttgcg                                              19

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 182
tcttccactg tgacttcct                                              19

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 183
accacctccc acttcttcc                                              19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 184
aaagcctgag tttgggagc                                              19

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 185
ccaacaagca acaatgccc                                              19

<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 186
tgaaatgcct gagttaatg                                              19

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 187
taattctttc cccttctag                                              19

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 188
tatcacgtta gagcattaa                                              19

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 189
cgttgggaat atacctcaa                                              19

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 190
gcagagtggt cagagagaa                                              19

<210> SEQ ID NO 191
<211> LENGTH: 19
<212> TYPE: DNA
<213> ORGANISM: Artificial Sequence
<220> FEATURE:

```
<223> OTHER INFORMATION: Description of Artificial Sequence: Synthetic
      siRNA, sense, 19 bp core sequence without 3' overhang

<400> SEQUENCE: 191
gcaagagcct ggacgcatt                                                    19

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 192
gaggatttct gtcggcaca                                                    19

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 193
gagtatcagc agaagatca                                                    19

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 194
gtacatggct tcctggaca                                                    19

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 195
ggctacaggc caaggatga                                                    19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 196
gctctgcggt ctcactgta                                                    19

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
``` siRNA, sense, 19 bp core sequence without 3' overhang

<400> SEQUENCE: 197
ggagcttcct gtccaaatt                                              19

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 198
ggagaaggat gtccatgca                                              19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 199
gaccacaaat cctccaaat                                              19

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 200
gcctcatcca caacaatgt                                              19

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 201
gccatctcac gtgtacata                                              19

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 202
gagccacaat aaattctat                                              19

<210> SEQ ID NO 203
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 203
gtcgacaggt caaggctga                                                19

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 204
ttgaggtata ttcccaacg                                                19

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 205
ttctctctga ccactctgc                                                19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 206
aatgcgtcca ggctcttgc                                                19

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 207
tgtgccgaca gaaatcctc                                                19

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 208
tgatcttctg ctgatactc                                                19

<210> SEQ ID NO 209
<211> LENGTH: 19
<212> TYPE: DNA

```
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 209
tgtccaggaa gccatgtac                                                  19

<210> SEQ ID NO 210
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 210
tcatccttgg cctgtagcc                                                  19

<210> SEQ ID NO 211
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 211
tacagtgaga ccgcagagc                                                  19

<210> SEQ ID NO 212
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 212
aatttggaca ggaagctcc                                                  19

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 213
tgcatggaca tccttctcc                                                  19

<210> SEQ ID NO 214
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 214
atttggagga tttgtggtc                                                  19
```

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 215
acattgttgt ggatgaggc                                                19

<210> SEQ ID NO 216
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 216
tatgtacacg tgagatggc                                                19

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 217
atagaattta ttgtggctc                                                19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 218
tcagccttga cctgtcgac                                                19

<210> SEQ ID NO 219
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 219
tcgatggact ggagacaga                                                19

<210> SEQ ID NO 220
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

```
<400> SEQUENCE: 220
ggcagagtgg tcagagaga                                                19

<210> SEQ ID NO 221
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 221
cagcagacat gtggcgctt                                                19

<210> SEQ ID NO 222
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 222
gtgagctggt gggagcaaa                                                19

<210> SEQ ID NO 223
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 223
cagcccgctt cctgcagaa                                                19

<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 224
gaggagtatc agcagaaga                                                19

<210> SEQ ID NO 225
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 225
caaagctgaa cgaggccaa                                                19

<210> SEQ ID NO 226
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 226
```
ttgcacggct acaggccaa                                    19

<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 227
cactgtagat cctgagaaa                                    19

<210> SEQ ID NO 228
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 228
tggaggaagt ggagaagga                                    19

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 229
agacgcagga ggaggacaa                                    19

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 230
cgactggagc agctgggaa                                    19

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 231
ccgagaggaa ggtggccaa                                    19

<210> SEQ ID NO 232
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 232
catctcacgt gtacataat                                          19

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 233
cataatcaga gccacaata                                          19

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 234
tctgtctcca gtccatcga                                          19

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 235
tctctctgac cactctgcc                                          19

<210> SEQ ID NO 236
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 236
aagcgccaca tgtctgctg                                          19

<210> SEQ ID NO 237
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 237
tttgctccca ccagctcac                                          19

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without 3' overhang

<400> SEQUENCE: 238
ttctgcagga agcgggctg                                                      19

<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 239
tcttctgctg atactcctc                                                      19

<210> SEQ ID NO 240
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 240
ttggcctcgt tcagctttg                                                      19

<210> SEQ ID NO 241
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 241
ttggcctgta gccgtgcaa                                                      19

<210> SEQ ID NO 242
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 242
tttctcagga tctacagtg                                                      19

<210> SEQ ID NO 243
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 243
tccttctcca cttcctcca                                                      19

<210> SEQ ID NO 244
<211> LENGTH: 19

```
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 244
ttgtcctcct cctgcgtct                                              19

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 245
ttcccagctg ctccagtcg                                              19

<210> SEQ ID NO 246
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ttggccacct tcctctcgg                                              19

<210> SEQ ID NO 247
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 247
attatgtaca cgtgagatg                                              19

<210> SEQ ID NO 248
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 248
tattgtggct ctgattatg                                              19

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 249
ccgtgtccat cttcgtcta                                              19
```

<210> SEQ ID NO 250
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 250
cttcaaaact ctacggcac                                               19

<210> SEQ ID NO 251
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 251
tggcttacat cgatggact                                               19

<210> SEQ ID NO 252
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 252
ccctcagctt cctggtcaa                                               19

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 253
gtggcagagt ggtcagaga                                               19

<210> SEQ ID NO 254
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 254
tcaaagagcc agccgagaa                                               19

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 255
aggagtatca gcagaagat                                               19

```
<210> SEQ ID NO 256
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 256
ctgtggtggt caagatgtt                                                  19

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 257
tcaatgtgga gctgatgaa                                                  19

<210> SEQ ID NO 258
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 258
ctgagaaatc cgtgcgaga                                                  19

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 259
caggaggagg acaaggaca                                                  19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 260
tgacagatgg gacgacgaa                                                  19

<210> SEQ ID NO 261
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 261
ccaagtgagc cgtgctagt                                                  19

<210> SEQ ID NO 262
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 262
ccaggccatc tcacgtgta                                                    19

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 263
gtacataatc agagccaca                                                    19

<210> SEQ ID NO 264
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 264
tagacgaaga tggacacgg                                                    19

<210> SEQ ID NO 265
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 265
gtgccgtaga gttttgaag                                                    19

<210> SEQ ID NO 266
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 266
agtccatcga tgtaagcca                                                    19

<210> SEQ ID NO 267
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 267
ttgaccagga agctgaggg                                                    19
```

<210> SEQ ID NO 268
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 268
tctctgacca ctctgccac                                              19

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 269
ttctcggctg gctctttga                                              19

<210> SEQ ID NO 270
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 270
atcttctgct gatactcct                                              19

<210> SEQ ID NO 271
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 271
aacatcttga ccaccacag                                              19

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 272
ttcatcagct ccacattga                                              19

<210> SEQ ID NO 273
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without 3' overhang

<400> SEQUENCE: 273
tctcgcacgg atttctcag                                                19

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 274
tgtccttgtc ctcctcctg                                                19

<210> SEQ ID NO 275
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 275
ttcgtcgtcc catctgtca                                                19

<210> SEQ ID NO 276
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 276
actagcacgg ctcacttgg                                                19

<210> SEQ ID NO 277
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 277
tacacgtgag atggcctgg                                                19

<210> SEQ ID NO 278
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 278
tgtggctctg attatgtac                                                19

<210> SEQ ID NO 279
<211> LENGTH: 19

```
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 279
catcgatgga ctggagaca                                             19

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 280
tgaaggagct ggagatctc                                             19

<210> SEQ ID NO 281
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 281
gctacaccag atcgtgaaa                                             19

<210> SEQ ID NO 282
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 282
gcagcctcat ccacaacaa                                             19

<210> SEQ ID NO 283
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 283
ctggtggctt catgagcaa                                             19

<210> SEQ ID NO 284
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 284
acgcattccc tgaggattt                                             19

<210> SEQ ID NO 285
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 285
agtatcagca gaagatcat                                                 19

<210> SEQ ID NO 286
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 286
ggctcctacc tcagtgcta                                                 19

<210> SEQ ID NO 287
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 287
ctgtagatcc tgagaaatc                                                 19

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 288
aggaagtgga gaaggatgt                                                 19

<210> SEQ ID NO 289
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 289
ggacaaggac acagcagag                                                 19

<210> SEQ ID NO 290
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 290
acagatggga cgacgaaga                                                 19

<210> SEQ ID NO 291
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      siRNA, sense, 19 bp core sequence without 3' overhang

<400> SEQUENCE: 291
gccccacaga tgtatttat                                                    19

<210> SEQ ID NO 292
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 292
aggccatctc acgtgtaca                                                    19

<210> SEQ ID NO 293
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 293
taatcagagc cacaataaa                                                    19

<210> SEQ ID NO 294
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 294
tgtctccagt ccatcgatg                                                    19

<210> SEQ ID NO 295
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 295
gagatctcca gctccttca                                                    19

<210> SEQ ID NO 296
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 296
tttcacgatc tggtgtagc                                                    19

<210> SEQ ID NO 297
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 297
ttgttgtgga tgaggctgc                                                19

<210> SEQ ID NO 298
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 298
ttgctcatga agccaccag                                                19

<210> SEQ ID NO 299
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 299
aaatcctcag ggaatgcgt                                                19

<210> SEQ ID NO 300
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 300
atgatcttct gctgatact                                                19

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 301
tagcactgag gtaggagcc                                                19

<210> SEQ ID NO 302
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 302
```
gatttctcag gatctacag                                          19

<210> SEQ ID NO 303
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 303
acatccttct ccacttcct                                          19

<210> SEQ ID NO 304
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 304
ctctgctgtg tccttgtcc                                          19

<210> SEQ ID NO 305
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 305
tcttcgtcgt cccatctgt                                          19

<210> SEQ ID NO 306
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 306
ataaatacat ctgtggggc                                          19

<210> SEQ ID NO 307
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 307
tgtacacgtg agatggcct                                          19

<210> SEQ ID NO 308
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without
3' overhang

<400> SEQUENCE: 308
tttattgtgg ctctgatta                                                19

<210> SEQ ID NO 309
<211> LENGTH: 6
<212> TYPE: DNA
<213> ORGANISM: Artificial Sequence
<220> FEATURE:
<223> OTHER INFORMATION: Description of Artificial Sequence: Synthetic
      5 base loop sequence

<400> SEQUENCE: 309 agtttg                                                               6

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: Synthetic
      minimal T7 RNA polymerase promoter sequence

<400> SEQUENCE: 310
taatacgact cactatagg                                                19

<210> SEQ ID NO 311
<211> LENGTH: 6
<212> TYPE: DNA
<213> ORGANISM: Artificial Sequence
<220> FEATURE:
<223> OTHER INFORMATION: Description of Artificial Sequence: Synthetic
      HindIII restriction site

<400> SEQUENCE: 311 aagctt                                                               6

<210> SEQ ID NO 312
<211> LENGTH: 6
<212> TYPE: DNA
<213> ORGANISM: Artificial Sequence
<220> FEATURE:
<223> OTHER INFORMATION: Description of Artificial Sequence: Synthetic
      EcoRI restriction site

<400> SEQUENCE: 312 gaattc                                                               6

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, PolG OT, sense

<400> SEQUENCE: 313
gggugaagcg cuggauauut t                                             21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic siRNA, PolG OT, reverse complement antisense

<400> SEQUENCE: 314
aauauccagc gcuucaccct t                                             21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, Scyl1 OT, sense

<400> SEQUENCE: 315
gccucaucca caacaaugut t                                             21

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, Scyl1 OT, reverse complement antisense

<400> SEQUENCE: 316
acauuguugu ggaugaggct t                                             21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, negative control, sense

<400> SEQUENCE: 317
uugucuugca uucgacuaat t                                             21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, negative control, reverse complement antisense

<400> SEQUENCE: 318
uuagucgaau gcaagacaat t                                             21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, Mad2, sense

<400> SEQUENCE: 319
ggaacaacug aaagauuggt t                                             21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, Mad2, reverse complement antisense

```
<400> SEQUENCE: 320
ccaaucuuuc aguuguucct t                                              21

<210> SEQ ID NO 321
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, first of the smart pools for PolG, sense

<400> SEQUENCE: 321
gguaucggcu gucggauga                                                 19

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, first of the smart pools for PolG, reverse complement
      antisense

<400> SEQUENCE: 322
ucauccgaca gccgauacc                                                 19

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, second of the smart pools for PolG, sense

<400> SEQUENCE: 323
agugggaccu gcaagaauu                                                 19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, second of the smart pools for PolG, reverse complement
      antisense

<400> SEQUENCE: 324
aauucuugca ggucccacu                                                 19

<210> SEQ ID NO 325
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, third of the smart pools for PolG, sense

<400> SEQUENCE: 325
ucacaaggau gguaauagc                                                 19

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
              siRNA, third of the smart pools for PolG, reverse complement
              antisense

<400> SEQUENCE: 326
gcuauuacca uccuuguga                                                    19

<210> SEQ ID NO 327
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, fourth of the smart pools for PolG, sense

<400> SEQUENCE: 327
gcuuacuaau gcaguuuaa                                                    19

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, fourth of the smart pools for PolG, reverse complement
      antisense

<400> SEQUENCE: 328
uuaaacugca uuaguaagc                                                    19

<210> SEQ ID NO 329
<211> LENGTH: 255
<212> TYPE: DNA
<213> ORGANISM: Artificial Sequence
<220> FEATURE:
<223> OTHER INFORMATION: Description of Artificial Sequence: Synthetic
      dsRNA of a fragment of human POLG

<400> SEQUENCE: 329
ggaagaagtg ggaggtggtt gctgaacggg catggaaggg gggcacagag tcagaaatgt        60
tcaataagct tgagagcatt gctacgtctg acataccacg tacccggtg ctgggctgct        120 gcatcagccg agccctggag ccctcggctg tccaggaaga gtttatgacc agccgtgtga      180
attgggtggt acagagctct gctgttgact acttacacct catgcttgtg gccatgaagt      240
ggctgtttga agagt                                                       255

<210> SEQ ID NO 330
<211> LENGTH: 426
<212> TYPE: DNA
<213> ORGANISM: Artificial Sequence
<220> FEATURE:
<223> OTHER INFORMATION: Description of Artificial Sequence: Synthetic
      dsRNA of a fragment of human SCYL1

<400> SEQUENCE: 330
cagccgagaa gcaaaaattc ttccaggagc tgagcaagag cctggacgca ttccctgagg        60
atttctgtcg gcacaaggtg ctgccccagc tgctgaccgc cttcgagttc ggcaatgctg      120
gggccgttgt cctcacgccc ctcttcaagg tgggcaagtt cctgagcgct gaggagtatc      180
agcagaagat catccctgtg gtggtcaaga tgttctcatc cactgaccgg gccatgcgca      240
tccgcctcct gcagcagatg gagcagttca tccagtacct tgacgagcca acagtcaaca      300
cccagatctt cccccacgtc gtacatggct tcctggacac caaccctgcc atccgggagc      360
agacggtcaa gtccatgctg ctcctggccc caaagctgaa cgaggccaac ctcaatgtgg      420
``` agctga 426

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, POLG forward

<400> SEQUENCE: 331
ttccaggacc tgatgcagta                                              20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, POLG reverse

<400> SEQUENCE: 332
acaggcaggt aggagacacc                                              20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, SCYL1 forward

<400> SEQUENCE: 333
ctggaggaag tggagaagga                                              20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, SCYL1 reverse

<400> SEQUENCE: 334
tcagcttgga ggtgagtgag                                              20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, GAPDH forward

<400> SEQUENCE: 335
atgggtgtga accatgagaa                                              20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, GAPDH reverse

<400> SEQUENCE: 336
gtgctaagca gttggtggtg                                                 20

<210> SEQ ID NO 337
<211> LENGTH: 692
<212> TYPE: DNA
<213> ORGANISM: Homo sapiens

<400> SEQUENCE: 337
ggatgacatg aggaaaataa tgtaattgta attttgaaat gtggttttcc tgaaatcaag     60
tcatctatag ttgatatgtt ttatttcatt ggttaatttt tacatggaga aaaccaaaat    120
gatacttact gaactgtgtg taattgttcc ttttattttt ttggtaccta tttgacttac    180
catggagtta acatcatgaa tttattgcac attgttcaaa aggaaccagg aggttttttt    240
gtcaacattg tgatgtatat tcctttgaag atagtaactg tagatggaaa aacttgtgct    300
ataaagctag atgctttcct aaatcagatg ttttggtcaa gtagtttgac tcagtatagg    360
tagggagata tttaagtata aaatacaaca aaggaagtct aaatattcag aatctttgtt    420
aaggtcctga aagtaactca taatctataa acaatgaaat attgctgtat agctcctttt    480
gaccttcatt tcatgtatag ttttccctat tgaatcagtt tccaattatt tgactttaat    540
ttatgtaact tgaacctatg aagcaatgga tatttgtact gtttaatgtt ctgtgataca    600
gaactcttaa aaatgttttt tcatgtgttt tataaaatca agttttaagt gaaagtgagg    660
aaataaagtt aagtttgttt taaatttgtc tt                                  692

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, Mad2 forward

<400> SEQUENCE: 338
agatgacagt gcacccagag                                                 20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, Mad2 reverse

<400> SEQUENCE: 339
tccaacagtg gcagaaatgt                                                 20

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first of the smart pools for Scyl1, sense

<400> SEQUENCE: 340
uuucucagga ucuacaguga g                                               21

<210> SEQ ID NO 341
<211> LENGTH: 21
<212> TYPE: DNA
<213> ORGANISM: Artificial Sequence
<220> FEATURE:

```
<223> OTHER INFORMATION: Description of Artificial Sequence: Synthetic
      siRNA, second of the smart pools for Scyl1, sense

<400> SEQUENCE: 341
uugagguaua ucccaacgg g                                             21

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, third of the smart pools for Scyl1, sense

<400> SEQUENCE: 342
uugguuucua caaagcgguu g                                            21

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, fourth of the smart pools for Scyl1, sense

<400> SEQUENCE: 343
uuguacaaua aauacaucug u                                            21

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, PolG forward

<400> SEQUENCE: 344
ttccaggacc tgatgcagta                                              20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      primer, PolG reverse

<400> SEQUENCE: 345
acaggcaggt aggagacacc                                              20

<210> SEQ ID NO 346
<211> LENGTH: 30
<212> TYPE: DNA
<213> ORGANISM: Artificial Sequence
<220> FEATURE:
<223> OTHER INFORMATION: Description of Artificial Sequence: Synthetic
      primer, Mad2 forward

<400> SEQUENCE: 346
gatcgagctc ggatgacatg aggaaaataa                                   30

<210> SEQ ID NO 347
<211> LENGTH: 35
<212> TYPE: DNA
<213> ORGANISM: Artificial Sequence
<220> FEATURE:
<223> OTHER INFORMATION: Description of Artificial Sequence: Synthetic
``` primer, Mad2 reverse

<400> SEQUENCE: 347
gatcgtttaa acaagacaaa tttaaaacaa actta    35

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      PolG Pool #1 siRNA off-T guide

<400> SEQUENCE: 348
gggtgaagcg ctggatatt    19

<210> SEQ ID NO 349
<211> LENGTH: 19
<212> TYPE: DNA
<213> ORGANISM: Artificial Sequence
<220> FEATURE:
<223> OTHER INFORMATION: Description of Artificial Sequence: Synthetic
      PolG Pool #1 siRNA off-T passenger

<400> SEQUENCE: 349
aatatccagc gcttcaccc    19

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      Scyl1 Pool #1 siRNA off-T guide

<400> SEQUENCE: 350
gcctcatcca caacaatgt    19

<210> SEQ ID NO 351
<211> LENGTH: 19
<212> TYPE: DNA
<213> ORGANISM: Artificial Sequence
<220> FEATURE:
<223> OTHER INFORMATION: Description of Artificial Sequence: Synthetic
      Scyl1 Pool #1 siRNA off-T passenger

<400> SEQUENCE: 351
acattgttgt ggatgaggc    19

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 352
gcagggattt agtgcaaga    19

<210> SEQ ID NO 353
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 353
gcctcggtat cctcgtgaa                                                    19

<210> SEQ ID NO 354
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 354
gcagtgcttt aacaaatca                                                    19

<210> SEQ ID NO 355
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 355
ggacctgtgt cttctacaa                                                    19

<210> SEQ ID NO 356
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 356
gagttggctt cagaatgta                                                    19

<210> SEQ ID NO 357
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 357
gcactggact tggttccca                                                    19

<210> SEQ ID NO 358
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 358
ggatgctcct gaaagcaaa                                                    19

<210> SEQ ID NO 359
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

```
<400> SEQUENCE: 359
ggccagtatt agagaacaa                                              19

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 360
ggaaacttgt gaatctgaa                                              19

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 361
ggaggctctt atggtacta                                              19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 362
gacaaatgtt caggccta                                               19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 363
ggcactaact ttcaagtta                                              19

<210> SEQ ID NO 364
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 364
gcagcaaact cccagagta                                              19

<210> SEQ ID NO 365
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 365
```
ggcgcaaatt ctggaggaa                                                    19

<210> SEQ ID NO 366
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 366
ggaacaaact gcctagcaa                                                    19

<210> SEQ ID NO 367
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 367
ggatcagggt tctgccaca                                                    19

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 368
ggagagcgat ggtagtaca                                                    19

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 369
gaagatgatt ctgctgcta                                                    19

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 370
ggagaaactt caaggaata                                                    19

<210> SEQ ID NO 371
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 371
cgtttccggt tggaacgaa                                              19

<210> SEQ ID NO 372
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 372
ggataatggt acttcagca                                              19

<210> SEQ ID NO 373
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 373
ggaacccatt gctgcggca                                              19

<210> SEQ ID NO 374
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 374
gatatgccat tgcctggaa                                              19

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 375
gccaccatat acaaagaaa                                              19

<210> SEQ ID NO 376
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 376
cgaagggtct gagtggcaa                                              19

<210> SEQ ID NO 377
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 377
gatgaaaggt ggaaacaaa                                              19

<210> SEQ ID NO 378
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 378
ggaggaatgt tacaagaca                                              19

<210> SEQ ID NO 379
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 379
ggcctcagat ttccaaaga                                              19

<210> SEQ ID NO 380
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 380
gcagcagcct ccagcacaa                                              19

<210> SEQ ID NO 381
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 381
ggcttgaact caaacttga                                              19

<210> SEQ ID NO 382
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 382
tcttgcacta aatccctgc                                              19

<210> SEQ ID NO 383
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, reverse complement antisense, 19 bp core sequence without
    3' overhang

<400> SEQUENCE: 383
ttcacgagga taccgaggc                                                    19

<210> SEQ ID NO 384
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 384
tgatttgtta aagcactgc                                                    19

<210> SEQ ID NO 385
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 385
ttgtagaaga cacaggtcc                                                    19

<210> SEQ ID NO 386
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 386
tacattctga agccaactc                                                    19

<210> SEQ ID NO 387
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 387
tgggaaccaa gtccagtgc                                                    19

<210> SEQ ID NO 388
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 388
tttgctttca ggagcatcc                                                    19

<210> SEQ ID NO 389
<211> LENGTH: 19
<212> TYPE: DNA
<213> ORGANISM: Artificial Sequence
<220> FEATURE:
<223> OTHER INFORMATION: Description of Artificial Sequence: Synthetic siRNA, reverse complement antisense, 19 bp core sequence without
3' overhang

<400> SEQUENCE: 389
ttgttctcta atactggcc                                              19

<210> SEQ ID NO 390
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 390
ttcagattca caagtttcc                                              19

<210> SEQ ID NO 391
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 391
tagtaccata agagcctcc                                              19

<210> SEQ ID NO 392
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 392
tagggcctga acatttgtc                                              19

<210> SEQ ID NO 393
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 393
taacttgaaa gttagtgcc                                              19

<210> SEQ ID NO 394
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 394
tactctggga gtttgctgc                                              19

<210> SEQ ID NO 395

```
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 395
ttcctccaga atttgcgcc                                              19

<210> SEQ ID NO 396
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 396
ttgctaggca gtttgttcc                                              19

<210> SEQ ID NO 397
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 397
tgtggcagaa ccctgatcc                                              19

<210> SEQ ID NO 398
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 398
tgtactacca tcgctctcc                                              19

<210> SEQ ID NO 399
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 399
tagcagcaga atcatcttc                                              19

<210> SEQ ID NO 400
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 400
```
tattccttga agtttctcc                                              19

<210> SEQ ID NO 401
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 401
ttcgttccaa ccggaaacg                                              19

<210> SEQ ID NO 402
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 402
tgctgaagta ccattatcc                                              19

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 403
tgccgcagca atgggttcc                                              19

<210> SEQ ID NO 404
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 404
ttccaggcaa tggcatatc                                              19

<210> SEQ ID NO 405
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 405
tttctttgta tatggtggc                                              19

<210> SEQ ID NO 406
<211> LENGTH: 19
<212> TYPE: DNA
<213> ORGANISM: Artificial Sequence
<220> FEATURE:

```
<223> OTHER INFORMATION: Description of Artificial Sequence: Synthetic
      siRNA, reverse complement antisense, 19 bp core sequence without
      3' overhang

<400> SEQUENCE: 406
ttgccactca gacccttcg                                                    19

<210> SEQ ID NO 407
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 407
tttgtttcca cctttcatc                                                    19

<210> SEQ ID NO 408
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 408
tgtcttgtaa cattcctcc                                                    19

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 409
tctttggaaa tctgaggcc                                                    19

<210> SEQ ID NO 410
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 410
ttgtgctgga ggctgctgc                                                    19

<210> SEQ ID NO 411
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 411
tcaagtttga gttcaagcc                                                    19
```

<210> SEQ ID NO 412
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 412
gcatcagatt ccaaatcta                                                19

<210> SEQ ID NO 413
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 413
ggaggagtct ggaacacca                                                19

<210> SEQ ID NO 414
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 414
ggcagtgctt cctcccaca                                                19

<210> SEQ ID NO 415
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 415
ggatgaatcc tcttgccaa                                                19

<210> SEQ ID NO 416
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 416
ccgtccacct aattccaaa                                                19

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 417
ccagttatct cctcaacaa                                                19

<210> SEQ ID NO 418

```
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 418
cccagacctt caaaccaaa                                                 19

<210> SEQ ID NO 419
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 419
ggatatggtt ctggcttca                                                 19

<210> SEQ ID NO 420
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 420
ggaaccgagt ctcgcttta                                                 19

<210> SEQ ID NO 421
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 421
gctgccctct gtagccaca                                                 19

<210> SEQ ID NO 422
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 422
ggaagccaat atgcacaaa                                                 19

<210> SEQ ID NO 423
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 423
gatagctggt tacctgcca                                                 19

<210> SEQ ID NO 424
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 424
cctgccaaat ctccaccaa                                              19

<210> SEQ ID NO 425
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 425
ggagtgccat ggaaaggta                                              19

<210> SEQ ID NO 426
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 426
gctgcgggat aacaccaca                                              19

<210> SEQ ID NO 427
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 427
gggtctaatt cttccctca                                              19

<210> SEQ ID NO 428
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 428
cagcaaagtt ccctgatta                                              19

<210> SEQ ID NO 429
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 429
cagatcccat aggacacaa                                              19

<210> SEQ ID NO 430
<211> LENGTH: 19
<212> TYPE: DNA
```

<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 430
ccactcatct ctccaacaa                                                    19

<210> SEQ ID NO 431
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 431
gggtcaacct tgagaacga                                                    19

<210> SEQ ID NO 432
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 432
gcccactgct gacattcca                                                    19

<210> SEQ ID NO 433
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 433
gacattccat ctgaatcta                                                    19

<210> SEQ ID NO 434
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 434
gcactgccct gatccgata                                                    19

<210> SEQ ID NO 435
<211> LENGTH: 19
<212> TYPE: DNA
<213> ORGANISM: Artificial Sequence
<220> FEATURE:
<223> OTHER INFORMATION: Description of Artificial Sequence: Synthetic
    siRNA, sense, 19 bp core sequence without 3' overhang

<400> SEQUENCE: 435
gcacatgtgt gtgttggga                                                    19

<210> SEQ ID NO 436
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 436
gtttgccact gatgatgaa                                                    19

<210> SEQ ID NO 437
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 437
cagccgcttt ctggcacaa                                                    19

<210> SEQ ID NO 438
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 438
ccagtcagat cccgtggga                                                    19

<210> SEQ ID NO 439
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 439
cgatcttgct ggcgcttca                                                    19

<210> SEQ ID NO 440
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 440
gggcagccct gctccttta                                                    19

<210> SEQ ID NO 441
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 441
ggaggagggt cggattcaa                                                    19

<210> SEQ ID NO 442
<211> LENGTH: 19
<212> TYPE: DNA
<213> ORGANISM: Artificial Sequence
<220> FEATURE:

```
<223> OTHER INFORMATION: Description of Artificial Sequence: Synthetic
      siRNA, reverse complement antisense, 19 bp core sequence without
      3' overhang

<400> SEQUENCE: 442
tagatttgga atctgatgc                                               19

<210> SEQ ID NO 443
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 443
tggtgttcca gactcctcc                                               19

<210> SEQ ID NO 444
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 444
tgtgggagga agcactgcc                                               19

<210> SEQ ID NO 445
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 445
ttggcaagag gattcatcc                                               19

<210> SEQ ID NO 446
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 446
tttggaatta ggtggacgg                                               19

<210> SEQ ID NO 447
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 447
ttgttgagga gataactgg                                               19
```

```
<210> SEQ ID NO 448
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 448
tttggtttga aggtctggg                                              19

<210> SEQ ID NO 449
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 449
tgaagccaga accatatcc                                              19

<210> SEQ ID NO 450
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 450
taaagcgaga ctcggttcc                                              19

<210> SEQ ID NO 451
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 451
tgtggctaca gagggcagc                                              19

<210> SEQ ID NO 452
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 452
tttgtgcata ttggcttcc                                              19

<210> SEQ ID NO 453
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang
```

```
<400> SEQUENCE: 453
tggcaggtaa ccagctatc                                                19

<210> SEQ ID NO 454
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 454
ttggtggaga tttggcagg                                                19

<210> SEQ ID NO 455
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 455
tacctttcca tggcactcc                                                19

<210> SEQ ID NO 456
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 456
tgtggtgtta tcccgcagc                                                19

<210> SEQ ID NO 457
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 457
tgagggaaga attagaccc                                                19

<210> SEQ ID NO 458
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 458
taatcaggga actttgctg                                                19

<210> SEQ ID NO 459
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      siRNA, reverse complement antisense, 19 bp core sequence without
      3' overhang

<400> SEQUENCE: 459
ttgtgtccta tgggatctg                                              19

<210> SEQ ID NO 460
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 460
ttgttggaga gatgagtgg                                              19

<210> SEQ ID NO 461
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 461
tcgttctcaa ggttgaccc                                              19

<210> SEQ ID NO 462
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 462
tggaatgtca gcagtgggc                                              19

<210> SEQ ID NO 463
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 463
tagattcaga tggaatgtc                                              19

<210> SEQ ID NO 464
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 464
tatcggatca gggcagtgc                                              19
```

<210> SEQ ID NO 465
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 465
tcccaacaca cacatgtgc                                                19

<210> SEQ ID NO 466
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 466
ttcatcatca gtggcaaac                                                19

<210> SEQ ID NO 467
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 467
ttgtgccaga aagcggctg                                                19

<210> SEQ ID NO 468
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 468
tcccacggga tctgactgg                                                19

<210> SEQ ID NO 469
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 469
tgaagcgcca gcaagatcg                                                19

<210> SEQ ID NO 470
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

```
<400> SEQUENCE: 470
taaaggagca gggctgccc                                              19

<210> SEQ ID NO 471
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 471
ttgaatccga ccctcctcc                                              19

<210> SEQ ID NO 472
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 472
ggcctgtact tggacatga                                              19

<210> SEQ ID NO 473
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 473
gaaacttgct gccacaaga                                              19

<210> SEQ ID NO 474
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 474
gaatgtgtct ttcagcgca                                              19

<210> SEQ ID NO 475
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 475
gcagacaaat ggactgcca                                              19

<210> SEQ ID NO 476
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang
```

```
<400> SEQUENCE: 476
gggcagtgct gaaggaata                                                19

<210> SEQ ID NO 477
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 477
cgtacagcct ggtggtgaa                                                19

<210> SEQ ID NO 478
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 478
gcggcatctt ctggaacta                                                19

<210> SEQ ID NO 479
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 479
gaatgatctt gacccaaga                                                19

<210> SEQ ID NO 480
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 480
ccctaggtct gaaaggaaa                                                19

<210> SEQ ID NO 481
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 481
gggtctggtt ggaatgaca                                                19

<210> SEQ ID NO 482
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang
```

<400> SEQUENCE: 482
cggtaccggt caaacagaa						19

<210> SEQ ID NO 483
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 483
gtaaacatgt gggatagaa						19

<210> SEQ ID NO 484
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 484
ggtggataat ggcacagca						19

<210> SEQ ID NO 485
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 485
gaataatgct gcttcccaa						19

<210> SEQ ID NO 486
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 486
gaaagcacct cctcctgca						19

<210> SEQ ID NO 487
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 487
gatgaggcct ggatcatga						19

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 488
gaggaggcct tgaagagta                                            19

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 489
gcccgccaat ctccaaaga                                            19

<210> SEQ ID NO 490
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 490
gcagcaagtt gcgcgcaca                                            19

<210> SEQ ID NO 491
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 491
ccggtggctt gtcggtgaa                                            19

<210> SEQ ID NO 492
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 492
gcatggtgct atccctgga                                            19

<210> SEQ ID NO 493
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 493
ggtacgattt aatccagaa                                            19

<210> SEQ ID NO 494
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 494
cctcaagagt ggaggtaaa                                              19

<210> SEQ ID NO 495
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 495
gaggccacct ccagggtta                                              19

<210> SEQ ID NO 496
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 496
gctggctcgt tcttcgaaa                                              19

<210> SEQ ID NO 497
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 497
ggcctcttat cacattcca                                              19

<210> SEQ ID NO 498
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 498
ccacctgaat ctgactcaa                                              19

<210> SEQ ID NO 499
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 499
gcaatgctgt ggtccggta                                              19

<210> SEQ ID NO 500
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, sense, 19 bp core sequence without 3' overhang

<400> SEQUENCE: 500
gcccagaagt ctctgcaca                                              19

<210> SEQ ID NO 501
<211> LENGTH: 19
<212> TYPE: DNA
<213> ORGANISM: Artificial Sequence
<220> FEATURE:
<223> OTHER INFORMATION: Description of Artificial Sequence: Synthetic
     siRNA, sense, 19 bp core sequence without 3' overhang

<400> SEQUENCE: 501
cgagttcgct ggtgaagaa                                              19

<210> SEQ ID NO 502
<211> LENGTH: 19
<212> TYPE: DNA
<213> ORGANISM: Artificial Sequence
<220> FEATURE:
<223> OTHER INFORMATION: Description of Artificial Sequence: Synthetic
     siRNA, reverse complement antisense, 19 bp core sequence without
     3' overhang

<400> SEQUENCE: 502
tcatgtccaa gtacaggcc                                              19

<210> SEQ ID NO 503
<211> LENGTH: 19
<212> TYPE: DNA
<213> ORGANISM: Artificial Sequence
<220> FEATURE:
<223> OTHER INFORMATION: Description of Artificial Sequence: Synthetic
     siRNA, reverse complement antisense, 19 bp core sequence without
     3' overhang

<400> SEQUENCE: 503
tcttgtggca gcaagtttc                                              19

<210> SEQ ID NO 504
<211> LENGTH: 19
<212> TYPE: DNA
<213> ORGANISM: Artificial Sequence
<220> FEATURE:
<223> OTHER INFORMATION: Description of Artificial Sequence: Synthetic
     siRNA, reverse complement antisense, 19 bp core sequence without
     3' overhang

<400> SEQUENCE: 504
tgcgctgaaa gacacattc                                              19

<210> SEQ ID NO 505
<211> LENGTH: 19
<212> TYPE: DNA
<213> ORGANISM: Artificial Sequence
<220> FEATURE:
<223> OTHER INFORMATION: Description of Artificial Sequence: Synthetic
     siRNA, reverse complement antisense, 19 bp core sequence without
     3' overhang

<400> SEQUENCE: 505
tggcagtcca tttgtctgc                                              19

<210> SEQ ID NO 506
<211> LENGTH: 19
<212> TYPE: DNA
<213> ORGANISM: Artificial Sequence
<220> FEATURE:
<223> OTHER INFORMATION: Description of Artificial Sequence: Synthetic
     siRNA, reverse complement antisense, 19 bp core sequence without
     3' overhang

<400> SEQUENCE: 506
tattccttca gcactgccc                                                    19

<210> SEQ ID NO 507
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 507
ttcaccacca ggctgtacg                                                    19

<210> SEQ ID NO 508
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 508
tagttccaga agatgccgc                                                    19

<210> SEQ ID NO 509
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 509
tcttgggtca agatcattc                                                    19

<210> SEQ ID NO 510
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 510
tttcctttca gacctaggg                                                    19

<210> SEQ ID NO 511
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 511
tgtcattcca accagaccc                                                    19

<210> SEQ ID NO 512
<211> LENGTH: 19
<212> TYPE: DNA

```
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 512
ttctgtttga ccggtaccg                                              19

<210> SEQ ID NO 513
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 513
ttctatccca catgtttac                                              19

<210> SEQ ID NO 514
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 514
tgctgtgcca ttatccacc                                              19

<210> SEQ ID NO 515
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 515
ttgggaagca gcattattc                                              19

<210> SEQ ID NO 516
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 516
tgcaggagga ggtgctttc                                              19

<210> SEQ ID NO 517
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 517
tcatgatcca ggcctcatc                                              19
```

<210> SEQ ID NO 518
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 518
tactcttcaa ggcctcctc                                              19

<210> SEQ ID NO 519
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 519
tctttggaga ttggcgggc                                              19

<210> SEQ ID NO 520
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 520
tgtgcgcgca acttgctgc                                              19

<210> SEQ ID NO 521
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 521
ttcaccgaca agccaccgg                                              19

<210> SEQ ID NO 522
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 522
tccagggata gcaccatgc                                              19

<210> SEQ ID NO 523
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without

```
                                  3' overhang

<400> SEQUENCE: 523
ttctggatta aatcgtacc                                                  19

<210> SEQ ID NO 524
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 524
tttacctcca ctcttgagg                                                  19

<210> SEQ ID NO 525
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 525
taaccctgga ggtggcctc                                                  19

<210> SEQ ID NO 526
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 526
tttcgaagaa cgagccagc                                                  19

<210> SEQ ID NO 527
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 527
tggaatgtga taagaggcc                                                  19

<210> SEQ ID NO 528
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 528
ttgagtcaga ttcaggtgg                                                  19

<210> SEQ ID NO 529
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 529
taccggacca cagcattgc                                                  19

<210> SEQ ID NO 530
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 530
tgtgcagaga cttctgggc                                                  19

<210> SEQ ID NO 531
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA, reverse complement antisense, 19 bp core sequence without
      3' overhang

<400> SEQUENCE: 531
ttcttcacca gcgaactcg                                                  19

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, negative control (ctrl.), sense

<400> SEQUENCE: 532
uugucuugca uucgacuaau t                                               21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, negative control (ctrl.), reverse complement antisense

<400> SEQUENCE: 533
uuagucgaau gcaagacaau t                                               21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first control for TNRC6A (siRNA A1), sense

<400> SEQUENCE: 534
uaaugccaag cgagcuacau t                                               21
```

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first control for TNRC6A (siRNA A1), reverse complement
      antisense

<400> SEQUENCE: 535
uguagcucgc uggcauuau t                                            21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, second control for TNRC6A (siRNA A2), sense

<400> SEQUENCE: 536
uauaguacug cacugaauau t                                           21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, second control for TNRC6A (siRNA A2), reverse complement
      antisense

<400> SEQUENCE: 537
uauucagugc aguacuauau t                                           21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first control for TNRC6B (siRNA B1), sense

<400> SEQUENCE: 538
ggagugccau ggaaaggurau t                                          21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first control for TNRC6B (siRNA B1), reverse complement
      antisense

<400> SEQUENCE: 539
uaccuuucca uggcacuccu t                                           21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, second control for TNRC6B (siRNA B2), sense

<400> SEQUENCE: 540
ggaaguuguu gcuaagaaau t                                           21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, second control for TNRC6B (siRNA B2), reverse complement
      antisense

<400> SEQUENCE: 541
uuucuuagca acaacuuccu t                                            21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first control for TNRC6C (siRNA C1), sense

<400> SEQUENCE: 542
caauggcguu gguaauaucu t                                            21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, first control for TNRC6C (siRNA C1), reverse complement
      antisense

<400> SEQUENCE: 543
gauauuacca acgccauugu t                                            21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, second control for TNRC6C (siRNA C2), sense

<400> SEQUENCE: 544
caauaugaau cuugaucagu t                                            21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA, second control for TNRC6C (siRNA C2), reverse complement
      antisense

<400> SEQUENCE: 545
cugaucaaga uucauauugu t                                            21

<210> SEQ ID NO 546
<211> LENGTH: 130
<212> TYPE: PRT
<213> ORGANISM: Artificial Sequence
<220> FEATURE:
<223> OTHER INFORMATION: Description of Artificial Sequence: Synthetic
      RNase T1

<400> SEQUENCE: 546

```
Met Met Tyr Ser Lys Leu Leu Thr Leu Thr Thr Leu Leu Leu Pro Thr
1               5                   10                  15

Ala Leu Ala Leu Pro Ser Leu Val Glu Arg Ala Cys Asp Tyr Thr Cys
            20                  25                  30

Gly Ser Asn Cys Tyr Ser Ser Ser Asp Val Ser Thr Ala Gln Ala Ala
        35                  40                  45

Gly Tyr Gln Leu His Glu Asp Gly Thr Val Gly Ser Asn Ser Tyr
    50                  55                  60

Pro His Lys Tyr Asn Asn Tyr Glu Gly Phe Asp Phe Ser Val Ser Ser
65                  70                  75                  80

Pro Tyr Tyr Glu Trp Pro Ile Leu Ser Ser Gly Asp Val Tyr Ser Gly
                85                  90                  95

Gly Ser Pro Gly Ala Asp Arg Val Val Phe Asn Glu Asn Asn Gln Leu
            100                 105                 110

Ala Gly Val Ile Thr His Thr Gly Ala Ser Gly Asn Asn Phe Val Glu
        115                 120                 125

Cys Thr
    130
```

<210> SEQ ID NO 547
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
ugccuuaguu gggcagu                                                    17

<210> SEQ ID NO 548
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
acugccaguu gaaggca                                                    17

<210> SEQ ID NO 549
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
ugccuuaguu ugggcagu                                                   18

<210> SEQ ID NO 550
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
acugccaguu ugaaggca                                                   18

```
<210> SEQ ID NO 551
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
ccuuuguuug ggca                                                         14

<210> SEQ ID NO 552
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
ugccuguuug aagg                                                         14

<210> SEQ ID NO 553
<211> LENGTH: 19
<212> TYPE: DNA
<213> ORGANISM: Bacteriophage T7

<400> SEQUENCE: 553
taatacgact cactatagg                                                    19
```